United States Patent
Abbot et al.

(10) Patent No.: US 8,969,315 B2
(45) Date of Patent: Mar. 3, 2015

(54) ENHANCEMENT OF PLACENTAL STEM CELL POTENCY USING MODULATORY RNA MOLECULES

(75) Inventors: Stewart Abbot, Warren, NJ (US); Kathy E. Karasiewicz-Mendez, Hillsborough, NJ (US); Vanessa Voskinarian-Berse, Millington, NJ (US); Xiaokui Zhang, Livingston, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 0 days.

(21) Appl. No.: 13/340,589

(22) Filed: Dec. 29, 2011

(65) Prior Publication Data

US 2012/0230959 A1    Sep. 13, 2012

Related U.S. Application Data

(60) Provisional application No. 61/429,070, filed on Dec. 31, 2010.

(51) Int. Cl.
| | | |
|---|---|---|
| A61K 48/00 | (2006.01) | |
| A61K 35/50 | (2006.01) | |
| A61K 31/7088 | (2006.01) | |
| A61K 31/7105 | (2006.01) | |
| A61K 31/713 | (2006.01) | |
| C12N 5/073 | (2010.01) | |
| C12N 5/0775 | (2010.01) | |
| C12N 15/113 | (2010.01) | |
| A61K 35/12 | (2006.01) | |

(52) U.S. Cl.
CPC ............ *A61K 35/50* (2013.01); *A61K 31/7088* (2013.01); *A61K 31/7105* (2013.01); *A61K 31/713* (2013.01); *C12N 5/0605* (2013.01); *C12N 5/0668* (2013.01); *C12N 15/1138* (2013.01); *A61K 2035/122* (2013.01); *C12N 2501/38* (2013.01); *C12N 2501/65* (2013.01); *C12N 2310/141* (2013.01)
USPC .......................................... 514/44; 536/24.5

(58) Field of Classification Search
None
See application file for complete search history.

(56) References Cited

U.S. PATENT DOCUMENTS

| | | | |
|---|---|---|---|
| 3,862,002 A | 1/1975 | Sanders | |
| 4,060,081 A | 11/1977 | Yannas et al. | |
| 4,458,678 A | 7/1984 | Yannas et al. | |
| 4,485,097 A | 11/1984 | Bell | |
| 4,520,821 A | 6/1985 | Schmidt et al. | |
| 4,798,824 A | 1/1989 | Belzer et al. | |
| 4,829,000 A | 5/1989 | Kleinman et al. | |
| 5,004,681 A | 4/1991 | Boyse et al. | |
| 5,192,312 A | 3/1993 | Orton | |
| 5,192,553 A | 3/1993 | Boyse et al. | |
| 5,197,985 A | 3/1993 | Caplan et al. | |
| 5,226,914 A | 7/1993 | Caplan et al. | |
| 5,272,071 A | 12/1993 | Chappel | |
| 5,284,766 A | 2/1994 | Okano et al. | |
| 5,318,025 A | 6/1994 | Dumoulin et al. | |
| 5,356,373 A | 10/1994 | Dracker et al. | |
| 5,372,581 A | 12/1994 | Anderson | |
| 5,385,901 A | 1/1995 | Kaplan | |
| 5,415,665 A | 5/1995 | Hessel et al. | |
| 5,426,098 A | 6/1995 | Carlino | |
| 5,437,994 A | 8/1995 | Emerson et al. | |
| 5,443,950 A | 8/1995 | Naughton et al. | |
| 5,460,964 A | 10/1995 | McGlave et al. | |
| 5,464,764 A | 11/1995 | Capecchi et al. | |
| 5,486,359 A | 1/1996 | Caplan et al. | |
| 5,487,992 A | 1/1996 | Capecchi et al. | |
| 5,516,532 A | 5/1996 | Atala et al. | |
| 5,552,267 A | 9/1996 | Stern et al. | |
| 5,580,724 A | 12/1996 | Alter et al. | |
| 5,580,777 A | 12/1996 | Bernard | |
| 5,591,625 A | 1/1997 | Gerson et al. | |
| 5,605,822 A | 2/1997 | Emerson et al. | |
| 5,613,982 A | 3/1997 | Goldstein | |
| 5,627,059 A | 5/1997 | Capecchi et al. | |
| 5,635,386 A | 6/1997 | Palsson et al. | |
| 5,635,387 A | 6/1997 | Fei et al. | |
| 5,643,741 A | 7/1997 | Tsukamoto et al. | |
| 5,646,043 A | 7/1997 | Emerson et al. | |
| 5,654,186 A | 8/1997 | Cerami et al. | |
| 5,654,381 A | 8/1997 | Hrkach et al. | |
| 5,665,557 A | 9/1997 | Murray et al. | |
| 5,668,104 A | 9/1997 | Nakahata et al. | |
| 5,670,147 A | 9/1997 | Emerson et al. | |
| 5,670,351 A | 9/1997 | Emerson et al. | |

(Continued)

FOREIGN PATENT DOCUMENTS

| | | |
|---|---|---|
| CA | 2381292 | 8/2000 |
| CN | 1407088 | 4/2003 |

(Continued)

OTHER PUBLICATIONS

Turini et al. (Annu. Rev. Med. 2002, 53:35-57).*
Sanchez-Munoz et al. (World J. Gastroenterol 2008 14(27): 4280-4288).*
U.S. Appl. No. 13/584,612, filed Aug. 13, 2012, Hariri et al.
U.S. Appl. No. 13/650,803, filed Oct. 12, 2012, Heidaran et al.
U.S. Appl. No. 13/711,331, filed Dec. 11, 2012, Hariri et al.
U.S. Appl. No. 13/727,217, filed Dec. 26, 2012, Hariri et al.
U.S. Appl. No. 13/777,391, filed Feb. 26, 2013, Bhatia et al.
U.S. Appl. No. 13/863,308, filed Apr. 15, 2013, Hariri.
U.S. Appl. No. 13/875,650, filed May 2, 2013, Heidaran et al.
U.S. Appl. No. 13/542,269, filed Jul. 5, 2012, Seehra et al.

(Continued)

*Primary Examiner* — Kimberly Chong
(74) *Attorney, Agent, or Firm* — Jones Day

(57) ABSTRACT

Provided herein are methods of producing enhanced placental stem cells by modulatory RNA molecules. Also provided herein are methods of using enhanced placental stem cells, for example, to treat individuals having a disease, disorder or condition caused by, or relating to, an unwanted or harmful immune response. Further provided herein are compositions comprising said enhanced placental stem cells.

8 Claims, 4 Drawing Sheets

(56) References Cited

U.S. PATENT DOCUMENTS

Figure 1:
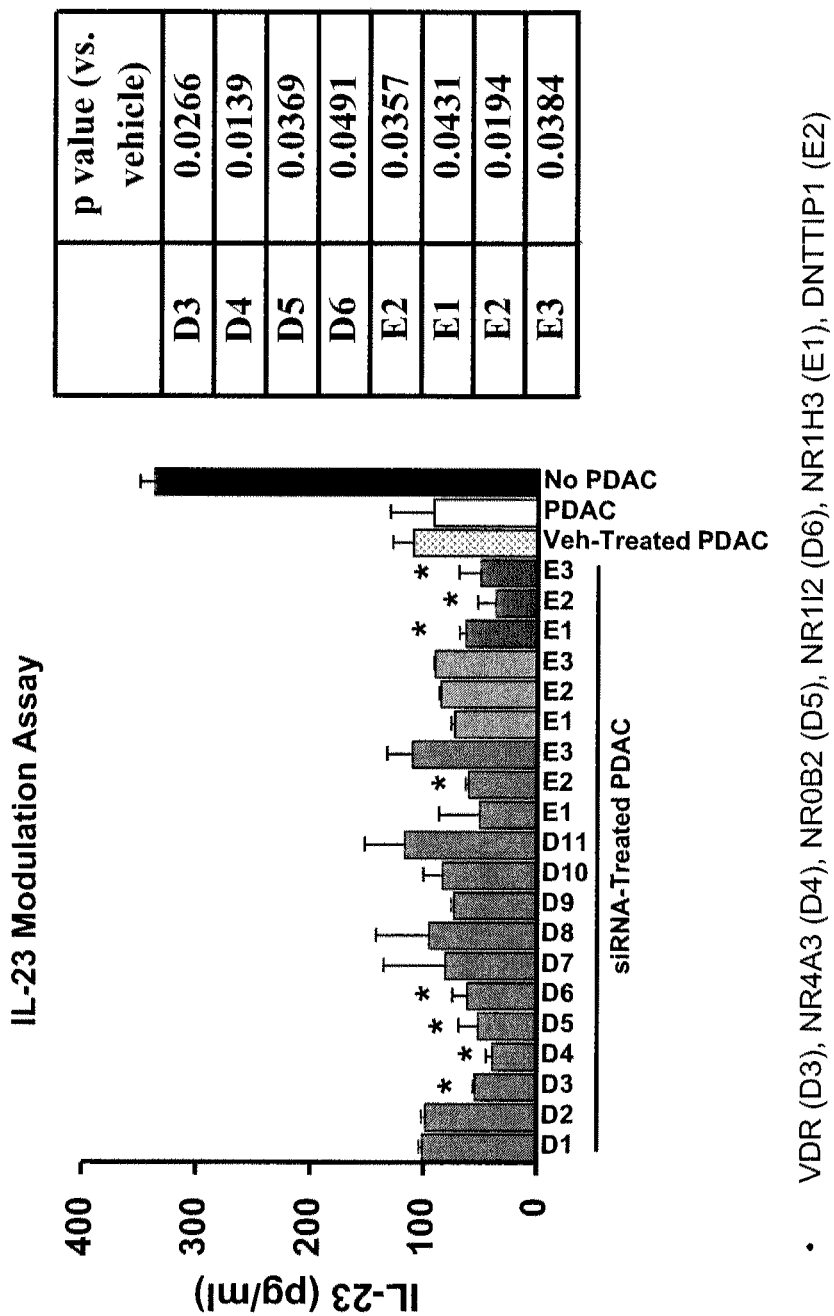

| | | |
|---|---|---|
| 5,672,346 A | 9/1997 | Srour et al. |
| 5,677,139 A | 10/1997 | Johnson |
| 5,704,361 A | 1/1998 | Seward et al. |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,744,361 A | 4/1998 | Hoffman et al. |
| 5,750,376 A | 5/1998 | Weiss et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,800,539 A | 9/1998 | Waller |
| 5,806,529 A | 9/1998 | Reisner et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,840,502 A | 11/1998 | Vlasselaer et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,861,315 A | 1/1999 | Nakahata et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,899,936 A | 5/1999 | Goldstein |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Varfaille et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,387 A | 11/1999 | Moore et al. |
| 5,993,429 A | 11/1999 | Kuypers et al. |
| 5,997,860 A | 12/1999 | Brauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,102,871 A | 8/2000 | Coe |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswell |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Matapurkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,291,240 B1 | 9/2001 | Mansbridge |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,762 B1 | 12/2001 | Anderson |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,365,362 B1 | 4/2002 | Terstappen et al. |
| 6,368,636 B1 | 4/2002 | McIntosh et al. |
| 6,379,953 B1 | 4/2002 | Bruder et al. |
| 6,384,105 B1 | 5/2002 | He |
| 6,387,367 B1 | 5/2002 | Davis-Sproul et al. |
| 6,387,369 B1 | 5/2002 | Pittenger et al. |
| 6,455,306 B1 | 9/2002 | Goldstein |
| 6,455,678 B1 | 9/2002 | Yin et al. |
| 6,458,810 B1 | 10/2002 | Muller et al. |
| 6,461,615 B1 | 10/2002 | Srivastava |
| 6,461,645 B1 | 10/2002 | Boyse et al. |
| 6,497,875 B1 | 12/2002 | Sorrell et al. |
| 6,528,245 B2 | 3/2003 | Sanchez-Ramos et al. |
| 6,534,084 B1 | 3/2003 | Vyakamam et al. |
| 6,541,024 B1 | 4/2003 | Kadiyala et al. |
| 6,548,299 B1 | 4/2003 | Pykett |
| 6,645,731 B2 | 11/2003 | Terstappen et al. |
| 6,685,936 B2 | 2/2004 | McIntosh et al. |
| 6,709,864 B1 | 3/2004 | Pittenger et al. |
| 6,753,181 B2 | 6/2004 | Atala et al. |
| 6,797,269 B2 | 9/2004 | Mosca et al. |
| 6,800,480 B1 | 10/2004 | Bodnar |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,875,607 B1 | 4/2005 | Reubinoff et al. |
| 6,916,655 B2 | 7/2005 | Yasumoto |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,153,500 B2 | 12/2006 | Qasba et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,410,773 B2 | 8/2008 | Abujadayel |
| 7,455,983 B2 | 11/2008 | Xu et al. |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,909,806 B2 | 3/2011 | Goodman |

(56) References Cited

U.S. PATENT DOCUMENTS

| | | |
|---|---|---|
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 8,202,703 B2 | 6/2012 | Edinger et al. |
| 8,263,065 B2 | 9/2012 | Zhang et al. |
| 8,293,223 B2 | 10/2012 | Hariri |
| 8,367,409 B2 | 2/2013 | Abbot et al. |
| 8,435,788 B2 | 5/2013 | Hariri |
| 8,455,250 B2 | 6/2013 | Heidaran et al. |
| 8,460,650 B2 | 6/2013 | Edinger et al. |
| 2001/0005591 A1 | 6/2001 | Qasba et al. |
| 2001/0038836 A1 | 11/2001 | During et al. |
| 2001/0044124 A1 | 11/2001 | Bacus |
| 2002/0022676 A1 | 2/2002 | He |
| 2002/0028510 A1 | 3/2002 | Sanberg et al. |
| 2002/0045643 A1 | 4/2002 | Muller et al. |
| 2002/0059106 A1 | 5/2002 | Tani |
| 2002/0061300 A1 | 5/2002 | Gokcen |
| 2002/0086005 A1 | 7/2002 | Chiu et al. |
| 2002/0102239 A1 | 8/2002 | Koopmans |
| 2002/0103542 A1 | 8/2002 | Bilbo |
| 2002/0110544 A1 | 8/2002 | Goldberg et al. |
| 2002/0123141 A1 | 9/2002 | Hariri et al. |
| 2002/0132343 A1 | 9/2002 | Lum |
| 2002/0160510 A1 | 10/2002 | Hariri et al. |
| 2003/0007954 A1 | 1/2003 | Naughton et al. |
| 2003/0032179 A1 | 2/2003 | Hariri |
| 2003/0044976 A1 | 3/2003 | Dominko et al. |
| 2003/0044977 A1 | 3/2003 | Sakuragawa et al. |
| 2003/0045552 A1 | 3/2003 | Robarge et al. |
| 2003/0059414 A1 | 3/2003 | Ho et al. |
| 2003/0068306 A1 | 4/2003 | Dilber |
| 2003/0096841 A1 | 5/2003 | Robarge et al. |
| 2003/0109042 A1 | 6/2003 | Wu |
| 2003/0152558 A1 | 8/2003 | Luft |
| 2003/0161818 A1 | 8/2003 | Weiss et al. |
| 2003/0180269 A1 | 9/2003 | Hariri |
| 2003/0187515 A1 | 10/2003 | Hariri |
| 2003/0215942 A1 | 11/2003 | Chow et al. |
| 2003/0235090 A1 | 12/2003 | Lee |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0166097 A1 | 8/2004 | Prockop |
| 2004/0171147 A1 | 9/2004 | Hariri |
| 2004/0176434 A1 | 9/2004 | Bennett et al. |
| 2004/0180040 A1 | 9/2004 | Phillips et al. |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0058641 A1 | 3/2005 | Siemionow |
| 2005/0074435 A1 | 4/2005 | Casper |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118147 A1 | 6/2005 | Oh |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0142118 A1 | 6/2005 | Wernet |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0282272 A1 | 12/2005 | Bhatia et al. |
| 2005/0283844 A1 | 12/2005 | Furcht et al. |
| 2006/0004043 A1 | 1/2006 | Bhagwat et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0122179 A1 | 6/2006 | Zeldis et al. |
| 2006/0128012 A1 | 6/2006 | Arinzeh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0205771 A1 | 9/2006 | Noble et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0060616 A1 | 3/2007 | Bennett et al. |
| 2007/0077652 A1 | 4/2007 | Peled et al. |
| 2007/0092497 A1 | 4/2007 | Hariri |
| 2007/0092967 A1 | 4/2007 | Han et al. |
| 2007/0116682 A1 | 5/2007 | Atala et al. |
| 2007/0122903 A1 | 5/2007 | Rezania et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0224174 A1 | 9/2007 | Kang et al. |
| 2007/0243172 A1 | 10/2007 | Ra et al. |
| 2007/0253931 A1 | 11/2007 | Varney et al. |
| 2007/0258963 A1 | 11/2007 | Danilkovitch et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2008/0032401 A1 | 2/2008 | Edinger et al. |
| 2008/0044392 A1 | 2/2008 | Kues et al. |
| 2008/0044848 A1 | 2/2008 | Heidaran |
| 2008/0050347 A1 | 2/2008 | Ichim |
| 2008/0050814 A1 | 2/2008 | Allickson |
| 2008/0064098 A1 | 3/2008 | Allickson |

(56) References Cited

U.S. PATENT DOCUMENTS

| | | |
|---|---|---|
| 2008/0069895 A1 | 3/2008 | Liu et al. |
| 2008/0095749 A1 | 4/2008 | Aggarwal et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0159998 A1 | 7/2008 | Ichim |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226612 A1 | 9/2008 | Treves et al. |
| 2008/0248005 A1 | 10/2008 | Phan |
| 2008/0254005 A1 | 10/2008 | Riordan et al. |
| 2008/0254538 A1 | 10/2008 | Messina et al. |
| 2008/0260694 A1 | 10/2008 | Gronthos et al. |
| 2008/0260703 A1 | 10/2008 | Riordan et al. |
| 2008/0260704 A1 | 10/2008 | Riordan et al. |
| 2008/0274087 A1 | 11/2008 | Li et al. |
| 2008/0279956 A1 | 11/2008 | Lin |
| 2008/0286249 A1 | 11/2008 | Varney et al. |
| 2008/0286267 A1 | 11/2008 | Sing et al. |
| 2008/0292597 A1 | 11/2008 | Steenblock |
| 2008/0299090 A1 | 12/2008 | Weiss et al. |
| 2008/0305148 A1 | 12/2008 | Fu |
| 2008/0311087 A1 | 12/2008 | Gosiewska et al. |
| 2009/0004738 A1 | 1/2009 | Merchav et al. |
| 2009/0016999 A1 | 1/2009 | Cohen et al. |
| 2009/0053182 A1 | 2/2009 | Ichim et al. |
| 2009/0053805 A1 | 2/2009 | Hariri |
| 2009/0074728 A1 | 3/2009 | Gronthos et al. |
| 2009/0074731 A1 | 3/2009 | Librach et al. |
| 2009/0075381 A1 | 3/2009 | Clarke et al. |
| 2009/0081171 A1 | 3/2009 | Fu et al. |
| 2009/0092653 A1 | 4/2009 | Colter et al. |
| 2009/0104158 A1 | 4/2009 | Young et al. |
| 2009/0104163 A1 | 4/2009 | Deans et al. |
| 2009/0104164 A1 | 4/2009 | Zhang et al. |
| 2009/0123437 A1 | 5/2009 | Takebe |
| 2009/0124007 A1 | 5/2009 | Cho |
| 2009/0124573 A1 | 5/2009 | Mazmanian et al. |
| 2009/0136457 A1 | 5/2009 | Sing et al. |
| 2009/0136471 A1 | 5/2009 | Heidaran et al. |
| 2009/0142831 A1 | 6/2009 | Hariri |
| 2009/0149371 A1 | 6/2009 | Mistry et al. |
| 2009/0169522 A1 | 7/2009 | Danilkovitch et al. |
| 2009/0169597 A1 | 7/2009 | Brown et al. |
| 2009/0170200 A1 | 7/2009 | Yeh et al. |
| 2009/0186006 A1 | 7/2009 | Murphy |
| 2009/0202479 A1 | 8/2009 | Shi et al. |
| 2009/0208463 A1 | 8/2009 | Pittenger et al. |
| 2009/0214484 A1 | 8/2009 | Mironov |
| 2009/0214493 A1 | 8/2009 | Pittenger et al. |
| 2009/0220464 A1 | 9/2009 | Aggarwal et al. |
| 2009/0226406 A1 | 9/2009 | Hariri et al. |
| 2009/0232781 A1 | 9/2009 | Fu |
| 2009/0232782 A1 | 9/2009 | Fu |
| 2009/0238801 A1 | 9/2009 | Woodbury et al. |
| 2009/0252710 A1 | 10/2009 | Zhang et al. |
| 2009/0257989 A1 | 10/2009 | Vanguri et al. |
| 2009/0263361 A1 | 10/2009 | Lee et al. |
| 2009/0274665 A1 | 11/2009 | Akabutu et al. |
| 2009/0280093 A1 | 11/2009 | Friedlander |
| 2009/0285842 A1 | 11/2009 | Davies et al. |
| 2009/0291061 A1 | 11/2009 | Riordan et al. |
| 2009/0304639 A1 | 12/2009 | Yokoo et al. |
| 2009/0305406 A1 | 12/2009 | Pytlik et al. |
| 2009/0311223 A1 | 12/2009 | Ichim |
| 2009/0311782 A1 | 12/2009 | Chiou et al. |
| 2009/0324609 A1 | 12/2009 | Lodie et al. |
| 2010/0008890 A1 | 1/2010 | Mays et al. |
| 2010/0008992 A1 | 1/2010 | Ichim |
| 2010/0015705 A1 | 1/2010 | Vodyanyk et al. |
| 2010/0015712 A1 | 1/2010 | Skuragawa |
| 2010/0021434 A1 | 1/2010 | Melamed et al. |
| 2010/0028306 A1 | 2/2010 | Clarke et al. |
| 2010/0028346 A1 | 2/2010 | Lutz et al. |
| 2010/0028997 A1 | 2/2010 | Lin |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0105132 A1 | 4/2010 | Totey et al. |
| 2010/0120015 A1 | 5/2010 | Hariri |
| 2010/0143312 A1 | 6/2010 | Hariri |
| 2010/0172830 A1 | 7/2010 | Heidaran |
| 2010/0183571 A1 | 7/2010 | Paludan et al. |
| 2010/0291679 A1 | 11/2010 | Edinger et al. |
| 2010/0297689 A1 | 11/2010 | Edinger et al. |
| 2010/0311036 A1 | 12/2010 | He |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0121550 A1 | 5/2012 | Heidaran |
| 2012/0148553 A1 | 6/2012 | Hariri et al. |
| 2012/0171160 A1 | 7/2012 | Johnson, Jr. et al. |
| 2012/0171161 A1 | 7/2012 | Abramson et al. |
| 2012/0171295 A1 | 7/2012 | Abramson et al. |
| 2012/0230959 A1 | 9/2012 | Abbot et al. |
| 2012/0269774 A1* | 10/2012 | Ichim et al. ............... 424/93.7 |
| 2012/0328583 A1 | 12/2012 | Herzberg et al. |
| 2013/0022581 A1 | 1/2013 | Edinger et al. |
| 2013/0028871 A1 | 1/2013 | Edinger et al. |
| 2013/0071362 A1 | 3/2013 | Bhatia et al. |
| 2013/0172531 A1 | 7/2013 | Bhatia et al. |
| 2013/0259845 A1 | 10/2013 | Heidaran et al. |

FOREIGN PATENT DOCUMENTS

| | | |
|---|---|---|
| CN | 1548529 | 5/2003 |
| CN | 1597937 | 3/2005 |
| CN | 1786154 | 6/2006 |
| CN | 1810959 | 8/2006 |
| CN | 100344757 | 10/2007 |
| CN | 101210232 | 7/2008 |
| CN | 101270349 | 9/2008 |
| EP | 0333328 | 9/1989 |
| EP | 0529421 | 3/1993 |
| EP | 0529751 | 3/1993 |
| EP | 0552380 | 7/1993 |
| EP | 1110957 | 6/2001 |
| EP | 1264877 | 12/2002 |
| EP | 1288293 | 3/2003 |
| EP | 1384775 | 1/2004 |
| EP | 1405649 | 4/2004 |
| EP | 1535994 | 6/2005 |
| EP | 1775341 | 4/2007 |
| EP | 1974013 | 12/2007 |
| JP | 2000-516616 | 12/2000 |
| JP | 2003-235549 | 12/2002 |
| JP | 2003-323558 | 11/2003 |
| JP | 2005-151907 | 11/2003 |
| JP | 2004-528021 | 9/2004 |
| JP | 2005-517402 | 6/2005 |
| JP | 2005-522215 | 7/2005 |
| JP | 2005-528105 | 9/2005 |
| JP | 3934539 | 6/2007 |

(56) References Cited

FOREIGN PATENT DOCUMENTS

| | | |
|---|---|---|
| KR | 20040024170 | 3/2004 |
| WO | WO 89/04168 | 5/1989 |
| WO | WO 90/11354 | 10/1990 |
| WO | WO 91/01140 | 2/1991 |
| WO | WO 91/06666 | 5/1991 |
| WO | WO 91/06667 | 5/1991 |
| WO | WO 91/16062 | 10/1991 |
| WO | WO 93/04169 | 3/1993 |
| WO | WO 95/22611 | 8/1995 |
| WO | WO 96/32905 | 10/1996 |
| WO | WO 96/34035 | 10/1996 |
| WO | WO 96/39101 | 12/1996 |
| WO | WO 98/37903 | 9/1998 |
| WO | WO 98/54170 | 12/1998 |
| WO | WO 99/03973 | 1/1999 |
| WO | WO 99/64566 | 12/1999 |
| WO | WO 99/65470 | 12/1999 |
| WO | WO 00/17325 | 3/2000 |
| WO | WO 00/27995 | 5/2000 |
| WO | WO 00/27999 | 5/2000 |
| WO | WO 00/38762 | 7/2000 |
| WO | WO 00/69355 | 11/2000 |
| WO | WO 00/73421 | 12/2000 |
| WO | WO 01/21767 | 3/2001 |
| WO | WO 01/87307 | 11/2001 |
| WO | WO 01/93909 | 12/2001 |
| WO | WO 02/46373 | 6/2002 |
| WO | WO 02/059106 | 8/2002 |
| WO | WO 02/063962 | 8/2002 |
| WO | WO 02/064083 | 8/2002 |
| WO | WO 02/064755 | 8/2002 |
| WO | WO 02/066450 | 8/2002 |
| WO | WO 02/097052 | 12/2002 |
| WO | WO 03/042405 | 5/2003 |
| WO | WO 03/068937 | 8/2003 |
| WO | WO 03/080822 | 10/2003 |
| WO | WO 03/086373 | 10/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/035064 | 4/2004 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/097190 | 10/2005 |
| WO | WO 2005/105992 | 11/2005 |
| WO | WO 2005/055929 | 1/2006 |
| WO | WO 2006/015214 | 2/2006 |
| WO | WO 2006/111706 | 10/2006 |
| WO | WO 2006/117889 | 11/2006 |
| WO | WO 2007/024441 | 3/2007 |
| WO | WO 2007/047465 | 4/2007 |
| WO | WO 2007/047468 | 4/2007 |
| WO | WO 2007/056578 | 5/2007 |
| WO | WO 2007/059007 | 5/2007 |
| WO | WO 2007/071048 | 6/2007 |
| WO | WO 2007/073552 | 6/2007 |
| WO | WO 2007/076522 | 7/2007 |
| WO | WO 2007/079183 | 7/2007 |
| WO | WO 2007/079184 | 7/2007 |
| WO | WO 2007/079185 | 7/2007 |
| WO | WO 2007/087292 | 8/2007 |
| WO | WO 2007/087293 | 8/2007 |
| WO | WO 2007/124594 | 11/2007 |
| WO | WO 2007/136673 | 11/2007 |
| WO | WO 2008/019148 | 2/2008 |
| WO | WO 2008/036374 | 3/2008 |
| WO | WO 2008/036447 | 3/2008 |
| WO | WO 2008/051568 | 5/2008 |
| WO | WO 2008/060541 | 5/2008 |
| WO | WO 2008/100497 | 8/2008 |
| WO | WO 2008/100498 | 8/2008 |
| WO | WO 2008/148105 | 12/2008 |
| WO | WO 2008/152640 | 12/2008 |
| WO | WO 2008/156659 | 12/2008 |
| WO | WO 2009/007979 | 1/2009 |
| WO | WO 2009/028870 | 3/2009 |
| WO | WO 2009/035612 | 3/2009 |
| WO | WO 2009/037690 | 3/2009 |
| WO | WO 2009/045360 | 4/2009 |
| WO | WO 2009/046346 | 4/2009 |
| WO | WO 2009/046377 | 4/2009 |
| WO | WO 2009/052132 | 4/2009 |
| WO | WO 2009/134532 | 11/2009 |
| WO | WO 2009/144720 | 12/2009 |
| WO | WO 2010/021714 | 2/2010 |
| WO | WO 2012/009422 | 1/2012 |
| WO | WO 2013/012698 | 1/2013 |

OTHER PUBLICATIONS

U.S. Appl. No. 13/654,191, filed Oct. 17, 2012, Heidaran et al.
Abbott, "ABCG2 (BCRP) Expression in Normal and Malignant Hematopoietic Cells," Hematol. Oncol. 21:115-130 (2003).
Abe, "Therapeutic Potential of Neurotrophic Factors and Neural Stem Cells Against Ischemic Brain Injury," Journal of Cerebral Blood Flow and Metabolism, Raven Press, Ltd., New York, 20(10): 1393-1408 (2000).
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).
Addison, et al., "Metabolism of Prednisolone by the Isolated Perfused Human Placental Lobule," J. Ster. Biochem. Mol. Biol., 39(1):83-90 (1991).
Adinolfi et al., 1982, "Expression of HLA antigents, $\beta_2$-microglobulin and enzymes by human amniotic epithelial cells," Nature 295:325-327.
Aerbajinai, ct al., "Thalidomide Induces gamma-Globin Gene Expression through Increased Reactive Oxygen Species-Mediated p38 MAPK Signaling and Histone H4 Acetylation in Adult Erythropoiesis," Blood 110(8):2864-2871 (2007).
Aggarwal, et al., "Human Mesenchymal Stem Cells Modulate Allogeneic Immune Cell Responses," Blood 105(4):1815-22 (2005).
Al-Khaldi, et al., "Postnatal Bone Marrow Stromal Cells Elicit a Potent VEGF-Dependent Neoangiogenic Response in Vivo," Gene Therapy 10:621-629, 2003.
Al-Khaldi, et al., "Therapeutic Angiogenesis Using Autologous Bone Marrow Stromal Cells: Improved Blood Flow in a Chronic Limb Ischemia Model," Ann. Thoracic Surgeons 75:204-209, 2003.
Allikmets et al., Cancer Res. 58(23):5337-5339 (1998).
Alviano, et al., "Term amniotic membrane is a high throughput source for multipotent mesenchymal stem cells with the ability to differentiate into endothelial cells in vitro," BMC Developmental Biology, vol. 7, No. 1, Feb. 2007.
American Heritage Dictionary of the English Language, Second Edition, Houghton Mifflin Company, p. 68 (1991).
Anderson, "Moving disease biology from the laboratory to the clinic," *Seminars in Oncology*, 2002 29:17-20.
Anderson, "Thalidomide: Therapeutic potential in hematologic malignancies," Seminars in Hematology 37(1 Supp 3): 1-4 (2000).
Anker In'T P, et al., "Isolation of Mesenchymal Stem Cells of Fetal or Maternal Origin from Human Placenta," Stem Cells 22(7): 1338-45 (2004).
Anseth et aL., J. Control Release 78(1-3): 199-209 (2002).
Aplin, "Implantation, trophoblast Differentiation and Haemochorial Placentation: Mechanistic Evidence in vivo and in vitro," Journal of Cell Science 99:681-692 (1991).
Ashihara, et al., "Successful Peripheral Blood Stem Cell Transplantation for Myelodysplastic Syndrome," Bone Marrow Transplantation 24(12): 1343-1345 (1999).
Bach 1963, "Studies on the Possible Anti-Neoplastic Effect of Thalidomide," *Acta Pathologica Et Microbiologica Scandinavica* 59:491-499.
Bach 1963, "Thalidomide in Cancer Chemotherapy," *The Lancet*, No. 1271, p. 71.

(56) References Cited

OTHER PUBLICATIONS

Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barkholt, et al., "Resetting the immune system in refractory Crohn's disease: Is autologous hematopoietic stem cell transplantation the way forward?" Gastroenterology 128:786-789 (2005).
Barlogie et al., "High-dose therapy immunomodulatory drugs in multiple myeloma," *Seminars in Oncology*, 2002, 29 (6):26-33.
Barlogie et al., "Introduction: Thalidomide and the IMiDs in multiple myeloma," *Seminars in Hematology*, 2003, 40 (4):1-2.
Barlogie et al., "Total Therapy II (TTII) for newly diagnosed multiple myeloma (MM): preliminary data on feasibility and efficacy in the first 231 enrolled patients; comparison with predecessor trial total therapy I ((TTI) (N=231)," Blood, Abstract # 2857, Dec. 7-11, 2001, *American Society of Hematology*.
Barlogie, "Thalidomide and CC-5013 in Multiple Myeloma: The University of Arkansas experience," *Seminars in Hematology*, 2003, 40 (4):33-38.
Barlogie, B., Desikan, R., Munshi, N., Siegel, D., Mehta, J., Singhal, S., Anaissie, E., Single Course D.T. Pace Anti-Angiochemotherapy Effects CR in Plasma Cell Leukemia and Fulminant Multiple Myeloma (MM). Abstract #4180. American Society of Hematology, Dec. 4-9, 1998.
Barlow et al., "Comparison of Human Placenta- and Bone Marrow-Derived Multipotent Mesenchymal Stem Cells," Stem Cells and Development 17:1095-1108 (2008).
Barry et al., Birth Defect Research (Part C) 69:250-256, (2003).
Barry et al., "The Monoclonal Antibody SH-2, Raised Against Human Mesenchymal Stem Cells, Recognizes an Epitope on Endoglin (CD105)," Osiris Therapeutics Inc., 2001 Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Bartholomew et al., "Mesenchymal Stem Cells Suppress Lymphocyte Proliferation In Vitro and Prolong Skin Graft Survival in Vivo," Experimental Hematology 30:42-48 (2002).
Bartlett et al., "Phase 1 study to determine the safety, tolerability and immunostimulatory activity of thalidomide analogue CC-5013 in patients with metastatic malignant melanoma and other advanced cancers," *British Journal of Cancer*, 2004, 90:955-961.
Batchelor et al., "HLA Matching and Corneal Grafting." Lancet 13(7959):551-554 (1976).
Battegay, "Angiogenesis: mechanistic insights, neovascular diseases, and therapeutic prospects," *J. Mol. Med.,* 1995, 73:333-346.
Battula et al., "Prospective Isolation and Characterization of Mesenchymal Stem Cells from Human Placenta Using a Firzzled-9-Specific Monoclonal Antibody," Differentiation 76:326-336 (2008).
Bauer et al., "Inhibition of Angiogenesis by Thalidomide Requires Metabolic Activation, Which is Species-Dependent," Biochem. Pharmacol. 55(11):1827-1834 (1998).
Baz et al., "Doxil (D), vincristine (V), reduced frequency dexamethasone (d) and revlimid (R) (DVd-R) results in a high response rate in patients with refractory multiple myeloma (RMM)," *Blood, Abstract # 2559, American Society of Hematology,* Dec. 10-13, 2005.
Beltrami, et al., "Adult Cardiac Stem Cells Are Multipotent and Support Myocardial Regenerationl," 114:763-776 (2003).
Belvedere, et al., "Increased Blood Volume and CD34(+)CD38(−) Progenitor Cell Recovery Using a Novel Umbilical Cord Blood Collection System," Stem Cells 18(4):245-251 (2000).
Bernardeschi et al., 2003, J. Exp. Clin. Cancer Res. 22(4):129-133.
Bersinger, et al., "Effect of Late Pregnancy Serum on the Synthesis and Release of Pregnancy Proteins by the Perfused Human Term Placenta," Reprod. Fertil. Dev. 4:585-588 (1992).

Bertolini, et al., "Retrovirus-Mediated Transfer of the Multidrug Resistance Gene into Human Haemopoietic Progenitor Cells." Haemolotol. 88:318-324 (1994).
Bingham, John A.C., "Multicarrier Modulation for Data Transmission: An Idea Whose Time Has Come." May 1990. pp. 5-14.
Blanc et al , "Immunobiology of Human Mesenchymal Stem Cells and Future Use in Hematopoietic Stem Cell Transplantation," Biology of Blood and marrow transplantation 11 :321-334 (2005).
Bloxam et al., "Culture of Syncytiotrophoblast for the Study of Human Placental Transfer. Part I: Isolation and Purification of Cytotrophoblast,"Placenta 18:93-98 (1997).
Bloxam, "Human Placental Trophoblast. Culture: One-Sided and Two-Sided Models," Proceedings of the Nutrition Society 50:349-354 (1991).
Bossolasco et al., "Molecular and phenotypic characterization of human amniotic fluid cells and their differentiation potential," Cell Research 16:329-336 (2006).
Bostian and Betts, 1978, "Kinetics and reaction of potassium-activated aldehyde dehydrogenase from *Saccharomyces cerevisiae*," Biochem J; 173:787-798.
Brittan, "Gastrointestinal Stem Cells," J. Pathol. 197:492-509 (2002).
Broudy, "Stem Cell Factor and Hematopoiesis," Blood 90(4):1345 (1997).
Broxmeyer et al., "Human Umbilical Cord Blood as a Potential Source of Transplantable Hematopoietic Stem/Progenitor Cells," Proc Natl Acad Sci U S A. 86(10):3828-32 (1989).
Buelens, "Treatment of a Grade 11 Astrocytoma with Thalidomide," Arzneimittel-Forschung 17:646-648 (1967).
Bullen ct al., "Two-Sided Culture of Human Placental Trophoblast. Morphology, Immunocytochemistry and Permeability Properties," Placenta 11:431-450 (1990).
Burger et al., 1999, "Development of an infusible-grade solution for non-cryopreserved hematopoietic cell storage", Cytotherapy, 1(2):123-133.
Buttery et al., 2001, Differentiation of osteoblasts and in vitro bone formation from murine embryonic stem cells, Tissue Eng. 7:89-99.
Campagnoli, et al., "Identification of Mesenchymal Stem/Progenitor Cells in Human First-Trimester Fetal Blood, Liver, and Bone Marrow." Blood 98(8):2396-402 (2001).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," Clin. Plast. Surg. 21(3):429-435 (1994).
Cardoso, et al., "Release from Quiescence of CD34+ CD38− Human Umbilical Cord Blood Cells Reveals Their Potentiality to Engraft Adults," Proc. Natl. Acad. Sci. USA 90(18):8707-8711 (1993).
Carter, et al., "Characterization of MSC Potential to Treat GVHD Using Molecular Markers Linked to MSC-Mediated Immunosuppression in Vitro," Blood, 106(11) part 2, Abstract No. 4322,160B (2005).
Cavanagh, et al. "Dendritic Epidermal T-Cell Involvement in Induction of CD* T Cell-Mediated Immunity Against and Ultraviolet Radiation-Induced Skin Tumor," Int. J. Cancer 70:98-105 (1997).
Celgene Corporation, "Celgene Corporation receives orphan drug designation for Revimid™ for multiple myeloma," Press Release, Oct. 2001.
Celgene Corporation, "Celgene corporation reports record operating performance in third quarter as total revenue increases 117% and profits rise," Press Release, Oct. 2003.
Celgene Corporation, "Celgene corporation reviews 2003 achievements and announces 2004 financial outlook," Press Release, Jan. 2004.
Celgene Corporation, "Celgene expands clinical development program for Revimid™. Five additional trials of Revimid initiated in hematological and solid tumor cancers," Press Release, Jun. 2002.
Celgene Corporation, "Celgene receives fast track status from FDA for Revimid™ in multiple myloma," Press Release, Feb. 2003.
Celgene Corporation, "Celgene receives fast track status from FDA for Revimid™ in myelodysplastic sydromes," Press Release, Apr. 2003.

(56) References Cited

OTHER PUBLICATIONS

Celgene Corporation, "Initial Phase I solid tumor data on Celgene's lead IMiD™, Revimid™," Press Release, Jun. 2001.
Celgene Corporation, "Revlimid™ receives orphan drug designation from the European commission for multiple myeloma," Press Release, Feb. 2004.
Celgene Corporation, "Revlimid™ receives orphan drug designation from the European commission for myelodysplastic sydromes," Press Release, Mar. 2004.
Cester et al., "Cation Transport Across Cultured Trophoblast Membrane in Preeclampsia," Clin. and Exper. Hyper. in Pregnancy, B11(1):59-69 (1992).
Chan, et al., "Placental Mesenchymal Stem Cells," Am. J. Obstet. Gynecol. 196(2):e18-e19 (2007).
Chang C Medium (Irvine Scientific, downloaded 2012).
Chang, et al., "Placenta-Derived Multipotent Cells Exhibit Immunosuppressive Properties That Are Enhanced in the Presence of Interferon-gamma," Stem Cells 24:2466-2477 (2006).
Chao, et al., "Stem Cell Transplantation (Cord Blood Transplants)." American Society of Hematology p. 354-371 (2004).
Chaundhry, *Cancer Research*, "Effect of Prednisolone and Thalidomide on Induced Submandibular Gland Tumors in Hamster," 26(part 1)1884-86 (1966).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al., "Therapeutic Benefit of Intravenous Administration of Bone Marrow Stromal Cells after Cerebral Ischemia in Rats," Stroke, 32(4):1005-11 (2001).
Chien, "Red Cell Deformability and Its Relevance to Blood Flow," Ann. Rev. Physiol. 49:177-192 (1987).
Chies et al., "Sickle Cell Disease: A Chronic Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1988).
Clark, et al., "Placental Trophoblast from Successful Human Pregnancies Expresses the Tolerance Signaling Molecule, CD200 (OX-2)" Am. J. Reprod. Immunol., 50(3):187-195 (2003).
Conget ct al., "Phenotypical and functional properties of human bone marrow mesenchymal progenitor cells" Journal of Cellular Physiology 181:67-73 (1999).
Contractor, et al., "A comparison of the effects of different perfusion regimens on the structure of the isolated human placental lobule," Cell Tissue Res. 237:609-617 (1984).
Cord Blood Stem Cell, Mesh Term Database 2003.
Corral et al., Ann Rheum Dis 58(suppl. 1):1107-1113 (1999).
Cosma, et al., "Use and Application of Stem Cells in Toxicology," SOT 2003 Annual Meeting, p. 4, Abstract 19 (2003).
Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Craig et al., "Potential anticancer agents. III. 2-phthalimidoaldehydes and derivatives," Potential Anticancer Agents III 10:1071-1073 (1967).
Cul et al., "Pod1 is Required in Stromal Cells for Glomerulogenesis," Developmental Dynamics 226(3):512-522 (2003).
Czarneski, et al., "Effects of Cord Blood Transfer on the Hematopoietic Recovery Following Sublethal Irradiation in MRL 1pr/1pr Mice," Proc. Soc. Exp. Biol. Med. 220(2):79-87 (1999).
D'Amato et al., 1994, "Thalidomide is an Inhibitor of Angiogenesis", Proc. Natl. Acad. Sci. 91:4082-4085.
D'Amato et al., 2001, "Mechanism of action of thalidomide and 3-aminothalidomide in multiple myeloma," Semin. Oncol. 28:597-601.
Dalgleish et al., "Thalidomide analogues CC-5013 and CC-4047 induce T cell activation and IL-12 production in patients with both solid tumours and relapsed and refractory multiple myeloma,"*British Journal of Cancer*, 2003, 88(Suppl I), S25-S54.
Dalgleish, et al., "New thalidomide analogues; anti-cancer, anti-angiogenic and immunostimulatory," *British Journal of Cancer*, 2001, 85 (1)25.
Dallas, et al., "Enhanced T Cell Reconstitution by Hematopoietic Progenitors Expanded ex vivo Using The Notch Ligand Delta 1," Blood 109:3579-3587 (2007).
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies et al., "Thalidomide (Thal) and immunomodulatory derivatives (IMiDs) augment natural killer (NK) cell cytotoxicity in multiple myeloma ~MM)," Abstract # P222, *VIIIth International Myeloma Workshop*, May 4-8, 2001.
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: A Report from the National Marrow Donor Program," Blood, 96(13): 4096-4102, (2000).
Davies, et al., Thalidomide (THAL) and Immunomodulatory Derivatives (IMiDS) Augment Natural Killer (NK) Cell Cytotocixity in Multiple Myeloma (MM). Abstract #3617. American Society of Hematology, Dec. 1-5, 2000.
Davila, et al., "Use and Application of Stem Cells in Toxicology," Toxicological Sciences 79:214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, p. 21, Abstract 81 (2004).
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS Meeting Abstracts, A1366, Abstract 781.7 (2005).
De et al., 1976, "Possible antineoplastic agents: III. Synthesis of 6-alkyl-2-[4'-methoxyphthalimido] and 6-alkyl-3-[3'-4'-dimethoxyphenyl] glutarimides," J. Indian Chem. Soc. L.III:1122-1125.
De Filippo, et al., "Total Penile Urethra Replacement with Autologous Cell-Seeded Collagen Matrices." Urology and Reproductive Surgery, vol. 195, No. 3S, Sep. 2002, p. S95.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Deans et al., "Mesenchymal stem cells: Biology and potential clinical uses," Exp. Hematol. 28: 875-84 (2000).
DeLorme et al., Blood 111:2631-2635, Online Dec. 17, 2007 (2008).
Denison et al., "Cytokine secretion by human fetal membranes, decidua and placenta at term" Human Reproduction 13(12):3560-3565 (1998).
Dimopoulos et al., "Study of lenalidomide plus dexamethasone versus dexamethasone alone in relapsed or refractory multiple myeloma (MM): Results of a phase 3 Study (MM-010),", *Abstract # 6, American Society of Hematology*, Dec. 10-13, 2005.
Dimopoulos et al., "Treatment of plasma cell dyscrasias with thalidomide and its derivatives," *Journal of Clinical Oncology*, Dec. 1, 2003, 21 (23)4444-4454.
Dimopoulos et al., 2004, "Primary treatment with puilsed melphalan, dexamethasone, thalidomide (MDT) for symptomatic patients with multiple myeloma ≥75 years of age," Am. Soc. Hematol. 46th Ann. Meeting Dec. 4-7, 2004, San Diego, CA Abstract #1482.
Dinarello, 2010, "Anti-inflammatory agents: present and future."

(56) References Cited

OTHER PUBLICATIONS

DiPaolo, 1963, "In vitro Test Systems for Cancer Chemotherapy, II. Correlation of in vitro Inhibition of Dehydrogenase and Growth with in vivo Inhibition of Ehrlich Asoites Tumor," *Proceedings of the Society for Experimental Biology & Medicine*, 114:384-387.
DiPaolo, 1963, "Effect of Thalidomide on a Variety of Transplantable Tumors," *Cancer Chemotherapy Reports* No. 29, p. 99-102.
DiPaolo, 1964, "Thalidomide: Effects on Ehrlich Ascites Tumor Cells in vitro" Science 144:1583.
Djouad, et al., Immunosuppressive effect of mesenchymal stem cells favors tumor growth in allogeneic animals. Blood 102, 3837-3844 (2003).
Djouad, et al., "Reversal of the Immunosuppressive Properties of Mesenchymal Stem Cells by Tumor Necrosis Factor alpha in Collagen-Induced Arthritis," Arthritis & Rheumatism 52(5):1595-1603 (2005).
Dominici, et al., "Minimal Criteria for Defining Multipotent Mesenchymal Stromal Cells. The International Society for Cellular Therapy Position Statement," Cytotherapy 8(4):315-317 (2006).
Donovan et al., "The End of the Beginning for Pluripotent Stem Cells," Nature 414:92-97 (2001).
Dorrel "Expansion of Human Cord Blood CD34+CD38− Cells in ex vivo Culture during Retroviral Transduction without a Corresponding Increase in SCID Repopulation cell (SRC) Frequency: Dissociation of SRC Phenotype and Function," Blood 95(1):102-110 (2000).
Drake, et al., "Human Placental Cytotrophoblasts Attract Monocytes and CD56 (Bright) Natural Killer Cells via the Actions of Monocyte Inflammatory Protein 1Alpha," J. Exp. Med. 193(10):1199-1212 (2001).
Dredge et al., A costimulatory thalidomide analog enhances the partial anti-tumor immunity of an autologous vaccination in a model of colorectal cancer, *Abstract # 491, American Association for Cancer Research*, Apr. 6-10, 2002.
Dredge et al., "Adjuvants and the promotion of Th1-type cytokines in tumour immunotherapy," *Cancer Immunol. Immunother.*, 2002, 51:521-531.
Dredge et al., "Protective antitumor immunity induced by a costimulatory thalidomide analog in conjunction with whole tumor cell vaccination is mediated by increased Th1-type immunity," *The Journal of Immunology*, 2002, 168(10):4914-4919.
Dredge et al., "Recent developments in antiangiogenic therapy," *Expert Opin. Biol. Ther.*, 2002, 2 (8):953-966.
Dredge et al., 2002, "Novel thalidomide analogues display antiangiogenic activity independently of immunomodulatory effects," Br. J. Cancer 87(10):1166-1172.
Drela et al., 2013, "Human mesenchymal stem cells in the treatment of neurological diseases," Acta Neurobiol Exp, 73:38-56.
Dubick, et al., "Issues of Concern Regarding the Use of Hypertonic/Hyperoncotic Fluid Resuscitation of Hemorrhagic Hypotension," Shock 25(4):321-8 (2006).
Dubick, et al., "Small-Volume Fluid Resuscitation for the Far-Forward Combat Environment: Current Concepts." J. Trauma. 54(5):S43-S45 (2003).
Dushnik-Levinson, et al. "Embryogenesis in vitro: study of differentiation of embryonic stem cells." Biol Neonate. 67(2):77-83 (1995).
Eisen et al., 2000, "Continuous low dose Thalidomide: a phase II study in advanced melanoma, renal cell, ovarian and breast cancer," Br. J. Cancer 82(4):812-817.
Elchalal, et al., "Postpartum Umbilical Cord Blood Collection for Transplantation: a Comparison of Three Methods," Am. J. of Obstetrics & Gyn. 182(1 Pt 1):227-232 (2000).
Emerson, et al., "Ex vivo Expansion of Hematopoietic Precursors, Progenitors and Stem Cells: the Next Generation of Cellular Therapeutics," Blood 87(8):3082-3088 (1996).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C.) Cord Blood, Unmatched for HLA for Marrow Transplantation," Am. J. Clin. Pathol. 111:773-781 (1999).
Ende, et al., "Human Umbilical Cord Blood Cells Amerliorate Alzheimer's Disease in Transgenic Mice," J. Med. 32(3-4):241-7 (2001).
Ende, et al., "Hemapoetic Transplantation by Means of Fetal (Cord) Blood: A New Method," Va. Med. Mon. 99:276-280 (1972).
Ende, et al., "Human Umbilical Cord Blood Cells Ameliorate Huntington's Disease in Transgenic Mice," J. Med. 32(3-4):231-240 (2001).
Ende, et al., "Human Umbilical Cord Blood Effect on SOD Mice (Amyotrophic Lateral Sclerosis)," Life Sci. 67(1):53-59 (2000).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and Irradiation and Its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Ernst, et al., "Blood Rheology in Patients with Transient Ischemic Attacks," Stroke 19:634-636 (1988).
Evans, "Stem Cell Therapy: Moving towards Reality," Am. J. Obstet. Gynecol. 194:662-663 (2006).
Fasouliotis, et al., "Human umbilical cord blood banking and transplantation: a state of the art," Eur. J. Obstet. Gynecol. Reprod. Biol. 90(1):13-25 (2000).
Fassas et al., "Autologous Stem Cell Transplantation in Progressive Multiple Sclerosis—An Interim Analysis of Efficacy," J. Clin. Immunol., 20(1):24-30 (2000).
Fauriat et al., Blood 109: 323-330 (2007).
Fenk et al., 2005, "Single-agent thalidomide for treatment of first relapse following high-dose chemotherapy in patients with multiple myeloma," Leukemia 19(1):156-159.
Fickentscher et al., "Stereochemical properties and teratogenic activity of some tetrahydrophthalimides," *Molecular Pharmacology*, 1976, 13:133-141.
Figg et al., "Inhibition of angiogenesis: treatment options for patients with metastatic prostate cancer," *Investigational New Drugs*, 2002, 20(2):183-194.
Fisher et al., "Adhesive and Degradatie Properties of Human Placental Cytotrophoblast Cells In Vitro," Journal od Cell Biology 109:891-902 (1989).
Flaminio, MJB., et al. "Inhibition of Lymphocyte Proliferation and Activation: A Mechanism Used by Equine Invasive Trophoblast to Escape the Maternal Immune Response," Placent, W.B. Saunders(2005) 26(2-3): 148-159.
Folkman et al., 1983, "Angiogenesis inhibition and tumor regression caused by heparin or a heparin fragment in the presence of cortisone," Science 221(4612):719-725.
Forbes et al., 2009, "Methods for siRNA-mediated reduction of mRNA and protein expression in human placental explants, isolated primary cells and cell lines," Placenta, 30(2):124-129.
Frank H G, et al., "Cell culture models of human trophoblast: primary culture of trophoblast—a workshop report." Placent Apr. 2001, vol. 22 Suppl A, pp. S107-S109, XP002443188 ISSN: 0143-4004 (Apr. 2001).
Freud et al., "Evidence for Discrete Stages of Human Natural Killer Cell Differentiation In Vivo," Journal of Eperimental Medicine 203(4):1033-1043 (2006).
Friedman et al., "Temozolomide and Treatment of Malignant Glioma," Clinical Cancer Research 6:2585-2597 (2000).
Gait et al., 1998, "Applications of chemically synthesized RNA, in RNA: Protein Interactions", A Practical Approach, Oxford University Press, Oxford and New York, pp. 1-36.
Gallo et al., 2001, "2'-C-methyluridine phosphoramidite: a new building block for the preparation of RNA analogues carrying the 2'-dydroxyl group", Tetrahedron, 57:5707-5713.
Galustian et al., "Thalidomide-derived immunomodulatory drugs as therapeutic agents," *Expert Opin. Biol. Ther.*, 2004, 4 (12):1-8.

(56) References Cited

OTHER PUBLICATIONS

Galvin et al., "Adult Human Neural Stem Cells for Cell-Replacement Therapies in the Central Nervous System," MJA 177:316-318 (2002).
Gamba, Physiol. Rev. 85:423-493 (2005).
Garcia-Olmo et al., "A Phase I Clinical Trial of the Treatment of Crohn's Fistula by Adipose Mesenchymal Stem Cell Transplantation," Stem Cells in Chron's Fistula 48(7): 1417-1423 (2005).
Garcia-Olmo et al., "Autologous Stem Cell Transplantation for Treatment of Rectovaginal Fistula in Perianal Crohn's Disease: A New Cell-based Therapy", Int. J. Colorectal Dis. 18:451-454 (2003).
Genbacev et al., "Regulation of Human Placental Development by Oxygen Tension," 277(5332):1669-1672 (1997).
Gerlach, et al., "Current State of Stem Cell Research for the Treatment of Parkinson's Disease", J. Neurol. (Suppl 3):III/33-III/35 (2002).
Gerlach, et al., "Use of Primary Human Liver Cells Originating from Discarded Grafts in a Bioreactor for Liver Support Therapy and the Prospects of Culturing Adult Liver Stem Cells in Bioreactors—a Morphologica Study," Transplantation 76(5):781-786 (2003).
Gershbein, 1991, "The thalidomide analog, EM 12, enhances 1,2-dimethylhydrazine-induction of rat colon adenocarcinomas," Cancer Letters 60: 129-133.
Giarratana, et al., "Ex vivo Generation of Fully Mature Human Red Blood Cells from Hematopoietic Stem Cells," Nat. Biotech. 23:69-74 (2005).
Glaspy et al., "The potential role of thalidomide and thalidomide analogs in melanoma," *Clinical Advances in Hematology & Oncology*, 2004, 1-7.
Gluckman et al., "Umbilical Cord Blood Biology and Transplantation," Current Opinion in Hematology, 2(6):413-416 (1995).
Gluckman, et al., "Cord Blood Heamatopoietic Stem Cells: Biology and Transplantation," In: Hematology, American Society of Hematology Education Program Book p. 1-14 (1998).
Gluckman, et al., "Results of Unrelated Umbilical Cord Blood Hematipoeietic Stem Cell Transplant," Transfusion Cinique et Biologique 8(3):146-154 (2001).
Goncalves, Bioessays 27: 506-517 (2005).
Gossen et al., Proc. Natl. Acad. Sci. USA 89:5547-5551 (1992).
Gould et al., Dermatologic Manifestations of Sarcoidosis. Medscape Reference: Drugs, Diseases, and Procedures. Downloaded from the Medscape websites on Nov. 27, 2012: <http://emedicine.medscape.com/article/1123970-overview#aw2 aab6b8>.
Govindarajan et al., 2000, "Effect of thalidomide on gastrointestinal toxic effects of irinotecan," *The Lancet*, 356:566-567.
Grabstald et al., "Clinical experiences with thalidomide in patients with cancer," Clinical Pharmacology and Therapeutics 6:298-302 (1965).
Graham, Med Device Technol 9(1):18-22 (1998).
Greenwood et al., "Membrane Potential Difference and Intracellular Cation Concentrations in Human Placental Trophoblast Cells in Culture," Journal of Physiology 492.3:629-640 (1996).
Groh, et al., Human mesenchymal stem cells require monocyte-mediated activation to suppress alloreactive T cells. Exp. Hematol. 33, 928-934 (2005).
Groner et al., "New Optical Technique for Measuring Erythrocyte Deformability with the Ektacytometer," CHn. Chern. 26:1435 (1980).
Gupta et al., 2001, "Adherence of multiple myeloma cells to bone marrow stromal cells upregulates vascular endothelial growth factor secretion: therapeutic applications," Leukemia 15(12):1950-1961.
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Hanahan, 1985, Nature 315: 115.
Hansen et al., "Differential Alteration by Thalidomide of the Glutathione Content of Rat vs. Rabbit Conceptuses in Vitro," Reprod Toxicol13: 547-554 (1999).
Harbacheuski, et al., "Placenta Derived Adherent Cells (PDACs) Supress Tumor Cells of Diverse Origin." Blood 108(11):288 (2006).
Hardingham, et al., Cancer Research 53:3455-3458 (1993).
Harduin-Lepers et al., "The Animal Sialyltransferases and Sialyltransferase-Related Genes: a Phylogenetic Approach," Glycobiology, OxFord University Press, 15(8):805-817 (2005).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos, et al. "Isolation and characterization of endothelial progenitor cells from mouse embryos," Development. 125(8):1457-68 (1998).
Hayashi et al., "Mechanisms whereby immunomodulatory analogs of thalidomide augment autologous NK cell anti-myeloma immunity," Blood, Abstract #3219, Dec. 6-10, 2002, *American Society of Hematology*.
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.
Helm et al., "Comparative teratological investigation of compounds of structurally and pharmacologically related to thalidomide," *Arzneimittel Forschung/Drug Research*, 1981, 31 (I)941-949.
Hemmoranta et al., N-Glycan Structures and Associated Gene Expressions Reflect the Characteristic N-Glycosylation Pattern of Human Hematopoietic Stem and Progenitor Cells, Experimental Hematology, Elsevier Inc., 35(8):1279-1292 (2007).
Hennink et al., Adv Drug Deliv Rev 54(1):13-36 (2004).
Hernandez-Llizaliturr, et al., "Immunomodulatory Drug CC-5013 or CC-4047 and Rituximab Enhance Antitumor Activity in a Severe Combined Immunodeficient. Mouse Lymphoma Model," Clin. Cancer Res. 11(16):5984-5992 (2005).
Herrera, et al., "Mesenchymal Stem Cells Contribute to the Renal Repair of Acute Tubular Epithelial Injury," Int. J. Mol. Med., 14(6):1035-41 (2004).
Hidai et al., "Cloning of Capsulin, a Basic Helix-Loop-Helix Factor Expressed in Progenitor Cells of the Pericardium and the Coronary Arteries," Mechanisms of Development, 73(1):33-43 (1998).
Hideshima et al., Thalidome (THAL) and its Analogs Overcome Drug Resistance of Human Multiple Myeloma (MM) Cells to Conventional Therapy. Abstract #1313. American Society of Hematology, Dec. 1-5, 2000.
Hideshima et al., "Thalidomide and its analogs overcome drug resistance of human multiple myeloma cells to conventional therapy," Blood, 2000, 96:2943-2950, *American Society of Hematology*.
Hideshima et al., NF-KB as a Therapeutic Target in Multiple Myeloma (MM). Abstract #1581. American Society of Hematology, Dec. 7-11, 2001.
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirano et al., "CD9 is Expressied in Extravillous Trophoblasts in Association with Integrin $\alpha 3$ and integrin $\alpha 5$," Molecular Human Reproduction 5(2):162-167 (1999).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075.
Hori et al, J. Surgical Research 102:156-160 (2002).
Hoshimaru et al., Proc. Natl. Acad. Sci. USA 93:1518-1523 (1996).
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells," Biochemical and Biophysical Research Communications, 2007; 362:347-53.

(56) References Cited

OTHER PUBLICATIONS

Hsieh et al., "Effects of glucose on placental hormones in the human term placenta in vitro" J. Formos. Med. Assoc. 96(5):309-313 (1997).
Hüffmeier et al., "Systematic Linkage Disequilibrium Analysis of SLC12A8 at PSORS5 Confirms a Role in Susceptibility to Psoriasis Vulgaris," J Invest Dermatol 125:906-912 (2005).
Hume et al., "Red Blood Cell Transfusions for Preterm Infants: The Role of Evidence-Based Medicine," Seminars in Perinatology, W.B. Saunders, GB 21(1):14-15 (1997).
Hung, et al. "Mesenchymal Stem Cell Targeting of Microscopic Tumors and Tumor Stroma Development Monitored by Noninvasive In vivo Positron Emission tomography Imaging," Clin. Cancer Res. 11(21):7749-7756 (2005).
Hunt et al., "Markers of endothelial and haemostatic activation in the use of CC-4047, a structural analogue of thalidamide, in relapsed myeloma," Blood, Abstract # 3216, Dec. 6-10, 2002, *American Society of Hematology*.
Huss, "Isolation of Primary and Immortalized CD34-Hematopoietic and Mesenchymal Stem Cells from Various Sources," Stem Cells 18:1-9 (2000).
Huss, "Perspectives on the Morphology and Biology of CD34-Negative Stem Cells," J. Hematother. Stem. Cell Res. 9(6):783-793 (2000).
Hussein et al., "Doxil (D), vincristine (V), reduced frequency dexamethasone (d) and Revlimid (DVd-R) a phase I/II trial in advanced relapsed/refractory multiple myeloma (Rmm) patients," *Blood, Abstract #208, American Society of Hematology*, Dec. 4-7, 2004.
Hwu et al., "Thalidomide and its analogues in the treatment of metastatic melanoma," *Chemotherapy Foundation Symposium, Abstract #44*, 2002.
Iacovitti et al., "Differentiation of Human Dopamine Neurons from an Embryonic Carcinomal Stem Cell Line," Brain Research, 912:99-104 (2001).
Igura, et al., "Isolation and Characterization of Mesencymal Progenitor Cells from Chorionic Villi of Human Placenta," Cytotherapy 6(6): 543-553 (2004).
Ikehara, "Bone Marrow Transplantation: A New Strategy for Intractable Diseases," Drugs of Today 38(2): 103-111 (2002).
Ilan, et al., Hepatology29(2):553-562 (1999).
Ilan, et al., Journal of Infectious Diseases185(2):153-161 (2002).
Ilancheran, et al., "Stem Cells Derived from Human Fetal Membranes Display Multilineage Differentiation Potential," Biology of Reproduction, 77, 577-588 (2007).
Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
Twasakt, "Recent Advances in the Treatment of Graft-Versus-Host Disease,"• Clin. Med. Res., 2004; 2(4):243-52.
Iyamu & Asakura, Expert Opin. Ther. Patents 13(6):807-813 (2003).
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jaroscak et al., "Preliminary characterization of the surface staining of placental derived adherent cells: a potential new source of stroma for umbilical cord blood (UCB) expansion," Blood 96(11, Pt 2) (2000).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2000).
Jiang et al., 2002, "Pluripotency of mesenchymal stem cells derived from adult marrow," Nature 418:41-49.

Jing, et al., "Blood Progenitor Cell Separation from Clinical Leukapheresis Product by Magnetic Nanoparticle Binding and Magnetophoresis," Biotechnol. Bioeng. 96(6):1139-1154 (2007).
Joggerst et al., "Stem Cell Therapy for Cardiac Repair: Benefits and Barriers," Expert Rev. Mol. Med. 11(e20):1-19 (2009).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).
Jonsson, 1972, "Chemical Structure and Teratogenic Properties," Acta Pharm., pp. 521-542.
Jorgensen, et al., "Mesenchymal Stem Cells and Rheumatoid Arthritis," Joint Bone Spine 483-485 (2003).
Jorgensen, et al., "Intercellular Calcium Signaling Occurs between Human Osteoblasts and Osteoclasts and Requires Activation of Osteoclast P2X7 Receptors," J. of Biol. Chem. 277:7574-7580 (2002).
Kai, Shunro, "A New Approach of Umbilical Cord Blood Transplantation," Japanese Journal of Clinical Pathology, Review, No. 122, pp. 75-80 (2002).
Kalka et al., "Transplantation of Ex Vivo Expanded Endothelial Progenitor Cells for Therapeutic Neovascularization," Proc. Natl. Acad. Sci. USA 97: 3422-3427 (2000).
Kamarch, 1987, Methods Enzymol, 151: 150-165.
Kamenva, et al., "Heparin Effect on Red Blood Cell Aggregation," Biorheology, 31(3):297-304 (1994).
Kamenva, et al., "Mechanical Trauma to Blood," In: Handbook of Hemorheology and Hemodynamics 206-227 (IOS Press, 2007).
Kamenva, et al., "Mechanisms of Red Blood Cell Trauma in Assisted Circulation. Rheologic Similarities of Red Blood Cell Transfoiuiations due to Natural Aging and Mechanical Stress," ASAIO J. 41:457-460 (1995).
Kamenva, et al., "Red Blood Cell Aging and Risk of Cardiovascular Diseases," Clin. Hemorheol. Microcirc. 8:67-74 (1998).
Kamenva, et al., "Rheologic Dissimilarities in Female and Male Blood: Potential Link to Development of Cardiovascular Diseases," Advances in Experimental Medicine and Biology 530:689-696 (2003).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kassem et al., Cloning Stem Cells 6:369-74 (2004).
Kato et al., "Discordant Secretion of Placental Protein Hormones in Differentiating Trophoblasts in Vitro," Journal of Clinical Endocrinology and Metabolism 68(4):814-820 (1989).
Kaufman et al., 1987, "Translational efficiency of polycistronic mRNAs and their utilization to express heterologous genes in mammalian cells," EMBO J, 6:187-195.
Kaufmann et al., "Extravillous Trophoblast in The Human Placenta," Trophoblast Research 10:21-65 (1997).
Kavalerchik E et al. "Chronic myeloid leukemia stem cells," J Clin Oncol 26:2911-2915(2008).
Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Keskin et al., 2007, "TGFβ promotes conversion of CD16+ peripheral blood NK cells into CD16 NK cells with similarities to decidual NK cells," Proc Natl Acad Sci USA, 104(9):3378-3383.
Kihm et al., "An Abundant Erythroid Protein That Stabilizes Free .alpha. Hemoglobin," Nature 417:758-763 (2002).
Kliman et al., "Purification, Characterization, and In Vitro Differentiation of Cytotropholblasts from Human Term Placentae," Endocrinology 118(4):1567-1582 (1986).
Koc et al., 1999, "Bone marrow-derived mesenchymal stem cells remain host-derived despite successful hematopoietic engraftment after allogeneic transplantation in patients with lysosomal and peroxisomal storage diseases," Experimental Hematology, 27:1675-1681.
Koc, et al., "Rapid Hematopoietic Recovery After Coinfusion of Autologous-Blood Stem Cells and Culture-Expanded Marrow

(56) References Cited

OTHER PUBLICATIONS

Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81.
Kojima et al., "Induction of Graft-versus-Autoimmune (GVA) Disease Effect Against Refractory Psoriasis by Complete Donor-Type Chimerism and Graft-versus-Host Disease After Allogenic Hematopoietic Stem Cell Transportation," Bone Marrow Transplantation 32:439-442 (2003).
Kolf 2007, 9:204.
Kon-nichi no Chiryou Shishin, 1997 [Pocket Edition], Igaku Shoin, 1997, 513-514 (in Japanese).
Korbling, et al. "Peripheral Blood Stem Cell Versus Bone Marrow Marrow Allotransplantation: Does the Source of Hematapoietic Stem Cells Matter?" Blood 98(10):2900-2908 (2001).
Korbling, et al., "Hepatocytes and Epithelial Cells of Donor Origin in Recipients of Peripheral-Blood Stem Cells," N. Engl. J. Med. 346(10):738-746 (2002).
Krampera, et al. Bone marrow mesenchymal stem cells inhibit the response of naive and memory antigen-specific T cells to their cognate peptide. Blood 101, 3722-3729 (2003).
Kucia et al., "Bone Marrow as a Home of Heterogenous Populations of Non Hematopoietic Stem Cells," Leukemia vol. 19: 1118-1127 (2005).
Kurtzberg, "Placental Bood as a Source of Hmatopoietic Sem Cells for Transplantation into Unrelated Recipients," N. Engl. J. Med. 335:157-166 (1996).
Kurzrock, R., "Myelodysplastic syndrome overview," *Seminars in Hematology* (Abstract only), 2002, 39(3)(suppl. 2):18-25 Abstract only.
Kyle et al., "Multiple myeloma," *New England Journal of Medicine*, 2004, 351:1860-1873.
Lacerda et al., "Human Epstein-Barr Virus (EBV)-Specific Cytotoxic T Lymphocytes Home Preferentially to and Induce Selective Regressions of Autologous EBV-Induced B Lymphoproliferations in Xenografted C.B-17 Scid/Scid Mice," J Exp. Med. 183: 1215-1228 (1996).
Landon et al., "The Effects of Ethanol Methotrexate and Diphenylhydantoin on [$^{14}$C] Leucine Incorporation by Human Troplioblasst Cells Cultured In Vitro," British Journal of Obstetrics and Gynaecology 94:252-255 (1987).
Lapchak et al., Expert Opin. Emerging Drugs 12:389-406 (2007).
Larsson, et al., "Serum and Plasma Levels of FGF-2 and VEGF in Healthy Blood Donors," Angiogenesis 5:107-110 (2002).
Lavelle et al., "Effects of Hydroxyurea Stem Cell Factor, and Erythropoietin in Combination on Fetal Hemoglobin in the Baboon," Experimental Hematology 29:156-162 (2001).
Law, E., et al., Stem Cell Symposium, State of New Jersey Commission on Science & Technology 2005 (Abstract).
Lazarus, et al., "Cotransplantation of HLA-Identical Sibling Culture-Expanded Mesenchymal Stem Cells and Hematopoietic Stem Cells in Hematologic Malignancy Patients," Blood Marrow Transplant, 11(5):389-398 (2005).
Le Blanc et al., "Treatment of Severe Acute Graft-Versus-Host Disease With Third Party Haploidentical Mesenchymal Stem Cells,"• Lancet, 363(9419):1439-41 (2004).
Lebkowski, et al., "Serum and Plasma Levels of FGF-2 and VEGF in Healthy Blood Donors," Cancer J. 7(Suppl 2):S83-S93 (2001).
Leblanc et al , "Immunomodulatory drug costimulates T cells via the B7-CD28 pathway," Blood, 2004, 103:1787-1790, *American Society of Hematology*.
Lee et al., "Clinical Efficacy of Granulocyte Transfusion Therapy in Patients With Neutropenia-Related Infections," Leukemia 15(2):203-7 (2001).
Lee-Macary et al, J Immunol Methods 252(1-2):83-92 (2001).
Lentsch, S., Rogers, M., Leblanc, R., Birsner, A., Shah, J., Anderson K., D'Amato R., 3-Amino-Phthalimido-Glutarimide (S-3APG) Inhibits Angiogenesis and Growth in Drug Resistant Multiple Myeloma (MM) in vivo. Abstract #1976, American Society of Hematology, Dec. 7-11, 2001.
Lentzsch et al., "immunomodulatory derivative of thalidomide (IMiD CC-4047) determine the lineage commitment of hematopoietic progenitors by down regulation of GATA-1 and modulation of cytokine secretion," *Abstract # 3073, American Society of Hematology*, Dec. 6-9, 2003.
Lentzsch et al , "Immunomodulatory derivative of thalidomide (IMiD CC-4047) down regulates CAAT/enhancer-binding protein $^\beta$(C/EBP$^\beta$) in multiple myeloma (MM)," *Abstract # 3456, American Society of Hematology*, Dec. 6-9, 2003.
Lentzsch et al., "In vivo activity of thalidomide and immunomodulatory drugs against multiple myeloma," *VIIIth International Myeloma Workshop, Abstract #P225*, May 4-8, 2001.
Lentzsch et al., 2002, "S-3-amino-phthalimido-glutarimide inhibits angiogenesis and growth of B-cell neoplasias in mice", Cancer Research 62:2300-2305.
Leonard, et al., "Identification and Expression of Mammalian Long-Chain Pufa Elongation Enzymes," Lipids, Springer, 37(8):733-740 (2002).
Leonard, et al., "The Role of ABC Transporters in Clinical Practice," Oncologist. 8:411-424 (2003).
Lew and Ferreira, 1978, "Calcium transport and the properties of a calcium-activated potassium channel in red cell membranes," Current Topics in Membranes and Transport, 10:217-277.
Li et al., "Human Placenta-Derived Adherent Stem Cells Prevent Bone Loss and Stimulate Bone Formation in Myelomatous Bones, and Suppress Growth of Primary Multiple Myeloma," Blood 112(11):240-241, XP002631697 (2008).
Li et al., "Human Placenta-Derived Adherent Stem Cells Prevent Bone Loss, Stimulate Bone Formation, and Suppress Growth of Multiple Myeloma in Bone," XP002631698, Stem Cells 29(2):263-273 (2011).
Li et al., "Adult bone-marrow-derived mesenchymal stem cells contribute to wound healing of skin appendages," Cell Tissue Res 326:725-733 (2006).
Li et al., "Mesenchymal Stem Cells Derived from Human Placenta Suppress Allogenic Umbilical Cord Blood Lymphocyte Proliferation." Cell Res. 15(7): 539-547 (2005).
Li et al., Br. J. Haematology 138(6):802-811 (2007).
Lin et al. "Murine CD200(+)CK7(+) trophoblasts in a poly (I:C)-induced embryo resorption model." Reproduction (Cambridge), vol. 130, No. 4, pp. 529-537, XP002443406 ISSN: 1470-1626 (2005).
Lindberg et al., "Apoptosis in Refractory Anaemia With Ringed Sideroblasts Is Initiated a the Stem Cell Level and Associated With Increased Activation of Caspases," British Journal of Haematology 112(3):714-726 (2001).
Lipinski et al., "Human Trophoblast Cell-Surface Antigen Defined by Monoclonal Antibodies," Proc. Natl. Acad. Sci. USA, Medical Sciences 78(8):5147-5150 (1981).
List et al., "Efficacy and Safety of CC5013 for Treatment of Anemia in Patients With Myelodysplastic Syndromes (MDS)," Blood, American Society of Hematology 102(11):184A (2003).
Liu et al, "Phase I study of CC-5013 (Revimid), a thalidomide derivative, in patients with refractory metastatic cancer," *American Society of Clinical Oncology, Abstract #927*, 2003.
Liu et al., "Ex vivo expansion of enriched CD34+ cells from neonatal blood in the presence of thrombopoietin, a comparison with cord blood and bone marrow", Bone Marrow Transplantation 24:247-252 (1999).
Loke et al., "Identification of Cytotrophoblast Colonies in Cultures of Human Placental Cells Using Monoclonal Antibodies," Placenta 7:221-231 (1986).
Looijenga, et al., Cancer Research, 63: 2244-2250 (2003).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Luzzio et al., "Thalidomide analogues: derivatives of an orphan drug with diverse biological activity," *Expert Opin. Ther. Patents*, 2004, 14 (2):215-229.

(56) References Cited

OTHER PUBLICATIONS

Ma et al., "Development of an in vitro Human Placenta Model by the Cultivation of Human Trophoblasts in a Fiber-Based Bioreactor System," Tissue Engineering 5, 91-102 (1999).
Ma et al., "Human Umbilical Cord Wharton's Jelly-Derived Mesenchymal Stem Cells Differentiation into Nerve-Like Cells," Chinese Med. Jour., 118(23):1987-1993 (2005).
Ma et al., "Synthetic Nano-Scale Fibrous Extracellular Matrix," J. biomed. Mater. Res. 46:60-72 (1999).
MacKay, et al., "Chondrogenic Differentiation of Cultured Human Mesenchymal Stem Cells from Marrow," Tissue Engineering 4(4):415-28 (1998).
MacKenzie et al., Blood Cells, Molecules and Diseases 27:601-604 (2001).
Maclaren, et al., 1992, Inter- and Intraspecific Palcentae in Sheep, Goats and Sheep-Goat Chimaeras, J Comp Pathol, 106:279-297.
Madri, et al., "Capillary Endothelial Cell Cultures: Phenotypic Modulation by Matrix Components," J. Cell Biol. 97:153-165 (1983).
Magatti, et al., "Human Amnion Mesenchyme Harbors Cells with Allogeneic T-Cell Suppression and Stimulation Capabilities," Stem Cells 26:182-192 (2008).
Malek et al. "Lack of transport of crythropoictin across the human placenta as studied by an in vitro perfusion system," European Journal of Physiology 427:157-161 (1994).
Malik, et al., "An in vitro Model of Human Red Blood Cell Production from Hematopoietic Progenitor Cells:," Blood 91:2664-2671 (1998).
Man et al., "α-Fluoro-substituted thalidomide analogues," Bioorganic & Medicinal Chemistry Letters 13, 2003, 3415-3417.
Marascalco, et al., "Development of Standard Tests to Examine Viscoelastic Properties of Blood of Experimental Animals for Pediatric Mechanical Support Device Evaluation," ASAIO J. 52:567-574 (2006).
Marino, "International Standards for Neurological Classification of Spinal Cord Injury," J Spinal Cord Med. 26 Suppl 1 :S50-6 (2003).
Marmont, "New Horizons in the Treatment of Autoimmune Diseases. Immunoablation and Stem Cell Transplantation," Ann. Rev. Medicine 51:115-134 (2000).
Marriott et al., "Thalidomide analogue CDC-501 is safe and well tolerated by patients with end stage cancer and shows evidence of clinical responses and extensive immune activation," Br. J. Cancer, 2002, 86(Supp. 1):Abst 6.4.
Mauad, 1963, "Clinical Improvements Obtained in Advanced Caner Patients with Treatment with Thalidomide Associated with Hormones," Anais *Paulistas de Medicina e Cirurgia* 86:13-40.
Mazzini et al., 2008, "Stem cell treatment in Amyotrophic Lateral Sclerosis", J Neuro Sci, 265:78-83.
Mazzini et al., 2010, "Mesenchymal stem cell transplantation in amyotrophic lateral sclerosis: a phaseI clinical trial,"Exp Neurol, 223:229-237.
Mazzini et al., 2012, "Transplantation of myesenchymal stem cells in ALS," Prog Brain Res, 201:333-359.
McMaster et al, "Human Placental HLA-G Expression is Restricted to Differentiated Cytotrophoblasts," J. Immunol. 154(8):3771-3778 (1995).
Meiler, et al., "Pomalidomide Augments Erythropoiesis and Fetal Hemoglobin Production in a Humanized Mouse Model of Sickle Cell Disease," American Society of Hematology, 2008 Annual Meeting, San Francisco, CA (12 pages), Abstract # 536.
Melchner, et al., "Human Placental Conditioned Medium Reverses Apparent Commitment to Differentiation of Human Promyelocytic Leukemia Cells (HL60)," Blood 66(6):1469-1472 (1985).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Melville, et al., 1975, "Direct Magnetic Separation of Red Cells from Whole Blood," Nature 255:706.
Meng et al., Biomaterials Sci., Polymer Edition 18(1):81-94 (2007).

Mercanti et al., "Mitogenic Effect of a Human Placental Factor on Astrocytes and Glial Precursors," Experimental Cell Research, 168,(1):182-190 (1987).
Merck Manual of Diagonstic and Therapy, 17th Ed., Merck Research Laboratories, Whitehouse Station, N.J., p. 878 (1999).
Meregalli et al., "High-dose dexamethasone as first line therapy of multiple myeloma?", Recenti Progressi in Medicina, 1998, 89(1):18-20.
Miki et al., "Isolation of Multipotent Stem Cells from Placenta." AASLD Abstracts, Hepatology 38(1):290 Abstract 279, (Oct. 2003).
Miki et al., "Production of Hepatocytes from Human Amniotic Stem Cells." Hepatology, Abstract 20, vol. 36, No. 4, Pt. 2 (2002).
Miki et al., "Stem Cell Characteristics of Amniotic Epithelial Cells." Stem Cells Express, published online Aug. 9, 2005; doi:10. 1634/stemcells:2004-0357, 32 pages (2005).
Minguell et al., 2013, "Mesenchymal stem cells and the treatment of conditions and diseases: the less glittering side of a conspicuous stem cell for basic research," Stem Cells Dev, 22:193-203.
Minguell, et al., "Mesenchymal Stem Cells," Exp. Biol. Med. 226:507-520 (2001).
Mitsiades et al., Apoptotic Signaling Induced by Immunomodulatory Thalidomide Analogs (Imids) in Human Multiple Myeloma Cells; Therapeutic Implications. Abstract #3224. American Society of Hematology, Dec. 7-11, 2001.
Miyachi et al., 1997, "Novel biological response modifiers: phthalimides with tumor necrosis factor-alpha production-regulating activity," J. Med. Chem. 40:2858-2865.
Mohandas et al., "Analysis ofFactors Regulating Erythrocyte Deformability," J. Clin. Invest. 66:563-573 (1980).
Möller et al., 1998, "A distinct distribution of natural killer cell subgroups in human tissues and blood," Int J Cancer, 78:533-538.
Mombaerts et al., 1991, Proc. Nat. Acad. Sci. U.S.A. 88:3084.
Monroig et al., Biochim. Biophys. Acta 1791(11): 1093-1101 (2009).
Moore, et al., "A Simple Perfusion Technique for Isolation of Maternal Intervillous Blood Mononuclear Cells from Human Placentae," J. Immunol. Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Moretra et aI., "Thalidomide Exerts its Inhibitory Action on Tumor Necrosis Factoraby Enhancing mRNA Degradation," J. Expr. Med. 177: 1675-1680 (1993).
Morgan et al., "Human Placental Cell Culture," Biochemical Society Transactions 12 (1984).
Morgan et al., "Long-Tenn Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol., 15(7):1794-1804 (2004).
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-06.
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Mostow et al., "Effectiveness of an Extracellular Matrix Graft (OASIS Wound Matrix) in the Treatment of Chronic Leg Ulcers: A Randomized Clinical Trail," Journal of Vascular Surgery, St. Louis, MO., US, vol. 41(5):837-843 (2005).
Moutouh De Parseval et al., "Pomalidomide and Lenalidomide Regulate Erythropoiesis and Fetal Hemoglobin Production in Human CD34+ Cells," The Journal of Clinical Investigation, 118(1): 248-258 (2008).
Moutsatos et al., Molecular Therapy 3:449-461 (2001).
Muhlemann, et al., "Cytomegalovirus in the Perfused Human Term Placenta in vitro," Placenta 16:367-373 (1995).

(56) References Cited

OTHER PUBLICATIONS

Muller et al., "Amino-Substituted Thalidomide Analogs: Potent Inhibitors of TNF-.alpha. Production," Bioorganic & Medicinal Chemistry Letters 9:1625-1630 (1999).
Muller et al., FASEB J, vol. 14: 2540-2548 (2000).
Myllynen "In Search of Models for Hepatic and Placental Pharmacokinetics," [Dissertation] University of Oulu, (2003).
Nadkarni, et al., "Effect of Retinoic Acid on Bone-Marrow Committed Stem Cells (CFU-c) from Chronic myeloid Leukemia Patients," Tumori. 70(6):503-505 (1984).
Nagayama et al., "Immunological reconstitution after cord blood transplantation for an adult patient", Bone Marrow Transplantation 24: 211-213 (1999).
Nakamura, K, et al. "Antitumor effect of genetically engineered mesenchymal stem cells in a rat glioma model." Gene Therapy(2004) vol. 11, No. 14. pp. 1155-1164.
Nguyen et al., Biomaterials 23(22):4307-4314 (2002).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int., 2006; 70(1):121-29.
Nishishita, et al., "A Potential Pro-Angiogenic Cell Therapy with Human Placenta-Derived Mesenchymal Cells," Biochem. Biophys. Res. Commun. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Oda et al., "Trophoblast Stem Cells," Methods in Enxymology 419(15):387-400 (2006).
Ohlsson et al., "Mesenchymal Progenitor Call-Mediated Inhibition of Tumor Growth in Vivo and In Vitro in Gelatin Matrix," Experimental and Molecular pathology 75:248-255 (2003).
Okajima et al., "Molecular Cloning of a Novel Alpha2,3-Sialyltransferase (ST3Ga1VI) that Sialylates Type II Lactosamine Structures on Glycoproteins and Glycolipids," Journal of Biological Chemistry, 274(17):11479-11486 (1999).
Okamoto et al., Nature Medicine 8:1011-1017 (2002).
Olson et al., 1965, "Thalidomide (N-phthaloylglutamimide) in the treatment of advanced cancer," Clinical Pharmacology and Therapeutics 6(3):292-297.
Omitz et al., 1986, Cold Spring Harbor Symp. Quant. Biol. 50:399;.
Oppenheim, et al., 2001, Evidence against humoral immune attach as the cause of sheep-goat interspecies and hybrid pregnancy failure in the doe, Theriogenology 55:1567-1581.
Ordi, et al., "Massive Chronic Intervilllositis of the Placenta Associated with Malaria Infection," Am. J. Surg. Pathol. 8:1006-1011 (1998).
Ortiz et al, "Mesenchymal Stem Cell Engraftment in Lung is Enhanced in Response to Bleomycin Exposure and Ameliorates Its Fibrotic Effects," Proc. Nat. Acad. Sci. (USA) 14:8407-8411 (2003).
Paludan, et al., "Immune Suppression by Placenta Derived Adherent Cells (PDAC) Correlate with Monocyte Chemoattractant Protein-1 and 1L-2 Secretion," Blood 108(11) Part II, p. 48B (2006) (abstract only).
Paludan, et al., "Placental Derived Stem Cells (PDAC) Suppress the Allo-MLR and the EBV Regression Assay," http://www.call4abstract.com/hem/finalpreview.php?absnum=552996 (2006).
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci, et al., "Comparison of Gene Expression of Umbilical Cord Vein and Bone Marrow-Derived Mesenchymal Stem Cells," Stem Cells, 2004; 22(7):1263-78.
Papaioannou, et al., "Stem Cells from Early Mammalian Embryos" Stem Cells Handbook:19-31 (2004).
Parolini, et al., "Concise Review: Isolation and Characterization of Cells from Human Term Placenta: Outcome of the First International Workshop on Placenta Derived Stem Cells," Stem Cells 26(2):300-311 (2008).
Patt et al., *Durable Clinical Response of Refractory Hepatocellular Carcinoma to Orally Administered Thalidomide*. American Journal of Clinical Oncology, 319-321 (2000).
Patten et al., "The early use of the serum free light chain assay in patients with relapsed refractory myeloma receiving treatment with a thalidomide analogue (CC-4047)," *Abstract # 1640, American Society of Hematology*, Dec. 6-9, 2003.
Pauling, et al., "The Magnetic Properties and Structure of the Hemochromogens and Related Substances," Proc. Natl. Acad. Sci. USA 22:159-163 (1936).
Payvandi et al., Effects of a Thalidomide Analog on Binding Activity of Transcription Factors and Cell Cycle Progression of Multiple Myeloma Cell Lines. Abstract #2487. American Society of Hematology, Dec. 1-5, 2000.
Pellegrini, et al., "FADD and Caspase-8 Are Required for Cytokine-Induced Proliferation of Hemopoietic Progenitor Cells," Blood 106(5):1581-1589 (2005).
Peppas et al., Eur J Pharm Biopharm 50(1):27-46 (2000).
Pera, et al., "Human Embryonic Stem Cells," J. Cell. Sci. 113:5-10 (2000).
Pesce, et al., "oct-4: Gatekeeper in the Beginnings of Mammalian Development," Stem Cells 19:271-278 (2001).
Petroff et al., "Isolation and Culture of Teru1 Human Trophoblast Cells," Methods in Molecular Medicine, Placenta and Trophoblast, 1(16):203-217 (2006).
Pinho-Ribeiro et al., "Human Umbilical Cord Blood Cells in Infarcted Rats," Braz. J. Med. Biol. Res. 43(3):290-296 (2010).
Pittenger et al., "Multilineage Potential of Adult Human Mesenchymal Stem Cells," Science 284(5411):143-147 (1999).
Pluchino, et al., "Neural Stem Cells and Their Use as Therapeutic Tool in Neurological Disorders," Brain Res Brain Res. Rev. 48(2):211-219 (2005).
Pluristem. Pluristem Therapeutics Receives DSMB Approval to Advance to Final Dose Level with PLX-PAD [online] Mar. 2, 2010 [retrieved Jun. 22, 2011], Available on the Internet: <URL:http://www.pluristem.com/index.php?option=com_content&view=article&id=148:march-2&catid=5:2010>.
Potgens, et al., "A Positive Immunoselection Method to Isolate Villous Cytotrophoblast Cells from First Trimester and Term Placenta to High Purity," 24(4):412-423 (2003).
Ponticiello et al., "Gelatin-based resorbable sponge as a carrier matrix for human mesenchymal stem cells in cartilage regeneration therapy" Journal of Biomedical Materials Research 52:246-255 (2000).
Portmann-Lanz, et al., "Placental Mesenchymal Stem Cells as Potential Autologous Graft for Pre- and Perinatal Neuroregeneration" Am. J. Obstet Gynecol. 194:664-673 (2006).
Potgens et al., "Human Trophoblast Contains an Intracellular Protein Reactive with and Antibody against CD133—A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured, 2007; 38(Supp. 4):S23-33.
Quinn et al., "Mouse Trophoblast Stem Cells," Methods in Molecular Medicine 121(1):125-148 (2005).
Rachmilewitz et al., "intermediate Cells During Cytotrphoblast Differentiation in Vitro," Cell Growth & Differentiation 4:395-402 (1993).
Raje et al., 1999, "Thalidomide—a revival story," N. Engl. J. Med. 341(21):1606-1609.
Rajkumar et al., "Combination therapy with thalidomide plus dexamethasone for newly diagnosed multiple myclonia," *American Society of Hematology*, 43rd Annual Meeting, Dec. 7-11, 2001, Abstract #3525.
Ramasethu and Luban, 1999, "Red blood cell transfusions in the newborn," Semin Neonatol, 4:5-16.
Rao and Georgieff, 2007, "Iron in fetal and neonatal nutrition," Seminars in Fetal & Neonatal Medicine, 12:54-53.

(56) References Cited

OTHER PUBLICATIONS

Raza et al., 2001, "Thalidomide produces transfusion independence in long-standing refractory anemias of patients with myelodysplastic syndromes," Blood, 98(4):958-985.
Readhead et al., 1987, Cell 48:703.
Reubinoff, "Neural Progenitors from Human Embryonic Stem Cells," Nature Biotech. 19(12):1134-1140 (2001).
Reyes, et al., "Purification and ex vivo Expansion of Postnatal Human Marrow Mesodermanl Progenitor Cells," Blood 98(9):2615-2625 (2001).
Reyes, et al., Origin of endothelial progenitors in human postnatal bone marrow.J Clin Invest. 109(3):337-46 (2002).
Richardson et al., *Thalidomide: Emerging Role in Cancer Medicine*; Annual Review of Medicine, 53:629-657 (2002).
Rielland et al., "Trophoblast Stem Cell Derivation, Cross-species Comparison and Use of Nuclear Transfer: New Tools to Study Trophoblast Growth and Differentiation," Developmental Biology 322: 1-10 (2008).
Ringler et al., "In Vitro Systems for the Study of Human Placental Endocrine Function," Endocrine Reviews 11(1):105-123, 1990.
Rong-Hao et al., "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Roussev et al., 1993, "Phenotypic characterization of normal human placental mononuclear cells," J Reproductive Immunol, 25:15-29.
Rubin et al, "Principles of Cancer Treatment—1", 12 ONCO IV 1, May 2003.
Rubenstein, et al., "Processing and Cryopreservation of Placental/Umbilical Cord Blood for Unrelated Bone Marrow Reconstitution," Proc. Natl. Acad. Sci. USA 92:10119-10122 (1995).
Rudel, "Caspase Inhibitors in Prevention of Apoptosis," Herz 24:236-241 (1999).
Russo, "Fighting Darwin's Battles. Symposium Marks Evolutionist Victory, Anti-Evolution Growth" The Scientist 15:6 (2001).
Sakabe, et al., "Functional Differences Between Subpopulations of Mobilized Peripheral Blood-Derived CD34+ Cells Expressing Different Levels of HLA-DR, CD33, CD38 and c-kit Antigens," Stem Cells 15(11):73-81 (1997).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Sanchez-Muñoz et al., 2008, "Role of cytokines in inflammatory bowel disease," World J Gastroenterol, 14(27):4280-4288.
Sapin, "Esterification of Vitamin A by the Human Placenta Involves Villous Mesenchymal Fibrlboasts," pediatric Research 48(4):565-572 (2000).
Saric et al., "An IFN-γ-induced Aminopeptidase in the ER, ERAP I, Trims Precursors to MHC Class I-presented Peptides," Nature Immunology 3(12):1169-1176 (2002).
Sauer, et al., "Thalidomide Inhibits Angiogenesis in Embryoid Bodies by the Generation of Hydroxyl Radicals." American Journal of Pathology, vo. 156, No. 1, pp. 151-158 (Jan. 2000).
Savicki, et al., "Magnetic Susceptibility of Oxy- and Carbonmonoxyhemoglobins," Proc. Natl. Acad. Sci. USA 81:5417-5419 (1984).
Scaringe, 2001, "RNA oligonucleotide synthesis via 5'-silyl-2'-orthoester chemistry," Methods, 23:206-217.
Schmedlen et al., Biomaterials 23:4325-4332 (2002).
Schulz et al., "Human Embryonic Stem Cells as Models for Trophoblast Differentiation," Placenta 29(Suppl A): S10-S16 (2008).
Schutz, et al., "Isolation and Cultivation of Endothelial Cells Derived from Human Placenta," Eur. J. Cell Biol. 395-401 (1996).
Schwab, "Fast and Reliable Culture Method for Cells from 8-10 Week Trophoblast Tissue," Lancet 323:1082 (1984).
Schwarz, "The Mixed Lymphocyte Reaction: An In Vitro Test for Tolerance," J Exp. Med. 127(5):879-890 (1968).
ScienCell—Human Amniotic Epithelial Cells. http://www.sciencellonline.com/products/7100.htm.
Seed, 1987, "An LFA-3 cDNA encodes a phospholipid-linked membrane protein homologous to its receptor CD2Nature," 329(6142):840-842.
Semenov et al. "Multipotent mesenchymal stem cells from human placenta: critical parameters for isolation and maintenance of stemness after isolation" American Journal of Obstetrics & Gynecolocy 202:193.e1-13 (2010).
Serafini, et al., "Pluripotency in Adult Stem Cells: State of the Art," Semi. Reprod. Med. 24:379-388 (2006).
Seyfried et al., J. Neurosurg. 104:313-318 (2006).
Shah et al., 1999, "Synthesis and enantiomeric separation of 2-phthalimidino-glutaric acid analogues: potent inhibitors of tumor metastasis," J. Med. Chem. 42:3014-3017.
Shamblott, et al., "Derivation of Pluripotent Stem Cells from Cultured Human Primordial Germ Cells," Proc. Natl. Acad. Sci. USA 95(23):13726-13731 (1998).
Shani, 1985, Nature 314:283.
Sherley, "Asymmetric Cell Kinetics Genes: The Key to Expansion of Adult Stem Cells in Culture", Stem Cell 20:561-72 (2002).
Shi et al., "BAX and Caspase Activity Limit Adult Neural Stem Cell Persistence," Society for Neuroscience Abstract Viewer and Itinerary Planner, vol. 2003, Abstract No. 356-7, & 33rd Annual Meeting of the Society of Neuroscience; New Orleans, LA, USANov. 8-12, 2003.
Shimazawa et al., "Antiangiogenic activity of tumor necrosis factor-alpha production regulators derived from thalidomide," Biol. Pharm. Bull. 22(2): 224-226 (1999).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sikkema-Raddatz, "Four Years' Cytogenetic Experience with the Culture of Chorionic Villi," Prenatal Diagnosis 20:950-955 (2000).
Sirchia, et al., "Placental/Umbilical Cord Blood Transplantation," Haematologica 84:738-747 (1999).
Skelhorne et al., Med Device Technol 13(9):19-23 (2002).
Slager, Transforming growth factor-beta in the early mouse embryo: implications for the regulation of muscle formation and implantation. Dev Genet. 14(3):212-24 (1993).
Snowden, et al, "Long-term Outcome of Autoimmune Disease Following Allogeneic Bone Marrow Transplanation," American College of Rheumatology, vol. 41:453-459 (1998).
Soma, "Human Trophoblast in Tissue Culture," Obstetrics and Gynaecology 18(6):704-718 (1961).
Soncini, et al., "Isolation and Characterization of Mesenchymal Cells from Human Fetal Membranes," J. Tissue Eng. Regen. Med. (2007) 1:296-305.
Southard et al., Transplantation 49(2):251-257 (1990).
Srour, "Ex vivo Expansion of Hematopoietic Stem and Progenitor Cells. Are We There Yet?" J. Hematother. 8:93-102 (1999).
Stanworth, et al., "Stem Cells: Progress in Research and Edging towards the Clinical Setting," Clin. Med. 1(5):378-382 (2001).
Stromberg et al., "Isolation of Functional Human Trophoblast Cells and Their Partial Characterization in Primary Cell Culture," In Vitro 14(7):631-638 (1978).
Stromberg et al., "Methods in Cell Biology, Chapter 10: The Human Placenta in Cell and Organ Culture," 21:227-252 (1980).
Studeny, et al., "Bone Marrow-Derived Mesenchymal Stem Cells as Vehicles for Interferon-B Delivery into Tumors," Cancer Res. 62:3603-3608 (2002).
Sudo et al., 2003, "Phenotypical analysis of effector cells on nonspecific cancer cell therapy," Japanese Journal of Cancer and Chemotherapy, 30(11):1817-1820.
Sudo, et al., "Mesenchymal Progenitors Able to Differentiate into Osteogenic, Chondrogenic, and/or Adipogenic Cells In Vitro Are Present in Most Primary Fibroblast-Like Cell Populations," Stem Cells, 25: 1610-1617, Publically available Mar. 29, 2007.

(56) References Cited

OTHER PUBLICATIONS

Sunderland et al., "HLA A, B, C Antigens Are Expressed on Nonvillous Trophoblast of the Early Human Placenta," Journal of Immunology 127(6):2614-2615 (1981).
Takahashi et al., 2007, "Induction of $CD16^+$ $CD56^{bright}$ NK cells with antitumour cytotoxicity not only from $CD16^-$ $CD56^{bright}$ NK cells but also from $CD16^-$ $CD56^{dim}$ NK cells," J Immunol 65:126-138.
Tarrade et al., "Characterization of Human Villous and Extravillous Trophoblasts Isolated from First Trimester Placenta," Laboratory Investigation 81(9):1199-1211 (2001).
Teo et al., "Chiral inversion of the second generation 1MiD™ CC-4047 (ACTIMID™) in human plasma and phosphate-buffered saline," *Chirality*, 2003, 15:348-351.
Thomson, et al., Embryonic stem cell lines derived from human blastocysts. Science. 282 (5391): 1145-1147 (1998).
Toma et al., "Human Mesenchymal Stem Cells Differentiate to a Cardiomyocyte Phenotype in the Adult Murine Heart," Circulation 105:93-98 (2002).
Travis, "Advances in Therapeutic Approaches to Ulcerative Colitis and Crohn's Disease," Current Gastroenterology Reports 7(6):475-484 (2005).
Truman et al., "Human Placental Cytotrophoblast Cells: Identification and Culture," Arch Gynecol. Obstet. 246:39-49 (1989).
Truman et al., "The Effects of Substrate and Epidermal Growth Factor on Human Placental Trophoblast Cells in Culture," In Vitro Cellular & Developmental Biology 22(9):525-528 (1986).
Tsai et al., "Functional network analysis of the transcriptomes of mesenchymal stem cells derived from amniotic fluid, amniotic membrane, cord blood, and bone marrow", Stem Cells 25:2511-2523 (2007).
Tse et al., "Suppression of Allogeneic T-Cell Proliferation by Human Marrow Stromal Cells: Implications in Transplantation", Transplantation 75(3):389-397 (2003).
Turini and Dubois, 2002, "Cyclooxygenase-2: a therapeutic target," Annu Rev Med, 53:35-57.
Turner, et al., "A modified Harvest Technique for Cord Blood Hematopoietic Stem Cells," Bone Marrow Transplantation 10:89-91 (1992).
Uchida et al., Direct Isolation of Human Central Nervous System Stem Cells, Proc. Natl. Acad. Sci. USA 97(26): 14720-5 (2000).
Ulloa-Montoya, et al., "Culture Systems for Pluripotent Stem Cells," Journal of Bioscience and Bioengineering, 2005; 100(1):12-27.
Vacanti, et al. "Selective Cell Transportation Using Bioabsorbable Artifical Polymers as Matrices," J. Pediatric Surg. (1998) 23:3.
Vacca et al., 1999, "Bone marrow neovascularization, plasma cell angiogenic potential, and matrix metalloproteinase-2 secretion parallel progression of human multiple myeloma," Blood 93(9):3064-3073.
Van Bekkum, "The Pluripotent Hemopoietic Stem Cell: It's Identification and Applications," Verh. Dtsch. Ges. Patol. 74:19-24 (1990).
Vawda et al., "Stem Cell Therapies for Perinatal Brain Injuries", Seminars in Fetal and Neonatal Medicine, Elsevier, GB 12(4):259-272 (2007).
Viacord, Umblicical cord blood can save lives (Informational brochure), Boston: ViaCell CENTR-BRO R1 Oct. 2001.
Wang et al., "Enhanced Recovery of Hematopoietic Progenitor and Stem Cells from Cultivated, Postpartum Human Placenta," Blood 98(11/1):183a Abstract No. 769 (2001).
Wang et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Wang et al., 2003, "Synthesis and characterization of a novel degradable phosphate-containing hydrogen," Biomaterials, 24(22):3969-3980.
Wang, 2005, "Altered glycosylation in cancer: sialic acids and sialyltransferases," Journal of Cancer Molecules, 1(2):73-81.
Watanabe et al, "Multilineage Potential of Human Placenta-Derived Mesenchymal Cells," Blood 100(11):517a, Abstract 2022 (2002).

Weber et al., "A multicenter, randomized, parallel-group, double-blind, placebo-controlled study of lenalidomide plus dexamethasone versus dexamethasone alone in previously treated subjects with multiple myeloma," *Abstract # PO.738, International Multiple Myeloma Workshop*, Apr. 10-14, 2005.
Weber, "Thalidomide and Its Derivatives: New Promise for Multiple Myeloma," *Cancer Control*, vol. 10, No. 5, 375-383, 2003.
Weiss et al., 2006, "Human Umbilical Cord Matrix Stem Cells: Preliminary Characterization and Effect of Transplantation in a Rodent Model of Parkinson's Disease," Stem Cells, 24:781-792.
Weissman et al., "Stem and Progenitor Cells: Origins, Phenotypes, Lineage Commitments, and Transdifferentiations", Annu. Rev. Cell Dev. Biol. 17:387-403 (2001).
Widness and Strauss, 1998, "Recombinant erythropoietin in treatment of the premature newborn," Semin Neonatol, 3:163-171.
Wiesmann, et al., "Effects of Caspase Inhibitors on Hematopoietic Engraftment After Short-Term Culture," Cell. Transplant. 11(4):351-358 (2002).
Wiesmann, et al., "No Reduction of TGF-Beta Induced Apoptosis on Hematopoietic Stem and Progenitor Cells in Vitro by Caspase Inhibitors," Blood 98(11) Part 2, p. 141b (2001).
Wikipedia: Organ 2010.
Woods et al., "Osomometric and permeability characteristics of human placental/umbilical cord blood CD34+ cells and their application to cryopreservation," J. Hematother. Stem Cell Res. 9(2):161-173 (2000).
Wulf et al., "Mesengenic Progenitor Cells Derived from Human Placenta," Tissue Engineering 10(7/8): 1136-1147 (2004).
Xu et al., "BMP4 Initiates Human Embryonic Stem Cell Differentiation to Trophoblast," Nature Biology 20:1261-1264 (2002).
Xu et al., "High Sensitivity of Megakaryocytic Progenitor Cells Contained in Placental/Umbilical Cord Blood to the Stresses During Cryopreservation," Bone Marrow Transplantation 34: 537-543 (2004).
Xu et al., "Feeder-free growth of undifferentiated human embryonic stem cells" Nature Biotechnology 19(10):971-974 (2001).
Xu et al., 2004, "Aligned biodegradable nanofibrous structure: a potential scaffold for blood vessel engineering," Biomaterials 25:877-886.
Xu et al., 2004, "Electrospun nanofiber fabrication as synthetic extracellular matrix and its potential for vascular tissue engineering," Tissue Engineering 10(7): 1160-1168.
Yaccoby et al., "Inhibitory Effects of Osteoblasts and Increased Bone Formation on Myeloma in Novel Culture Systems and a Myelomatous Mouse Model," Haematologica 91:192-199 (2006).
Yan et al., Retinoic acid promotes differentiation of trophoblast stem cells to a giant cell fate.Dev Biol. 235(2): 422-32 (2001).
Ye et al., "Novel IMiD drugs enhance expansion and regulate differentiation of human cord blood CD34+ cells with cytokines," *Blood, Abstract #4099, American Society of Hematology* (Dec. 6-10, 2002).
Ye et al., "Recovery of Placental-Derived Adherent Cells with Mesenchymal Stem Cell Characteristics," Blood 98(11):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yen et al, "Isolation of multipotent cells from human term placenta" Stem Cells (Dayton, Ohio) 2005, vol. 23(1):3-9, XP002443187 ISSN: 1065-5099 (Jan. 2005).
Yin et al., "AC133, a novel marker for human hematopoietic stem and progenitor cells" Blood 90(12):5002-5012 (1997).
Yoo et al., 2013, "Stem cells as promising therapeutic options for neurological disorders," J Cell Biochem, 114:743-753.
Young, et al., "Human Pluripotent and Progenitor Cells Display Cell Surface Cluster Differentiation Markers CD10, CD13, CD56, and MHC class—I," Proc Soc Exp Biol Med. 221(1):63-71 (1999).
Young, et al., "Use of Mesenchymal Stem Cells in a Collagen Matrix for Achilles Tendon Repair," 16:4:406-413 (1998).

(56) References Cited

OTHER PUBLICATIONS

Yui et al., "Functional, Long-term Cultures of Human Term Trophoblasts Purified by Column-elimination of CD9 Expressing Cells," Placenta 15:231-246 (1994).

Zhang, et al., "Comparison of Mesenchymal Stem Cells from Human Placenta and Bone Marrow," Chinese Medical Journal, 117(6):882-87 (2004).

Zhang, et al., "Efficient Adena-Associated Virus-Mediated Gene Expression in Human Placenta-Derived Mesenchymal Cells," Microbiol. Immunol. 47(1):109-16 (2003).

Zhang, et al., "Human Placenta-Derived Mesenchymal Progenitor Cells Support Culture Expansion of Long-Term Culture-Initiating Cells from Cord Blood CD34+ Cells." Exp. Hematol. 32(7): 657-664 (2004).

Zhao et al., "Transplanted Human Bone Marrow-Derived Adult Stem Cells Survive and Improve Functional Outcome in a Rat Model of Cortical Ischemic Brain Injury," Experimental Neurology, Academic Press, New York, 164(2):465-466, XP001159669 (2000).

Zhao, et al., "Human Bone Marrow Stem Cells Exhibit Neural Phenotypes After Transplantation and Ameliorate Neurological Deficits with Ischemic Brain Injury in Rats," Abstract of the Annual Meeting of the Society for Neuroscience, Society of Neuroscience, Washington, DC, 26(1/02): 860.01, XP001159670 (2000).

Zhao, et al., "Microscopic Investigation of Erythrocyte Deformation Dynamics," Biorheology 43(6):747-65 (2006).

Zhu, et al., "Mesenchymal Stem Cells Derived from Bone Marrow Favor Tumor Cell Growth in vivo," Exp Mol Pathol. 80(3):267-274 (2006).

* cited by examiner

US 8,969,315 B2

ENHANCEMENT OF PLACENTAL STEM CELL POTENCY USING MODULATORY RNA MOLECULES

CROSS-REFERENCE TO RELATED APPLICATIONS

This application claims the benefit of U.S. Provisional Patent Application Ser. No. 61/429,070, filed Dec. 31, 2010, the disclosure of which is incorporated by reference herein in its entirety.

1. FIELD

Provided herein are methods of increasing the immunomodulatory (e.g., immunosuppressive) activity of placental stem cells, e.g., human placental stem cells using oligomeric or polymeric regulatory molecules, e.g., modulatory RNA molecules. Also provided herein are methods of using human placental stem cells having enhanced immunomodulatory (e.g., immunosuppressive) activity (referred to as "enhanced placental stem cells" or "ePSCs") to treat individuals having a disease, disorder or condition caused by, or relating to, an unwanted or harmful immune response, for instance, a disease, disorder or condition having an inflammatory component. Additionally provided herein are compositions comprising said enhanced placental stem cells.

2. BACKGROUND

Because mammalian placentas are plentiful and are normally discarded as medical waste, they represent a unique source of medically-useful stem cells that are immunomodulatory (e.g., immunosuppressive). However, there exists a need for populations of placental stem cells that have improved immunosuppressive activity. Provided herein are such improved placental stem cells, populations of the placental stem cells, and methods of using the same.

3. SUMMARY

In one aspect, provided herein is a method of modifying placental stem cells to enhance their immunomodulatory (e.g., immunosuppressive) activity. In certain embodiments, provided herein is a method of modifying placental stem cells to enhance their immunomodulatory (e.g., immunosuppressive) activity, comprising contacting the placental stem cells with an effective amount of oligomeric or polymeric molecules, such that the immunomodulatory (e.g., immunosuppressive) activity of the placental stem cells is enhanced, as compared to placental stem cells that have not been modified, e.g., that have not been contacted with said molecules. Such modified placental stem cells are referred to herein as "enhanced placental stem cells (ePSCs)." In certain embodiments, said oligomeric or polymeric molecules are modulatory molecules. In specific embodiments, the modulatory molecules are small interfering RNAs (siRNAs), microRNA inhibitors (miR inhibitors), miR mimics, antisense RNAs, small hairpin RNAs (shRNAs), microRNA-adapted shRNA (shRNAmirs), or any combinations thereof.

In another aspect, provided herein is a method of producing enhanced placental stem cells having enhanced immunomodulatory (e.g., immunosuppressive) activity, comprising contacting the placental stem cells with an effective amount of oligomeric or polymeric molecules, such that the immunomodulatory (e.g., immunosuppressive) activity of the placental stem cells is enhanced, as compared to placental stem cells that have not been modified, e.g., that have not been contacted with said molecules.

In another aspect, provided herein are placental stem cells that have been treated or modified by contacting said placental stem cells with an effective amount of oligomeric or polymeric molecules (e.g., modulatory RNA molecules), to enhance their immunomodulatory (e.g., immunosuppressive) activity over that of untreated or unmodified placental stem cells. As used herein, such treated or modified placental stem cells are referred to as enhanced placental stem cells, or ePSCs.

In certain embodiments, said modulatory RNA molecules target one or more genes in said ePSCs that modulate the production of interleukin-23 (IL-23) by peripheral blood mononuclear cells (PBMCs) such that the production of IL-23 by said PBMCs in the presence of the ePSCs is reduced, e.g., as compared to PBMCs in the presence of an equivalent number of unmodified placental stem cells. In a specific embodiment, said one or more genes in said ePSCs that modulate the production of IL-23 by PBMCs comprise one or more of Twinfilin-1, human nuclear receptor subfamily 1, group H, member 3 (NR1H3), deoxynucleotidyltransferase, terminal, interacting protein 1 (DNTTIP1), vitamin D (1,25-dihydroxyvitamin D3) receptor (VDR), nuclear receptor subfamily 4, group A, member 3 (NR4A3), nuclear receptor subfamily 4, group A, member 2 (NR4A2), nuclear receptor subfamily 0, group B, member 2 (NR0B2), and nuclear receptor subfamily 1, group I, member 2 (NR1I2). In another specific embodiment, said one or more genes comprise NR4A2. In another specific embodiment, said one or more genes comprise NR4A3.

In one embodiment, said modulatory RNA molecules are small interfering RNAs (siRNAs). In a specific embodiment, said siRNAs are double-stranded, wherein one strand of said siRNAs have a sequence at least about 70%, 80%, 90%, 95%, 98% or 100% identical to SEQ ID NOS: 1, 3, 5, 7, 9, 11 or 13, e.g., wherein said ePSCs contacted with said siRNAs suppress IL-23 production in PBMCs contacted with said ePSCs. In a specific embodiment, said siRNAs are double-stranded, wherein one strand of said siRNAs have a sequence at least about 70%, 80%, 90%, 95%, 98% or 100% identical to SEQ ID NOS: 2, 4, 6, 8, 10, 12 or 14, e.g., wherein said ePSCs contacted with said siRNAs suppress IL-23 production in PBMCs contacted with said ePSCs.

In certain embodiments, said modulatory molecules, e.g., modulatory RNA molecules, target one or more microRNAs (miRNAs) in said ePSCs that act to modulate the production of IL-23 by PBMCs, such that, when said PBMCs are contacted with said ePSCs, production of IL-23 by said PBMCs is reduced, e.g., as compared to PBMCs contacted with an equivalent number of unmodified placental stem cells. In one embodiment, said modulatory RNA molecules are miR inhibitors. In another embodiment, said modulatory RNA molecules are miR mimics. In various specific embodiments, said one or more miRNAs comprise hsa-miR-183, hsa-miR-491-5p, hsa-miR-132*, hsa-miR-129-5p, hsa-miR-636, hsa-miR-100, hsa-miR-181a, hsa-miR-519a, hsa-miR-338-3p, hsa-miR-1179, hsa-miR-521, hsa-miR-608, hsa-miR-1306, hsa-miR-543, hsa-miR-542-3p, hsa-miR-23b, hsa-miR-299-3p, hsa-miR-597, hsa-miR-1976, hsa-miR-1252, hsa-miR-510, hsa-miR-1207-5p, hsa-miR-518a-3p, hsa-miR-1250, hsa-miR-1274a, hsa-miR-141*, hsa-miR-9*, hsa-miR-566, hsa-miR-142-5p, hsa-miR-23a*, hsa-miR-519e*, hsa-miR-1292, hsa-miR-96, hsa-miR-886-3p, hsa-miR-216b, hsa-miR-218-2*, hsa-miR-182, hsa-miR-545*, hsa-miR-517a, hsa-miR-541*, hsa-miR-1293, hsa-miR-339-5p, hsa-miR-494, hsa-miR-196a*, hsa-miR-371-5p, hsa-miR-136*, hsamiR-214, hsa-miR-25*, hsa-miR-452*, hsa-miR-454*, hsa-miR-548b-5p, hsa-miR-10b*, hsa-miR-218, hsa-miR-548m, hsa-miR-520a-3p, hsa-miR-1323, hsa-miR-24-2*, hsa-miR-613, hsa-miR-26a, hsa-miR-193a-3p, hsa-miR-1208, hsa-miR-767-5p, hsa-miR-491-3p, hsa-miR-626, hsa-miR-216a, hsa-miR-151-5p, hsa-miR-1282, hsa-miR-497*, hsa-miR-129-3p, hsa-miR-1, hsa-miR-129*, hsa-miR-24, hsa-miR-24-1*, hsa-miR-218-1*, hsa-miR-183, and/or hsa-miR-183*.

In some embodiments, said miR inhibitors or said miR mimics have a sequence at least about 70%, 80%, 90%, 95%, 98% or 100% identical to any of SEQ ID NOS: 15-83 and 228-234, or the complement thereof, e.g., wherein said ePSCs contacted with said miR inhibitors suppress IL-23 production in PBMCs contacted with said ePSCs. In a specific embodiment, said miR inhibitors have a sequence at least about 70%, 80%, 90%, 95%, 98% or 100% identical to any of SEQ ID NOS: 59-83 and 228-234, or the complement thereof, e.g., wherein said ePSCs contacted with said miR inhibitors suppress IL-23 production in PBMCs contacted with said ePSCs. In another specific embodiment, said miR mimics have a sequence at least about 70%, 80%, 90%, 95%, 98% or 100% identical to any of SEQ ID NOS: 19-58 and 228-234, e.g., wherein said ePSCs contacted with said miR mimics suppress IL-23 production in PBMCs contacted with said ePSCs.

In certain embodiments, the enhanced placental stem cells (ePSCs) have increased cyclooxygenase II (Cox-2) activity, e.g., as compared to an equivalent number of unmodified placental stem cells. In a specific embodiment, said contacting of said modulatory RNA with said placental stem cells causes an increase in Cox-2 activity in said placental stem cells (i.e., in the ePSCs), as compared to an equivalent number of placental stem cells not contacted with said modulatory RNA. In another specific embodiment, said Cox-2 activity is induced by IL-1β. In a specific embodiment, said modulatory molecules target one or more genes in said ePSCs that modulate the activity of Cox-2 such that the activity of Cox-2 in said ePSCs is increased, e.g., as compared to an equivalent number of unmodified placental stem cells.

In certain embodiments, the enhanced placental stem cells (ePSCs) have been modified to produce an increased amount of PGE2, e.g., as compared to an equivalent number of unmodified placental stem cells. In one embodiment, said production of PGE2 production is induced by IL-1β.

In certain embodiments, said modulatory molecules target one or more genes in said ePSCs that modulate the production of PGE2 by said ePSCs such that the production of PGE2 by said ePSCs is increased, e.g., as compared to an equivalent number of unmodified placental stem cells. In a specific embodiment, said one or more genes comprise one or more of cholinergic receptor, nicotinic beta 1 (muscle) (CHRNB1), chloride channel 6 (CLCN6), chloride intracellular channel 4 (CLIC4), casein kinase 1, gamma 3 (CSNK1G3), casein kinase 2, alpha prime polypeptide (CSNK2A2), dual specificity phosphatase 1 (DUSP1), potassium channel modulatory factor 1 (KCMF1), potassium voltage-gated channel, shaker-related subfamily, member 3 (KCNA3), potassium inwardly-rectifying channel, subfamily J, member 14 (KCNJ14), potassium voltage-gated channel, delayed-rectifier, subfamily S, member 3 (KCNS3), potassium channel tetramerisation domain containing 13 (KCTD13), hepatocyte growth factor (hepapoietin A; scatter factor) (HGF), nuclear receptor subfamily 2, group C, member 2 (NR2C2), phosphodiesterase 1B, calmodulin-dependent (PDE1B), phosphodiesterase 7B (PDE7B), phosphatidylinositol 4-kinase type 2 beta (PI4K2B), phosphoinositide-3-kinase, regulatory subunit 1 (alpha) (PIK3R1), phospholipase C, eta 2 (PLCH2), protein phosphatase, Mg2+/Mn2+ dependent, 1D (PPM1D), protein phosphatase, Mg2+/Mn2+ dependent, 1G (PPM1G), protein phosphatase 1, regulatory (inhibitor) subunit 2 pseudogene 9 (PPP1R2P9), protein phosphatase 1, regulatory (inhibitor) subunit 3B (PPP1R3B), protein phosphatase 1, regulatory (inhibitor) subunit 9B (PPP1R9B), protein phosphatase 2, catalytic subunit, beta isozyme (PPP2CB), protein tyrosine phosphatase type IVA, member 1 (PTP4A1), protein tyrosine phosphatase, receptor type, K (PTPRK), regulator of G-protein signaling 4 (RGS4), regulator of G-protein signaling 7 binding protein (RGS7BP), regulator of G-protein signaling 8 (RGS8), solute carrier family 16, member 3 (monocarboxylic acid transporter 4) (SLC16A3), solute carrier family 30 (zinc transporter), member 1 (SLC30A1), solute carrier family 35, member A4 (SLC35A4), solute carrier family 38, member 7 (SLC38A7), solute carrier family 41, member 1 (SLC41A1), solute carrier family 45, member 3 (SLC45A3), solute carrier family 7 (cationic amino acid transporter, y+ system), member 1 (SLC7A1), ubiquitin associated protein 2 (UBAP2), ubiquitin-conjugating enzyme E2D 3 (UBC4/5 homolog, yeast) (UBE2D3), ubiquitin-conjugating enzyme E2E 3 (UBC4/5 homolog, yeast) (UBE2E3), ubiquitin-conjugating enzyme E2R 2 (UBE2R2), ubiquitin-conjugating enzyme E2W (putative) (UBE2W), ubiquitin-like with PHD and ring finger domains 2 (UHRF2), ubiquitin specific peptidase 9, X-linked (USP9X), or hypoxia inducible factor 1, alpha subunit (HIF1A). In another specific embodiment, said one or more genes comprise HIF1A. In another specific embodiment, said one or more genes comprise DUSP1. In another specific embodiment, said one or more genes comprise PDE7B.

In certain embodiments, said modulatory molecules target one or more miRNAs in said ePSCs that modulate the production of PGE2 by ePSCs such that production of PGE2 by said ePSCs is increased, e.g., as compared to an equivalent number of unmodified placental stem cells. In a specific embodiment, said one or more miRNAs comprise one or more of hsa-miR-886-3p, hsa-miR-371-3p, hsa-miR-25*, hsa-miR-376c, hsa-miR-888, hsa-miR-517b, hsa-miR-433, hsa-miR-200a*, hsa-miR-520a-5p, hsa-miR-1286, hsa-miR-182*, hsa-miR-1273, hsa-miR-1280, hsa-miR-563, hsa-miR-501-5p, hsa-miR-448, hsa-miR-485-3p, hsa-miR-29c, hsa-miR-548f, hsa-miR-1248, hsa-let-7d*, hsa-miR-618, hsa-miR-30c, hsa-miR-136, hsa-miR-181a, hsa-miR-26a, hsa-miR-10a, hsa-miR-557, hsa-miR-564, hsa-miR-520g, hsa-miR-122*, hsa-miR-548k, hsa-miR-423-3p, hsa-miR-548j, hsa-miR-340*, hsa-miR-573, hsa-miR-548i, hsa-miR-555, hsa-miR-144, hsa-miR-567, hsa-miR-191*, hsa-miR-566, hsa-miR-335, hsa-miR-126*, hsa-miR-22*, hsa-miR-572, hsa-miR-517c, hsa-miR-380*, hsa-miR-106a*, hsa-miR-519e, hsa-miR-520c-3p, hsa-miR-517*, hsa-miR-432*, hsa-miR-520e, hsa-miR-9*, hsa-miR-551a, hsa-miR-1471, hsa-miR-613, hsa-miR-562, hsa-miR-922, hsa-miR-216a, hsa-miR-499-5p, hsa-miR-25, hsa-miR-197, hsa-miR-500*, hsa-miR-365*, hsa-miR-1247, hsa-miR-586, hsa-miR-548d-3p, hsa-miR-27a*, hsa-miR-598, hsa-miR-609, hsa-miR-132, hsa-miR-411*, hsa-miR-135a, hsa-miR-31, hsa-miR-181a*, hsa-miR-1245, hsa-miR-758, hsa-miR-924, hsa-miR-1246, hsa-miR-23b, hsa-miR-631, hsa-miR-1, hsa-miR-920, hsa-miR-589*, hsa-miR-638, hsa-miR-1244, hsa-miR-328, hsa-let-71, hsa-miR-429, hsa-miR-380, hsa-let-7b*, hsa-miR-614, hsa-miR-1225-5p, hsa-miR-545*, hsa-miR-320c, hsa-miR-579, hsa-miR-1282, hsa-miR-455-5p, hsa-miR-615-3p, hsa-miR-585, hsa-miR-559, hsa-miR-561, hsa-miR-191, hsa-miR-187, hsa-miR-29b, hsa-miR-769-5p, hsa-miR-495, hsa-miR-516a-3p, hsa-miR-938, hsa-miR-936, hsa-miR-373*, hsa-miR-1184, hsa-miR-122, hsa-miR-208b, hsa-miR-223*, hsa-miR-1972, hsa-miR-520h, hsa-miR-330-3p, hsamiR-149, hsa-miR-7, hsa-miR-29b-2*, hsa-miR-520d-5p, hsa-miR-592, hsa-miR-940, hsa-miR-146b-3p, hsa-miR-518e*, hsa-miR-1255a, hsa-miR-935, hsa-miR-633, hsa-miR-513a-5p, hsa-miR-361-3p, hsa-miR-194, hsa-miR-1185, hsa-miR-875-3p, hsa-miR-200a, hsa-miR-1201, hsa-miR-629, hsa-miR-139-5p, hsa-miR-504, hsa-miR-452, hsa-miR-517a, hsa-miR-543, hsa-miR-616*, hsa-miR-651, hsa-miR-1254, hsa-miR-339-3p, hsa-miR-510, hsa-miR-181c*, hsa-miR-19b-1*, hsa-miR-1274a, hsa-miR-1294, hsa-miR-1306, hsa-miR-1226*, and hsa-miR-541* in said enhanced placental stem cells. In one embodiment, said modulatory RNA molecules are miR inhibitors. In another embodiment, said modulatory RNA molecules are miR mimics. In a some embodiments, said miR inhibitors or miR mimics have a sequence at least about 70%, 80%, 90%, 95%, 98% or 100% identical to any of SEQ ID NO: 21, 27, 28, 30, 35, 39, 41, 42, 48, 52-54, 62, 72, 73, 79, 81, and 84-222, or the complement thereof, e.g., wherein said ePSCs contacted with said miR inhibitors or miR mimics show reduced production of PGE2 as compared with an equivalent number of placental stem cells not contacted with said miR inhibitors or miR mimics. In a specific embodiment, said miR inhibitors have a sequence at least about 70%, 80%, 90%, 95%, 98% or 100% identical to any of SEQ ID NO: 27, 28, 35, 39, 53-54, and 181-222, or the complement thereof e.g., wherein said ePSCs contacted with said miR inhibitors show reduced production of PGE2 as compared with an equivalent number of placental stem cells not contacted with said miR inhibitors. In another specific embodiment, said miR mimics have a sequence at least about 70%, 80%, 90%, 95%, 98% or 100% identical to any of SEQ ID NO: 21, 30, 41, 42, 48, 52, 62, 72, 73, 79, 81, 84-180, e.g., wherein said ePSCs contacted with said miR inhibitors show reduced production of PGE2 as compared with an equivalent number of placental stem cells not contacted with said miR mimics.

In certain embodiments, the enhanced placental stem cells (ePSCs) have reduced production of a pro-inflammatory cytokine (e.g., extracellular pro-inflammatory cytokine), e.g., as compared to an equivalent number of unmodified placental stem cells. In certain embodiments, said pro-inflammatory cytokine is IL-1, IL-6, IL-8, TNF-α, or any combinations thereof. In a specific embodiment, said pro-inflammatory cytokine is IL-6, IL-8, or a combination thereof. In another specific embodiment, said pro-inflammatory cytokine is IL-6. In another specific embodiment, said modulatory RNA molecules target (e.g., modulate) one or more genes in said ePSCs that modulate the production of said pro-inflammatory cytokine such that the production of said pro-inflammatory cytokine of is reduced, e.g., as compared to an equivalent number of unmodified placental stem cells. In another specific embodiment, said one or more genes comprise a gene that encodes IL-1, IL-1, IL-6, IL-8, or TNF-α. In another specific embodiment, said one or more genes comprise a gene that encodes IL-6.

In certain embodiments, the enhanced placental stem cells (ePSCs) display a suppressed interferon-gamma (IFN-γ)-induced response, as compared to an equivalent number of unmodified placental stem cells. In one specific embodiment, said modulatory RNA molecules target (e.g., modulate) one or more genes in said ePSCs that modulate an IFN-γ-induced response of said ePSCs such that the IFN-γ-induced response is suppressed, e.g., as compared to an equivalent number of unmodified placental stem cells. In another specific embodiment, said one or more genes comprise one or more of protein inhibitors of activated STAT, 1 (PIAS1) and TYRO protein tyrosine kinase binding protein (TYROBP).

In a specific embodiment, said enhanced placental stem cells are CD10$^+$, CD34$^-$, CD105$^+$, and CD200$^+$. In another specific embodiment, said enhanced placental stem cells express CD200 and do not express HLA-G; or express CD73, CD105, and CD200; or express CD200 and OCT-4; or express CD73 and CD105 and do not express HLA-G; or express CD73 and CD105 and facilitate the formation of one or more embryoid-like bodies in a population of placental cells comprising said stem cell when said population is cultured under conditions that allow for the formation of an embryoid-like body; or express OCT-4 and facilitate the formation of one or more embryoid-like bodies in a population of placental cells comprising said stem cell when said population is cultured under conditions that allow for the formation of an embryoid-like body. In another specific embodiment, said placental stem cells are additionally CD90$^+$ and CD45$^-$. In another specific embodiment, said placental stem cells are additionally CD80$^-$ and CD86$^-$. In yet other embodiments, said placental stem cells express one or more of CD44, CD90, HLA-A,B,C or ABC-p, and/or do not express one or more of CD45, CD117, CD133, KDR, CD80, CD86, HLA-DR, SSEA3, SSEA4, or CD38. In certain embodiments, the enhanced placental stem cells suppress the activity of an immune cell, e.g., suppress proliferation of a T cell to a detectably greater degree than an untreated or unmodified placental stem cells, e.g., as determinable by a mixed leukocyte reaction assay, regression assay, or bead T cell assay.

In another aspect, provided herein is a method for the modulation, e.g., suppression, of the activity, e.g., proliferation, of an immune cell, or plurality of immune cells, by contacting the immune cell(s) with a plurality of enhanced placental stem cells.

In certain embodiments, provided herein is a method of inhibiting a pro-inflammatory response, comprising contacting T cells (e.g., CD4$^+$ T lymphocytes or leukocytes) that are associated with or part of an immune response with enhanced placental stem cells, e.g., the enhanced placental stem cells described herein, either in vivo or in vitro. In a specific embodiment, the inflammatory response is a Th1 response or a Th17 response. In another specific embodiment, said contacting detectably reduces Th1 cell maturation. In a specific embodiment of the method, said contacting detectably reduces the production of one or more of interleukin-1β (IL-1β), IL-12, IL-17, IL-21, IL-23, tumor necrosis factor alpha (TNFα) and/or interferon gamma (IFNγ) by said T cells. In another specific embodiment of the method, said contacting potentiates or upregulates a regulatory T cell (Treg) phenotype. In another specific embodiment, said contacting downregulates dendritic cell (DC) and/or macrophage expression of markers (e.g., CD80, CD83, CD86, ICAM-1, HLA-II) that promote Th1 and/or Th17 immune response.

In another embodiment, provided herein is a method of reducing the production of pro-inflammatory cytokines from macrophages, comprising contacting the macrophages with an effective amount of enhanced placental stem cells. In another embodiment, provided herein is a method of upregulating tolerogenic cells and/or cytokines, e.g., from macrophages, comprising contacting immune system cells with an effective amount of enhanced placental stem cells. In a specific embodiment, said contacting causes activated macrophages to produce detectably more IL-10 than activated macrophages not contacted with said enhanced placental stem cells. In another embodiment, provided herein is a method of upregulating, or increasing the number of, anti-inflammatory T cells, comprising contacting immune system cells with enhanced placental stem cells in an amount sufficient to upregulate, or increase the number of, anti-inflammatory T cells.

In one embodiment, provided herein is a method of inhibiting a Th1 response in an individual comprising administering to the individual an effective amount of enhanced placental stem cells, wherein said effective amount is an amount that results in a detectable decrease in said Th1 response in the individual, e.g., a decrease that is also detectably more than that achieved by comparable untreated or unmodified placental stem cells. In another embodiment, provided herein is a method of inhibiting a injury-associated Th17 response in an individual comprising administering to the individual an effective amount of enhanced placental stem cells, wherein said effective amount is an amount that results in a detectable decrease in a Th17 response in the individual, e.g., a decrease that is also detectably more than that achieved by comparable untreated or unmodified placental stem cells. In specific embodiments of these methods, said administering detectably reduces the production, by T cells, or an antigen presenting cell (e.g., DC, macrophage or monocyte) in said individual, of one or more of lymphotoxins-1a (LT-1a), IL-1β, IL-12, IL-17, IL-21, IL-23, TNFα and/or IFNγ. In another specific embodiment of the method, said administering potentiates or upregulates a regulatory T cell (Treg). In another embodiment, said administering modulates (e.g., reduces) production by dendritic cells (DC) and/or macrophages in said individual of markers that promote a Th1 or Th17 response (e.g., CD80, CD83, CD86, ICAM-1, HLA-II). In another specific embodiment, the method comprises additionally administering IL-10 to said individual.

In one embodiment, provided herein is a method of inhibiting a Th1 response in an individual comprising administering to the individual an effective amount of enhanced placental stem cells, wherein said effective amount is an amount that results in a detectable decrease in said Th1 response in the individual, e.g., a decrease that is also detectably more than that achieved by comparable untreated or unmodified placental stem cells. In another embodiment, provided herein is a method of inhibiting a injury-associated Th17 response in an individual comprising administering to the individual an effective amount of enhanced placental stem cells, wherein said effective amount is an amount that results in a detectable decrease in a Th17 response in the individual, e.g., a decrease that is also detectably more than that achieved by comparable untreated or unmodified placental stem cells. In specific embodiments of these methods, said administering detectably reduces the production, by T cells, or an antigen presenting cell (e.g., DC, macrophage or monocyte) in said individual, of one or more of lymphotoxins-1α (LT-1α), IL-1β, IL-12, IL-17, IL-21, IL-23, TNFα and/or IFNγ. In another specific embodiment of the method, said administering potentiates or upregulates a regulatory T cell (Treg). In another embodiment, said administering modulates (e.g., reduces) production by dendritic cells (DC) and/or macrophages in said individual of markers that promote a Th1 or Th17 response (e.g., CD80, CD83, CD86, ICAM-1, HLA-II). In another specific embodiment, the method comprises additionally administering IL-10 to said individual.

In another aspect, provided herein is a method of inhibiting a pro-inflammatory response, e.g., a Th1 response or a Th17 response, either in vivo or in vitro, comprising contacting T cells (e.g., CD4+ T lymphocytes or leukocytes) with enhanced placental stem cells, e.g., the enhanced placental stem cells described herein. In a specific embodiment, said contacting detectably reduces Th1 cell maturation. In a specific embodiment of the method, said contacting detectably reduces the production of one or more of interleukin-1β (IL-1β), IL-12, IL-17, IL-21, IL-23, tumor necrosis factor alpha (TNFα) and/or interferon gamma (IFNγ) by said T cells. In another specific embodiment of the method, said contacting potentiates or upregulates a regulatory T cell (Treg) phenotype. In another specific embodiment, said contacting downregulates DC and/or macrophage expression of markers (e.g., CD80, CD83, CD86, ICAM-1, HLA-II) that promote Th1 and/or Th17 immune response.

In another embodiment, provided herein is a method of reducing the production of pro-inflammatory cytokines from macrophages, comprising contacting the macrophages with an effective amount of enhanced placental stem cells. In another embodiment, provided herein is a method of upregulating tolerogenic cells and/or cytokines, e.g., from macrophages, comprising contacting immune system cells with an effective amount of enhanced placental stem cells. In a specific embodiment, said contacting causes activated macrophages to produce detectably more IL-10 than activated macrophages not contacted with said enhanced placental stem cells. In another embodiment, provided herein is a method of upregulating, or increasing the number of, anti-inflammatory T cells, comprising contacting immune system cells with an effective amount of enhanced placental stem cells.

In one embodiment, provided herein is a method of inhibiting a Th1 response in an individual comprising administering to the individual an effective amount of enhanced placental stem cells, wherein said effective amount is an amount that results in a detectable decrease in a Th1 response in the individual. In another embodiment, provided herein is a method of inhibiting a Th17 response in an individual comprising administering to the individual an effective amount of enhanced placental stem cells, wherein said effective amount is an amount that results in a detectable decrease in a Th17 response in the individual. In specific embodiments of these methods, said administering detectably reduces the production, by T cells, or an antigen presenting cell (e.g., DC, macrophage or monocyte) in said individual, of one or more of lymphotoxins-1α (LT-1α), IL-1β, IL-12, IL-17, IL-21, IL-23, TNFα and/or IFNγ. In another specific embodiment of the method, said contacting potentiates or upregulates a regulatory T cell (Treg). In another embodiment, said contacting modulates (e.g., reduces) production by dendritic cells (DC) and/or macrophages in said individual of markers that promote a Th1 or Th17 response (e.g., CD80, CD83, CD86, ICAM-1, HLA-II). In another specific embodiment, the method comprises additionally administering IL-10 to said individual.

3.1 DEFINITIONS

As used herein, the term "amount," when referring to the placental stem cells, e.g., enhanced placental stem cells described herein, means a particular number of placental cells.

As used herein, the term "derived" means isolated from or otherwise purified. For example, placental derived adherent cells are isolated from placenta. The term "derived" encompasses cells that are cultured from cells isolated directly from a tissue, e.g., the placenta, and cells cultured or expanded from primary isolates.

As used herein, "immunolocalization" means the detection of a compound, e.g., a cellular marker, using an immune protein, e.g., an antibody or fragment thereof in, for example, flow cytometry, fluorescence-activated cell sorting, magnetic cell sorting, in situ hybridization, immunohistochemistry, or the like.

As used herein, the term "SH2" refers to an antibody that binds an epitope on the marker CD105. Thus, cells that are referred to as SH2+ are CD105+.

As used herein, the terms "SH3" and SH4" refer to antibodies that bind epitopes present on the marker CD73. Thus, cells that are referred to as SH3+ and/or SH4+ are CD73+.

As used herein, a stem cell is "isolated" if at least 50%, 60%, 70%, 80%, 90%, 95%, or at least 99% of the other cells with which the stem cell is naturally associated are removed from the stem cell, e.g., during collection and/or culture of the stem cell. A population of "isolated" cells means a population of cells that is substantially separated from other cells of the tissue, e.g., placenta, from which the population of cells is derived. In some embodiments, a population of, e.g., stem cells is "isolated" if at least 50%, 60%, 70%, 80%, 90%, 95%, or at least 99% of the cells with which the population of stem cells are naturally associated are removed from the population of stem cells, e.g., during collection and/or culture of the population of stem cells.

As used herein, the term "placental stem cell" refers to a stem cell or progenitor cell that is derived from, e.g., isolated from, a mammalian placenta, regardless of the number of passages after a primary culture, which adheres to a tissue culture substrate (e.g., tissue culture plastic or a fibronectin-coated tissue culture plate). The term "placental stem cell" as used herein does not, however, refer to a trophoblast, a cytotrophoblast, embryonic germ cell, or embryonic stem cell, as those cells are understood by persons of skill in the art. The terms "placental stem cell" and "placenta-derived stem cell" may be used interchangeably. Unless otherwise noted herein, the term "placental" includes the umbilical cord. The placental stem cells disclosed herein are, in certain embodiments, multipotent in vitro (that is, the cells differentiate in vitro under differentiating conditions), multipotent in vivo (that is, the cells differentiate in vivo), or both.

As used herein, a stem cell is "positive" for a particular marker when that marker is detectable. For example, a placental stem cell is positive for, e.g., CD73 because CD73 is detectable on placental stem cells in an amount detectably greater than background (in comparison to, e.g., an isotype control or an experimental negative control for any given assay). A cell is also positive for a marker when that marker can be used to distinguish the cell from at least one other cell type, or can be used to select or isolate the cell when present or expressed by the cell.

As used herein, the term "stem cell" defines a cell that retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like.

As used herein, "immunomodulation" and "immunomodulatory" mean causing, or having the capacity to cause, a detectable change in an immune response, and the ability to cause a detectable change in an immune response.

As used herein, "immunosuppression" and "immunosuppressive" mean causing, or having the capacity to cause, a detectable reduction in an immune response, and the ability to cause a detectable suppression of an immune response.

As used herein, the term "oligomeric or polymeric molecule" refers to a biomolecule that are capable of targeting a gene, RNA or protein of interest (e.g., by binding or hybridizing to a region of a gene, RNA or protein of interest). This term includes, for example, oligonucleotides, oligonucleosides, oligonucleotide analogs, oligonucleotide mimetics, oligopeptides or polypeptides, and any combinations (e.g., chimeric combinations) thereof. As such, these compounds may be single-stranded, double-stranded, circular, branched or have hairpins and can comprise structural elements such as internal or terminal bulges or loops. Oligomeric or polymeric double-stranded molecules can be two strands hybridized to form double-stranded compounds or a single strand with sufficient self complementarity to allow for hybridization and formation of a fully or partially double-stranded molecule.

As used herein, the term "modulatory RNA molecule" refers to an RNA molecule that modulates, (e.g., up-regulates or down-regulates) directly or indirectly, the expression or activity of the selectable target(s) (e.g., a target gene, RNA or protein). In certain embodiments, a "modulatory RNA molecule" is a siRNA, miR inhibitor, miR mimic, antisense RNA, shRNA, shRNAmir, or a hybrid or a combination thereof that modulates the expression of the selectable target in a host cell. In certain embodiments, the modulatory RNA molecules provided herein comprise about 1 to about 100, from about 8 to about 80, 10 to 50, 13 to 80, 13 to 50, 13 to 30, 13 to 24, 18 to 22, 19 to 23, 20 to 80, 20 to 50, 20 to 30, or 20 to 24 nucleobases (i.e. from about 1 to about 100 linked nucleosides).

4. BRIEF DESCRIPTION OF THE FIGURES

FIG. 1: siRNAs targeting six human nuclear hormone receptor (HNR) genes enhanced placental stem cell suppression of IL-23 production by PBMCs. Compared to the vehicle-treated placental stem cell, placental stem cells treated with siRNAs targeting vitamin D (1,25-dihydroxyvitamin D3) receptor (VDR), nuclear receptor subfamily 4, group A, member 3 (NR4A3), nuclear receptor subfamily 0, group B, member 2 (NR0B2), nuclear receptor subfamily 1, group I, member 2 (NR1I2), human nuclear receptor subfamily 1, group H, member 3 (NR1H3) and deoxynucleotidyltransferase, terminal, interacting protein 1 (DNTTIP1) significantly reduced the amount of IL-23 produced by PBMCs. ePSCs in which VDR was targeted: D3. ePSCs in which NR4A3 was targeted: D4. ePSCs in which NR0B2 was targeted: D5. ePSCs in which NR1I2 was targeted: D6. ePSCs in which NR1H3 was targeted: E1. ePSCs in which DNTTIP1 was targeted: E2.

Figure 2:
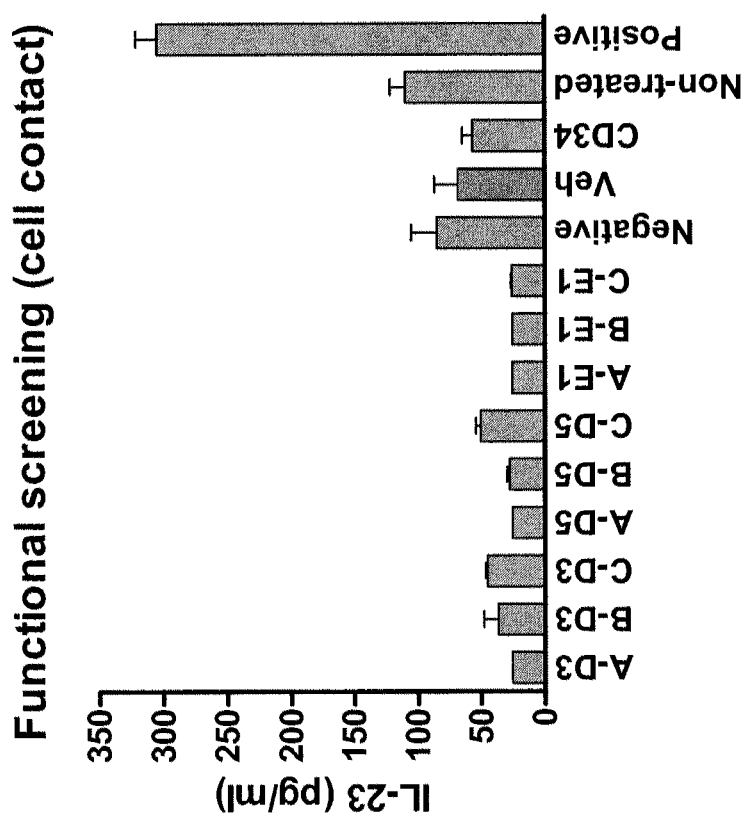

FIG. 2: Suppression of PBMC IL-23 production by enhanced placental stem cells treated with siRNAs targeting VDR, NR0B2 and NR1H3. Placental stem cells treated with siRNAs targeting VDR, NR0B2 and NR1H3 PDAC reduced the amount of IL-23 produced by PBMCs. VDR-treated placental stem cells: A-D3, B-D3 and C-D3. NR0B2-treated placental stem cells: A-D5, B-D5 and C-D5. NR1H3-treated placental stem cells: A-E1, B-E1 and C-E1.

Figure 3:
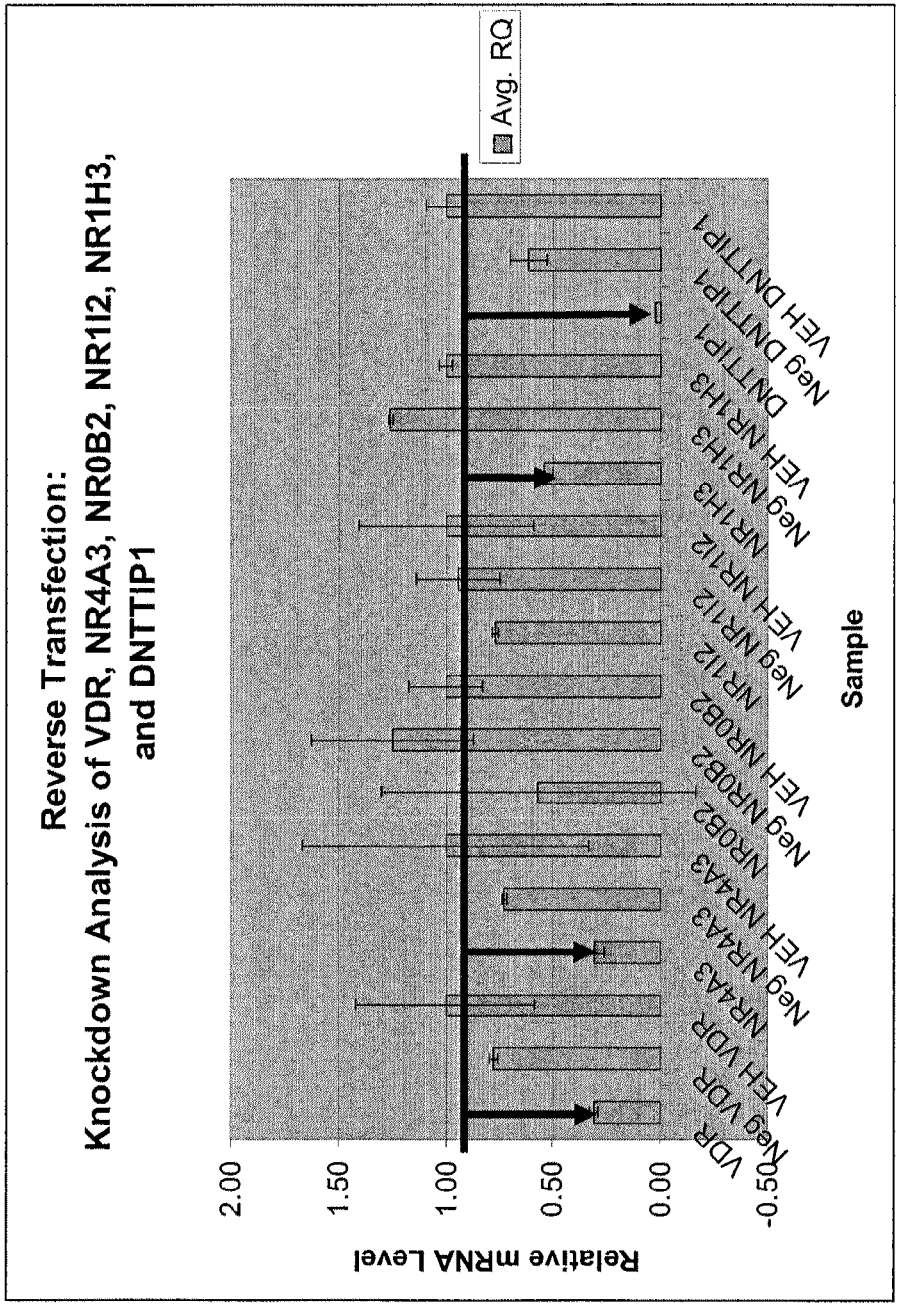

FIG. 3. Quantitative RT-PCR analysis of gene silencing efficiency by siRNAs. siRNAs were delivered to placental stem cells by reverse transfection. siRNAs targeting VDR, NR4A3, NR1H3 showed more than 50% gene silencing, and siRNAs against DNTTIP1 showed ~95% of gene silencing.

Figure 4:
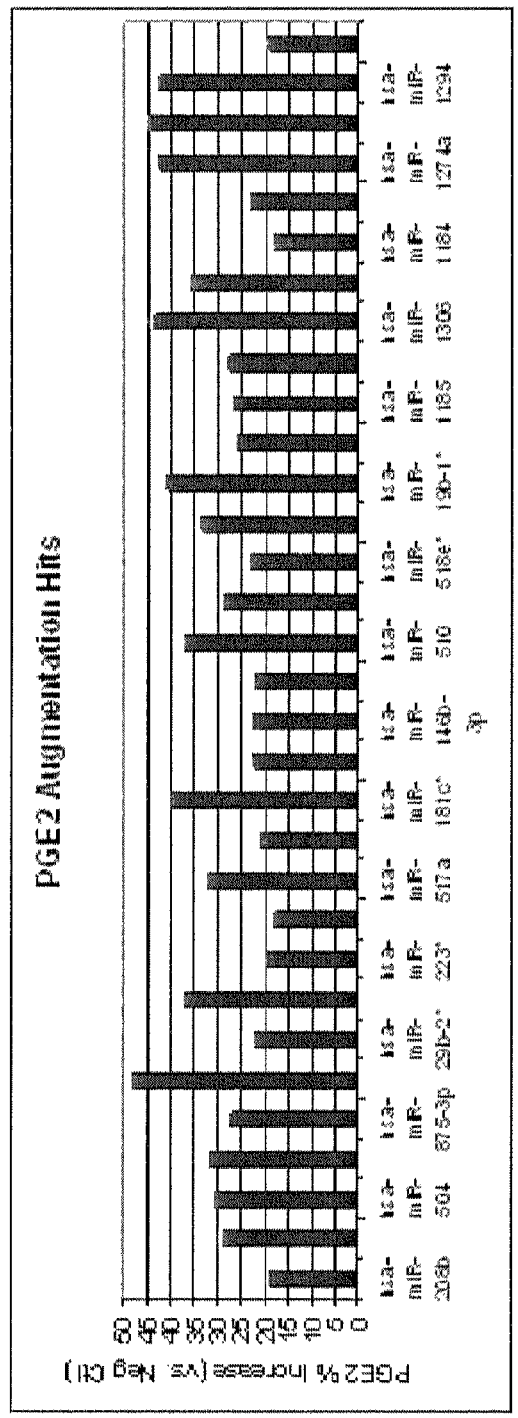

FIG. 4. Enhancement of PGE2 secretion of placental stem cells by anti-miR inhibitors. Anti-miR inhibitors treated PDACs showed 15-50% increase of PGE2 production compared to the negative control group (P<0.05; unpaired t-Test)

5. DETAILED DESCRIPTION 5.1 Production of Enhanced Placental Stem Cells

In one aspect, provided herein are methods of modifying placental stem cells to enhance their immunomodulatory (e.g., immunosuppressive) activity. In certain embodiments, provided herein is a method of modifying placental stem cells to enhance their immunomodulatory (e.g., immunosuppressive) activity, comprising contacting the placental stem cells with an effective amount of oligomeric or polymeric molecules, such that the immunomodulatory (e.g., immunosuppressive) activity of the placental stem cells is enhanced, as compared to placental stem cells that have not been modified, e.g., that have not been contacted with said molecules.

In another aspect, provided herein are methods for the production of enhanced placental stem cells. Such enhanced placental stem cells are placental stem cells that have been modified to have increased immunomodulatory (e.g., immunosuppressive) activity. In certain embodiments, the methods provided herein for the production of enhanced placental stem cells comprise contacting the placental stem cells with an effective amount of oligomeric or polymeric molecules, such that the immunomodulatory (e.g., immunosuppressive) activity of the placental stem cells is enhanced, as compared to placental stem cells that have not been modified, e.g., that have not been contacted with said molecules. In some embodiments, said oligomeric or polymeric molecules comprise nucleotides (e.g., DNA or RNA molecules), nucleosides, nucleotide analogs, nucleotide mimetics, polypeptides, nucleotide analogs, nucleotide mimetics, and any combinations (e.g., chimeric combinations) thereof.

In one embodiment, the nucleotide analog is an RNA analog, for example, an RNA analog that has been modified in the 2'-OH group, e.g. by substitution with a group, for example —O—CH$_3$, —O—CH$_2$—CH$_2$—O—CH$_3$, —O—CH$_2$—CH$_2$—CH$_2$—NH$_2$, —O—CH$_2$—CH$_2$—CH$_2$—OH or —F.

In some embodiments, the oligomeric or polymeric molecules provided herein comprise one or more modifications (e.g., chemical modifications) in the sugars, bases, or internucleoside linkages. As used herein, the term "internucleoside linkage group" refers to a group capable of covalently coupling together two nucleotides, such as between RNA units. Examples include phosphate, phosphodiester groups and phosphorothioate groups. In one embodiment, the oligomeric or polymeric molecules provided herein comprise at least one phosphate internucleoside linkage group. In one embodiment, the oligomeric or polymeric molecules provided herein comprise at least one phosphodiester internucleoside linkage group. In another embodiment, the oligomeric or polymeric molecules provided herein comprise at least one internucleoside linkage group selected from the following: (—O—P(O)$_2$—O—) include —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, —PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$—CO—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is hydrogen or C$_{1-4}$-alkyl.

In one embodiment, the oligomeric or polymeric molecules are single-stranded oligonucleotides or polynucleotides. In another embodiment, the oligomeric or polymeric molecules are double-stranded oligonucleotides or polynucleotides. In some embodiments, the oligonucleotides or polynucleotides comprise one or more modifications (e.g., chemical modifications) in the sugars, bases, or internucleoside linkages.

In a specific embodiment, said oligomeric molecules are modulatory RNA molecules. In certain embodiments, the modulator RNA molecules are small interfering RNAs (siRNAs), microRNA inhibitors (anti-miRs), other modulatory RNA molecules such as antisense RNAs, miR mimics, small hairpin RNAs (shRNAs), microRNA-adapted shRNA (shRNAmirs), or any combination thereof.

5.1.1 siRNAs

In certain embodiments, the methods provided herein for the production of enhanced placental stem cells or modification of placental stem cells to enhance their immunomodulatory (e.g., immunosuppressive) activity comprise contacting the placental stem cells with an effective amount of small interfering RNAs (siRNAs), such that the immunomodulatory (e.g., immunosuppressive) activity of the placental stem cells is enhanced, e.g., as compared to placental stem cells that have not been modified, e.g., that have not been contacted with siRNAs.

As used herein, the term "small interfering RNA" or "siRNA" refers to an RNA molecule that interferes with the expression of a specific gene.

In certain embodiments, a method of producing ePSCs or modifying placental stem cells to enhance their immunomodulatory (e.g., immunosuppressive) activity comprises contacting the placental stem cells with an effective amount of siRNAs, such that the immunomodulatory (e.g., immunosuppressive) activity of the placental stem cells is enhanced, as described in the embodiments herein, compared to placental stem cells that have not been modified, e.g., that have not been contacted with siRNAs.

Interleukin (IL)-23 acts to promote the Th17 immune response, which is associated with unwanted or harmful immune response, such as autoimmune diseases or disorders. Thus, in certain embodiments, the enhanced placental stem cells (ePSCs), when contacted with (e.g., co-cultured with) peripheral blood mononuclear cells (PBMCs), reduce an amount of interleukin-23 (IL-23) produced by said PBMCs, e.g., as compared to an equivalent number of unmodified placental stem cells. In a specific embodiment, the PBMCs are contacted with said ePSCs in vivo, e.g. within an individual to whom the ePSCs are administered. In another specific embodiment, the PBMCs are contacted with said ePSCs in vitro.

In one embodiment, said enhanced placental stem cells (ePSCs), when contacted with (e.g., co-cultured with) peripheral blood mononuclear cells (PBMCs), reduce an amount of interleukin-23 (IL-23) produced by said PBMCs, e.g., as compared to an equivalent number of unmodified placental stem cells. In a specific embodiment, the PBMCs are contacted with said ePSCs in vivo, e.g. within an individual to whom the ePSCs are administered. In another specific embodiment, the PBMCs are contacted with said ePSCs in vitro. In another specific embodiment, said siRNAs target (e.g., modulate) one or more genes in said ePSCs that modulate the production of IL-23 by PBMCs such that the production of IL-23 by said PBMCs is reduced, e.g., as compared to an equivalent number of unmodified placental stem cells.

In another embodiment, said enhanced placental stem cells (ePSCs) have increased cyclooxygenase II (Cox-2) activity, e.g., as compared to an equivalent number of unmodified placental stem cells. In one embodiment, said Cox-2 activity is induced by IL-1β. In a specific embodiment, said siRNAs target (e.g., modulate) one or more genes in said ePSCs that modulate the activity of Cox-2 in said ePSCs such that the activity of said Cox-2 in said ePSCs increased, e.g., as compared to an equivalent number of unmodified placental stem cells.

Prostaglandin E2 (PGE2), secreted by placental stem cells, acts to reduce serum tumor necrosis factor-alpha (TNF-α), which in turn is implicated in a variety of diseases and disorders relating to an unwanted or harmful immune response. Thus, in certain embodiments, the enhanced placental stem cells (ePSCs) have been modified to produce an increased amount of PGE2, e.g., as compared to an equivalent number of unmodified placental stem cells. In one embodiment, said production of PGE2 production is induced by IL-1β.

In another embodiment, said enhanced placental stem cells (ePSCs) have increased production of prostaglandin E2 (PGE2), e.g., as compared to an equivalent number of unmodified placental stem cells. In one embodiment, said production of PGE2 production is induced by IL-1β. In a specific embodiment, said siRNAs target (e.g., modulate) one or more genes in said ePSCs that modulate the production of PGE2 by said ePSCs such that the production of PGE2 by said ePSCs is increased, e.g., as compared to an equivalent number of unmodified placental stem cells.

In another embodiment, the enhanced placental stem cells (ePSCs) have reduced production of a pro-inflammatory cytokine (e.g., extracellular pro-inflammatory cytokine), e.g., as compared to an equivalent number of unmodified placental stem cells. In one embodiment, said pro-inflammatory cytokine is IL-1, IL-6, IL-8, TNF-α, or any combinations thereof. In a specific embodiment, said pro-inflammatory cytokine is IL-6, IL-8, or a combination thereof. In another specific embodiment, said pro-inflammatory cytokine is IL-6. In another specific embodiment, said siRNAs target (e.g., modulate) one or more genes in said ePSCs that modulate the production of said pro-inflammatory cytokine such that the production of said pro-inflammatory cytokine of is reduced, e.g., as compared to an equivalent number of unmodified placental stem cells. In another specific embodiment, said one or more genes comprise a gene that encodes IL-1, IL-1, IL-6, IL-8, TNF-α. In another specific embodiment, said one or more genes comprise a gene that encodes IL-6.

In another embodiment, the enhanced placental stem cells (ePSCs) have suppressed response induced by interferon-gamma (IFN-γ), as compared to an equivalent number of unmodified placental stem cells. In one specific embodiment, said siRNAs target (e.g., modulate) one or more genes in said ePSCs that modulate IFN-γ-induced response of said ePSCs such that the IFN-γ-induced response is suppressed, e.g., as compared to an equivalent number of unmodified placental stem cells. In another specific embodiment, said one or more genes comprise one or more of protein inhibitor of activated STAT, 1 (PIAS1) and TYRO protein tyrosine kinase binding protein (TYROBP).

In certain embodiments, a method of producing ePSCs comprises contacting the placental stem cells with an effective amount of siRNAs, such that the immunomodulatory (e.g., immunosuppressive) activity of the placental stem cells is enhanced, as described in the embodiments herein, compared to placental stem cells that have not been modified, e.g., that have not been contacted with siRNAs.

The siRNAs can be single-stranded or double-stranded, and can be modified or unmodified. In one embodiment, the siRNAs have one or more 2'-deoxy or 2'-O-modified bases. In some embodiments, the siRNAs have one or more base substitutions and inversions (e.g., 3-4 nucleobases inversions).

In some embodiments, the siRNAs useful in producing ePSCs are double-stranded. In one embodiment, one strand of the siRNA is antisense to the target nucleic acid, while the other strand is complementary to the first strand. In certain embodiments, said siRNAs comprise a central complementary region between the first and second strands and terminal regions that are optionally complementary between said first and second strands or with the target RNA.

In certain embodiments, the siRNAs have a length of about 2 to about 50 nucleobases. In some embodiments, the siRNAs are double-stranded, and have a length of about 5 to 45, about 7 to 40, or about 10 to about 35 nucleobases. In some embodiments, the siRNAs are double-stranded, and are about 10, 11, 12, 13, 14, 15, 16, 17, 18, 19, 20, 21, 22, 23, 24, 25, 26, 27, 28, 29, 30, 31, 32, 33, 34, or 35 nucleobases in length.

In certain embodiments, one or both ends of the first and/or second strands of the siRNAs are modified by adding one or more natural or modified nucleobases to form an overhang. In certain embodiments, one or both ends of the first and/or second strands of the siRNAs are blunt. It is possible for one end of the first and/or second strands of the siRNAs to be blunt and the other to have overhanging nucleobases.

In one embodiment, said overhangs are about 1 to about 10, about 2 to about 8, about 3 to about 7, about 4 to about 6 nucleobase(s) in length. In another embodiment, said overhangs are about 1, 2, 3, 4, 5, 6, 7, 8, 9, or 10 nucleobase(s) in length. In a specific embodiment, the siRNAs are double-stranded, and have a length of about 21 nucleobases. In another specific embodiment, the siRNAs are double-stranded, and have a length of about 21 nucleobases comprising dinucleotide 3' overhangs (e.g., dinucleotide 3' DNA overhangs such as UU or TT 3'-overhangs) such that there is a 19 nt complementary region between the sense and anti-sense strands.

In a specific embodiment, said one or more genes targeted (e.g., modulated) by said siRNAs comprise one or more of Twinfilin-1, human nuclear receptor subfamily 1, group H, member 3 (NR1H3), deoxynucleotidyltransferase, terminal, interacting protein 1 (DNTTIP1), vitamin D (1,25-dihydroxyvitamin D3) receptor (VDR), nuclear receptor subfamily 4, group A, member 2 (NR4A2), nuclear receptor subfamily 4, group A, member 3 (NR4A3), nuclear receptor subfamily 0, group B, member 2 (NR0B2), or nuclear receptor subfamily 1, group I, member 2 (NR1I2). In another specific embodiment, said one or more gene comprise NR4A3. In another specific embodiment, said one or more gene comprise NR4A2.

In another specific embodiment, said one or more genes targeted (e.g., modulated) by said siRNAs comprise one or more of cholinergic receptor, nicotinic beta 1 (muscle) (CHRNB1), chloride channel 6 (CLCN6), chloride intracellular channel 4 (CLIC4), casein kinase 1, gamma 3 (CSNK1G3), casein kinase 2, alpha prime polypeptide (CSNK2A2), dual specificity phosphatase 1 (DUSP1), potassium channel modulatory factor 1 (KCMF1), potassium voltage-gated channel, shaker-related subfamily, member 3 (KCNA3), potassium inwardly-rectifying channel, subfamily J, member 14 (KCNJ14), potassium voltage-gated channel, delayed-rectifier, subfamily S, member 3 (KCNS3), potassium channel tetramerisation domain containing 13 (KCTD13), hepatocyte growth factor (hepapoietin A; scatter factor) (HGF), nuclear receptor subfamily 2, group C, member 2 (NR2C2), phosphodiesterase 1B, calmodulin-dependent (PDE1B), phosphodiesterase 7B (PDE7B), phosphatidylinositol 4-kinase type 2 beta (PI4K2B), phosphoinositide-3-kinase, regulatory subunit 1 (alpha) (PIK3R1), phospholipase C, eta 2 (PLCH2), protein phosphatase, $Mg^{2+}/Mn^{2+}$ dependent, 1D (PPM1D), protein phosphatase, $Mg^{2+}/Mn^{2+}$ dependent, 1G (PPM1G), protein phosphatase 1, regulatory (inhibitor) subunit 2 pseudogene 9 (PPP1R2P9), protein phosphatase 1, regulatory (inhibitor) subunit 3B (PPP1R3B), protein phosphatase 1, regulatory (inhibitor) subunit 9B (PPP1R9B), protein phosphatase 2, catalytic subunit, beta isozyme (PPP2CB), protein tyrosine phosphatase type IVA, member 1 (PTP4A1), protein tyrosine phosphatase, receptor type, K (PTPRK), regulator of G-protein signaling 4 (RGS4), regulator of G-protein signaling 7 binding protein (RGS7BP), regulator of G-protein signaling 8 (RGS8), solute carrier family 16, member 3 (monocarboxylic acid transporter 4) (SLC16A3), solute carrier family 30 (zinc transporter), member 1 (SLC30A1), solute carrier family 35, member A4 (SLC35A4), solute carrier family 38, member 7 (SLC38A7), solute carrier family 41, member 1 (SLC41A1 (includes EG:254428)), solute carrier family 45, member 3 (SLC45A3), solute carrier family 7 (cationic amino acid transporter, y+ system), member 1 (SLC7A1), ubiquitin associated protein 2 (UBAP2), ubiquitin-conjugating enzyme E2D 3 (UBC4/5 homolog, yeast) (UBE2D3 (includes EG:7323)), ubiquitin-conjugating enzyme E2E 3 (UBC4/5 homolog, yeast) (UBE2E3), ubiquitin-conjugating enzyme E2R 2 (UBE2R2 (includes EG:54926)), ubiquitin-conjugating enzyme E2W (putative) (UBE2W), ubiquitin-like with PHD and ring finger domains 2 (UHRF2), ubiquitin specific peptidase 9, X-linked (USP9X), or hypoxia inducible factor 1, alpha subunit (HIF1A). In another specific embodiment, said one or more genes comprise HIF1A. In another specific embodiment, said one or more genes comprise DUSP1. In another specific embodiment, said one or more genes comprise PDE7B. In another specific embodiment, said siRNAs decrease the mRNA level of said one or more genes in said ePSCs. In various embodiments, said decrease is a decrease of about, up to, or no more than, 5%, 10%, 15%, 20%, 25%, 30%, 35%, 40%, 45%, 50%, 55%, 60%, 65%, 70%, 75%, 80%, 85%, 90%, 95%, 98% or 99%, as compared to expression of said genes in unmodified placental stem cells.

In certain embodiments, the siRNAs modulate (e.g., suppress the expression of) one or more genes listed in Table 1 (see the column designated as "Full Gene Name (Human)") and Table 7.

nuclear receptor subfamily 1, group H, member 3 (NR1H3) (e.g., NCBI Ref Seq Accession Number NM_005693). In one embodiment, said siRNAs are double-stranded. In a specific embodiment, one strand (e.g., sense strand) of said double-stranded siRNAs has a sequence at least about 70%, 80%, 90%, 95%, 98% or 100% identical to SEQ ID NO: 1, wherein said ePSCs contacted with said siRNAs suppress IL-23 production in PBMCs contacted with said ePSCs. In another embodiment, one strand (e.g., antisense strand) of said double-stranded siRNAs has a sequence at least about 70%, 80%, 90%, 95%, 98% or 100% identical to SEQ ID NO: 2, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
GGAUGCUAAUGAAACUGGUtt   SEQ ID NO: 1
||||||||||||||||||||
tgCCUACGAUUACUUUGACCA   SEQ ID NO: 2
```

In another specific embodiment, said siRNAs target (e.g., modulate) a gene encoding NR1H3 (e.g., NCBI Ref Seq Accession Number NM_005693) such that the production of IL-23 by said PBMCs is reduced when contacted with ePSCs, e.g., as compared to an equivalent number of unmodified placental stem cells.

In certain embodiments, the siRNAs target (e.g., modulate) a gene encoding deoxynucleotidyltransferase, terminal, interacting protein 1 (DNTTIP1) (e.g., NCBI Ref Seq Accession

TABLE 1

Suppression of soluble IL-23 protein produced by peripheral blood mononuclear cells (PBMCs) in the presence of enhanced placental stem cells by siRNAs (0.25 nmoles).

| RefSeq Accession Number | Gene Symbol | Full Gene Name (Human) | Gene ID | siRNA ID | Sense (S)/ antisense (AS) | Sequence (Upper case denotes RNA-bases, and lower case denotes DNA-bases) | SEQ ID NO |
|---|---|---|---|---|---|---|---|
| NM_005693 | NR1H3 | nuclear receptor subfamily 1, group H, member 3 | 10062 | s19568 | S | GGAUGCUAAUGAAACUGGUtt | 1 |
|  |  |  |  |  | AS | ACCAGUUUCAUUAGCAUCCgt | 2 |
| NM_052951 | DNTTIP1 | deoxynucleotidyl-transferase, terminal, interacting protein 1 | 116092 | s41922 | S | GGAACAUAAUGAUAAAGCAtt | 3 |
|  |  |  |  |  | AS | UGCUUUAUCAUUAUGUUCCaa | 4 |
| NM_000376 | VDR | vitamin D (1,25-dihydroxyvitamin D3) receptor | 7421 | s14779 | S | AGAUCACUGUAUCACCUCUtt | 5 |
|  |  |  |  |  | AS | AGAGGUGAUACAGUGAUCUga | 6 |
| NM_173198 | NR4A3 | nuclear receptor subfamily 4, group A, member 3 | 8013 | s15543 | A | AGAUCUUGAUUAUUCCAGAtt | 7 |
|  |  |  |  |  | AS | UCUGGAAUAAUCAAGAUCUct | 8 |
| NM_021969 | NR0B2 | nuclear receptor subfamily 0, group B, member 2 | 8431 | s15988 | S | CGGUGCCCAGCAUACUCAAtt | 9 |
|  |  |  |  |  | AS | UUGAGUAUGCUGGGCACCCgg | 10 |
| NM_022002 | NR1I2 | nuclear receptor subfamily 1, group I, member 2 | 8856 | s16911 | S | GGCUAUCACUUCAAUGUCAtt | 11 |
|  |  |  |  |  | AS | UGACAUUGAAGUGAUAGCCag | 12 |
| NM_052951 | DNTTIP1 | deoxynucleotidyl-transferase, terminal, interacting protein 1 | 116092 | s41924 | S | CCUUGGAACAUAAUGAUAAtt | 13 |
|  |  |  |  |  | AS | UUAUCAUUAUGUUCCAAGGgt | 14 |

In certain embodiments, the siRNAs target (e.g., modulate) a gene (e.g., a nucleic acid molecule) encoding human Number NM_052951).). In one embodiment, said siRNAs are double-stranded. In a specific embodiment, one strand (e.g., sense strand) of said double-stranded siRNAs has a sequence at least about 70%, 80%, 90%, 95%, 98% or 100% identical to SEQ ID NO 3, wherein said ePSCs contacted with said siRNAs suppress IL-23 production in PBMCs contacted with said ePSCs. In another embodiment, one strand (e.g., antisense strand) of said double-stranded siRNAs has a sequence at least about 70%, 80%, 90%, 95%, 98% or 100% identical to SEQ ID NO 4, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
GGAACAUAAUGAUAAAGCAtt   SEQ ID NO: 3
||||||||||||||||||
aaCCUUGUAUUACUAUUUCGU    SEQ ID NO: 4
```

In another specific embodiment, one strand (e.g., sense strand) of said double-stranded siRNAs have a sequence at least about 70%, 80%, 90%, 95%, 98% or 100% identical to SEQ ID NO 13, wherein said ePSCs contacted with said siRNAs suppress IL-23 production in PBMCs contacted with said ePSCs. In another embodiment, one strand (e.g., antisense strand) of said double-stranded siRNAs have a sequence at least about 70%, 80%, 90%, 95%, 98% or 100% identical to SEQ ID NO 14, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
CCUUGGAACAUAAUGAUAAtt    SEQ ID NO: 13
||||||||||||||||||
tgGGAACCUUGUAUUACUAUU    SEQ ID NO: 14
```

In a specific embodiment, said siRNAs target (e.g., modulate) a gene encoding DNTTIP1 (e.g., NCBI Ref Seq Accession Number NM_052951) such that the production of IL-23 by said PBMCs is reduced when contacted with ePSCs, e.g., as compared to an equivalent number of unmodified placental stem cells.

In certain embodiments, the siRNAs target (e.g., modulate) a gene encoding vitamin D (1,25-dihydroxyvitamin D3) receptor (VDR) (e.g., NCBI Ref Seq Accession Number NM_000376). In one embodiment, said siRNAs are double-stranded. In a specific embodiment, one strand (e.g., sense strand) of said double-stranded siRNAs has a sequence at least about 70%, 80%, 90%, 95%, 98% or 100% identical to SEQ ID NO 5, wherein said ePSCs contacted with said siRNAs suppress IL-23 production in PBMCs contacted with said ePSCs. In another embodiment, one strand (e.g., antisense strand) of said double-stranded siRNAs has a sequence at least about 70%, 80%, 90%, 95%, 98% or 100% identical to SEQ ID NO 6, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
AGAUCACUGUAUCACCUCUtt    SEQ ID NO: 5
||||||||||||||||||
gaUCUAGUGACAUAGUGGAGA    SEQ ID NO: 6
```

In a specific embodiment, said siRNAs target (e.g., modulate) a gene encoding VDR (e.g., NCBI Ref Seq Accession Number NM_000376) such that the production of IL-23 by said PBMCs is reduced when contacted with ePSCs, e.g., as compared to an equivalent number of unmodified placental stem cells.

In certain embodiments, the siRNAs target (e.g., modulate) a gene encoding nuclear receptor subfamily 4, group A, member 3 (NR4A3) (e.g., NCBI Ref Seq Accession Number NM_173198). In one embodiment, said siRNAs are double-stranded. In a specific embodiment, one strand (e.g., sense strand) of said double-stranded siRNAs has a sequence at least about 70%, 80%, 90%, 95%, 98% or 100% identical to SEQ ID NO 7, wherein said ePSCs contacted with said siRNAs suppress IL-23 production in PBMCs contacted with said ePSCs. In another embodiment, one strand (e.g., antisense strand) of said double-stranded siRNAs has a sequence at least about 70%, 80%, 90%, 95%, 98% or 100% identical to SEQ ID NO 8, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
AGAUCUUGAUUAUUCCAGAtt    SEQ ID NO: 7
||||||||||||||||||
tcUCUAGAACUAAUAAGGUCU    SEQ ID NO: 8
```

In a specific embodiment, said siRNAs target (e.g., modulate) a gene encoding NR4A3 (e.g., NCBI Ref Seq Accession Number NM_173198) such that the production of IL-23 by said PBMCs is reduced when contacted with ePSCs, e.g., as compared to an equivalent number of unmodified placental stem cells.

In certain embodiments, the siRNAs target (e.g., modulate) a gene encoding nuclear receptor subfamily 0, group B, member 2 (NR0B2) (e.g., NCBI Ref Seq Accession Number NM_021969). In one embodiment, said siRNAs are double-stranded. In a specific embodiment, one strand (e.g., sense strand) of said double-stranded siRNAs has a sequence at least about 70%, 80%, 90%, 95%, 98% or 100% identical to SEQ ID NO 9, wherein said ePSCs contacted with said siRNAs suppress IL-23 production in PBMCs contacted with said ePSCs. In another embodiment, one strand (e.g., antisense strand) of said double-stranded siRNAs has a sequence at least about 70%, 80%, 90%, 95%, 98% or 100% identical to SEQ ID NO 10, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
CGGUGCCCAGCAUACUCAAtt    SEQ ID NO: 9
||||||||||||||||||
ggGCCACGGGUCGUAUGAGUU    SEQ ID NO: 10
```

In a specific embodiment, said siRNAs target (e.g., modulate) a gene encoding NR0B2 (e.g., NCBI Ref Seq Accession Number NM_021969) such that the production of IL-23 by said PBMCs is reduced when contacted with ePSCs, e.g., as compared to an equivalent number of unmodified placental stem cells.

In certain embodiments, the siRNAs target (e.g., modulate) a gene encoding nuclear receptor subfamily 1, group I, member 2 (NR1I2) (e.g., NCBI Ref Seq Accession Number NM_022002). In one embodiment, said siRNAs are double-stranded. In a specific embodiment, one strand (e.g., sense strand) of said double-stranded siRNAs has a sequence at least about 70%, 80%, 90%, 95%, 98% or 100% identical to SEQ ID NO 11, wherein said ePSCs contacted with said siRNAs suppress IL-23 production in PBMCs contacted with said ePSCs. In another embodiment, one strand (e.g., antisense strand) of said double-stranded siRNAs has a sequence at least about 70%, 80%, 90%, 95%, 98% or 100% identical to SEQ ID NO 12, wherein said ePSCs contacted with said siRNAs suppress IL-23 production in PBMCs contacted with said ePSCs. In another embodiment, said double-stranded siRNAs form a duplex comprising a two-nucleobase overhang and the following structure:

```
    GGCUAUCACUUCAAUGUCAtt    SEQ ID NO: 11
    |||||||||||||||||||
    gaCCGAUAGUGAAGUUACAGU    SEQ ID NO: 12
```

In a specific embodiment, said siRNAs target (e.g., modulate) a gene encoding NR1I2 (e.g., NCBI Ref Seq Accession Number NM_022002) such that the production of IL-23 by said PBMCs is reduced when contacted with ePSCs, e.g., as compared to an equivalent number of unmodified placental stem cells.

The siRNAs can be supplied by a commercial vendor (e.g., Ambion; Dharmacon), or be synthesized by, e.g., solid phase synthesis, or according to the procedures as described in, e.g., Protocols for Oligonucleotides and Analogs, Ed. Agrawal (1993), Humana Press; Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

siRNAs useful for the production of enhanced placental stem cells can be identified by a variety of methods known in the art. In certain embodiments, such siRNAs are identified and obtained from one or more siRNA libraries, e.g., a commercially available library (e.g., Ambion, Silencer® Select Human Nuclear Hormone Receptor (HNR) siRNA Library V4; Dharmacon, siRNA library Human ON-TARGETplus siRNA Nuclear Receptors Sub-Library), optionally by a screening method, e.g., medium or high-throughput screening. In one embodiment, such a library can encompass a wide range of genes (e.g., human genome-wide siRNA library), or pre-defined to encompass specific target genes or gene families (e.g., human nuclear receptor siRNA library, phosphatase siRNA library, etc.)

The screening method can be carried out, for example, using automated robotics, liquid handling equipments, data processing software, and/or sensitive detectors, e.g., Precision XS Automated Pipettor System, EL406 liquid handling system, or synergy plate reader.

5.1.2 miR Inhibitors and miR Mimics

In certain embodiments, the methods provided herein for the production of enhanced placental stem cells or modification of placental stem cells to enhance their immunomodulatory (e.g., immunosuppressive) activity comprise contacting the placental stem cells with an effective amount of microRNA inhibitors (miR inhibitors), such that the immunomodulatory (e.g., immunosuppressive) activity of the placental stem cells is enhanced, e.g., as compared to placental stem cells that have not been modified, e.g., that have not been contacted with miR inhibitors.

In certain embodiments, the methods provided herein for the production of enhanced placental stem cells or modification of placental stem cells to enhance their immunomodulatory (e.g., immunosuppressive) activity comprise contacting the placental stem cells with an effective amount of microRNA mimics (miR mimics), such that the immunomodulatory (e.g., immunosuppressive) activity of the placental stem cells is enhanced, e.g., as compared to placental stem cells that have not been modified, e.g., that have not been contacted with miR mimics.

As used herein, the term "microRNA," "miRNA," or "miR" refers to short ribonucleic acid (RNA) molecules, including, but not limited to, mature single stranded miRNAs, precursor miRNAs (pre-miR), and variants thereof. As used herein, the term "microRNA inhibitor," "miRNA inhibitor," "miR inhibitor" or "anti-miR" refer to a ribonucleic acid molecule designed to inhibit miRNAs (e.g., endogenous miRNAs). In some embodiments, the miR inhibitors up-regulate a target gene by inhibition of one or more endogenous miRs. In one embodiment, the microRNAs are naturally occurring. In certain embodiments, the microRNAs are post-transcriptional regulators that bind to complementary sequences on target messenger RNA transcripts (mRNAs) and result in translational repression and gene silencing. In certain embodiments, a single precursor contains more than one mature miRNA sequence. In other embodiments, multiple precursor miRNAs contain the same mature sequence. In some embodiments, when the relative abundances clearly indicate which is the predominantly expressed miRNA, the term "microRNA," "miRNA," or "miR" refers to the predominant product, and the term "microRNA*," "miRNA*," or "miR*" refers to the opposite arm of the precursor. In one embodiment, miRNA is the "guide" strand that eventually enters RNA-Induced Silencing Complex (RISC), and miRNA* is the other "passenger" strand. In another embodiment, the level of miRNA* present in the cell at a lower level (e.g., <15%) relative to the corresponding miRNA. In some embodiments where there is a higher proportion of passenger strand present in the cell, the nomenclature miRNA-3p (i.e., miRNA derived from the 3' arm of the precursor miRNA) and miRNA-5p (i.e., miRNA-5p is the miRNA derived from the 5' arm of the precursor miRNA) is used instead of miRNA/miRNA*.

As used herein, the term "microRNA mimic(s)" or "miR mimic(s)" refers to molecules that can be used to imitate or mimic the gene silencing ability of one or more miRNAs. In one embodiment, the miR mimics down-regulate a target gene by imitating one or more endogenous miRs. In certain embodiments, miRNA mimics are synthetic non-coding RNAs (i.e., the miRNA is not obtained by purification from a source of the endogenous miRNA). In certain embodiments, the miRNA mimics are capable of entering the RNAi pathway and regulating gene expression. In certain embodiments, miRNA mimics can be designed as mature molecules (e.g. single stranded) or mimic precursors (e.g., pri- or pre-miR-NAs).

In some embodiments, the miR inhibitors or miRNA mimics provided herein comprise nucleic acid (modified or modified nucleic acids) including oligonucleotides comprising, e.g., RNA, DNA, modified RNA, modified DNA, locked nucleic acids, or 2'-O,4'-C-ethylene-bridged nucleic acids (ENA), or any combination of thereof.

The miR inhibitors or miR mimics can be single-stranded or double-stranded, and can be modified or unmodified. In certain embodiments, the miR inhibitors or miR mimics have a length of about 2 to about 30 nucleobases. In certain embodiments, the miR inhibitors or miR mimics are single-stranded, and have a length of about 15 to about 30 nucleobases. In some embodiments, the miR inhibitors are single-stranded, and are about 15, 16, 17, 18, 19, 20, 21, 22, 23, 24, 25, 26, 27, 28, 29 or 30 nucleobases in length.

In certain embodiments, a method of producing ePSCs comprises contacting the placental stem cells with an effective amount of miR inhibitors or miR mimics, such that the immunomodulatory (e.g., immunosuppressive) activity of the placental stem cells is enhanced compared to placental stem cells that have not been modified, e.g., that have not been contacted with miR inhibitors or miR mimics.

In one embodiment, said enhanced placental stem cells (ePSCs), when contacted with (e.g., co-cultured with) peripheral blood mononuclear cells (PBMCs), reduce an amount of interleukin-23 (IL-23) produced by said PBMCs, e.g., as compared to an equivalent number of unmodified placental stem cells. In a specific embodiment, the PBMCs are contacted with said ePSCs in vivo, e.g. within an individual to whom the ePSCs are administered. In another specific embodiment, the PBMCs are contacted with said ePSCs in vitro.

In another specific embodiment, said miR inhibitors target (e.g., modulate, reduce the level of, up-regulate) one or more miRs in said ePSCs that modulate the production of IL-23 by PBMCs such that the production of IL-23 by said PBMCs contacted with said ePSCs is reduced, e.g., as compared to PBMCs contacted with an equivalent number of unmodified placental stem cells. In another specific embodiment, said miR inhibitors target (e.g., modulate, up-regulate) one or more genes in said ePSCs that modulate the production of IL-23 by PBMCs such that the production of IL-23 by said PBMCs contacted with said ePSCs is reduced, e.g., as compared to PBMCs contacted with an equivalent number of unmodified placental stem cells.

In another specific embodiment, said miR mimics imitate or mimic one or more miRs in said ePSCs that modulate the production of IL-23 by PBMCs such that the production of IL-23 by said PBMCs contacted with said ePSCs is reduced, e.g., as compared to PBMCs contacted with an equivalent number of unmodified placental stem cells. In another specific embodiment, said miR mimics target one or more genes in said ePSCs that modulate the production of IL-23 by PBMCs such that the production of IL-23 by said PBMCs contacted with said ePSCs is reduced, e.g., as compared to PBMCs contacted with an equivalent number of unmodified placental stem cells.

In certain embodiments, said miR inhibitors target (e.g., modulate) one or more miRs listed in Table 2 (see the column designated as "Target miR"). In a specific embodiment, said miR inhibitors target (e.g., modulate, reduce the level of) one or more miRs listed in Table 2 (see the column designated as "Target miR") in said ePSCs such that the production of IL-23 by said PBMCs contacted with said ePSCs is reduced, e.g., as compared to PBMCs contacted with an equivalent number of unmodified placental stem cells. In another specific embodiment, said miR inhibitors have a sequence that is at least about 70%, 80%, 90%, 95%, 98% or 100% identical to SEQ ID NO. 15-83 and 228-234, or the complement thereof.

In certain embodiments, said miR mimics imitate or mimic one or more miRs listed in Table 2 (see the column designated as "Target miR"). In a specific embodiment, said miR mimics imitate or mimic one or more miRs listed in Table 2 (see the column designated as "Target miR") in said ePSCs such that the production of IL-23 by said PBMCs contacted with said ePSCs is reduced, e.g., as compared to PBMCs contacted with an equivalent number of unmodified placental stem cells. In another specific embodiment, said miR mimics have a sequence at least about 70%, 80%, 90%, 95%, 98% or 100% identical to SEQ ID NO. 15-83 and 228-234, or the complement thereof.

In one embodiment, said miR inhibitors target (e.g., modulate) hsa-miR-371-5p, wherein said miR inhibitors have a sequence at least about 70%, 80%, 90%, 95%, 98% or 100% identical to SEQ ID NO. 59, or the complement thereof. In another embodiment, said miR inhibitors target (e.g., modulate) hsa-miR-136*, wherein said miR inhibitors have a sequence at least about 70%, 80%, 90%, 95%, 98% or 100% identical to SEQ ID NO. 60, or the complement thereof. In another embodiment, said miR inhibitors target (e.g., modulate) hsa-miR-214, wherein said miR inhibitors have a sequence at least about 70%, 80%, 90%, 95%, 98% or 100% identical to SEQ ID NO. 61, or the complement thereof. In another embodiment, said miR inhibitors target (e.g., modulate) hsa-miR-25*, wherein said miR inhibitors have a sequence at least about 70%, 80%, 90%, 95%, 98% or 100% identical to SEQ ID NO.62, or the complement thereof. In another embodiment, said miR inhibitors target (e.g., modulate) hsa-miR-452*, wherein said miR inhibitors have a sequence at least about 70%, 80%, 90%, 95%, 98% or 100% identical to SEQ ID NO.63, or the complement thereof. In another embodiment, said miR inhibitors target (e.g., modulate) hsa-miR-454*, wherein said miR inhibitors have a sequence at least about 70%, 80%, 90%, 95%, 98% or 100% identical to SEQ ID NO.64, or the complement thereof.

In another embodiment, said miR inhibitors target (e.g., modulate) hsa-miR-548b-5p, wherein said miR inhibitors have a sequence at least about 70%, 80%, 90%, 95%, 98% or 100% identical to SEQ ID NO.65, or the complement thereof. In another embodiment, said miR inhibitors target (e.g., modulate) hsa-miR-10b*, wherein said miR inhibitors have a sequence at least about 70%, 80%, 90%, 95%, 98% or 100% identical to SEQ ID NO: 66, or the complement thereof. In another embodiment, said miR inhibitors target (e.g., modulate) hsa-miR-218, wherein said miR inhibitors have a sequence at least about 70%, 80%, 90%, 95%, 98% or 100% identical to SEQ ID NO: 67, or the complement thereof. In another embodiment, said miR inhibitors target (e.g., modulate) hsa-miR-548m, wherein said miR inhibitors have a sequence at least about 70%, 80%, 90%, 95%, 98% or 100% identical to SEQ ID NO: 68, or the complement thereof. In another embodiment, said miR inhibitors target (e.g., modulate) hsa-miR-520a-3p, wherein said miR inhibitors have a sequence at least about 70%, 80%, 90%, 95%, 98% or 100% identical to SEQ ID NO: 69, or the complement thereof. In another embodiment, said miR inhibitors target (e.g., modulate) hsa-miR-1323, wherein said miR inhibitors have a sequence at least about 70%, 80%, 90%, 95%, 98% or 100% identical to SEQ ID NO: 70, or the complement thereof.

In another embodiment, said miR inhibitors target (e.g., modulate) hsa-miR-24-2*, wherein said miR inhibitors have a sequence at least about 70%, 80%, 90%, 95%, 98% or 100% identical to SEQ ID NO: 71, or the complement thereof. In another embodiment, said miR inhibitors target (e.g., modulate) hsa-miR-613, wherein said miR inhibitors have a sequence at least about 70%, 80%, 90%, 95%, 98% or 100% identical to SEQ ID NO: 72, or the complement thereof. In another embodiment, said miR inhibitors target (e.g., modulate) hsa-miR-26a, wherein said miR inhibitors have a sequence at least about 70%, 80%, 90%, 95%, 98% or 100% identical to SEQ ID NO: 73, or the complement thereof. In another embodiment, said miR inhibitors target (e.g., modulate) hsa-miR-193a-3p, wherein said miR inhibitors have a sequence at least about 70%, 80%, 90%, 95%, 98% or 100% identical to SEQ ID NO: 74, or the complement thereof. In another embodiment, said miR inhibitors target (e.g., modulate) hsa-miR-1208, wherein said miR inhibitors have a sequence at least about 70%, 80%, 90%, 95%, 98% or 100% identical to SEQ ID NO: 75, or the complement thereof. In another embodiment, said miR inhibitors target (e.g., modulate) hsa-miR-767-5p, wherein said miR inhibitors have a sequence at least about 70%, 80%, 90%, 95%, 98% or 100% identical to SEQ ID NO: 76, or the complement thereof. In another embodiment, said miR inhibitors target (e.g., modulate) hsa-miR-491-3p, wherein said miR inhibitors have a sequence at least about 70%, 80%, 90%, 95%, 98% or 100% identical to SEQ ID NO: 77, or the complement thereof.

In another embodiment, said miR inhibitors target (e.g., modulate) hsa-miR-626, wherein said miR inhibitors have a sequence at least about 70%, 80%, 90%, 95%, 98% or 100% identical to SEQ ID NO: 78, or the complement thereof. In another embodiment, said miR inhibitors target (e.g., modulate) hsa-miR-216a, wherein said miR inhibitors have a sequence at least about 70%, 80%, 90%, 95%, 98% or 100% identical to SEQ ID NO: 79, or the complement thereof. In another embodiment, said miR inhibitors target (e.g., modulate) hsa-miR-151-5p, wherein said miR inhibitors have a sequence at least about 70%, 80%, 90%, 95%, 98% or 100% identical to SEQ ID NO: 80, or the complement thereof. In another embodiment, said miR inhibitors target (e.g., modulate) hsa-miR-1282, wherein said miR inhibitors have a sequence at least about 70%, 80%, 90%, 95%, 98% or 100% identical to SEQ ID NO: 81, or the complement thereof. In another embodiment, said miR inhibitors target (e.g., modulate) hsa-miR-497*, wherein said miR inhibitors have a sequence at least about 70%, 80%, 90%, 95%, 98% or 100% identical to SEQ ID NO: 82, or the complement thereof. In another embodiment, said miR inhibitors target (e.g., modulate) hsa-miR-129-3p, wherein said miR inhibitors have a sequence at least about 70%, 80%, 90%, 95%, 98% or 100% identical to SEQ ID NO.83, or the complement thereof. In another embodiment, said miR inhibitors target (e.g., modulate) hsa-miR-1, wherein said miR inhibitors have a sequence at least about 70%, 80%, 90%, 95%, 98% or 100% identical to SEQ ID NO.228, or the complement thereof. In another embodiment, said miR inhibitors target (e.g., modulate) hsa-miR-129*, wherein said miR inhibitors have a sequence at least about 70%, 80%, 90%, 95%, 98% or 100% identical to SEQ ID NO.229, or the complement thereof. In another embodiment, said miR inhibitors target (e.g., modulate) hsa-miR-24, wherein said miR inhibitors have a sequence at least about 70%, 80%, 90%, 95%, 98% or 100% identical to SEQ ID NO. 230, or the complement thereof. In another embodiment, said miR inhibitors target (e.g., modulate) hsa-miR-24-1*, wherein said miR inhibitors have a sequence at least about 70%, 80%, 90%, 95%, 98% or 100% identical to SEQ ID NO. 231, or the complement thereof. In another embodiment, said miR inhibitors target (e.g., modulate) hsa-miR-218-1*, wherein said miR inhibitors have a sequence at least about 70%, 80%, 90%, 95%, 98% or 100% identical to SEQ ID NO. 232, or the complement thereof. In another embodiment, said miR inhibitors target (e.g., modulate) hsa-miR-183, wherein said miR inhibitors have a sequence at least about 70%, 80%, 90%, 95%, 98% or 100% identical to SEQ ID NO. 233, or the complement thereof. In another embodiment, said miR inhibitors target (e.g., modulate) hsa-miR-183*, wherein said miR inhibitors have a sequence at least about 70%, 80%, 90%, 95%, 98% or 100% identical to SEQ ID NO. 234, or the complement thereof.

In one embodiment, said miR mimics imitate or mimic hsa-miR-183, wherein said miR mimics have a sequence at least about 70%, 80%, 90%, 95%, 98% or 100% identical to SEQ ID NO. 15. In another embodiment, said miR mimics imitate or mimic hsa-miR-491-5p, wherein said miR mimics have a sequence at least about 70%, 80%, 90%, 95%, 98% or 100% identical to SEQ ID NO. 16. In another embodiment, said miR mimics imitate or mimic hsa-miR-132*, wherein said miR mimics have a sequence at least about 70%, 80%, 90%, 95%, 98% or 100% identical to SEQ ID NO. 17. In another embodiment, said miR mimics imitate or mimic hsa-miR-129-5p, wherein said miR mimics have a sequence at least about 70%, 80%, 90%, 95%, 98% or 100% identical to SEQ ID NO. 18. In another embodiment, said miR mimics imitate or mimic hsa-miR-636, wherein said miR mimics have a sequence at least about 70%, 80%, 90%, 95%, 98% or 100% identical to SEQ ID NO. 19. In another embodiment, said miR mimics imitate or mimic hsa-miR-100, wherein said miR mimics have a sequence at least about 70%, 80%, 90%, 95%, 98% or 100% identical to SEQ ID NO. 20.

In another embodiment, said miR mimics imitate or mimic hsa-miR-181a, wherein said miR mimics have a sequence at least about 70%, 80%, 90%, 95%, 98% or 100% identical to SEQ ID NO. 21. In another embodiment, said miR mimics imitate or mimic hsa-miR-519a, wherein said miR mimics have a sequence at least about 70%, 80%, 90%, 95%, 98% or 100% identical to SEQ ID NO. 22. In another embodiment, said miR mimics imitate or mimic hsa-miR-338-3p, wherein said miR mimics have a sequence at least about 70%, 80%, 90%, 95%, 98% or 100% identical to SEQ ID NO. 23. In another embodiment, said miR mimics imitate or mimic hsa-miR-1179, wherein said miR mimics have a sequence at least about 70%, 80%, 90%, 95%, 98% or 100% identical to SEQ ID NO. 24. In another embodiment, said miR mimics imitate or mimic hsa-miR-521, wherein said miR mimics have a sequence at least about 70%, 80%, 90%, 95%, 98% or 100% identical to SEQ ID NO. 25. In another embodiment, said miR mimics imitate or mimic hsa-miR-608, wherein said miR mimics have a sequence at least about 70%, 80%, 90%, 95%, 98% or 100% identical to SEQ ID NO. 26. In another embodiment, said miR mimics imitate or mimic hsa-miR-1306, wherein said miR mimics have a sequence at least about 70%, 80%, 90%, 95%, 98% or 100% identical to SEQ ID NO. 27.

In another embodiment, said miR mimics imitate or mimic hsa-miR-543, wherein said miR mimics have a sequence at least about 70%, 80%, 90%, 95%, 98% or 100% identical to SEQ ID NO. 28. In another embodiment, said miR mimics imitate or mimic hsa-miR-542-3p, wherein said miR mimics have a sequence at least about 70%, 80%, 90%, 95%, 98% or 100% identical to SEQ ID NO. 29. In another embodiment, said miR mimics imitate or mimic hsa-miR-23b, wherein said miR mimics have a sequence at least about 70%, 80%, 90%, 95%, 98% or 100% identical to SEQ ID NO. 30. In another embodiment, said miR mimics imitate or mimic hsa-miR-299-3p, wherein said miR mimics have a sequence at least about 70%, 80%, 90%, 95%, 98% or 100% identical to SEQ ID NO. 31. In another embodiment, said miR mimics imitate or mimic hsa-miR-597, wherein said miR mimics have a sequence at least about 70%, 80%, 90%, 95%, 98% or 100% identical to SEQ ID NO. 32. In another embodiment, said miR mimics imitate or mimic hsa-miR-1976, wherein said miR mimics have a sequence at least about 70%, 80%, 90%, 95%, 98% or 100% identical to SEQ ID NO. 33. In another embodiment, said miR mimics imitate or mimic hsa-miR-1252, wherein said miR mimics have a sequence at least about 70%, 80%, 90%, 95%, 98% or 100% identical to SEQ ID NO. 34.

In another embodiment, said miR mimics imitate or mimic hsa-miR-510, wherein said miR mimics have a sequence at least about 70%, 80%, 90%, 95%, 98% or 100% identical to SEQ ID NO. 35. In another embodiment, said miR mimics imitate or mimic hsa-miR-1207-5p, wherein said miR mimics have a sequence at least about 70%, 80%, 90%, 95%, 98% or 100% identical to SEQ ID NO. 36. In another embodiment, said miR mimics imitate or mimic hsa-miR-518a-3p, wherein said miR mimics have a sequence at least about 70%, 80%, 90%, 95%, 98% or 100% identical to SEQ ID NO. 37. In another embodiment, said miR mimics imitate or mimic hsa-miR-1250, wherein said miR mimics have a sequence at least about 70%, 80%, 90%, 95%, 98% or 100% identical to SEQ ID NO. 38. In another embodiment, said miR mimics imitate or mimic hsa-miR-1274a, wherein said miR mimics have a sequence at least about 70%, 80%, 90%, 95%, 98% or 100% identical to SEQ ID NO. 39. In another embodiment, said miR mimics imitate or mimic hsa-miR-141*, wherein said miR mimics have a sequence at least about 70%, 80%, 90%, 95%, 98% or 100% identical to SEQ ID NO. 40. In another embodiment, said miR mimics imitate or mimic hsa-miR-9*, wherein said miR mimics have a sequence at least about 70%, 80%, 90%, 95%, 98% or 100% identical to SEQ ID NO. 41.

In another embodiment, said miR mimics imitate or mimic hsa-miR-566, wherein said miR mimics have a sequence at least about 70%, 80%, 90%, 95%, 98% or 100% identical to SEQ ID NO. 42. In another embodiment, said miR mimics imitate or mimic hsa-miR-142-5p, wherein said miR mimics have a sequence at least about 70%, 80%, 90%, 95%, 98% or 100% identical to SEQ ID NO. 43. In another embodiment, said miR mimics imitate or mimic hsa-miR-23a*, wherein said miR mimics have a sequence at least about 70%, 80%, 90%, 95%, 98% or 100% identical to SEQ ID NO. 44. In another embodiment, said miR mimics imitate or mimic hsa-miR-519e*, wherein said miR mimics have a sequence at least about 70%, 80%, 90%, 95%, 98% or 100% identical to SEQ ID NO. 45. In another embodiment, said miR mimics imitate or mimic hsa-miR-1292, wherein said miR mimics have a sequence at least about 70%, 80%, 90%, 95%, 98% or 100% identical to SEQ ID NO. 46. In another embodiment, said miR mimics imitate or mimic hsa-miR-96, wherein said miR mimics have a sequence at least about 70%, 80%, 90%, 95%, 98% or 100% identical to SEQ ID NO. 47. In another embodiment, said miR mimics imitate or mimic hsa-miR-886-3p, wherein said miR mimics have a sequence at least about 70%, 80%, 90%, 95%, 98% or 100% identical to SEQ ID NO. 48. In another embodiment, said miR mimics imitate or mimic hsa-miR-216b, wherein said miR mimics have a sequence at least about 70%, 80%, 90%, 95%, 98% or 100% identical to SEQ ID NO. 49. In another embodiment, said miR mimics imitate or mimic hsa-miR-218-2*, wherein said miR mimics have a sequence at least about 70%, 80%, 90%, 95%, 98% or 100% identical to SEQ ID NO. 50.

In another embodiment, said miR mimics imitate or mimic hsa-miR-182, wherein said miR mimics have a sequence at least about 70%, 80%, 90%, 95%, 98% or 100% identical to SEQ ID NO. 51. In another embodiment, said miR mimics imitate or mimic hsa-miR-545*, wherein said miR mimics have a sequence at least about 70%, 80%, 90%, 95%, 98% or 100% identical to SEQ ID NO. 52. In another embodiment, said miR mimics imitate or mimic hsa-miR-517a, wherein said miR mimics have a sequence at least about 70%, 80%, 90%, 95%, 98% or 100% identical to SEQ ID NO. 53. In another embodiment, said miR mimics imitate or mimic hsa-miR-541*, wherein said miR mimics have a sequence at least about 70%, 80%, 90%, 95%, 98% or 100% identical to SEQ ID NO. 54. In another embodiment, said miR mimics imitate or mimic hsa-miR-1293, wherein said miR mimics have a sequence at least about 70%, 80%, 90%, 95%, 98% or 100% identical to SEQ ID NO. 55. In another embodiment, said miR mimics imitate or mimic hsa-miR-339-5p, wherein said miR mimics have a sequence at least about 70%, 80%, 90%, 95%, 98% or 100% identical to SEQ ID NO. 56. In another embodiment, said miR mimics imitate or mimic hsa-miR-494, wherein said miR mimics have a sequence at least about 70%, 80%, 90%, 95%, 98% or 100% identical to SEQ ID NO. 57. In another embodiment, said miR mimics imitate or mimic hsa-miR-196a*, wherein said miR mimics have a sequence at least about 70%, 80%, 90%, 95%, 98% or 100% identical to SEQ ID NO. 58. In another embodiment, said miR mimics imitate or mimic hsa-miR-1, wherein said miR mimics have a sequence at least about 70%, 80%, 90%, 95%, 98% or 100% identical to SEQ ID NO. 228. In another embodiment, said miR mimics imitate or mimic hsa-miR-129*, wherein said miR mimics have a sequence at least about 70%, 80%, 90%, 95%, 98% or 100% identical to SEQ ID NO. 229. In another embodiment, said miR mimics imitate or mimic hsa-miR-24, wherein said miR mimics have a sequence at least about 70%, 80%, 90%, 95%, 98% or 100% identical to SEQ ID NO. 230. In another embodiment, said miR mimics imitate or mimic hsa-miR-24-1*, wherein said miR mimics have a sequence at least about 70%, 80%, 90%, 95%, 98% or 100% identical to SEQ ID NO. 231. In another embodiment, said miR mimics imitate or mimic hsa-miR-218-1*, wherein said miR mimics have a sequence at least about 70%, 80%, 90%, 95%, 98% or 100% identical to SEQ ID NO. 232. In another embodiment, said miR mimics imitate or mimic hsa-miR-183, wherein said miR mimics have a sequence at least about 70%, 80%, 90%, 95%, 98% or 100% identical to SEQ ID NO. 233. In another embodiment, said miR mimics imitate or mimic hsa-miR-183*, wherein said miR mimics have a sequence at least about 70%, 80%, 90%, 95%, 98% or 100% identical to SEQ ID NO. 234.

TABLE 2

Sequences of miRs

| Target miR | Mature Sequence of Target miR | SEQ ID NO |
|---|---|---|
| hsa-miR-183 | UAUGGCACUGGUAGAAUUCACU | 15 |
| hsa-miR-491-5p | AGUGGGGAACCCUUCCAUGAGG | 16 |
| hsa-miR-132* | ACCGUGGCUUUCGAUUGUUACU | 17 |
| hsa-miR-129-5p | CUUUUUGCGGUCUGGGCUUGC | 18 |
| hsa-miR-636 | UGUGCUUGCUCGUCCCGCCCGCA | 19 |
| hsa-miR-100 | AACCCGUAGAUCCGAACUUGUG | 20 |
| hsa-miR-181a | AACAUUCAACGCUGUCGGUGAGU | 21 |
| hsa-miR-519a | AAAGUGCAUCCUUUUAGAGUGU | 22 |
| hsa-miR-338-3p | UCCAGCAUCAGUGAUUUUGUUG | 23 |
| hsa-miR-1179 | AAGCAUUCUUUCAUUGGUUGG | 24 |
| hsa-miR-521 | AACGCACUUCCCUUUAGAGUGU | 25 |
| hsa-miR-608 | AGGGGUGGUGUUGGGACAGCUCCGU | 26 |
| hsa-miR-1306 | ACGUUGGCUCUGGUGGUG | 27 |
| hsa-miR-543 | AAACAUUCGCGGUGCACUUCUU | 28 |
| hsa-miR-542-3p | UGUGACAGAUUGAUAACUGAAA | 29 |

TABLE 2-continued

Sequences of miRs

| Target miR | Mature Sequence of Target miR | SEQ ID NO |
|---|---|---|
| hsa-miR-23b | AUCACAUUGCCAGGGAUUACC | 30 |
| hsa-miR-299-3p | UAUGUGGGAUGGUAAACCGCUU | 31 |
| hsa-miR-597 | UGUGUCACUCGAUGACCACUGU | 32 |
| hsa-miR-1976 | CCUCCUGCCCUCCUUGCUGU | 33 |
| hsa-miR-1252 | AGAAGGAAAUUGAAUUCAUUUA | 34 |
| hsa-miR-510 | UACUCAGGAGAGUGGCAAUCAC | 35 |
| hsa-miR-1207-5p | UGGCAGGGAGGCUGGGAGGGG | 36 |
| hsa-miR-518a-3p | GAAAGCGCUUCCCUUUGCUGGA | 37 |
| hsa-miR-1250 | ACGGUGCUGGAUGUGGCCUUU | 38 |
| hsa-miR-1274a | GUCCCUGUUCAGGCGCCA | 39 |
| hsa-miR-141* | CAUCUUCCAGUACAGUGUUGGA | 40 |
| hsa-miR-9* | AUAAAGCUAGAUAACCGAAAGU | 41 |
| hsa-miR-566 | GGGCGCCUGUGAUCCCAAC | 42 |
| hsa-miR-142-5p | CAUAAAGUAGAAAGCACUACU | 43 |
| hsa-miR-23a* | GGGGUUCCUGGGGAUGGGAUUU | 44 |
| hsa-miR-519e* | UUCUCCAAAAGGGAGCACUUUC | 45 |
| hsa-miR-1292 | UGGGAACGGGUUCCGGCAGACGCUG | 46 |
| hsa-miR-96 | UUUGGCACUAGCACAUUUUGCU | 47 |
| hsa-miR-886-3p | CGCGGGUGCUUACUGACCCUU | 48 |
| hsa-miR-216b | AAAUCUCUGCAGGCAAAUGUGA | 49 |
| hsa-miR-218-2* | CAUGGUUCUGUCAAGCACCGCG | 50 |
| hsa-miR-182 | UUUGGCAAUGGUAGAACUCACACU | 51 |
| hsa-miR-545* | UCAGUAAAUGUUUAUUAGAUGA | 52 |
| hsa-miR-517a | AUCGUGCAUCCCUUUAGAGUGU | 53 |
| hsa-miR-541* | AAAGGAUUCUGCUGUCGGUCCCACU | 54 |
| hsa-miR-1293 | UGGGUGGUCUGGAGAUUUGUGC | 55 |
| hsa-miR-339-5p | UCCCUGUCCUCCAGGAGCUCACG | 56 |
| hsa-miR-494 | UGAAACAUACACGGGAAACCUC | 57 |
| hsa-miR-196a* | CGGCAACAAGAAACUGCCUGAG | 58 |
| hsa-miR-371-5p | ACUCAAACUGUGGGGGCACU | 59 |
| hsa-miR-136* | CAUCAUCGUCUCAAAUGAGUCU | 60 |
| hsa-miR-214 | ACAGCAGGCACAGACAGGCAGU | 61 |
| hsa-miR-25* | AGGCGGAGACUUGGGCAAUUG | 62 |
| hsa-miR-452* | CUCAUCUGCAAAGAAGUAAGUG | 63 |
| hsa-miR-454* | ACCCUAUCAAUAUUGUCUCUGC | 64 |
| hsa-miR-548b-5p | AAAAGUAAUUGUGGUUUUUGGCC | 65 |
| hsa-miR-10b* | ACAGAUUCGAUUCUAGGGGAAU | 66 |
| hsa-miR-218 | UUGUGCUUGAUCUAACCAUGU | 67 |
| hsa-miR-548m | CAAAGGUAUUUGUGGUUUUUG | 68 |
| hsa-miR-520a-3p | AAAGUGCUUCCCUUUGGACUGU | 69 |
| hsa-miR-1323 | UCAAAACUGAGGGGCAUUUUCU | 70 |
| hsa-miR-24-2* | UGCCUACUGAGCUGAAACACAG | 71 |
| hsa-miR-613 | AGGAAUGUUCCUUCUUUGCC | 72 |
| hsa-miR-26a | UUCAAGUAAUCCAGGAUAGGCU | 73 |
| hsa-miR-193a-3p | AACUGGCCUACAAAGUCCCAGU | 74 |
| hsa-miR-1208 | UCACUGUUCAGACAGGCGGA | 75 |
| hsa-miR-767-5p | UGCACCAUGGUUGUCUGAGCAUG | 76 |
| hsa-miR-491-3p | CUUAUGCAAGAUUCCCUUCUAC | 77 |
| hsa-miR-626 | AGCUGUCUGAAAAUGUCUU | 78 |
| hsa-miR-216a | UAAUCUCAGCUGGCAACUGUGA | 79 |
| hsa-miR-151-5p | UCGAGGAGCUCACAGUCUAGU | 80 |
| hsa-miR-1282 | UCGUUUGCCUUUUUCUGCUU | 81 |
| hsa-miR-497* | CAAACCACACUGUGGUGUUAGA | 82 |
| hsa-miR-129-3p | AAGCCCUUACCCCAAAAAGCAU | 83 |

In another embodiment, said enhanced placental stem cells (ePSCs) have increased cyclooxygenase II (Cox-2) activity, e.g., as compared to an equivalent number of unmodified placental stem cells. In one embodiment, said Cox-2 activity is induced by IL-1β. In a specific embodiment, said miR inhibitors target (e.g., modulate, reduce the level of) one or more miRs in said ePSCs that modulate the activity of said Cox-2 in said ePSCs such that the activity of said Cox-2 in said ePSCs is increased, e.g., as compared to an equivalent number of unmodified placental stem cells. In another specific embodiment, said miR inhibitors target (e.g., modulate, up-regulate) one or more genes in said ePSCs that modulate the activity of said Cox-2 such that the activity of said Cox-2 in said ePSCs is increased, e.g., as compared to an equivalent number of unmodified placental stem cells.

In another specific embodiment, said miR mimics imitate or mimic one or more miRs in said ePSCs that modulate the activity of Cox-2 in said ePSCs such that the activity of said Cox-2 in said ePSCs is increased, e.g., as compared to the activity of said Cox-2 in an equivalent number of unmodified placental stem cells. In another specific embodiment, said miR mimics target one or more genes in said ePSCs that modulate the activity of said Cox-2 in said ePSCs such that the activity of said Cox-2 in said ePSCs is increased, e.g., as compared to an equivalent number of unmodified placental stem cells.

In another embodiment, said enhanced placental stem cells (ePSCs) have increased production of prostaglandin E2 (PGE2), e.g., as compared to an equivalent number of unmodified placental stem cells. In one embodiment, said production of PGE2 production is induced by IL-1β. In a specific embodiment, said miR inhibitors target (e.g., modulate, reduce the level of) one or more miRs in said ePSCs that modulate the production of PGE2 by said ePSCs such that the production of PGE2 by said ePSCs is increased, e.g., as compared to an equivalent number of unmodified placental stem cells. In a specific embodiment, said miR inhibitors target (e.g., modulate, up-regulate) one or more genes in said ePSCs that modulate the production of PGE2 by said ePSCs such that the production of PGE2 by said ePSCs is increased, e.g., as compared to an equivalent number of unmodified placental stem cells.

In a specific embodiment, said miR mimics imitate or mimic one or more miRs in said ePSCs that modulate the production of PGE2 by said ePSCs such that the production of PGE2 by said ePSCs is increased, e.g., as compared to an equivalent number of unmodified placental stem cells. In a specific embodiment, said miR mimics target one or more genes in said ePSCs that modulate the production of PGE2 by said ePSCs such that the production of PGE2 by said ePSCs is increased, e.g., as compared to an equivalent number of unmodified placental stem cells.

In certain embodiments, said miR inhibitors target (e.g., modulate) one or more miRs listed in Table 3 (see the column designated as "Target miR"). In a specific embodiment, said miR inhibitors target (e.g., modulate, reduce the level of) one or more miRs listed in Table 3 (see the column designated as "Target miR") in said ePSCs such that the production of PGE2 by said ePSCs is increased, e.g., as compared to an equivalent number of unmodified placental stem cells. In another specific embodiment, said miR inhibitors have a sequence that is at least about 70%, 80%, 90%, 95%, 98% or 100% identical to any of SEQ ID NO: 21, 27, 28, 30, 35, 39, 41, 42, 48, 52-54, 62, 72, 73, 79, 81, and 84-222, or the complement thereof.

In certain embodiments, said miR mimics imitate or mimic one or more miRs listed in Table 3 (see the column designated as "Target miR"). In a specific embodiment, said miR mimics imitate or mimic one or more miRs listed in Table 3 (see the column designated as "Target miR") in said ePSCs such that the production of PGE2 by said ePSCs is increased, e.g., as compared to an equivalent number of unmodified placental stem cells. In another specific embodiment, said miR mimics have a sequence at least about 70%, 80%, 90%, 95%, 98% or 100% identical to any of SEQ ID NO: 21, 27, 28, 30, 35, 39, 41, 42, 48, 52-54, 62, 72, 73, 79, 81, and 84-222, or the complement thereof.

In another embodiment, said miR inhibitors target (e.g., modulate) hsa-miR-495, wherein said miR inhibitors have a sequence at least about 70%, 80%, 90%, 95%, 98% or 100% identical to SEQ ID NO. 181, or the complement thereof. In another embodiment, said miR inhibitors target (e.g., modulate) hsa-miR-516a-3p, wherein said miR inhibitors have a sequence at least about 70%, 80%, 90%, 95%, 98% or 100% identical to SEQ ID NO. 182, or the complement thereof. In another embodiment, said miR inhibitors target (e.g., modulate) hsa-miR-938, wherein said miR inhibitors have a sequence at least about 70%, 80%, 90%, 95%, 98% or 100% identical to SEQ ID NO. 183, or the complement thereof. In another embodiment, said miR inhibitors target (e.g., modulate) hsa-miR-936, wherein said miR inhibitors have a sequence at least about 70%, 80%, 90%, 95%, 98% or 100% identical to SEQ ID NO. 184, or the complement thereof. In another embodiment, said miR inhibitors target (e.g., modulate) hsa-miR-373*, wherein said miR inhibitors have a sequence at least about 70%, 80%, 90%, 95%, 98% or 100% identical to SEQ ID NO. 185, or the complement thereof. In another embodiment, said miR inhibitors target (e.g., modulate) hsa-miR-1184, wherein said miR inhibitors have a sequence at least about 70%, 80%, 90%, 95%, 98% or 100% identical to SEQ ID NO. 186, or the complement thereof. In another embodiment, said miR inhibitors target (e.g., modulate) hsa-miR-122, wherein said miR inhibitors have a sequence at least about 70%, 80%, 90%, 95%, 98% or 100% identical to SEQ ID NO. 187, or the complement thereof. In another embodiment, said miR inhibitors target (e.g., modulate) hsa-miR-208b, wherein said miR inhibitors have a sequence at least about 70%, 80%, 90%, 95%, 98% or 100% identical to SEQ ID NO. 188, or the complement thereof. In another embodiment, said miR inhibitors target (e.g., modulate) hsa-miR-223*, wherein said miR inhibitors have a sequence at least about 70%, 80%, 90%, 95%, 98% or 100% identical to SEQ ID NO. 189, or the complement thereof. In another embodiment, said miR inhibitors target (e.g., modulate) hsa-miR-1972, wherein said miR inhibitors have a sequence at least about 70%, 80%, 90%, 95%, 98% or 100% identical to SEQ ID NO. 190, or the complement thereof.

In another embodiment, said miR inhibitors target (e.g., modulate) hsa-miR-520h, wherein said miR inhibitors have a sequence at least about 70%, 80%, 90%, 95%, 98% or 100% identical to SEQ ID NO. 191, or the complement thereof. In another embodiment, said miR inhibitors target (e.g., modulate) hsa-miR-330-3p, wherein said miR inhibitors have a sequence at least about 70%, 80%, 90%, 95%, 98% or 100% identical to SEQ ID NO. 192, or the complement thereof. In another embodiment, said miR inhibitors target (e.g., modulate) hsa-miR-149, wherein said miR inhibitors have a sequence at least about 70%, 80%, 90%, 95%, 98% or 100% identical to SEQ ID NO. 193, or the complement thereof. In another embodiment, said miR inhibitors target (e.g., modulate) hsa-miR-7, wherein said miR inhibitors have a sequence at least about 70%, 80%, 90%, 95%, 98% or 100% identical to SEQ ID NO. 194, or the complement thereof. In another embodiment, said miR inhibitors target (e.g., modulate) hsa-miR-29b-2*, wherein said miR inhibitors have a sequence at least about 70%, 80%, 90%, 95%, 98% or 100% identical to SEQ ID NO. 195, or the complement thereof. In another embodiment, said miR inhibitors target (e.g., modulate) hsa-miR-520d-5p, wherein said miR inhibitors have a sequence at least about 70%, 80%, 90%, 95%, 98% or 100% identical to SEQ ID NO. 196, or the complement thereof.

In another embodiment, said miR inhibitors target (e.g., modulate) hsa-miR-592, wherein said miR inhibitors have a sequence at least about 70%, 80%, 90%, 95%, 98% or 100% identical to SEQ ID NO. 197, or the complement thereof. In another embodiment, said miR inhibitors target (e.g., modulate) hsa-miR-940, wherein said miR inhibitors have a sequence at least about 70%, 80%, 90%, 95%, 98% or 100% identical to SEQ ID NO. 198, or the complement thereof. In another embodiment, said miR inhibitors target (e.g., modulate) hsa-miR-146b-3p, wherein said miR inhibitors have a sequence at least about 70%, 80%, 90%, 95%, 98% or 100% identical to SEQ ID NO. 199, or the complement thereof. In another embodiment, said miR inhibitors target (e.g., modulate) hsa-miR-518e*, wherein said miR inhibitors have a sequence at least about 70%, 80%, 90%, 95%, 98% or 100% identical to SEQ ID NO. 200, or the complement thereof. In another embodiment, said miR inhibitors target (e.g., modulate) hsa-miR-1255a, wherein said miR inhibitors have a sequence at least about 70%, 80%, 90%, 95%, 98% or 100% identical to SEQ ID NO. 201, or the complement thereof. In another embodiment, said miR inhibitors target (e.g., modulate) hsa-miR-935, wherein said miR inhibitors have a sequence at least about 70%, 80%, 90%, 95%, 98% or 100% identical to SEQ ID NO. 202, or the complement thereof. In another embodiment, said miR inhibitors target (e.g., modulate) hsa-miR-633, wherein said miR inhibitors have a sequence at least about 70%, 80%, 90%, 95%, 98% or 100% identical to SEQ ID NO. 203, or the complement thereof. In another embodiment, said miR inhibitors target (e.g., modulate) hsa-miR-513a-5p, wherein said miR inhibitors have a sequence at least about 70%, 80%, 90%, 95%, 98% or 100% identical to SEQ ID NO. 204, or the complement thereof.

In another embodiment, said miR inhibitors target (e.g., modulate) hsa-miR-361-3p, wherein said miR inhibitors have a sequence at least about 70%, 80%, 90%, 95%, 98% or 100% identical to SEQ ID NO. 205, or the complement thereof. In another embodiment, said miR inhibitors target (e.g., modulate) hsa-miR-194, wherein said miR inhibitors have a sequence at least about 70%, 80%, 90%, 95%, 98% or 100% identical to SEQ ID NO. 206, or the complement thereof. In another embodiment, said miR inhibitors target (e.g., modulate) hsa-miR-1185, wherein said miR inhibitors have a sequence at least about 70%, 80%, 90%, 95%, 98% or 100% identical to SEQ ID NO. 207, or the complement thereof. In another embodiment, said miR inhibitors target (e.g., modulate) hsa-miR-875-3p, wherein said miR inhibitors have a sequence at least about 70%, 80%, 90%, 95%, 98% or 100% identical to SEQ ID NO. 208, or the complement thereof. In another embodiment, said miR inhibitors target (e.g., modulate) hsa-miR-200a, wherein said miR inhibitors have a sequence at least about 70%, 80%, 90%, 95%, 98% or 100% identical to SEQ ID NO. 209, or the complement thereof. In another embodiment, said miR inhibitors target (e.g., modulate) hsa-miR-1201, wherein said miR inhibitors have a sequence at least about 70%, 80%, 90%, 95%, 98% or 100% identical to SEQ ID NO. 210, or the complement thereof.

In another embodiment, said miR inhibitors target (e.g., modulate) hsa-miR-629, wherein said miR inhibitors have a sequence at least about 70%, 80%, 90%, 95%, 98% or 100% identical to SEQ ID NO. 211, or the complement thereof. In another embodiment, said miR inhibitors target (e.g., modulate) hsa-miR-139-5p, wherein said miR inhibitors have a sequence at least about 70%, 80%, 90%, 95%, 98% or 100% identical to SEQ ID NO. 212, or the complement thereof. In another embodiment, said miR inhibitors target (e.g., modulate) hsa-miR-504, wherein said miR inhibitors have a sequence at least about 70%, 80%, 90%, 95%, 98% or 100% identical to SEQ ID NO. 213, or the complement thereof. In another embodiment, said miR inhibitors target (e.g., modulate) hsa-miR-452, wherein said miR inhibitors have a sequence at least about 70%, 80%, 90%, 95%, 98% or 100% identical to SEQ ID NO. 214, or the complement thereof. In another embodiment, said miR inhibitors target (e.g., modulate) hsa-miR-517a, wherein said miR inhibitors have a sequence at least about 70%, 80%, 90%, 95%, 98% or 100% identical to SEQ ID NO. 53, or the complement thereof. In another embodiment, said miR inhibitors target (e.g., modulate) hsa-miR-543, wherein said miR inhibitors have a sequence at least about 70%, 80%, 90%, 95%, 98% or 100% identical to SEQ ID NO. 28, or the complement thereof. In another embodiment, said miR inhibitors target (e.g., modulate) hsa-miR-616*, wherein said miR inhibitors have a sequence at least about 70%, 80%, 90%, 95%, 98% or 100% identical to SEQ ID NO. 215, or the complement thereof. In another embodiment, said miR inhibitors target (e.g., modulate) hsa-miR-651, wherein said miR inhibitors have a sequence at least about 70%, 80%, 90%, 95%, 98% or 100% identical to SEQ ID NO. 216, or the complement thereof.

In another embodiment, said miR inhibitors target (e.g., modulate) hsa-miR-1254, wherein said miR inhibitors have a sequence at least about 70%, 80%, 90%, 95%, 98% or 100% identical to SEQ ID NO. 217, or the complement thereof. In another embodiment, said miR inhibitors target (e.g., modulate) hsa-miR-339-3p, wherein said miR inhibitors have a sequence at least about 70%, 80%, 90%, 95%, 98% or 100% identical to SEQ ID NO. 218, or the complement thereof. In another embodiment, said miR inhibitors target (e.g., modulate) hsa-miR-510, wherein said miR inhibitors have a sequence at least about 70%, 80%, 90%, 95%, 98% or 100% identical to SEQ ID NO. 35, or the complement thereof. In another embodiment, said miR inhibitors target (e.g., modulate) hsa-miR-181c*, wherein said miR inhibitors have a sequence at least about 70%, 80%, 90%, 95%, 98% or 100% identical to SEQ ID NO. 219, or the complement thereof. In another embodiment, said miR inhibitors target (e.g., modulate) hsa-miR-19b-1*, wherein said miR inhibitors have a sequence at least about 70%, 80%, 90%, 95%, 98% or 100% identical to SEQ ID NO. 220, or the complement thereof.

In another embodiment, said miR inhibitors target (e.g., modulate) hsa-miR-1274a, wherein said miR inhibitors have a sequence at least about 70%, 80%, 90%, 95%, 98% or 100% identical to SEQ ID NO. 39, or the complement thereof. In another embodiment, said miR inhibitors target (e.g., modulate) hsa-miR-1294, wherein said miR inhibitors have a sequence at least about 70%, 80%, 90%, 95%, 98% or 100% identical to SEQ ID NO. 221, or the complement thereof. In another embodiment, said miR inhibitors target (e.g., modulate) hsa-miR-1306, wherein said miR inhibitors have a sequence at least about 70%, 80%, 90%, 95%, 98% or 100% identical to SEQ ID NO. 27, or the complement thereof. In another embodiment, said miR inhibitors target (e.g., modulate) hsa-miR-1226*, wherein said miR inhibitors have a sequence at least about 70%, 80%, 90%, 95%, 98% or 100% identical to SEQ ID NO. 222, or the complement thereof. In another embodiment, said miR inhibitors target (e.g., modulate) hsa-miR-541*, wherein said miR inhibitors have a sequence at least about 70%, 80%, 90%, 95%, 98% or 100% identical to SEQ ID NO. 54, or the complement thereof.

In another embodiment, said miR mimics imitate or mimic hsa-miR-886-3p, wherein said miR mimics have a sequence at least about 70%, 80%, 90%, 95%, 98% or 100% identical to SEQ ID NO. 48. In another embodiment, said miR mimics imitate or mimic hsa-miR-371-3p, wherein said miR mimics have a sequence at least about 70%, 80%, 90%, 95%, 98% or 100% identical to SEQ ID NO. 84. In another embodiment, said miR mimics imitate or mimic hsa-miR-25*, wherein said miR mimics have a sequence at least about 70%, 80%, 90%, 95%, 98% or 100% identical to SEQ ID NO. 62. In another embodiment, said miR mimics imitate or mimic hsa-miR-376c, wherein said miR mimics have a sequence at least about 70%, 80%, 90%, 95%, 98% or 100% identical to SEQ ID NO. 85. In another embodiment, said miR mimics imitate or mimic hsa-miR-888, wherein said miR mimics have a sequence at least about 70%, 80%, 90%, 95%, 98% or 100% identical to SEQ ID NO. 86. In another embodiment, said miR mimics imitate or mimic hsa-miR-517b, wherein said miR mimics have a sequence at least about 70%, 80%, 90%, 95%, 98% or 100% identical to SEQ ID NO. 87. In another embodiment, said miR mimics imitate or mimic hsa-miR-433, wherein said miR mimics have a sequence at least about 70%, 80%, 90%, 95%, 98% or 100% identical to SEQ ID NO. 88.

In another embodiment, said miR mimics imitate or mimic hsa-miR-200a*, wherein said miR mimics have a sequence at least about 70%, 80%, 90%, 95%, 98% or 100% identical to SEQ ID NO. 89. In another embodiment, said miR mimics imitate or mimic hsa-miR-520a-5p, wherein said miR mimics have a sequence at least about 70%, 80%, 90%, 95%, 98% or 100% identical to SEQ ID NO. 90. In another embodiment, said miR mimics imitate or mimic hsa-miR-1286, wherein said miR mimics have a sequence at least about 70%, 80%, 90%, 95%, 98% or 100% identical to SEQ ID NO. 91. In another embodiment, said miR mimics imitate or mimic hsa-miR-182*, wherein said miR mimics have a sequence at least about 70%, 80%, 90%, 95%, 98% or 100% identical to SEQ ID NO. 92. In another embodiment, said miR mimics imitate or mimic hsa-miR-1273, wherein said miR mimics have a sequence at least about 70%, 80%, 90%, 95%, 98% or 100% identical to SEQ ID NO. 93. In another embodiment, said miR mimics imitate or mimic hsa-miR-1280, wherein said miR mimics have a sequence at least about 70%, 80%, 90%, 95%, 98% or 100% identical to SEQ ID NO. 94. In another embodiment, said miR mimics imitate or mimic hsa-miR-563, wherein said miR mimics have a sequence at least about 70%, 80%, 90%, 95%, 98% or 100% identical to SEQ ID NO. 95. In another embodiment, said miR mimics imitate or mimic hsa-miR-501-5p, wherein said miR mimics have a sequence at least about 70%, 80%, 90%, 95%, 98% or 100% identical to SEQ ID NO. 96. In another embodiment, said miR mimics imitate or mimic hsa-miR-448, wherein said miR mimics have a sequence at least about 70%, 80%, 90%, 95%, 98% or 100% identical to SEQ ID NO. 97. In another embodiment, said miR mimics imitate or mimic hsa-miR-485-3p, wherein said miR mimics have a sequence at least about 70%, 80%, 90%, 95%, 98% or 100% identical to SEQ ID NO. 98.

In another embodiment, said miR mimics imitate or mimic hsa-miR-29c, wherein said miR mimics have a sequence at least about 70%, 80%, 90%, 95%, 98% or 100% identical to SEQ ID NO. 99. In another embodiment, said miR mimics imitate or mimic hsa-miR-548f, wherein said miR mimics have a sequence at least about 70%, 80%, 90%, 95%, 98% or 100% identical to SEQ ID NO. 100. In another embodiment, said miR mimics imitate or mimic hsa-miR-1248, wherein said miR mimics have a sequence at least about 70%, 80%, 90%, 95%, 98% or 100% identical to SEQ ID NO. 101. In another embodiment, said miR mimics imitate or mimic hsa-let-7d*, wherein said miR mimics have a sequence at least about 70%, 80%, 90%, 95%, 98% or 100% identical to SEQ ID NO. 102. In another embodiment, said miR mimics imitate or mimic hsa-miR-618, wherein said miR mimics have a sequence at least about 70%, 80%, 90%, 95%, 98% or 100% identical to SEQ ID NO. 103. In another embodiment, said miR mimics imitate or mimic hsa-miR-30c, wherein said miR mimics have a sequence at least about 70%, 80%, 90%, 95%, 98% or 100% identical to SEQ ID NO. 104. In another embodiment, said miR mimics imitate or mimic hsa-miR-136, wherein said miR mimics have a sequence at least about 70%, 80%, 90%, 95%, 98% or 100% identical to SEQ ID NO. 105.

In another embodiment, said miR mimics imitate or mimic hsa-miR-181a, wherein said miR mimics have a sequence at least about 70%, 80%, 90%, 95%, 98% or 100% identical to SEQ ID NO. 21. In another embodiment, said miR mimics imitate or mimic hsa-miR-26a, wherein said miR mimics have a sequence at least about 70%, 80%, 90%, 95%, 98% or 100% identical to SEQ ID NO. 73. In another embodiment, said miR mimics imitate or mimic hsa-miR-10a, wherein said miR mimics have a sequence at least about 70%, 80%, 90%, 95%, 98% or 100% identical to SEQ ID NO. 106. In another embodiment, said miR mimics imitate or mimic hsa-miR-557, wherein said miR mimics have a sequence at least about 70%, 80%, 90%, 95%, 98% or 100% identical to SEQ ID NO. 107. In another embodiment, said miR mimics imitate or mimic hsa-miR-564, wherein said miR mimics have a sequence at least about 70%, 80%, 90%, 95%, 98% or 100% identical to SEQ ID NO. 108. In another embodiment, said miR mimics imitate or mimic hsa-miR-520g, wherein said miR mimics have a sequence at least about 70%, 80%, 90%, 95%, 98% or 100% identical to SEQ ID NO. 109. In another embodiment, said miR mimics imitate or mimic hsa-miR-122*, wherein said miR mimics have a sequence at least about 70%, 80%, 90%, 95%, 98% or 100% identical to SEQ ID NO. 110. In another embodiment, said miR mimics imitate or mimic hsa-miR-548k, wherein said miR mimics have a sequence at least about 70%, 80%, 90%, 95%, 98% or 100% identical to SEQ ID NO. 111. In another embodiment, said miR mimics imitate or mimic hsa-miR-423-3p, wherein said miR mimics have a sequence at least about 70%, 80%, 90%, 95%, 98% or 100% identical to SEQ ID NO. 112. In another embodiment, said miR mimics imitate or mimic hsa-miR-548j, wherein said miR mimics have a sequence at least about 70%, 80%, 90%, 95%, 98% or 100% identical to SEQ ID NO. 113.

In another embodiment, said miR mimics imitate or mimic hsa-miR-340*, wherein said miR mimics have a sequence at least about 70%, 80%, 90%, 95%, 98% or 100% identical to SEQ ID NO. 114. In another embodiment, said miR mimics imitate or mimic hsa-miR-573, wherein said miR mimics have a sequence at least about 70%, 80%, 90%, 95%, 98% or 100% identical to SEQ ID NO. 115. In another embodiment, said miR mimics imitate or mimic hsa-miR-548i, wherein said miR mimics have a sequence at least about 70%, 80%, 90%, 95%, 98% or 100% identical to SEQ ID NO. 116. In another embodiment, said miR mimics imitate or mimic hsa-miR-555, wherein said miR mimics have a sequence at least about 70%, 80%, 90%, 95%, 98% or 100% identical to SEQ ID NO. 117. In another embodiment, said miR mimics imitate or mimic hsa-miR-144, wherein said miR mimics have a sequence at least about 70%, 80%, 90%, 95%, 98% or 100% identical to SEQ ID NO. 118. In another embodiment, said miR mimics imitate or mimic hsa-miR-567, wherein said miR mimics have a sequence at least about 70%, 80%, 90%, 95%, 98% or 100% identical to SEQ ID NO. 119. In another embodiment, said miR mimics imitate or mimic hsa-miR-191*, wherein said miR mimics have a sequence at least about 70%, 80%, 90%, 95%, 98% or 100% identical to SEQ ID NO. 120. In another embodiment, said miR mimics imitate or mimic hsa-miR-566, wherein said miR mimics have a sequence at least about 70%, 80%, 90%, 95%, 98% or 100% identical to SEQ ID NO. 42.

In another embodiment, said miR mimics imitate or mimic hsa-miR-335, wherein said miR mimics have a sequence at least about 70%, 80%, 90%, 95%, 98% or 100% identical to SEQ ID NO. 121. In another embodiment, said miR mimics imitate or mimic hsa-miR-126*, wherein said miR mimics have a sequence at least about 70%, 80%, 90%, 95%, 98% or 100% identical to SEQ ID NO. 122. In another embodiment, said miR mimics imitate or mimic hsa-miR-22*, wherein said miR mimics have a sequence at least about 70%, 80%, 90%, 95%, 98% or 100% identical to SEQ ID NO. 123. In another embodiment, said miR mimics imitate or mimic hsa-miR-572, wherein said miR mimics have a sequence at least about 70%, 80%, 90%, 95%, 98% or 100% identical to SEQ ID NO. 124. In another embodiment, said miR mimics imitate or mimic hsa-miR-517c, wherein said miR mimics have a sequence at least about 70%, 80%, 90%, 95%, 98% or 100% identical to SEQ ID NO. 125. In another embodiment, said miR mimics imitate or mimic hsa-miR-380*, wherein said miR mimics have a sequence at least about 70%, 80%, 90%, 95%, 98% or 100% identical to SEQ ID NO. 126. In another embodiment, said miR mimics imitate or mimic hsa-miR-106a*, wherein said miR mimics have a sequence at least about 70%, 80%, 90%, 95%, 98% or 100% identical to SEQ ID NO. 127. In another embodiment, said miR mimics imitate or mimic hsa-miR-519e, wherein said miR mimics have a sequence at least about 70%, 80%, 90%, 95%, 98% or 100% identical to SEQ ID NO. 128. In another embodiment, said miR mimics imitate or mimic hsa-miR-520c-3p, wherein said miR mimics have a sequence at least about 70%, 80%, 90%, 95%, 98% or 100% identical to SEQ ID NO. 129.

In another embodiment, said miR mimics imitate or mimic hsa-miR-517*, wherein said miR mimics have a sequence at least about 70%, 80%, 90%, 95%, 98% or 100% identical to SEQ ID NO. 130. In another embodiment, said miR mimics imitate or mimic hsa-miR-432*, wherein said miR mimics have a sequence at least about 70%, 80%, 90%, 95%, 98% or 100% identical to SEQ ID NO. 131. In another embodiment, said miR mimics imitate or mimic hsa-miR-520e, wherein said miR mimics have a sequence at least about 70%, 80%, 90%, 95%, 98% or 100% identical to SEQ ID NO. 132. In another embodiment, said miR mimics imitate or mimic hsa-miR-9*, wherein said miR mimics have a sequence at least about 70%, 80%, 90%, 95%, 98% or 100% identical to SEQ ID NO. 41. In another embodiment, said miR mimics imitate or mimic hsa-miR-551a, wherein said miR mimics have a sequence at least about 70%, 80%, 90%, 95%, 98% or 100% identical to SEQ ID NO. 133. In another embodiment, said miR mimics imitate or mimic hsa-miR-1471, wherein said miR mimics have a sequence at least about 70%, 80%, 90%, 95%, 98% or 100% identical to SEQ ID NO. 134. In another embodiment, said miR mimics imitate or mimic hsa-miR-613, wherein said miR mimics have a sequence at least about 70%, 80%, 90%, 95%, 98% or 100% identical to SEQ ID NO. 72. In another embodiment, said miR mimics imitate or mimic hsa-miR-562, wherein said miR mimics have a sequence at least about 70%, 80%, 90%, 95%, 98% or 100% identical to SEQ ID NO. 135. In another embodiment, said miR mimics imitate or mimic hsa-miR-922, wherein said miR mimics have a sequence at least about 70%, 80%, 90%, 95%, 98% or 100% identical to SEQ ID NO. 136. In another embodiment, said miR mimics imitate or mimic hsa-miR-216a, wherein said miR mimics have a sequence at least about 70%, 80%, 90%, 95%, 98% or 100% identical to SEQ ID NO. 79. In another embodiment, said miR mimics imitate or mimic hsa-miR-499-5p, wherein said miR mimics have a sequence at least about 70%, 80%, 90%, 95%, 98% or 100% identical to SEQ ID NO. 137.

In another embodiment, said miR mimics imitate or mimic hsa-miR-25, wherein said miR mimics have a sequence at least about 70%, 80%, 90%, 95%, 98% or 100% identical to SEQ ID NO. 138. In another embodiment, said miR mimics imitate or mimic hsa-miR-197, wherein said miR mimics have a sequence at least about 70%, 80%, 90%, 95%, 98% or 100% identical to SEQ ID NO. 139. In another embodiment, said miR mimics imitate or mimic hsa-miR-500*, wherein said miR mimics have a sequence at least about 70%, 80%, 90%, 95%, 98% or 100% identical to SEQ ID NO. 140. In another embodiment, said miR mimics imitate or mimic hsa-miR-365*, wherein said miR mimics have a sequence at least about 70%, 80%, 90%, 95%, 98% or 100% identical to SEQ ID NO. 141. In another embodiment, said miR mimics imitate or mimic hsa-miR-1247, wherein said miR mimics have a sequence at least about 70%, 80%, 90%, 95%, 98% or 100% identical to SEQ ID NO. 142. In another embodiment, said miR mimics imitate or mimic hsa-miR-586, wherein said miR mimics have a sequence at least about 70%, 80%, 90%, 95%, 98% or 100% identical to SEQ ID NO. 143. In another embodiment, said miR mimics imitate or mimic hsa-miR-548d-3p, wherein said miR mimics have a sequence at least about 70%, 80%, 90%, 95%, 98% or 100% identical to SEQ ID NO. 144. In another embodiment, said miR mimics imitate or mimic hsa-miR-27a*, wherein said miR mimics have a sequence at least about 70%, 80%, 90%, 95%, 98% or 100% identical to SEQ ID NO. 145. In another embodiment, said miR mimics imitate or mimic hsa-miR-598, wherein said miR mimics have a sequence at least about 70%, 80%, 90%, 95%, 98% or 100% identical to SEQ ID NO. 146.

In another embodiment, said miR mimics imitate or mimic hsa-miR-609, wherein said miR mimics have a sequence at least about 70%, 80%, 90%, 95%, 98% or 100% identical to SEQ ID NO. 147. In another embodiment, said miR mimics imitate or mimic hsa-miR-132, wherein said miR mimics have a sequence at least about 70%, 80%, 90%, 95%, 98% or 100% identical to SEQ ID NO. 148. In another embodiment, said miR mimics imitate or mimic hsa-miR-411*, wherein said miR mimics have a sequence at least about 70%, 80%, 90%, 95%, 98% or 100% identical to SEQ ID NO. 149. In another embodiment, said miR mimics imitate or mimic hsa-miR-135a, wherein said miR mimics have a sequence at least about 70%, 80%, 90%, 95%, 98% or 100% identical to SEQ ID NO. 150. In another embodiment, said miR mimics imitate or mimic hsa-miR-31, wherein said miR mimics have a sequence at least about 70%, 80%, 90%, 95%, 98% or 100% identical to SEQ ID NO. 151. In another embodiment, said miR mimics imitate or mimic hsa-miR-181a*, wherein said miR mimics have a sequence at least about 70%, 80%, 90%, 95%, 98% or 100% identical to SEQ ID NO. 152. In another embodiment, said miR mimics imitate or mimic hsa-miR-1245, wherein said miR mimics have a sequence at least about 70%, 80%, 90%, 95%, 98% or 100% identical to SEQ ID NO. 153.

In another embodiment, said miR mimics imitate or mimic hsa-miR-758, wherein said miR mimics have a sequence at least about 70%, 80%, 90%, 95%, 98% or 100% identical to SEQ ID NO. 154. In another embodiment, said miR mimics imitate or mimic hsa-miR-924, wherein said miR mimics have a sequence at least about 70%, 80%, 90%, 95%, 98% or 100% identical to SEQ ID NO. 155. In another embodiment, said miR mimics imitate or mimic hsa-miR-1246, wherein said miR mimics have a sequence at least about 70%, 80%, 90%, 95%, 98% or 100% identical to SEQ ID NO. 156. In another embodiment, said miR mimics imitate or mimic hsa-miR-23b, wherein said miR mimics have a sequence at least about 70%, 80%, 90%, 95%, 98% or 100% identical to SEQ ID NO. 30. In another embodiment, said miR mimics imitate or mimic hsa-miR-631, wherein said miR mimics have a sequence at least about 70%, 80%, 90%, 95%, 98% or 100% identical to SEQ ID NO. 157. In another embodiment, said miR mimics imitate or mimic hsa-miR-1, wherein said miR mimics have a sequence at least about 70%, 80%, 90%, 95%, 98% or 100% identical to SEQ ID NO. 158. In another embodiment, said miR mimics imitate or mimic hsa-miR-920, wherein said miR mimics have a sequence at least about 70%, 80%, 90%, 95%, 98% or 100% identical to SEQ ID NO. 159. In another embodiment, said miR mimics imitate or mimic hsa-miR-589*, wherein said miR mimics have a sequence at least about 70%, 80%, 90%, 95%, 98% or 100% identical to SEQ ID NO. 160.

In another embodiment, said miR mimics imitate or mimic hsa-miR-638, wherein said miR mimics have a sequence at least about 70%, 80%, 90%, 95%, 98% or 100% identical to SEQ ID NO. 161. In another embodiment, said miR mimics imitate or mimic hsa-miR-1244, wherein said miR mimics have a sequence at least about 70%, 80%, 90%, 95%, 98% or 100% identical to SEQ ID NO. 162. In another embodiment, said miR mimics imitate or mimic hsa-miR-328, wherein said miR mimics have a sequence at least about 70%, 80%, 90%, 95%, 98% or 100% identical to SEQ ID NO. 163. In another embodiment, said miR mimics imitate or mimic hsa-let-71, wherein said miR mimics have a sequence at least about 70%, 80%, 90%, 95%, 98% or 100% identical to SEQ ID NO. 164. In another embodiment, said miR mimics imitate or mimic hsa-miR-429, wherein said miR mimics have a sequence at least about 70%, 80%, 90%, 95%, 98% or 100% identical to SEQ ID NO. 165. In another embodiment, said miR mimics imitate or mimic hsa-miR-380, wherein said miR mimics have a sequence at least about 70%, 80%, 90%, 95%, 98% or 100% identical to SEQ ID NO. 166. In another embodiment, said miR mimics imitate or mimic hsa-let-7b*, wherein said miR mimics have a sequence at least about 70%, 80%, 90%, 95%, 98% or 100% identical to SEQ ID NO. 167. In another embodiment, said miR mimics imitate or mimic hsa-miR-614, wherein said miR mimics have a sequence at least about 70%, 80%, 90%, 95%, 98% or 100% identical to SEQ ID NO. 168.

In another embodiment, said miR mimics imitate or mimic hsa-miR-1225-5p, wherein said miR mimics have a sequence at least about 70%, 80%, 90%, 95%, 98% or 100% identical to SEQ ID NO. 169. In another embodiment, said miR mimics imitate or mimic hsa-miR-545*, wherein said miR mimics have a sequence at least about 70%, 80%, 90%, 95%, 98% or 100% identical to SEQ ID NO. 52. In another embodiment, said miR mimics imitate or mimic hsa-miR-320c, wherein said miR mimics have a sequence at least about 70%, 80%, 90%, 95%, 98% or 100% identical to SEQ ID NO. 170. In another embodiment, said miR mimics imitate or mimic hsa-miR-579, wherein said miR mimics have a sequence at least about 70%, 80%, 90%, 95%, 98% or 100% identical to SEQ ID NO. 171. In another embodiment, said miR mimics imitate or mimic hsa-miR-1282, wherein said miR mimics have a sequence at least about 70%, 80%, 90%, 95%, 98% or 100% identical to SEQ ID NO. 81. In another embodiment, said miR mimics imitate or mimic hsa-miR-455-5p, wherein said miR mimics have a sequence at least about 70%, 80%, 90%, 95%, 98% or 100% identical to SEQ ID NO. 172.

In another embodiment, said miR mimics imitate or mimic hsa-miR-615-3p, wherein said miR mimics have a sequence at least about 70%, 80%, 90%, 95%, 98% or 100% identical to SEQ ID NO. 173. In another embodiment, said miR mimics imitate or mimic hsa-miR-585, wherein said miR mimics have a sequence at least about 70%, 80%, 90%, 95%, 98% or 100% identical to SEQ ID NO. 174. In another embodiment, said miR mimics imitate or mimic hsa-miR-559, wherein said miR mimics have a sequence at least about 70%, 80%, 90%, 95%, 98% or 100% identical to SEQ ID NO. 175. In another embodiment, said miR mimics imitate or mimic hsa-miR-561, wherein said miR mimics have a sequence at least about 70%, 80%, 90%, 95%, 98% or 100% identical to SEQ ID NO. 176. In another embodiment, said miR mimics imitate or mimic hsa-miR-191, wherein said miR mimics have a sequence at least about 70%, 80%, 90%, 95%, 98% or 100% identical to SEQ ID NO. 177. In another embodiment, said miR mimics imitate or mimic hsa-miR-187, wherein said miR mimics have a sequence at least about 70%, 80%, 90%, 95%, 98% or 100% identical to SEQ ID NO. 178. In another embodiment, said miR mimics imitate or mimic hsa-miR-29b, wherein said miR mimics have a sequence at least about 70%, 80%, 90%, 95%, 98% or 100% identical to SEQ ID NO. 179. In another embodiment, said miR mimics imitate or mimic hsa-miR-769-5p, wherein said miR mimics have a sequence at least about 70%, 80%, 90%, 95%, 98% or 100% identical to SEQ ID NO. 180.

TABLE 3

Sequences of miRs

| Target miR | Mature Sequence of Target miR | SEQ ID NO |
|---|---|---|
| hsa-miR-886-3p | CGCGGGUGCUUACUGACCCUU | 48 |
| hsa-miR-371-3p | AAGUGCCGCCAUCUUUUGAGUGU | 84 |
| hsa-miR-25* | AGGCGGAGACUUGGGCAAUUG | 62 |
| hsa-miR-376c | AACAUAGAGGAAAUUCCACGU | 85 |
| hsa-miR-888 | UACUCAAAAAGCUGUCAGUCA | 86 |
| hsa-miR-517b | UCGUGCAUCCCUUUAGAGUGUU | 87 |
| hsa-miR-433 | AUCAUGAUGGGCUCCUCGGUGU | 88 |
| hsa-miR-200a* | CAUCUUACCGGACAGUGCUGGA | 89 |
| hsa-miR-520a-5p | CUCCAGAGGGAAGUACUUUCU | 90 |
| hsa-miR-1286 | UGCAGGACCAAGAUGAGCCCU | 91 |
| hsa-miR-182* | UGGUUCUAGACUUGCCAACUA | 92 |
| hsa-miR-1273 | GGGCGACAAAGCAAGACUCUUUCUU | 93 |
| hsa-miR-1280 | UCCCACCGCUGCCACCC | 94 |
| hsa-miR-563 | AGGUUGACAUACGUUUCCC | 95 |
| hsa-miR-501-5p | AAUCCUUUGUCCCUGGGUGAGA | 96 |
| hsa-miR-448 | UUGCAUAUGUAGGAUGUCCCAU | 97 |
| hsa-miR-485-3p | GUCAUACACGGCUCUCCUCUCU | 98 |
| hsa-miR-29c | UAGCACCAUUUGAAAUCGGUUA | 99 |
| hsa-miR-548f | AAAAACUGUAAUUACUUUU | 100 |
| hsa-miR-1248 | ACCUUCUUGUAUAAGCACUGUGCUAAA | 101 |
| hsa-let-7d* | CUAUACGACCUGCUGCCUUUCU | 102 |
| hsa-miR-618 | AAACUCUACUUGUCCUUCUGAGU | 103 |
| hsa-miR-30c | UGUAAACAUCCUACACUCUCAGC | 104 |
| hsa-miR-136 | ACUCCAUUUGUUUUGAUGAUGGA | 105 |
| hsa-miR-181a | AACAUUCAACGCUGUCGGUGAGU | 21 |
| hsa-miR-26a | UUCAAGUAAUCCAGGAUAGGCU | 73 |
| hsa-miR-10a | UACCCUGUAGAUCCGAAUUUGUG | 106 |
| hsa-miR-557 | GUUUGCACGGGUGGGCCUUGUCU | 107 |
| hsa-miR-564 | AGGCACGGUGUCAGCAGGC | 108 |
| hsa-miR-520g | ACAAAGUGCUUCCCUUUAGAGUGU | 109 |
| hsa-miR-122* | AACGCCAUUAUCACACUAAAUA | 110 |
| hsa-miR-548k | AAAAGUACUUGCGGAUUUUGCU | 111 |
| hsa-miR-423-3p | AGCUCGGUCUGAGGCCCCUCAGU | 112 |
| hsa-miR-548j | AAAAGUAAUUGCGGUCUUUGGU | 113 |
| hsa-miR-340* | UCCGUCUCAGUUACUUUAUAGC | 114 |
| hsa-miR-573 | CUGAAGUGAUGUGUAACUGAUCAG | 115 |
| hsa-miR-548i | AAAAGUAAUUGCGGAUUUUGCC | 116 |

TABLE 3-continued

Sequences of miRs

| Target miR | Mature Sequence of Target miR | SEQ ID NO |
|---|---|---|
| hsa-miR-555 | AGGGUAAGCUGAACCUCUGAU | 117 |
| hsa-miR-144 | UACAGUAUAGAUGAUGUACU | 118 |
| hsa-miR-567 | AGUAUGUUCUUCCAGGACAGAAC | 119 |
| hsa-miR-191* | GCUGCGCUUGGAUUUCGUCCCC | 120 |
| hsa-miR-566 | GGGCGCCUGUGAUCCCAAC | 42 |
| hsa-miR-335 | UCAAGAGCAAUAACGAAAAAUGU | 121 |
| hsa-miR-126* | CAUUAUUACUUUUGGUACGCG | 122 |
| hsa-miR-22* | AGUUCUUCAGUGGCAAGCUUUA | 123 |
| hsa-miR-572 | GUCCGCUCGGCGGUGGCCCA | 124 |
| hsa-miR-517c | AUCGUGCAUCCUUUUAGAGUGU | 125 |
| hsa-miR-380* | UGGUUGACCAUAGAACAUGCGC | 126 |
| hsa-miR-106a* | CUGCAAUGUAAGCACUUCUUAC | 127 |
| hsa-miR-519e | AAGUGCCUCCUUUUAGAGUGUU | 128 |
| hsa-miR-520c-3p | AAAGUGCUUCCUUUUAGAGGGU | 129 |
| hsa-miR-517* | CCUCUAGAUGGAAGCACUGUCU | 130 |
| hsa-miR-432* | CUGGAUGGCUCCUCCAUGUCU | 131 |
| hsa-miR-520e | AAAGUGCUUCCUUUUGAGGG | 132 |
| hsa-miR-9* | AUAAAGCUAGAUAACCGAAAGU | 41 |
| hsa-miR-551a | GCGACCCACUCUUGGUUUCCA | 133 |
| hsa-miR-1471 | GCCCGCGUGUGGAGCCAGGUGU | 134 |
| hsa-miR-613 | AGGAAUGUUCCUUCUUUGCC | 72 |
| hsa-miR-562 | AAAGUAGCUGUACCAUUUGC | 135 |
| hsa-miR-922 | GCAGCAGAGAAUAGGACUACGUC | 136 |
| hsa-miR-216a | UAAUCUCAGCUGGCAACUGUGA | 79 |
| hsa-miR-499-5p | UUAAGACUUGCAGUGAUGUUU | 137 |
| hsa-miR-25 | CAUUGCACUUGUCUCGGUCUGA | 138 |
| hsa-miR-197 | UUCACCACCUUCUCCACCCAGC | 139 |
| hsa-miR-500* | AUGCACCUGGGCAAGGAUUCUG | 140 |
| hsa-miR-365* | AGGGACUUUCAGGGGCAGCUGU | 141 |
| hsa-miR-1247 | ACCCGUCCCGUUCGUCCCCGGA | 142 |
| hsa-miR-586 | UAUGCAUUGUAUUUUUAGGUCC | 143 |
| hsa-miR-548d-3p | CAAAAACCACAGUUUCUUUUGC | 144 |
| hsa-miR-27a* | AGGGCUUAGCUGCUUGUGAGCA | 145 |
| hsa-miR-598 | UACGUCAUCGUUGUCAUCGUCA | 146 |
| hsa-miR-609 | AGGGUGUUUCUCUCAUCUCU | 147 |
| hsa-miR-132 | UAACAGCUACAGCCAUGGUCG | 148 |
| hsa-miR-411* | UAUGUAACACGGUCCACUAACC | 149 |
| hsa-miR-135a | UAUGGCUUUUUAUUCCUAUGUGA | 150 |
| hsa-miR-31 | AGGCAAGAUGCUGGCAUAGCU | 151 |
| hsa-miR-181a* | ACCAUCGACCGUUGAUUGUACC | 152 |
| hsa-miR-1245 | AAGUGAUCUAAAGGCCUACAU | 153 |
| hsa-miR-758 | UUUGUGACCUGGUCCACUAACC | 154 |
| hsa-miR-924 | AGAGUCUUGUGAUGUCUUGC | 155 |
| hsa-miR-1246 | AAUGGAUUUUUGGAGCAGG | 156 |
| hsa-miR-23b | AUCACAUUGCCAGGGAUUACC | 30 |
| hsa-miR-631 | AGACCUGGCCCAGACCUCAGC | 157 |
| hsa-miR-1 | UGGAAUGUAAAGAAGUAUGUAU | 158 |
| hsa-miR-920 | GGGGAGCUGUGGAAGCAGUA | 159 |
| hsa-miR-589* | UCAGAACAAAUGCCGGUUCCCAGA | 160 |
| hsa-miR-638 | AGGGAUCGCGGGCGGGUGGCGGCCU | 161 |
| hsa-miR-1244 | AAGUAGUUGGUUUGUAUGAGAUGGUU | 162 |
| hsa-miR-328 | CUGGCCCUCUCUGCCCUUCCGU | 163 |
| hsa-let-7i | UGAGGUAGUAGUUUGUGCUGUU | 164 |
| hsa-miR-429 | UAAUACUGUCUGGUAAAACCGU | 165 |
| hsa-miR-380 | UAUGUAAUAUGGUCCACAUCUU | 166 |
| hsa-let-7b* | CUAUACAACCUACUGCCUUCCC | 167 |
| hsa-miR-614 | GAACGCCUGUUCUUGCCAGGUGG | 168 |
| hsa-miR-1225-5p | GUGGGUACGGCCCAGUGGGGGG | 169 |
| hsa-miR-545* | UCAGUAAAUGUUUAUUAGAUGA | 52 |
| hsa-miR-320c | AAAAGCUGGGUUGAGAGGGU | 170 |
| hsa-miR-579 | UUCAUUUGGUAUAAACCGCGAUU | 171 |
| hsa-miR-1282 | UCGUUUGCCUUUUUCUGCUU | 81 |
| hsa-miR-455-5p | UAUGUGCCUUUGGACUACAUCG | 172 |
| hsa-miR-615-3p | UCCGAGCCUGGGUCUCCCUCUU | 173 |
| hsa-miR-585 | UGGGCGUAUCUGUAUGCUA | 174 |
| hsa-miR-559 | UAAAGUAAAUAUGCACCAA AA | 175 |
| hsa-miR-561 | CAAAGUUUAAGAUCCUUGAAGU | 176 |
| hsa-miR-191 | CAACGGAAUCCCAAAAGCAGCUG | 177 |
| hsa-miR-187 | UCGUGUCUUGUGUUGCAGCCGG | 178 |
| hsa-miR-29b | UAGCACCAUUUGAAAUCAGUGUU | 179 |
| hsa-miR-769-5p | UGAGACCUCUGGGUUCUGAGCU | 180 |
| hsa-miR-495 | AAACAAACAUGGUGCACUUCUU | 181 |
| hsa-miR-516a-3p | UGCUUCCUUUCAGAGGGU | 182 |
| hsa-miR-938 | UGCCCUUAAAGGUGAACCCAGU | 183 |

TABLE 3-continued

Sequences of miRs

| Target miR | Mature Sequence of Target miR | SEQ ID NO |
|---|---|---|
| hsa-miR-936 | ACAGUAGAGGGAGGAAUCGCAG | 184 |
| hsa-miR-373* | ACUCAAAAUGGGGGCGCUUUCC | 185 |
| hsa-miR-1184 | CCUGCAGCGACUUGAUGGCUUCC | 186 |
| hsa-miR-122 | UGGAGUGUGACAAUGGUGUUUG | 187 |
| hsa-miR-208b | AUAAGACGAACAAAAGGUUUGU | 188 |
| hsa-miR-223* | CGUGUAUUUGACAAGCUGAGUU | 189 |
| hsa-miR-1972 | UCAGGCCAGGCACAGUGGCUCA | 190 |
| hsa-miR-520h | ACAAAGUGCUUCCCUUUAGAGU | 191 |
| hsa-miR-330-3p | GCAAAGCACACGGCCUGCAGAGA | 192 |
| hsa-miR-149 | UCUGGCUCCGUGUCUUCACUCCC | 193 |
| hsa-miR-7 | UGGAAGACUAGUGAUUUUGUUGU | 194 |
| hsa-miR-29b-2* | CUGGUUUCACAUGGUGGCUUAG | 195 |
| hsa-miR-520d-5p | CUACAAAGGGAAGCCCUUUC | 196 |
| hsa-miR-592 | UUGUGUCAAUAUGCGAUGAUGU | 197 |
| hsa-miR-940 | AAGGCAGGGCCCCCGCUCCCC | 198 |
| hsa-miR-146b-3p | UGCCCUGUGGACUCAGUUCUGG | 199 |
| hsa-miR-518e* | CUCUAGAGGGAAGCGCUUUCUG | 200 |
| hsa-miR-1255a | AGGAUGAGCAAAGAAAGUAGAUU | 201 |
| hsa-miR-935 | CCAGUUACCGCUUCCGCUACCGC | 202 |
| hsa-miR-633 | CUAAUAGUAUCUACCACAAUAAA | 203 |
| hsa-miR-513a-5p | UUCACAGGGAGGUGUCAU | 204 |
| hsa-miR-361-3p | UCCCCCAGGUGUGAUUCUGAUUU | 205 |
| hsa-miR-194 | UGUAACAGCAACUCCAUGUGGA | 206 |
| hsa-miR-1185 | AGAGGAUACCCUUUGUAUGUU | 207 |
| hsa-miR-875-3p | CCUGGAAACACUGAGGUUGUG | 208 |
| hsa-miR-200a | UAACACUGUCUGGUAACGAUGU | 209 |
| hsa-miR-1201 | AGCCUGAUUAAACACAUGCUCUGA | 210 |
| hsa-miR-629 | UGGGUUUACGUUGGGAGAACU | 211 |
| hsa-miR-139-5p | UCUACAGUGCACGUGUCUCCAG | 212 |
| hsa-miR-504 | AGACCCUGGUCUGCACUCUAUC | 213 |
| hsa-miR-452 | AACUGUUUGCAGAGGAAACUGA | 214 |
| hsa-miR-517a | AUCGUGCAUCCCUUUAGAGUGU | 53 |
| hsa-miR-543 | AAACAUUCGCGGUGCACUUCUU | 28 |
| hsa-miR-616* | ACUCAAAACCCUUCAGUGACUU | 215 |
| hsa-miR-651 | UUUAGGAUAAGCUUGACUUUUG | 216 |
| hsa-miR-1254 | AGCCUGGAAGCUGGAGCCUGCAGU | 217 |
| hsa-miR-339-3p | UGAGCGCCUCGACGACAGAGCCG | 218 |
| hsa-miR-510 | UACUCAGGAGAGUGGCAAUCAC | 35 |
| hsa-miR-181c* | AACCAUCGACCGUUGAGUGGAC | 219 |
| hsa-miR-19b-1* | AGUUUUGCAGGUUUGCAUCCAGC | 220 |
| hsa-miR-1274a | GUCCCUGUUCAGGCGCCA | 39 |
| hsa-miR-1294 | UGUGAGGUUGGCAUUGUUGUCU | 221 |
| hsa-miR-1306 | ACGUUGGCUCUGGUGGUG | 27 |
| hsa-miR-1226* | GUGAGGGCAUGCAGGCCUGGAUGGGG | 222 |
| hsa-miR-541* | AAAGGAUUCUGCUGUCGGUCCCACU | 54 |

In another embodiment, the enhanced placental stem cells (ePSCs) have reduced production of a pro-inflammatory cytokine (e.g., extracellular pro-inflammatory cytokine), e.g., as compared to an equivalent number of unmodified placental stem cells. In one embodiment, said pro-inflammatory cytokine is IL-1, IL-6, IL-8, TNF-α, or any combinations thereof. In a specific embodiment, said pro-inflammatory cytokine is IL-6, IL-8, or a combination thereof. In another specific embodiment, said pro-inflammatory cytokine is IL-6. In another specific embodiment, said miR inhibitors target (e.g., modulate, reduce the level of) one or more miRs in said ePSCs that modulate the production of said pro-inflammatory cytokine such that the production of said pro-inflammatory cytokine of is reduced, e.g., as compared to an equivalent number of unmodified placental stem cells. In another specific embodiment, said miR inhibitors target (e.g., modulate, up-regulate) one or more genes in said ePSCs that modulate the production of said pro-inflammatory cytokine such that the production of said pro-inflammatory cytokine of is reduced, e.g., as compared to an equivalent number of unmodified placental stem cells. In another specific embodiment, said miR mimics imitate or mimic one or more miRs in said ePSCs that modulate the production of said pro-inflammatory cytokine such that the production of said pro-inflammatory cytokine of is reduced, e.g., as compared to an equivalent number of unmodified placental stem cells. In another specific embodiment, said miR mimics target one or more genes in said ePSCs that modulate the production of said pro-inflammatory cytokine such that the production of said pro-inflammatory cytokine of is reduced, e.g., as compared to an equivalent number of unmodified placental stem cells. In another specific embodiment, said one or more genes comprise a gene that encodes IL-1, IL-1, IL-6, IL-8, TNF-α. In another specific embodiment, said one or more genes comprise a gene that encodes IL-6.

In certain embodiments, the enhanced placental stem cells (ePSCs) have suppressed response induced by interferon-gamma (IFN-γ), as compared to an equivalent number of unmodified placental stem cells. In a specific embodiment, said miR inhibitors target (e.g., modulate) one or more miRs in said ePSCs that modulate IFN-γ-induced response of said ePSCs such that the IFN-γ-induced response is suppressed, e.g., as compared to an equivalent number of unmodified placental stem cells. In another specific embodiment, said miR inhibitors target (e.g., modulate) one or more genes in said ePSCs that modulate IFN-γ-induced response of said ePSCs such that the IFN-γ-induced response is suppressed, e.g., as compared to an equivalent number of unmodified placental stem cells. In a specific embodiment, said miR mimics imitate or mimic one or more miRs in said ePSCs that modulate IFN-γ-induced response of said ePSCs such that the IFN-γ-induced response is suppressed, e.g., as compared to an equivalent number of unmodified placental stem cells. In another specific embodiment, said miR mimics target one or more genes in said ePSCs that modulate IFN-γ-induced response of said ePSCs such that the IFN-γ-induced response is suppressed, e.g., as compared to an equivalent number of unmodified placental stem cells. In another specific embodiment, said one or more genes comprise one or more of protein inhibitor of activated STAT, 1 (PIAS1) and TYRO protein tyrosine kinase binding protein (TYROBP).

In one embodiment, said one or more genes targeted (e.g., modulated) by said miR inhibitors or miR mimics comprise one or more of Twinfilin-1, human nuclear receptor subfamily 1, group H, member 3 (NR1H3), deoxynucleotidyltransferase, terminal, interacting protein 1 (DNTTIP1), vitamin D (1,25-dihydroxyvitamin D3) receptor (VDR), nuclear receptor subfamily 4, group A, member 3 (NR4A3), nuclear receptor subfamily 0, group B, member 2 (NR0B2), or nuclear receptor subfamily 1, group I, member 2 (NR1I2). In another specific embodiment, said one or more genes comprise NR4A3. In another specific embodiment, said one or more genes comprise NR4A2. In another specific embodiment, said miR inhibitors or miR mimics target (e.g., modulate) one or more of Twinfilin-1, NR1H3, DNTTIP1, VDR, NR4A3, NR0B2, or NR1I2 in said ePSCs such that the production of IL-23 by said PBMCs contacted with said ePSCs is reduced, e.g., as compared to PBMCs contacted with an equivalent number of unmodified placental stem cells. In one embodiment, said miR inhibitors have a sequence that is at least about 70%, 80%, 90%, 95%, 98% or 100% identical to SEQ ID NO. 15-83, or the complement thereof. In another embodiment, said miR mimics have a sequence at least about 70%, 80%, 90%, 95%, 98% or 100% identical to SEQ ID NO. 15-83, or the complement thereof. In a specific embodiment, said miR inhibitors have a sequence at least about 70%, 80%, 90%, 95%, 98% or 100% identical to any of SEQ ID NOS: 59-83. In another specific embodiment, said miR mimics have a sequence at least about 70%, 80%, 90%, 95%, 98% or 100% identical to any of SEQ ID NOS: 19-58.

In a specific embodiment, said one or more genes targeted (e.g., modulated) by said miR inhibitors or miR mimics comprise one or more genes listed in Table 4. In another specific embodiment, said one or more gene targeted (e.g., modulated) by said miR inhibitors or miR mimics comprise one or more of cholinergic receptor, nicotinic beta 1 (muscle) (CHRNB1), chloride channel 6 (CLCN6), chloride intracellular channel 4 (CLIC4), casein kinase 1, gamma 3 (CSNK1G3), casein kinase 2, alpha prime polypeptide (CSNK2A2), dual specificity phosphatase 1 (DUSP1), potassium channel modulatory factor 1 (KCMF1), potassium voltage-gated channel, shaker-related subfamily, member 3 (KCNA3), potassium inwardly-rectifying channel, subfamily J, member 14 (KCNJ14), potassium voltage-gated channel, delayed-rectifier, subfamily S, member 3 (KCNS3), potassium channel tetramerisation domain containing 13 (KCTD13), hepatocyte growth factor (hepapoietin A; scatter factor) (HGF), nuclear receptor subfamily 2, group C, member 2 (NR2C2), phosphodiesterase 1B, calmodulin-dependent (PDE1B), phosphodiesterase 7B (PDE7B), phosphatidylinositol 4-kinase type 2 beta (PI4K2B), phosphoinositide-3-kinase, regulatory subunit 1 (alpha) (PIK3R1), phospholipase C, eta 2 (PLCH2), protein phosphatase, $Mg^{2+}$/$Mn^{2+}$ dependent, 1D (PPM1D), protein phosphatase, $Mg^{2+}$/$Mn^{2+}$ dependent, 1G (PPM1G), protein phosphatase 1, regulatory (inhibitor) subunit 2 pseudogene 9 (PPP1R2P9), protein phosphatase 1, regulatory (inhibitor) subunit 3B (PPP1R3B), protein phosphatase 1, regulatory (inhibitor) subunit 9B (PPP1R9B), protein phosphatase 2, catalytic subunit, beta isozyme (PPP2CB), protein tyrosine phosphatase type IVA, member 1 (PTP4A1), protein tyrosine phosphatase, receptor type, K (PTPRK), regulator of G-protein signaling 4 (RGS4), regulator of G-protein signaling 7 binding protein (RGS7BP), regulator of G-protein signaling 8 (RGS8), solute carrier family 16, member 3 (monocarboxylic acid transporter 4) (SLC16A3), solute carrier family 30 (zinc transporter), member 1 (SLC30A1), solute carrier family 35, member A4 (SLC35A4), solute carrier family 38, member 7 (SLC38A7), solute carrier family 41, member 1 (SLC41A1), solute carrier family 45, member 3 (SLC45A3), solute carrier family 7 (cationic amino acid transporter, y+ system), member 1 (SLC7A1), ubiquitin associated protein 2 (UBAP2), ubiquitin-conjugating enzyme E2D 3 (UBC4/5 homolog, yeast) (UBE2D3), ubiquitin-conjugating enzyme E2E 3 (UBC4/5 homolog, yeast) (UBE2E3), ubiquitin-conjugating enzyme E2R 2 (UBE2R2), ubiquitin-conjugating enzyme E2W (putative) (UBE2W), ubiquitin-like with PHD and ring finger domains 2 (UHRF2), ubiquitin specific peptidase 9, X-linked (USP9X), and hypoxia inducible factor 1, alpha subunit (HIF1A). In another specific embodiment, said one or more genes comprise HIF1A. In another specific embodiment, said one or more genes comprise DUSP1. In another specific embodiment, said one or more genes comprise PDE7B. In another specific embodiment, said miR inhibitors target (e.g., modulate, up-regulate) one or more of CHRNB1, CLCN6, CLIC4, CSNK1G3, CSNK2A2, DUSP1, KCMF1, KCNA3, KCNJ14, KCNS3, KCTD13, HGF, NR2C2, PDE1B, PDE7B, PI4K2B, PIK3R1, PLCH2, PPM1D, PPM1G, PPP1R2P9, PPP1R3B, PPP1R9B, PPP2CB, PTP4A1, PTPRK, RGS4, RGS7BP, RGS8, SLC16A3, SLC30A1, SLC35A4, SLC38A7, SLC41A1, SLC45A3, SLC7A1, UBAP2, UBE2D3, UBE2E3, UBE2R2, UBE2W, UHRF2, or USP9X in said ePSCs such that the production of PGE2 by said ePSCs is increased, e.g., as compared to an equivalent number of unmodified placental stem cells.

TABLE 4

Targets of miRNAs which modulate PGE2 production

| Symbol | Entrez Gene Name | Location | Family |
|---|---|---|---|
| CHRNB1 | cholinergic receptor, nicotinic, beta 1 (muscle) | Plasma Membrane | transmembrane receptor |
| CLCN6 | chloride channel 6 | Plasma Membrane | ion channel |
| CLIC4 | chloride intracellular channel 4 | Plasma Membrane | ion channel |
| CSNK1G3 | casein kinase 1, gamma 3 | Cytoplasm | kinase |
| CSNK2A2 | casein kinase 2, alpha prime polypeptide | Cytoplasm | kinase |

TABLE 4-continued

Targets of miRNAs which modulate PGE2 production

| Symbol | Entrez Gene Name | Location | Family |
|---|---|---|---|
| DUSP1 | dual specificity phosphatase 1 | Nucleus | phosphatase |
| KCMF1 | potassium channel modulatory factor 1 | unknown | enzyme |
| KCNA3 | potassium voltage-gated channel, shaker-related subfamily, member 3 | Plasma Membrane | ion channel |
| KCNJ14 | potassium inwardly-rectifying channel, subfamily J, member 14 | Plasma Membrane | ion channel |
| KCNS3 | potassium voltage-gated channel, delayed-rectifier, subfamily S, member 3 | Plasma Membrane | ion channel |
| KCTD13 | potassium channel tetramerisation domain containing 13 | Nucleus | ion channel |
| HGF | hepatocyte growth factor (hepapoietin A; scatter factor) | Extracellular Space | growth factor |
| NR2C2 | nuclear receptor subfamily 2, group C, member 2 | Nucleus | ligand-dependent nuclear receptor |
| PDE1B | phosphodiesterase 1B, calmodulin-dependent | Cytoplasm | enzyme |
| PDE7B | phosphodiesterase 7B | Cytoplasm | enzyme |
| PI4K2B | phosphatidylinositol 4-kinase type 2 beta | Cytoplasm | kinase |
| PIK3R1 | phosphoinositide-3-kinase, regulatory subunit 1 (alpha) | Cytoplasm | kinase |
| PLCH2 | phospholipase C, eta 2 | Cytoplasm | enzyme |
| PPM1D | protein phosphatase, Mg2+/Mn2+ dependent, 1D | Cytoplasm | phosphatase |
| PPM1G | protein phosphatase, Mg2+/Mn2+ dependent, 1G | Nucleus | phosphatase |
| PPP1R2P9 | protein phosphatase 1, regulatory (inhibitor) subunit 2 pseudogene 9 | unknown | other |
| PPP1R3B | protein phosphatase 1, regulatory (inhibitor) subunit 3B | unknown | other |
| PPP1R9B | protein phosphatase 1, regulatory (inhibitor) subunit 9B | Cytoplasm | other |
| PPP2CB | protein phosphatase 2, catalytic subunit, beta isozyme | Cytoplasm | phosphatase |
| PTP4A1 | protein tyrosine phosphatase type IVA, member 1 | Nucleus | phosphatase |
| PTPRK | protein tyrosine phosphatase, receptor type, K | Plasma Membrane | phosphatase |
| RGS4 | regulator of G-protein signaling 4 | Cytoplasm | other |
| RGS7BP | regulator of G-protein signaling 7 binding protein | unknown | other |
| RGS8 | regulator of G-protein signaling 8 | unknown | other |
| SLC16A3 | solute carrier family 16, member 3 (monocarboxylic acid transporter 4) | Plasma Membrane | transporter |
| SLC30A1 | solute carrier family 30 (zinc transporter), member 1 | Plasma Membrane | transporter |
| SLC35A4 | solute carrier family 35, member A4 | unknown | transporter |
| SLC38A7 | solute carrier family 38, member 7 | unknown | transporter |
| SLC41A1 (includes EG: 254428) | solute carrier family 41, member 1 | unknown | transporter |
| SLC45A3 | solute carrier family 45, member 3 | Cytoplasm | other |
| SLC7A1 | solute carrier family 7 (cationic amino acid transporter, y+ system), member 1 | Plasma Membrane | transporter |
| UBAP2 | ubiquitin associated protein 2 | Cytoplasm | other |
| UBE2D3 (includes EG: 7323) | ubiquitin-conjugating enzyme E2D 3 (UBC4/5 homolog, yeast) | Cytoplasm | enzyme |
| UBE2E3 | ubiquitin-conjugating enzyme E2E 3 (UBC4/5 homolog, yeast) | Nucleus | enzyme |
| UBE2R2 | ubiquitin-conjugating enzyme E2R 2 | unknown | enzyme |
| UBE2W | ubiquitin-conjugating enzyme E2W (putative) | unknown | enzyme |
| UHRF2 | ubiquitin-like with PHD and ring finger domains 2 | Nucleus | enzyme |
| USP9X | ubiquitin specific peptidase 9, X-linked | Plasma Membrane | peptidase |

In certain embodiments, provided herein is a method of modifying, e.g., genetically engineering, placental stem cells to enhance their immunosuppressive activity to produce enhanced placental stem cells, or ePSCs. In certain embodiments, the ePSCs express 105%, 110%, 115%, 120%, 125%, 130%, 135%, 140%, 145%, 150%, 155%, 160%, 165%, 170%, 175%, 180%, 185%, 190%, 195%, or 200%, or more, of one or more miRs listed in Tables 2-3, e.g., as compared to an equivalent number of placental stem cells that have not been enhanced.

In certain embodiments, provided herein are ePSCs expressing 105%, 110%, 115%, 120%, 125%, 130%, 135%, 140%, 145%, 150%, 155%, 160%, 165%, 170%, 175%, 180%, 185%, 190%, 195%, or 200%, or more, of one or more of miRs listed in Tables 2 and 3 (see the column designated as "Target miR"), as compared to placental stem cells that have not been enhanced.

In certain embodiments, provided herein are enhanced placental stem cells, wherein said enhanced placental stem cells (ePSCs) are isolated placental stem cells that have been genetically engineered to express one or more of miRs listed in Tables 2 and 3 (see the column designated as "Target miR") that detectably enhances the immunosuppressive activity of the ePSCs as compared to placental stem cells that have not been so engineered.

The miR inhibitors or miR mimics can be supplied by a commercial vendor (e.g., Ambion; Dharmafect), or be synthesized by, e.g., solid phase synthesis, or according to the procedures as described in, e.g., Protocols for Oligonucleotides and Analogs, Ed. Agrawal (1993), Humana Press; Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

The miR inhibitors or miR mimics useful for the production of enhanced placental stem cells can be identified by a variety of methods known in the art. In certain embodiments, such miR inhibitors or miR mimics are identified and obtained from one or more miR inhibitors or miR mimics libraries, e.g., a commercially available library (e.g., Ambion, Anti-miR miRNA Precursor Library Human V13), optionally by a screening method, e.g., medium or high-throughput screening. In one embodiment, such a library can encompass a wide range of target miRs (e.g., human genome-wide siRNA library), or pre-defined to encompass specific target genes or gene families (e.g., nuclear receptor siRNA library, phosphatase siRNA library etc.)

The screening method can be carried out, for example, using automated robotics, liquid handling equipments, data processing software, and/or sensitive detectors, e.g., Precision XS Automated Pipettor System, EL406 liquid handling system, or synergy plate reader.

5.1.3 Other Modulatory RNA Molecules

Other modulatory RNA molecules useful for the production of ePSCs or modification of placental stem cells to enhance their immunomodulatory (e.g., immunosuppressive) activity comprise antisense RNAs, shRNAs, or shRNAmirs. These RNA molecules can be used in any combination and can be used in combination with siRNAs, miR mimics and/or miR inhibitors to produce the ePSCs as described herein.

As used herein, the term "antisense RNA" is an antisense ribonucleic acid molecule. By illustration only without limitation, the antisense RNAs hybridize to a target nucleic acid and modulates gene expression activities such as transcription or translation.

As used herein, the term "small hairpin RNA" or "shRNA" refers to an RNA molecule comprising a stem-loop structure; the term "shRNAmir" refers to "microRNA-adapted shRNA." In certain embodiments, said shRNA comprises a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The shRNA hairpin structure can be, for example, cleaved by the cellular machinery into siRNA, which is then bound to the RNA-induced silencing complex (RISC). This complex binds to and cleaves mRNAs which match the siRNA that is bound to it.

In some embodiments, shRNAmirs or microRNA-adapted shRNA provided herein are shRNA constructs that mimic naturally occurring primary transcript miRNA with the addition of an miRNA loop and a miRNA flanking sequence to a shRNA. Without wishing to be bound by any theory, the shRNAmir is first cleaved to produce shRNA by Drosha, and then cleaved again by Dicer to produce siRNA. The siRNA is then incorporated into the RISC for target mRNA degradation. This allows the shRNAmir to be cleaved by Drosha thereby allowing for a greater increase in knockdown efficiency. The addition of a miR30 loop and 125 nt of miR30 flanking sequence on either side of the shRNA hairpin has been reported to result in greater than 10-fold increase in Drosha and Dicer processing of the expressed hairpins when compared with conventional shRNA constructs without microRNA.

In one embodiment, the shRNAmirs provided herein target a gene encoding vitamin D (1,25-dihydroxyvitamin D3) receptor (VDR) (e.g., NCBI Ref Seq Accession Number NM_000376). In a specific embodiment, said shRNAmirs have a hairpin sequence encoded from a DNA sequence that is at least about 70%, 80%, 90%, 95%, 98% or 100% identical to SEQ ID NO: 224.

In another specific embodiment, said shRNAmirs have a mature sense sequence encoded from a DNA sequence that is at least about 70%, 80%, 90%, 95%, 98% or 100% identical to SEQ ID NO: 225.

In one embodiment, said shRNAmirs provided herein target a gene encoding nuclear receptor subfamily 4, group A, member 3 (NR4A3) (e.g., NCBI Ref Seq Accession Number NM_173198). In a specific embodiment, said shRNAmirs have a hairpin sequence encoded from a DNA sequence that is at least about 70%, 80%, 90%, 95%, 98% or 100% identical to SEQ ID NO: 226.

In another specific embodiment, said shRNAmirs have a mature sense sequence encoded from a DNA sequence that is at least about 70%, 80%, 90%, 95%, 98% or 100% identical to SEQ ID NO: 227.

The shRNAmir provided herein can be delivered to the cells by any known method. In a specific embodiment, said shRNAmir is incorporated into an eukaryotic expression vector. In another specific embodiment, said shRNAmir is incorporated into a viral vector for gene expression. Such viral vectors include, but are not limited to, retroviral vectors, e.g., lentivirus, and adenoviruses. In a specific embodiment, said shRNAmir is incorporated into a lentiviral vector.

The antisense RNAs, shRNAs and shRNAmirs can be supplied by a commercial vendor (e.g., Ambion; Dharmafect), or be synthesized by, e.g., solid phase synthesis, or according to the procedures as described in, e.g., Protocols for Oligonucleotides and Analogs, Ed. Agrawal (1993), Humana Press; Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense RNAs, shRNAs, shRNAmirs and other modulatory RNA molecules useful for the production of enhanced placental stem cells can be identified by a variety of methods known in the art. In certain embodiments, such antisense RNAs, shRNAs, shRNAmirs and other modulatory RNA molecules are identified and obtained from one or more libraries, e.g., a commercially available library (Thermo Scientific, shRNAmir libraries), optionally by a screening method, e.g., medium or high-throughput screening. In one embodiment, such a library can encompass a wide range of genes (e.g., human genome targeted library), or pre-defined to encompass specific target genes or gene families (e.g., human nuclear receptor targeted library, phosphatase targeted library, etc.)

The screening method can be carried out, for example, using automated robotics, liquid handling equipments, data processing software, and/or sensitive detectors, e.g., Precision XS Automated Pipettor System, EL406 liquid handling system, or synergy plate reader.

In certain embodiments, the antisense RNAs, shRNAs and shRNAmirs comprise about 1 to about 100, from about 8 to about 80, 10 to 50, 13 to 80, 13 to 50, 13 to 30, 13 to 24, 18 to 22, 19 to 23, 20 to 80, 20 to 50, 20 to 30, or 20 to 24 nucleobases (nucleobases (i.e. from about 1 to about 100 linked nucleosides).

The antisense RNAs, shRNAs and shRNAmirs can be single-stranded or double-stranded, modified or unmodified. In certain embodiments, said antisense RNAs, miR mimics, shRNAs, shRNAmirs and other modulatory RNA molecules comprise about 1 to about 100, from about 8 to about 80, 10 to 50, 13 to 80, 13 to 50, 13 to 30, 13 to 24, 18 to 22, 19 to 23, 20 to 80, 20 to 50, 20 to 30, or 20 to 24 nucleobases (i.e. from about 1 to about 100 linked nucleosides). In certain embodiment, said antisense RNAs, shRNAs and shRNAmirs are single-stranded, comprising from about 12 to about 35 nucleobases (i.e. from about 12 to about 35 linked nucleosides). In one embodiment, said antisense RNAs, miR mimics, shRNAs and shRNAmirs comprise about 10, 11, 12, 13, 14, 15, 16, 17, 18, 19, 20, 21, 22, 23, 24, 25, 26, 27, 28, 29, 30, 31, 32, 33, 34, or 35 nucleobases in length.

5.1.4 Delivery of Modulatory RNA Molecules to Placental Stem Cells

The modulatory RNA molecules can be delivered to placental stem cells by transfection (e.g., transient or stable transfection) or other means known in the art. In certain embodiments, said transfection can be carried out, e.g., using lipids (e.g., liposomes), calcium phosphate, cyclodextrin, dendrimers, or polymers (e.g., cationic polymers); by electroporation, optical transfection, gene electrotransfer, impalefection, gene gun, or magnetofection; via viruses (e.g., viral carriers); or a combination thereof. In one embodiment, said transfection is performed using commercially available transfection reagents or kits (e.g., Ambion, siPORT™ Amine, siPORT NeoFX's; Dharmafect, Dharmafect 3 Transfection Reagent or Dharmafect 1; Invitrogen, Lipofectamine RNAiMAX; Integrated DNA Technologies, Transductin; Minis Bio LLC, TransIT-siQUEST, TransIT-TKO). In some embodiments, said transfection can be set up in a medium or high-throughput manner, including, but not limited to, use of microtiter plate (e.g., 96-well plate) and microplate reader (e.g., synergy plate reader), or automation system, for example, Precision XS Automated Pipettor System, EL406 liquid handling system. In other embodiments, said transfection is set up in a large scale, including, but not limited to, the use of tissue culture dishes or culture flasks (e.g., T25, T75, or T225 flasks). Placental stem cells can be plated and cultured in tissue culture containers, e.g., dishes, flasks, multiwell plates, or the like, for a sufficient time for the placental stem cells to proliferate to about 20-80% confluence, or about 30-70% confluence at the time of transfection. For example, there can be about 2000, 2500, 3000, 3500, or 4000 placental stem cells per well in a 96-well plate at the time of transfection. In one embodiment, placental stem cells are about 50% confluence at the time of transfection. In another embodiment, there are about 3000 or 3500 placental stem cells per well in a 96-well plate at the time of direct transfection. In another embodiment, there are about 3500 placental stem cells per well in a 96-well plate at the time of reverse transfection.

The modulatory RNA molecules can be administered to the cells by transient transfection, or be stably transfected to the cell for long-term modulation (e.g., suppression) of genes to which the siRNAs are targeted. In one embodiment, stable transfection of modulatory RNA molecules can be carried out, for example, by the use of plasmids or expression vectors that express functional modulatory RNA molecules. In one embodiment, such plasmids or expression vectors comprise a selectable marker (e.g., an antibiotic selection marker). In another embodiment, such plasmids or expression vectors comprise a cytomegalovirus (CMV) promoter, an RNA polymerase III (RNA pol III) promoter (e.g., U6 or H1), or an RNA polymerase II (RNA pol II) promoter. In another embodiment, such plasmids or expression vectors are commercially available (e.g., Ambion, pSilencer™ 4.1-CMV vector).

Other examples of mammalian expression vectors include pLOC (Open Biosystems), which contains a cytomegalovirus promoter; pCDM8 (Seed, Nature 329:840 (1987)) and pMT2PC (Kaufman et al., EMBO J. 6:187-195 (1987)). Other example expression vectors that may be used include pFN10A (ACT) FLEXI® Vector (Promega), pFN11A (BIND) FLEXI® Vector (Promega), pGL4.31[luc2P/GAL4UAS/Hygro] (Promega), pFC14K (HALOTAG® 7) MCV FLEXI® Vector (Promega), pFC15A (HALOTAG® 7) MCV FLEXI® Vector (Promega), and the like.

When used in mammalian cells, an expression vector's control functions can be provided by viral regulatory elements. For example, commonly used promoters are derived from polyoma virus, adenovirus 2, cytomegalovirus, and simian virus 40. Other suitable expression systems for both prokaryotic and eukaryotic cells are described, e.g., in chapters 16 and 17 of Sambrook et al., eds., *Molecular Cloning: A Laboratory Manual,* 2nd, ed., Cold Spring Harbor Laboratory, Cold Spring Harbor Laboratory Press, Cold Spring Harbor, N.Y. (1989).

Recombinant expression vectors can include one or more control sequences that can be, for example, operably linked to the nucleic acid sequence encoding the gene to be expressed. Such control sequences are described, for example, in Goeddel, Gene Expression Technology: Methods in Enzymology 185, Academic Press, San Diego, Calif. (1990). In certain embodiments, the vector includes a control sequence that directs constitutive expression of the nucleotide sequence in the placental stem cells. In certain other embodiments, the control sequence directs expression of the nucleotide sequence only in cells of certain tissues in a recipient of the ePSCs, e.g., in lung, neural, muscle, skin, vascular system, or other tissues, within said recipient. In certain other embodiments, said vector comprises a control sequence that is inducible, e.g., by contact with a chemical agent, e.g., tetracycline.

The modulatory RNA molecules can be administered to the cells by any technique known to those of skill in the art, e.g., by direct transfection. For example, said direct transfection can involve the step of pre-plating the cells prior to transfection, allowing them to reattach and resume growth for a period of time (e.g., 24 hours) before exposure to transfection complexes. The modulatory RNA molecules can also be administered to the cells by reverse transfection. For example, said reverse transfection can involve the step of adding transfection complexes to the cells while they are in suspension, prior to plating.

In various embodiments, the effects of the modulatory molecules on the ePSCs, e.g., upregulation or downregulation of one or more genes in said ePSCs, effect of the ePSCs on IL-23 production by PBMCs contacted with the ePSCs, and the like) last for up to, about, or no more than, 1, 2, 3, 4, 5, 6, 7, 8, 9, 10, 11, 12, 13, 14, 15, 16, 17, 18, 19, 20, 21, 22 or 23 hours, or 1, 2, 3, 4, 5, 6, 7, 8, 9, 10, 11, 12, 13, 14, 15, 16, 17, 18, 19, 20, 21, 22, 23, 24, 25, 26, 27, or 28 days, or more. In various other embodiments, the ePSCs are used within no more than 1, 2, 3, 4, 5, 6, 7, 8, 9, 10, 11, 12, 13, 14, 15, 16, 17, 18, 19, 20, 21, 22 or 23 hours, or 1, 2, 3, 4, 5, 6, 7, 8, 9, 10, 11, 12, 13, 14, 15, 16, 17, 18, 19, 20, 21, 22, 23, 24, 25, 26, 27, or 28 days of the time the ePSCs are produced. In certain embodiments, the effects of the modulatory molecules on the ePSCs are inducible. In certain other embodiments, no, or substantially no, cellular expansion (culturing of the ePSCs, proliferation, etc.) is performed between the time the placental stem cells are modified to produce the ePSCs and the time the ePSCs are administered or cryopreserved.

Assessment of the function (e.g., silencing of genes, up-regulation of genes) of modulatory RNA molecules in the enhanced placental stem cells, e.g., the level or degree of gene silencing or up-regulation, can be accomplished by any art-recognized method for detection of protein production or nucleic acid production by cells. For example, assessment can be performed by determining the mRNA or protein level of a gene of interest in a sample of ePSCs (e.g., a sample of $10 \times 10^5$ to $10 \times 10^7$ ePSCs, or 1%, 2%, 3%, 4%, 5%, 6%, 7%, 8%, 9%, or 10% of said ePSCs) as compared to equivalent placental stem cells that have not been transfected or transformed with such a nucleic acid sequence. Such assessment can be performed using, e.g nucleic acid-based methods, e.g., northern blot analysis, reverse transcriptase polymerase chain reaction (RT-PCR), real-time PCR, quantitative PCR, and the like. In other embodiments, expression of protein can be assessed using antibodies that bind to the protein of interest, e.g., in an ELISA, sandwich assay, or the like. In specific embodiments, said enhanced placental stem cells produce 5%, 10%, 15%, 20%, 25%, 30%, 35%, 40%, 45%, 50%, 55%, 60%, 65%, 70%, 75%, 80%, 85%, 90%, 95%, 100% less of the mRNA of a target gene as compared to unmodified placental stem cells. In specific embodiments, said enhanced placental stem cells produce 5%, 10%, 15%, 20%, 25%, 30%, 35%, 40%, 45%, 50%, 55%, 60%, 65%, 70%, 75%, 80%, 85%, 90%, 95%, 100% more of the mRNA of a target gene expressed by a target gene as compared to unmodified placental stem cells. In a specific embodiment, said enhanced placental stem cells produce 5%, 10%, 15%, 20%, 25%, 30%, 35%, 40%, 45%, 50%, 55%, 60%, 65%, 70%, 75%, 80%, 85%, 90%, 95%, 100% less of the protein of a target gene as compared to unmodified placental stem cells. In another specific embodiment, said enhanced placental stem cells produce 5%, 10%, 15%, 20%, 25%, 30%, 35%, 40%, 45%, 50%, 55%, 60%, 65%, 70%, 75%, 80%, 85%, 90%, 95%, 100% more of the protein of a target gene as compared to unmodified placental stem cells.

5.2 Use of Enhanced Placental Stem Cells to Modulate an Immune Response

In another aspect, provided herein is a method of treating an individual having or at risk of developing a disease, disorder or condition caused by, or relating to, an unwanted or harmful immune response, for instance, a disease, disorder or condition having an inflammatory component, comprising administering to the individual a therapeutically effective amount of ePSCs. In certain embodiments, said cells comprise or have been contacted with an effective amount of modulatory RNA molecules that (i) suppress an amount of soluble IL-23 protein produced by peripheral blood mononuclear cells (PBMCs) in the presence of said enhanced placental stem cells; (ii) increase cyclooxygenase II (Cox-2) activity in said enhanced placental stem cells; (iii) increase an amount of PGE2 produced by said enhanced placental stem cells; or (iv) reduce the level a pro-inflammatory cytokine produced by enhanced placental stem cells, compared to placental stem cells not contacted with said modulatory RNA molecules, wherein the therapeutically effective amount is an amount sufficient to cause a detectable improvement in one or more symptoms of said disease, disorder or condition.

In another aspect, provided herein are methods for the modulation, e.g., suppression, of the activity, e.g., proliferation, of an immune cell, or plurality of immune cells, by contacting the immune cell(s) with a plurality of enhanced placental stem cells. Such enhanced placental stem cells are placental stem cells that have increased immunosuppressive activity, as described in the embodiments herein, compared to an equivalent number of unmodified or untreated placental stem cells (that it, placental stem cells that are not enhanced).

In one embodiment, provided herein is a method of suppressing an immune response comprising contacting a plurality of immune cells with a plurality of enhanced placental stem cells for a time sufficient for said enhanced placental stem cells to detectably suppress an immune response, wherein said enhanced placental stem cells detectably suppress T cell proliferation in a mixed lymphocyte reaction (MLR) assay or a regression assay.

Placental stem cells used to produce enhanced placental stem cells can be derived or obtained from a single placenta or multiple placentas. Such placental stem cells used for immunosuppression can also be derived from a single species, e.g., the species of the intended recipient or the species of the immune cells the function of which is to be reduced or suppressed, or can be derived from multiple species.

An "immune cell" in the context of this method means any cell of the immune system, particularly T cells and NK (natural killer) cells. Thus, in various embodiments of the method, enhanced placental stem cells are contacted with a plurality of immune cells, wherein the plurality of immune cells are, or comprises, a plurality of T cells (e.g., a plurality of $CD3^+$ T cells, $CD4^+$ T cells and/or $CD8^+$ T cells) and/or natural killer cells. An "immune response" in the context of the method can be any response by an immune cell to a stimulus normally perceived by an immune cell, e.g., a response to the presence of an antigen. In various embodiments, an immune response can be the proliferation of T cells (e.g., $CD3^+$ T cells, $CD4^+$ T cells and/or $CD8^+$ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, or the like. The immune response can also be a local, tissue- or organ-specific, or systemic effect of an activity of one or more classes of immune cells, e.g., the immune response can be graft versus host disease, inflammation, formation of inflammation-related scar tissue, an autoimmune condition (e.g., rheumatoid arthritis, Type I diabetes, lupus erythematosus, etc.). and the like.

"Contacting" in this context encompasses bringing the placental stem cells and immune cells together in a single container (e.g., culture dish, flask, vial, etc.) or in vivo, for example, in the same individual (e.g., mammal, for example, human). In a preferred embodiment, the contacting is for a time sufficient, and with a sufficient number of placental stem cells and immune cells, that a change in an immune function of the immune cells is detectable. More preferably, in various embodiments, said contacting is sufficient to suppress immune function (e.g., T cell proliferation in response to an antigen) by at least 50%, 60%, 70%, 80%, 90% or 95%, compared to the immune function in the absence of the placental stem cells. Such suppression in an in vivo context can be determined in an in vitro assay (see below); that is, the degree of suppression in the in vitro assay can be extrapolated, for a particular number of enhanced placental stem cells and a number of immune cells in a recipient individual, to a degree of suppression in the individual.

In certain embodiments, provided herein are methods of using enhanced placental stem cells to modulate an immune response, or the activity of a plurality of one or more types of immune cells, in vitro. Contacting the enhanced placental stem cells and plurality of immune cells can comprise combining the enhanced placental stem cells and immune cells in the same physical space such that at least a portion of the plurality of enhanced placental stem cells interacts with at least a portion of the plurality of immune cells; maintaining the enhanced placental stem cells and immune cells in separate physical spaces with common medium; or can comprise contacting medium from one or a culture of enhanced placental stem cells or immune cells with the other type of cell (for example, obtaining culture medium from a culture of enhanced placental stem cells and resuspending isolated immune cells in the medium). In a specific example, the contacting is performed in a Mixed Lymphocyte Reaction (MLR). In another specific example, the contacting is performed in a regression assay. In another specific example, the contacting is performed in a Bead T-lymphocyte reaction (BTR) assay.

Such contacting can, for example, take place in an experimental setting designed to determine the extent to which a particular plurality of enhanced placental stem cells is immunomodulatory, e.g., immunosuppressive. Such an experimental setting can be, for example, a mixed lymphocyte reaction (MLR) or regression assay. Procedures for performing the MLR and regression assays are well-known in the art. See, e.g. Schwarz, "The Mixed Lymphocyte Reaction An In Vitro Test for Tolerance," *J. Exp. Med.* 127(5):879-890 (1968); Lacerda et al., "Human Epstein-Barr Virus (EBV)-Specific Cytotoxic T Lymphocytes Home Preferentially to and Induce Selective Regressions of Autologous EBV-Induced B Lymphoproliferations in Xenografted C.B-17 Scid/Scid Mice," *J. Exp. Med.* 183:1215-1228 (1996). In a preferred embodiment, an MLR is performed in which pluralities of placental stem cells are contacted with a plurality of immune cells (e.g., lymphocytes, for example, $CD3^+$, $CD4^+$ and/or $CD8^+$ T lymphocytes).

For example, a plurality of enhanced placental stem cells can be tested in an MLR comprising combining $CD4^+$ or $CD8^+$ T cells, dendritic cells (DC) and enhanced placental stem cells in a ratio of about 10:1:2, wherein the T cells are stained with a dye such as, e.g., CFSE that partitions into daughter cells, and wherein the T cells are allowed to proliferate for about 6 days. The plurality of enhanced placental stem cells is immunosuppressive if the T cell proliferation at 6 days in the presence of enhanced placental stem cells is detectably reduced compared to T cell proliferation in the presence of DC and absence of placental stem cells. Additionally, a control using unmodified or untreated (i.e., non-enhanced) placental stem cells can be run in parallel to demonstrate that the enhanced placental stem cells are more immunosuppressive than unmodified or untreated placental stem cells. In such an MLR, for example, enhanced placental stem cells can be either thawed or harvested from culture. About 20,000 enhanced placental stem cells are resuspended in 100 μl of medium (RPMI 1640, 1 mM HEPES buffer, antibiotics, and 5% pooled human serum), and allowed to attach to the bottom of a well for 2 hours. $CD4^+$ and/or $CD8^+$ T cells are isolated from whole peripheral blood mononuclear cells Miltenyi magnetic beads. The cells are CFSE stained, and a total of 100,000 T cells ($CD4^+$ T cells alone, $CD8^+$ T cells alone, or equal amounts of $CD4^+$ and $CD8^+$ T cells) are added per well. The volume in the well is brought to 200 μl, and the MLR is allowed to proceed.

In one embodiment, therefore, provided herein is a method of suppressing an immune response comprising contacting a plurality of immune cells with a plurality of enhanced placental stem cells for a time sufficient for said enhanced placental stem cells to detectably suppress T cell proliferation in a mixed lymphocyte reaction (MLR) assay or in a regression assay. In one embodiment, said enhanced placental stem cells used in the MLR represent a sample or aliquot of placental stem cells from a larger population of placental stem cells.

Populations of placental stem cells obtained from different placentas, or different tissues within the same placenta, and thus enhanced placental stem cells produced therefrom, can differ in their ability to modulate an activity of an immune cell, e.g., can differ in their ability to suppress T cell activity or proliferation, macrophage activity, DC activity, or NK cell activity. It is also possible that different preparations of enhanced placental stem cells may vary in their ability to modulate an activity of an immune cell, e.g., can differ in their ability to suppress T cell activity or proliferation, macrophage activity, DC activity, or NK cell activity. It is thus desirable to determine, prior to use, the immunosuppressive activity of a particular population of placental stem cells or enhanced placental stem cells for immunosuppression. Such a activity can be determined, for example, by testing a sample of the placental stem cells or enhanced placental stem cells in, e.g., an MLR or regression assay. In one embodiment, an MLR is performed with the sample, and a degree of immunosuppression in the assay attributable to the placental stem cells or enhanced placental stem cells is determined. This degree of immunosuppression can then be attributed to the placental stem cell population or enhanced placental stem cell population that was sampled. Thus, the MLR can be used as a method of determining the absolute and relative ability of a particular population of placental stem cells or enhanced placental stem cells to suppress immune function. The parameters of the MLR can be varied to provide more data or to best determine the capacity of a sample of placental stem cells or enhanced placental stem cells to immunosuppress. For example, because immunosuppression by placental stem cells or enhanced placental stem cells appears to increase roughly in proportion to the number of placental stem cells or enhanced placental stem cells present in the assay, the MLR can be performed with, in one embodiment, two or more numbers of placental stem cells or enhanced placental stem cells, e.g., $1 \times 10^3$, $3 \times 10^3$, $1 \times 10^4$ and/or $3 \times 10^4$ placental stem cells or enhanced placental stem cells per reaction. The number of placental stem cells or enhanced placental stem cells relative to the number of T cells in the assay can also be varied. For example, placental stem cells or enhanced placental stem cells, and T cells, in the assay can be present in any ratio of, e.g. about 10:1 to about 1:10, preferably about 1:5, though a relatively greater number of placental stem cells or enhanced placental stem cells, or T cells, can be used.

The regression assay or BTR assay can be used in similar fashion.

Enhanced placental stem cells can be administered to an individual in a ratio, with respect to a known or expected number of immune cells, e.g., T cells, in the individual, of from about 10:1 to about 1:10, preferably about 1:5. However, enhanced placental stem cells can be administered to an individual in a ratio of, in non-limiting examples, about 10,000:1, about 1,000:1, about 100:1, about 10:1, about 1:1, about 1:10, about 1:100, about 1:1,000 or about 1:10,000. Generally, about $1 \times 10^5$ to about $1 \times 10^8$ enhanced placental stem cells per recipient kilogram, preferably about $1 \times 10^6$ to about $1 \times 10^7$ enhanced placental stem per recipient kilogram can be administered to effect immunosuppression. In various embodiments, a plurality of enhanced placental stem cells administered to an individual or subject comprises at least, about, or no more than, $1 \times 10^5$, $3 \times 10^5$, $1 \times 10^6$, $3 \times 10^6$, $1 \times 10^7$, $3 \times 10^7$, $1 \times 10^8$, $3 \times 10^8$, $1 \times 10^9$, $3 \times 10^9$ enhanced placental stem cells, or more.

The enhanced placental stem cells can also be administered with one or more second types of stem cells, e.g., mesenchymal stem cells from bone marrow. Such second stem cells can be administered to an individual with said enhanced placental stem cells in a ratio of, e.g., about 1:10 to about 10:1.

To facilitate contacting, or proximity of, enhanced placental stem cells and immune cells in vivo, the enhanced placental stem cells can be administered to an individual by any route sufficient to bring the enhanced placental stem cells and immune cells into contact with each other. For example, the enhanced placental stem cells can be administered to the individual, e.g., intravenously, intramuscularly, intraperitoneally, intraocularly, parenterally, intrathecally, or directly into an organ, e.g., pancreas. For in vivo administration, the enhanced placental stem cells can be formulated as a pharmaceutical composition, as described below.

The method of immunosuppression can additionally comprise the addition of one or more immunosuppressive agents, particularly in the in vivo context. In one embodiment, the enhanced placental stem cells are contacted with the immune cells in vivo in an individual, and a composition comprising an immunosuppressive agent is administered to the individual. Immunosuppressive agents are well-known in the art and include, e.g., anti-T cell receptor antibodies (monoclonal or polyclonal, or antibody fragments or derivatives thereof), anti-IL-2 receptor antibodies (e.g., Basiliximab (SIMULECT®) or daclizumab (ZENAPAX)®), anti T cell receptor antibodies (e.g., Muromonab-CD3), azathioprine, corticosteroids, cyclosporine, tacrolimus, mycophenolate mofetil, sirolimus, calcineurin inhibitors, and the like. In a specific embodiment, the immumosuppressive agent is a neutralizing antibody to macrophage inflammatory protein (MIP)-1α or MIP-1β. Preferably, the anti-MIP-1α or MIP-1β antibody is administered in an amount sufficient to cause a detectable reduction in the amount of MIP-1α and/or MIP-1β in said individual.

Placental stem cells, in addition to suppression of proliferation of T cells, have other anti-inflammatory effects on cells of the immune system which can be beneficial in the treatment of a CNS injury, e.g., a spinal cord injury or traumatic brain injury. For example, placental stem cells, e.g., in vitro or in vivo, as when administered to an individual, reduce an immune response mediated by a Th1 and/or a Th17 T cell subset. In another aspect, provided herein is a method of inhibiting a pro-inflammatory response, e.g., a Th1 response or a Th17 response, either in vivo or in vitro, comprising contacting T cells (e.g., CD4$^+$ T lymphocytes or leukocytes) with enhanced placental stem cells, e.g., the enhanced placental stem cells described herein. In a specific embodiment, said contacting detectably reduces Th1 cell maturation. In a specific embodiment of the method, said contacting detectably reduces the production of one or more of lymphotoxin-1α (LT-1α), interleukin-1β (IL-1β), IL-12, IL-17, IL-21, IL-23, tumor necrosis factor alpha (TNFα) and/or interferon gamma (IFNγ) by said T cells or by an antigen-producing cell. In another specific embodiment of the method, said contacting potentiates or upregulates a regulatory T cell (Treg) phenotype, and/or reduces expression in a dendritic cell (DC) and/or macrophage of biomolecules that promote a Th1 and/or Th17 response (e.g., CD80, CD83, CD86, ICAM-1, HLA-II).

In another embodiment, provided herein is a method of reducing the production of pro-inflammatory cytokines from macrophages, comprising contacting the macrophages with an effective amount of enhanced placental stem cells. In another embodiment, provided herein is a method of increasing a number of tolerogenic cells, promoting tolerogenic functions of immune cells, and/or upregulating tolerogenic cytokines, e.g., from macrophages, comprising contacting immune system cells with an effective amount of enhanced placental stem cells. In a specific embodiment, said contacting causes activated macrophages to produce detectably more IL-10 than activated macrophages not contacted with said enhanced placental stem cells. In another embodiment, provided herein is a method of upregulating, or increasing the number of, anti-inflammatory T cells, comprising contacting immune system cells with an effective amount of enhanced placental stem cells.

In one embodiment, provided herein is a method of inhibiting a Th1 response in an individual comprising administering to the individual an effective amount of placental stem cells, wherein said effective amount is an amount that results in a detectable decrease in a Th1 response in the individual. In another embodiment, provided herein is a method of inhibiting a Th17 response in an individual comprising administering to the individual an effective amount of placental stem cells, wherein said effective amount is an amount that results in a detectable decrease in a Th17 response in the individual. In specific embodiments of these methods, said administering detectably reduces the production, by T cells or antigen presenting cells in said individual, of one or more of IL-1β, IL-12, IL-17, IL-21, IL-23, TNFα and/or IFNγ.

In another specific embodiment of the method, said contacting potentiates or upregulates a regulatory T cell (Treg) phenotype, or modulates production in a dendritic cell (DC) and/or macrophage in said individual of markers the promote a Th1 or Th17 response. In another specific embodiment, the method comprises additionally administering IL-10 to said individual. In another specific embodiment, the individual has graft-versus-host disease. In another specific embodiment, the individual has rheumatoid arthritis, multiple sclerosis, psoriasis, inflammatory bowel disease (e.g., Crohn's disease), diabetes (e.g., diabetes mellitus), lupus (e.g., lupus erythematosus), scleroderma, or mycosis fungoides.

In another aspect, provided herein are enhanced placental stem cells, as described herein, that have been additionally genetically engineered to express one or more anti-inflammatory cytokines. In a specific embodiment, said anti-inflammatory cytokines comprise IL-10.

5.3 Placental Stem Cells and Placental Stem Cell Populations

The methods provided herein use enhanced placental stem cells, or ePSCs. In another aspect, provided herein are placental stem cells that have been treated or modified, according to methods of modifying placental stem cells provided herein, to enhance their immunomodulatory (e.g., immunosuppressive) activity over that of untreated or unmodified placental stem cells.

Enhanced placental stem cells are produced from placental stem cells, which are stem cells obtainable from a placenta or part thereof, that (1) adhere to a tissue culture substrate; (2)

have the capacity to differentiate into non-placental cell types; and (3) have, in sufficient numbers, the capacity to detectably suppress an immune function, e.g., proliferation of CD4+ and/or CD8+ T cells in a mixed lymphocyte reaction assay or regression assay. Enhancement of such placental stem cells by oligomeric or polymeric molecules (e.g., modulatory RNA molecules such as antisense RNAs, siRNAs, miR inhibitors, shRNAs, or a combination thereof) provided herein improves upon the native immunosuppressive capacity of such placental stem cells.

In certain embodiments, the enhanced placental stem cells (ePSCs), when contacted with (e.g., co-cultured with) peripheral blood mononuclear cells (PBMCs), reduce an amount of interleukin-23 (IL-23) produced by said PBMCs, e.g., as compared to an equivalent number of unmodified placental stem cells. In a specific embodiment, the PBMCs are contacted with said ePSCs in vivo, e.g. within an individual to whom the ePSCs are administered. In another specific embodiment, the PBMCs are contacted with said ePSCs in vitro.

In certain embodiments, said modulatory RNA molecules target one or more genes in said ePSCs that modulate the production of IL-23 by PBMCs such that the production of IL-23 by said PBMCs contacted with said ePSCs is reduced, e.g., as compared to PBMCs contacted with an equivalent number of unmodified placental stem cells. In a specific embodiment, said one or more genes comprise one or more of Twinfilin-1, human nuclear receptor subfamily 1, group H, member 3 (NR1H3), deoxynucleotidyltransferase, terminal, interacting protein 1 (DNTTIP1), vitamin D (1,25-dihydroxyvitamin D3) receptor (VDR), nuclear receptor subfamily 4, group A, member 3 (NR4A3), nuclear receptor subfamily 4, group A, member 2 (NR4A2), nuclear receptor subfamily 0, group B, member 2 (NR0B2), and nuclear receptor subfamily 1, group I, member 2 (NR1I2). In another specific embodiment, said one or more genes comprise NR4A2. In another specific embodiment, said one or more genes comprise NR4A3.

In one embodiment, said modulatory RNA molecules are small interfering RNAs (siRNAs). In a specific embodiment, said siRNAs are double-stranded, wherein one strand of said siRNAs have a sequence at least about 70%, 80%, 90%, 95%, 98% or 100% identical to SEQ ID NO: 1, 3, 5, 7, 9, 11 or 13, e.g., wherein said ePSCs contacted with said siRNAs suppress IL-23 production in PBMCs contacted with said ePSCs. In a specific embodiment, said siRNAs are double-stranded, wherein one strand of said siRNAs have a sequence at least about 70%, 80%, 90%, 95%, 98% or 100% identical to SEQ ID NO: 2, 4, 6, 8, 10, 12 or 14, e.g., wherein said ePSCs contacted with said siRNAs suppress IL-23 production in PBMCs contacted with said ePSCs.

In certain embodiments, said modulatory RNA molecules target one or more miRNAs in said ePSCs that modulate the production of IL-23 by PBMCs such that production of IL-23 by said PBMCs contacted with said ePSCs is reduced, e.g., as compared to PBMCs contacted with an equivalent number of unmodified placental stem cells. In a specific embodiment, said one or more miRNAs comprise hsa-miR-183, hsa-miR-491-5p, hsa-miR-132*, hsa-miR-129-5p, hsa-miR-636, hsa-miR-100, hsa-miR-181a, hsa-miR-519a, hsa-miR-338-3p, hsa-miR-1179, hsa-miR-521, hsa-miR-608, hsa-miR-1306, hsa-miR-543, hsa-miR-542-3p, hsa-miR-23b, hsa-miR-299-3p, hsa-miR-597, hsa-miR-1976, hsa-miR-1252, hsa-miR-510, hsa-miR-1207-5p, hsa-miR-518a-3p, hsa-miR-1250, hsa-miR-1274a, hsa-miR-141*, hsa-miR-9*, hsa-miR-566, hsa-miR-142-5p, hsa-miR-23a*, hsa-miR-519e*, hsa-miR-1292, hsa-miR-96, hsa-miR-886-3p, hsa-miR-216b, hsa-miR-218-2*, hsa-miR-182, hsa-miR-545*, hsa-miR-517a, hsa-miR-541*, hsa-miR-1293, hsa-miR-339-5p, hsa-miR-494, hsa-miR-196a*, hsa-miR-371-5p, hsa-miR-136*, hsa-miR-214, hsa-miR-25*, hsa-miR-452*, hsa-miR-454*, hsa-miR-548b-5p, hsa-miR-10b*, hsa-miR-218, hsa-miR-548m, hsa-miR-520a-3p, hsa-miR-1323, hsa-miR-24-2*, hsa-miR-613, hsa-miR-26a, hsa-miR-193a-3p, hsa-miR-1208, hsa-miR-767-5p, hsa-miR-491-3p, hsa-miR-626, hsa-miR-216a, hsa-miR-151-5p, hsa-miR-1282, hsa-miR-497*, hsa-miR-129-3p, hsa-miR-1, hsa-miR-129*, hsa-miR-24, hsa-miR-24-1*, hsa-miR-218-1*, hsa-miR-183, and/or hsa-miR-183*.

In one embodiment, said modulatory RNA molecules are miR inhibitors. In a specific embodiment, said miR inhibitors have a sequence of at least about 70%, 80%, 90%, 95%, 98% or 100% identical to any of SEQ ID NO: 59-83, e.g., wherein said ePSCs contacted with said miR inhibitors suppress IL-23 produced by said PBMCs contacted with said ePSCs.

In certain embodiments, the enhanced placental stem cells (ePSCs) have increased cyclooxygenase II (Cox-2) activity, e.g., as compared to an equivalent number of unmodified placental stem cells. In one embodiment, said Cox-2 activity is induced by IL-1β.

In certain embodiments, the enhanced placental stem cells (ePSCs) have increased production of prostaglandin E2 (PGE2), e.g., as compared to an equivalent number of unmodified placental stem cells. In one embodiment, said production of PGE2 production is induced by IL-1β.

In certain embodiments, said modulatory RNA molecules target one or more genes in said ePSCs that modulate the production of PGE2 by said ePSCs such that the production of PGE2 by said ePSCs is increased, e.g., as compared to an equivalent number of unmodified placental stem cells. In a specific embodiment, said one or more genes comprise one or more of cholinergic receptor, nicotinic beta 1 (muscle) (CHRNB1), chloride channel 6 (CLCN6), chloride intracellular channel 4 (CLIC4), casein kinase 1, gamma 3 (CSNK1G3), casein kinase 2, alpha prime polypeptide (CSNK2A2), dual specificity phosphatase 1 (DUSP1), potassium channel modulatory factor 1 (KCMF1), potassium voltage-gated channel, shaker-related subfamily, member 3 (KCNA3), potassium inwardly-rectifying channel, subfamily J, member 14 (KCNJ14), potassium voltage-gated channel, delayed-rectifier, subfamily S, member 3 (KCNS3), potassium channel tetramerisation domain containing 13 (KCTD13), hepatocyte growth factor (hepapoietin A; scatter factor) (HGF), nuclear receptor subfamily 2, group C, member 2 (NR2C2), phosphodiesterase 1B, calmodulin-dependent (PDE1B), phosphodiesterase 7B (PDE7B), phosphatidylinositol 4-kinase type 2 beta (PI4K2B), phosphoinositide-3-kinase, regulatory subunit 1 (alpha) (PIK3R1), phospholipase C, eta 2 (PLCH2), protein phosphatase, Mg2+/Mn2+ dependent, 1D (PPM1D), protein phosphatase, Mg2+/Mn2+ dependent, 1G (PPM1G), protein phosphatase 1, regulatory (inhibitor) subunit 2 pseudogene 9 (PPP1R2P9), protein phosphatase 1, regulatory (inhibitor) subunit 3B (PPP1R3B), protein phosphatase 1, regulatory (inhibitor) subunit 9B (PPP1R9B), protein phosphatase 2, catalytic subunit, beta isozyme (PPP2CB), protein tyrosine phosphatase type IVA, member 1 (PTP4A1), protein tyrosine phosphatase, receptor type, K (PTPRK), regulator of G-protein signaling 4 (RGS4), regulator of G-protein signaling 7 binding protein (RGS7BP), regulator of G-protein signaling 8 (RGS8), solute carrier family 16, member 3 (monocarboxylic acid transporter 4) (SLC16A3), solute carrier family 30 (zinc transporter), member 1 (SLC30A1), solute carrier family 35, member A4 (SLC35A4), solute carrier family 38, member 7 (SLC38A7), solute carrier family 41, member 1 (SLC41A1

(includes EG:254428)), solute carrier family 45, member 3 (SLC45A3), solute carrier family 7 (cationic amino acid transporter, y+ system), member 1 (SLC7A1), ubiquitin associated protein 2 (UBAP2), ubiquitin-conjugating enzyme E2D 3 (UBC4/5 homolog, yeast) (UBE2D3 (includes EG:7323)), ubiquitin-conjugating enzyme E2E 3 (UBC4/5 homolog, yeast) (UBE2E3), ubiquitin-conjugating enzyme E2R 2 (UBE2R2), ubiquitin-conjugating enzyme E2W (putative) (UBE2W), ubiquitin-like with PHD and ring finger domains 2 (UHRF2), ubiquitin specific peptidase 9, X-linked (USP9X), and hypoxia inducible factor 1, alpha subunit (HIF1A). In another specific embodiment, said one or more genes comprise HIF1A. In another specific embodiment, said one or more genes comprise DUSP1. In another specific embodiment, said one or more genes comprise PDE7B.

In certain embodiments, said modulatory RNA molecules target one or more miRNAs in said ePSCs that modulate the production of PGE2 by ePSCs such that production of IL-23 by said ePSCs is reduced, e.g., as compared to an equivalent number of unmodified placental stem cells. In a specific embodiment, said one or more miRNAs comprise one or more of hsa-miR-886-3p, hsa-miR-371-3p, hsa-miR-25*, hsa-miR-376c, hsa-miR-888, hsa-miR-517b, hsa-miR-433, hsa-miR-200a*, hsa-miR-520a-5p, hsa-miR-1286, hsa-miR-182*, hsa-miR-1273, hsa-miR-1280, hsa-miR-563, hsa-miR-501-5p, hsa-miR-448, hsa-miR-485-3p, hsa-miR-29c, hsa-miR-548f, hsa-miR-1248, hsa-let-7d*, hsa-miR-618, hsa-miR-30c, hsa-miR-136, hsa-miR-181a, hsa-miR-26a, hsa-miR-10a, hsa-miR-557, hsa-miR-564, hsa-miR-520g, hsa-miR-122*, hsa-miR-548k, hsa-miR-423-3p, hsa-miR-548j, hsa-miR-340*, hsa-miR-573, hsa-miR-548i, hsa-miR-555, hsa-miR-144, hsa-miR-567, hsa-miR-191*, hsa-miR-566, hsa-miR-335, hsa-miR-126*, hsa-miR-22*, hsa-miR-572, hsa-miR-517c, hsa-miR-380*, hsa-miR-106a*, hsa-miR-519e, hsa-miR-520c-3p, hsa-miR-517*, hsa-miR-432*, hsa-miR-520e, hsa-miR-9*, hsa-miR-551a, hsa-miR-1471, hsa-miR-613, hsa-miR-562, hsa-miR-922, hsa-miR-216a, hsa-miR-499-5p, hsa-miR-25, hsa-miR-197, hsa-miR-500*, hsa-miR-365*, hsa-miR-1247, hsa-miR-586, hsa-miR-548d-3p, hsa-miR-27a*, hsa-miR-598, hsa-miR-609, hsa-miR-132, hsa-miR-411*, hsa-miR-135a, hsa-miR-31, hsa-miR-181a*, hsa-miR-1245, hsa-miR-758, hsa-miR-924, hsa-miR-1246, hsa-miR-23b, hsa-miR-631, hsa-miR-1, hsa-miR-920, hsa-miR-589*, hsa-miR-638, hsa-miR-1244, hsa-miR-328, hsa-let-71, hsa-miR-429, hsa-miR-380, hsa-let-7b*, hsa-miR-614, hsa-miR-1225-5p, hsa-miR-545*, hsa-miR-320c, hsa-miR-579, hsa-miR-1282, hsa-miR-455-5p, hsa-miR-615-3p, hsa-miR-585, hsa-miR-559, hsa-miR-561, hsa-miR-191, hsa-miR-187, hsa-miR-29b, hsa-miR-769-5p, hsa-miR-495, hsa-miR-516a-3p, hsa-miR-938, hsa-miR-936, hsa-miR-373*, hsa-miR-1184, hsa-miR-122, hsa-miR-208b, hsa-miR-223*, hsa-miR-1972, hsa-miR-520h, hsa-miR-330-3p, hsa-miR-149, hsa-miR-7, hsa-miR-29b-2*, hsa-miR-520d-5p, hsa-miR-592, hsa-miR-940, hsa-miR-146b-3p, hsa-miR-518e*, hsa-miR-1255a, hsa-miR-935, hsa-miR-633, hsa-miR-513a-5p, hsa-miR-361-3p, hsa-miR-194, hsa-miR-1185, hsa-miR-875-3p, hsa-miR-200a, hsa-miR-1201, hsa-miR-629, hsa-miR-139-5p, hsa-miR-504, hsa-miR-452, hsa-miR-517a, hsa-miR-543, hsa-miR-616*, hsa-miR-651, hsa-miR-1254, hsa-miR-339-3p, hsa-miR-510, hsa-miR-181c*, hsa-miR-19b-1*, hsa-miR-1274a, hsa-miR-1294, hsa-miR-1306, hsa-miR-1226*, and hsa-miR-541* in said enhanced placental stem. In one embodiment, said modulatory RNA molecules are miR inhibitors. In a specific embodiment, said miR inhibitors have a sequence at least about 70%, 80%, 90%, 95%, 98% or 100% identical to any of SEQ ID NO: 27, 28, 35, 39, 53-54, and 181-222.

In certain embodiments, the enhanced placental stem cells (ePSCs) have reduced production of a pro-inflammatory cytokine (e.g., extracellular pro-inflammatory cytokine), e.g., as compared to an equivalent number of unmodified placental stem cells. In certain embodiments, said pro-inflammatory cytokine is IL-1, IL-6, IL-8, TNF-α, or any combinations thereof. In a specific embodiment, said pro-inflammatory cytokine is IL-6, IL-8, or a combination thereof. In another specific embodiment, said pro-inflammatory cytokine is IL-6.

In another embodiment, the enhanced placental stem cells (ePSCs) have suppressed response induced by interferon-gamma (IFN-γ), as compared to an equivalent number of unmodified placental stem cells. In one specific embodiment, said modulatory RNA molecules target (e.g., modulate) one or more genes in said ePSCs that modulate IFN-γ-induced response of said ePSCs such that the IFN-γ-induced response is suppressed, e.g., as compared to an equivalent number of unmodified placental stem cells. In another specific embodiment, said one or more genes comprise one or more of protein inhibitor of activated STAT, 1 (PIAS1) and TYRO protein tyrosine kinase binding protein (TYROBP).

Placental stem cells from which enhanced placental stem cells are produced are not derived from blood, e.g., placental blood or umbilical cord blood. The placental stem cells used to produce the enhanced placental stem cells used in the methods and compositions provided herein have the capacity, and can be selected for their capacity, to suppress the immune system of an individual.

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

5.3.1 Physical and Morphological Characteristics

The placental stem cells used as described herein, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cyotplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

5.3.2 Cell Surface, Molecular and Genetic Markers

The isolated placental stem cells, e.g., isolated multipotent placental stem cells or isolated placental stem cells, and populations of such isolated placental stem cells, useful in the methods disclosed herein, e.g., the methods of treatment of a CNS injury, are tissue culture plastic-adherent human placental stem cells that have characteristics of multipotent cells or stem cells, and express a plurality of markers that can be used to identify and/or isolate the cells, or populations of cells that comprise the stem cells. In certain embodiments, the placental stem cells are angiogenic, e.g., in vitro or in vivo. The isolated placental stem cells, and placental cell populations described herein (that is, two or more isolated placental stem cells) include placental stem cells and placental cell-containing cell populations obtained directly from the placenta, or any part thereof (e.g., chorion, placental cotyledons, or the like). Isolated placental cell populations also include populations of (that is, two or more) isolated placental stem cells in culture, and a population in a container, e.g., a bag. The isolated placental stem cells described herein are not bone marrow-derived mesenchymal cells, adipose-derived mesenchymal stem cells, or mesenchymal cells obtained from umbilical cord blood, placental blood, or peripheral blood. Placental cells, e.g., placental multipotent cells and placental stem cells, useful in the methods and compositions described herein are described herein and, e.g., in U.S. Pat. Nos. 7,311,904; 7,311,905; 7,468,276 and 8,057,788, the disclosures of which are hereby incorporated by reference in their entireties.

In certain embodiments, the isolated placental stem cells are $CD34^-$, $CD10^+$ and $CD105^+$ as detected by flow cytometry. In another specific embodiment, the isolated $CD34^-$, $CD10^+$, $CD105^+$ placental stem cells have the potential to differentiate into cells of a neural phenotype, cells of an osteogenic phenotype, and/or cells of a chondrogenic phenotype. In another specific embodiment, the isolated $CD34^-$, $CD10^+$, $CD105^+$ placental stem cells are additionally $CD200^+$. In another specific embodiment, the isolated $CD34^-$, $CD10^+$, $CD105^+$ placental stem cells are additionally $CD45^-$ or $CD90^+$. In another specific embodiment, the isolated $CD34^-$, $CD10^+$, $CD105^+$ placental stem cells are additionally $CD45^-$ and $CD90^+$, as detected by flow cytometry. In another specific embodiment, the isolated $CD34^-$, $CD10^+$, $CD105^+$, $CD200^+$ placental stem cells are additionally $CD90^+$ or $CD45^-$, as detected by flow cytometry. In another specific embodiment, the isolated $CD34^-$, $CD10^+$, $CD105^+$, $CD200^+$ placental stem cells are additionally $CD90^+$ and $CD45^-$, as detected by flow cytometry, i.e., the cells are $CD34^-$, $CD10^+$, $CD45^-$, $CD90^+$, $CD105^+$ and $CD200^+$. In another specific embodiment, said $CD34^-$, $CD10^+$, $CD45^-$, $CD90^+$, $CD105^+$, $CD200^+$ placental stem cells are additionally $CD80^-$ and $CD86^-$.

In certain embodiments, said placental stem cells are $CD34^-$, $CD10^+$, $CD105^+$ and $CD200^+$, and one or more of $CD38^-$, $CD45^-$, $CD80^-$, $CD86^-$, $CD133^-$, HLA-DR,DP,DQ$^-$, SSEA3$^-$, SSEA4$^-$, $CD29^+$, $CD44^+$, $CD73^+$, $CD90^+$, $CD105^+$, HLA-A,B,C$^+$, PDL1$^+$, ABC-p$^+$, and/or OCT-4$^+$, as detected by flow cytometry. In other embodiments, any of the $CD34^-$, $CD10^+$, $CD105^+$ placental stem cells described above are additionally one or more of $CD29^+$, $CD38^-$, $CD44^+$, $CD54^+$, SH3$^+$ or SH4$^+$. In another specific embodiment, the placental stem cells are additionally $CD44^+$. In another specific embodiment of any of the isolated $CD34^-$, $CD10^+$, $CD105^+$ placental stem cells above, the cells are additionally one or more of $CD117^-$, $CD133^-$, KDR$^-$ (VEGFR2$^-$), HLA-A,B,C$^+$, HLA-DP,DQ,DR$^-$, or Programmed Death-1 Ligand (PDL1)$^+$, or any combination thereof.

In another embodiment, the $CD34^-$, $CD10^+$, $CD105^+$ placental stem cells are additionally one or more of $CD13^+$, $CD29^+$, $CD33^+$, $CD38^-$, $CD44^+$, $CD45^-$, $CD54^+$, $CD62E^-$, $CD62L^-$, $CD62P^-$, SH3$^+$ ($CD73^+$), SH4$^+$ ($CD73^+$), $CD80^-$, $CD86^-$, $CD90^+$, SH2$^+$ ($CD105^+$), CD106/VCAM$^+$, $CD117^-$, CD144/VE-cadherin$^{low}$, CD184/CXCR4$-$, $CD200^+$, $CD133^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, or Programmed Death-1 Ligand (PDL1)$^+$, or any combination thereof. In another embodiment, the $CD34^-$, $CD10^+$, $CD105^+$ placental stem cells are additionally $CD13^+$, $CD29^+$, $CD33^+$, $CD38^-$, $CD44^+$, $CD45^-$, $CD54$/ICAM$^+$, $CD62E^-$, $CD62L^-$, $CD62L^-$, SH3$^+$ ($CD73^+$), SH4$^+$ ($CD73^+$), $CD80^-$, $CD86^-$, $CD90^+$, SH2$^+$ ($CD105^+$), CD106/VCAM$^+$, $CD117^-$, CD144/VE-cadherin$^{low}$, CD184/CXCR4$^-$, $CD200^+$, $CD133^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, and Programmed Death-1 Ligand (PDL1)$^+$.

In another specific embodiment, any of the placental stem cells described herein are additionally ABC-p$^+$, as detected by flow cytometry, or OCT-4$^+$ (POU5F1$^+$), as determined by reverse-transcriptase polymerase chain reaction (RT-PCR), wherein ABC-p is a placenta-specific ABC transporter protein (also known as breast cancer resistance protein (BCRP) or as mitoxantrone resistance protein (MXR)), and OCT-4 is the Octamer-4 protein (POU5F1). In another specific embodiment, any of the placental stem cells described herein are additionally SSEA3$^-$ or SSEA4$^-$, as determined by flow cytometry, wherein SSEA3 is Stage Specific Embryonic Antigen 3, and SSEA4 is Stage Specific Embryonic Antigen 4. In another specific embodiment, any of the placental stem cells described herein are additionally SSEA3$^-$ and SSEA4$^-$.

In another specific embodiment, any of the placental stem cells described herein are, or are additionally, one or more of MHC-I$^+$ (e.g., HLA-A,B,C$^+$), MHC-II$^-$ (e.g., HLA-DP,DQ,DR$^-$) or HLA-G$^-$. In another specific embodiment, any of the placental stem cells described herein are additionally MHC-I$^+$ (e.g., HLA-A,B,C$^+$), MHC-II$^-$ (e.g., HLA-DP,DQ,DR$^-$) and HLA-G$^-$.

Also provided herein are populations of the isolated placental stem cells, or populations of cells, e.g., populations of placental cells, comprising, e.g., that are enriched for, the isolated placental stem cells, that are useful in the methods and compositions disclosed herein. Preferred populations of cells are those comprising the isolated placental stem cells, wherein the populations of cells comprise, e.g., at least 10%, 15%, 20%, 25%, 30%, 35%, 40%, 45%, 50%, 55%, 60%, 65%, 70%, 75%, 80%, 85%, 90%, 95% or 98% isolated $CD10^+$, $CD105^+$ and $CD34^-$ placental stem cells; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated $CD10^+$, $CD105^+$ and $CD34^-$ placental stem cells. In a specific embodiment, the isolated $CD34^-$, $CD10^+$, $CD105^+$ placental stem cells are additionally $CD200^+$. In another specific embodiment, the isolated $CD34^-$, $CD10^+$, $CD105^+$, $CD200^+$ placental stem cells are additionally $CD90^+$ or $CD45^-$, as detected by flow cytometry. In another specific embodiment, the isolated $CD34^-$, $CD10^+$, $CD105^+$, $CD200^+$ placental stem cells are additionally $CD90^+$ and $CD45^-$, as detected by flow cytometry. In another specific embodiment, any of the isolated $CD34^-$, $CD10^+$, $CD105^+$ placental stem cells described above are additionally one or more of $CD29^+$, $CD38^-$, $CD44^+$, $CD54^+$, SH3$^+$ or SH4$^+$. In another specific embodiment, the isolated $CD34^-$, $CD10^+$, $CD105^+$ placental stem cells, or isolated $CD34^-$, $CD10^+$, $CD105^+$, $CD200^+$ placental stem cells, are additionally $CD44^+$. In a specific embodiment of any of the populations of cells comprising isolated $CD34^-$, $CD10^+$, $CD105^+$ placental stem cells above, the isolated placental stem cells are additionally one or more of $CD13^+$, $CD29^+$, $CD33^+$, $CD38^-$, $CD44^+$, $CD45^-$, $CD54^+$, $CD62E^-$, $CD62L^-$, $CD62P^-$, SH3$^+$ ($CD73^+$), SH4$^+$ ($CD73^+$), $CD80^-$, $CD86^-$, $CD90^+$, SH2$^+$ ($CD105^+$), CD106/VCAM$^+$, $CD117^-$, CD144/VE-cadherin$^{low}$, CD184/CXCR4$^-$, $CD200^+$, $CD133^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, or Programmed Death-1 Ligand (PDL1)$^+$, or any combination thereof. In another specific embodiment, the $CD34^-$, $CD10^+$, $CD105^+$ placental stem cells are additionally $CD13^+$, $CD29^+$, $CD33^+$, $CD38^-$, $CD44^+$, $CD45^-$, $CD54$/ICAM$^+$, $CD62E^-$, $CD62L^-$, $CD62P^-$, SH3$^+$ ($CD73^+$), SH4$^+$ ($CD73^+$), $CD80^-$, $CD86^-$, $CD90^+$, SH2$^+$ ($CD105^+$), CD106/VCAM$^+$, CD11T, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, and Programmed Death-1 Ligand (PDL1)$^+$.

In certain embodiments, the isolated placental stem cells in said population of cells are one or more, or all, of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, wherein said isolated placental stem cells are obtained by physical and/or enzymatic disruption of placental tissue. In a specific embodiment, the isolated placental stem cells are OCT-4$^+$ and ABC-p$^+$. In another specific embodiment, the isolated placental stem cells are OCT-4$^+$ and CD34$^-$, wherein said isolated placental stem cells have at least one of the following characteristics: CD10$^+$, CD29$^+$, CD44$^+$, CD45$^-$, CD54$^+$, CD90$^+$, SH3$^+$, SH4$^+$, SSEA3$^-$, and SSEA4$^-$. In another specific embodiment, the isolated placental stem cells are OCT-4$^+$, CD34$^-$, CD10$^+$, CD29$^+$, CD44$^+$, CD45$^-$, CD54$^+$, CD90$^+$, SH3$^+$, SH4$^+$, SSEA3$^-$, and SSEA4$^-$. In another embodiment, the isolated placental stem cells are OCT-4$^+$, CD34$^-$, SSEA3$^-$, and SSEA4$^-$. In another specific embodiment, the isolated placental stem cells are OCT-4$^+$ and CD34$^-$, and is either SH2$^+$ or SH3$^+$. In another specific embodiment, the isolated placental stem cells are OCT-4$^+$, CD34$^-$, SH2$^+$, and SH3$^+$. In another specific embodiment, the isolated placental stem cells are OCT-4$^+$, CD34$^-$, SSEA3$^-$, and SSEA4$^-$, and are either SH2$^+$ or SH3$^+$. In another specific embodiment, the isolated placental stem cells are OCT-4$^+$ and CD34$^-$, and either SH2$^+$ or SH3$^+$, and is at least one of CD10$^+$, CD29$^+$, CD44$^+$, CD45$^-$, CD54$^+$, CD90$^+$, SSEA3$^-$, or SSEA4$^-$. In another specific embodiment, the isolated placental stem cells are OCT-4$^+$, CD34$^-$, CD10$^+$, CD29$^+$, CD44$^+$, CD45$^-$, CD54$^+$, CD90$^+$, SSEA3$^-$, and SSEA4$^-$, and either SH2$^+$ or SH3$^+$.

In another embodiment, the isolated placental stem cells are SH2$^+$, SH3$^+$, SH4$^+$ and OCT-4$^+$. In another specific embodiment, the isolated placental stem cells are CD10$^+$, CD29$^+$, CD44$^+$, CD54$^+$, CD90$^+$, CD34$^-$, CD45$^-$, SSEA3$^-$, or SSEA4$^-$. In another embodiment, the isolated placental stem cells are SH2$^+$, SH3$^+$, SH4$^+$, SSEA3$^-$ and SSEA4$^-$. In another specific embodiment, the isolated placental stem cells are SH2$^+$, SH3$^+$, SH4$^+$, SSEA3$^-$ and SSEA4$^-$, CD10$^+$, CD29$^+$, CD44$^+$, CD54$^+$, CD90$^+$, OCT-4$^+$, CD34$^-$ or CD45$^-$.

In another embodiment, the isolated placental stem cells useful in the methods and compositions disclosed herein are CD10$^+$, CD29$^+$, CD34$^-$, CD44$^+$, CD45$^-$, CD54$^+$, CD90$^+$, SH2$^+$, SH3$^+$, and SH4$^+$; wherein said isolated placental stem cells are additionally one or more of OCT-4$^+$, SSEA3$^-$ or SSEA4$^-$.

In certain embodiments, isolated placental stem cells are CD200$^+$ or HLA-G$^-$. In a specific embodiment, the isolated placental stem cells are CD200$^+$ and HLA-G$^-$. In another specific embodiment, the isolated placental stem cells are additionally CD73$^+$ and CD105$^+$. In another specific embodiment, the isolated placental stem cells are additionally CD34$^-$, CD38$^-$ or CD45$^-$. In another specific embodiment, the isolated placental stem cells are additionally CD34$^-$, CD38$^-$ and CD45$^-$. In another specific embodiment, said placental stem cells are CD34$^-$, CD38$^-$, CD45$^-$, CD73$^+$ and CD105$^+$. In another specific embodiment, said isolated CD200$^+$ or HLA-G$^-$ placental stem cells facilitate the formation of embryoid-like bodies in a population of placental cells comprising the isolated placental stem cells, under conditions that allow the formation of embryoid-like bodies. In another specific embodiment, the isolated placental stem cells are isolated away from placental cells that are not said placental stem cells. In another specific embodiment, said isolated placental stem cells are isolated away from placental cells that do not display this combination of markers.

In another embodiment, a cell population useful in the methods and compositions described herein is a population of cells comprising, e.g., that is enriched for, CD200$^+$, HLA-G$^-$ placental stem cells. In a specific embodiment, said population is a population of placental cells. In various embodiments, at least about 10%, at least about 20%, at least about 30%, at least about 40%, at least about 50%, or at least about 60% of cells in said cell population are isolated CD200$^+$, HLA-G$^-$ placental stem cells. Preferably, at least about 70% of cells in said cell population are isolated CD200$^+$, HLA-G$^-$ placental stem cells. More preferably, at least about 90%, 95%, or 99% of said cells are isolated CD200$^+$, HLA-G$^-$ placental stem cells. In a specific embodiment of the cell populations, said isolated CD200$^+$, HLA-G$^-$ placental stem cells are also CD73$^+$ and CD105$^+$. In another specific embodiment, said isolated CD200$^+$, HLA-G$^-$ placental stem cells are also CD34$^-$, CD38$^-$ or CD45$^-$. In another specific embodiment, said isolated CD200$^+$, HLA-G$^-$ placental stem cells are also CD34$^-$, CD38$^-$, CD45$^-$, CD73$^+$ and CD105$^+$. In another embodiment, said cell population produces one or more embryoid-like bodies when cultured under conditions that allow the formation of embryoid-like bodies. In another specific embodiment, said cell population is isolated away from placental cells that are not placental stem cells. In another specific embodiment, said isolated CD200$^+$, HLA-G$^-$ placental stem cells are isolated away from placental cells that do not display these markers.

In another embodiment, the isolated placental stem cells useful in the methods and compositions described herein are CD73$^+$, CD105$^+$, and CD200$^+$. In another specific embodiment, the isolated placental stem cells are HLA-G$^-$. In another specific embodiment, the isolated placental stem cells are CD34$^-$, CD38$^-$ or CD45$^-$. In another specific embodiment, the isolated placental stem cells are CD34$^-$, CD38$^-$ and CD45$^-$. In another specific embodiment, the isolated placental stem cells are CD34$^-$, CD38$^-$, CD45$^-$, and HLA-G$^-$. In another specific embodiment, the isolated CD73$^+$, CD105$^+$, and CD200$^+$ placental stem cells facilitate the formation of one or more embryoid-like bodies in a population of placental cells comprising the isolated placental stem cells, when the population is cultured under conditions that allow the formation of embryoid-like bodies. In another specific embodiment, the isolated placental stem cells are isolated away from placental cells that are not the isolated placental stem cells. In another specific embodiment, the isolated placental stem cells are isolated away from placental cells that do not display these markers.

In another embodiment, a cell population useful in the methods and compositions described herein is a population of cells comprising, e.g., that is enriched for, isolated CD73$^+$, CD105$^+$, CD200$^+$ placental stem cells. In various embodiments, at least about 10%, at least about 20%, at least about 30%, at least about 40%, at least about 50%, or at least about 60% of cells in said cell population are isolated CD73$^+$, CD105$^+$, CD200$^+$ placental stem cells. In another embodiment, at least about 70% of said cells in said population of cells are isolated CD73$^+$, CD105$^+$, CD200$^+$ placental stem cells. In another embodiment, at least about 90%, 95% or 99% of cells in said population of cells are isolated CD73$^+$, CD105$^+$, CD200$^+$ placental stem cells. In a specific embodiment of said populations, the isolated placental stem cells are HLA-G$^-$. In another specific embodiment, the isolated placental stem cells are additionally CD34$^-$, CD38$^-$ or CD45$^-$. In another specific embodiment, the isolated placental stem cells are additionally CD34$^-$, CD38$^-$ and CD45$^-$. In another specific embodiment, the isolated placental stem cells are additionally CD34−, CD38−, CD45−, and HLA-G−. In another specific embodiment, said population of cells produces one or more embryoid-like bodies when cultured under conditions that allow the formation of embryoid-like bodies. In another specific embodiment, said population of placental stem cells is isolated away from placental cells that are not placental stem cells. In another specific embodiment, said population of placental stem cells is isolated away from placental cells that do not display these characteristics.

In certain other embodiments, the isolated placental stem cells are one or more of CD10+, CD29+, CD34−, CD38−, CD44+, CD45−, CD54+, CD90+, SH2+, SH3+, SH4+, SSEA3−, SSEA4−, OCT-4+, HLA-G− or ABC-p+. In a specific embodiment, the isolated placental stem cells are CD10+, CD29+, CD34−, CD38−, CD44+, CD45−, CD54+, CD90+, SH2+, SH3+, SH4+, SSEA3−, SSEA4−, and OCT-4+. In another specific embodiment, the isolated placental stem cells are CD10+, CD29+, CD34−, CD38−, CD45−, CD54+, SH2+, SH3+, and SH4+. In another specific embodiment, the isolated placental stem cells CD10+, CD29+, CD34−, CD38−, CD45−, CD54+, SH2+, SH3+, SH4+ and OCT-4+. In another specific embodiment, the isolated placental stem cells are CD10+, CD29+, CD34−, CD38−, CD44+, CD45−, CD54+, CD90+, HLA-G−, SH2+, SH3+, SH4+. In another specific embodiment, the isolated placental stem cells are OCT-4+ and ABC-p+. In another specific embodiment, the isolated placental stem cells are SH2+, SH3+, SH4+ and OCT-4+. In another embodiment, the isolated placental stem cells are OCT-4+, CD34−, SSEA3−, and SSEA4−. In a specific embodiment, said isolated OCT-4+, CD34−, SSEA3−, and SSEA4− placental stem cells are additionally CD10+, CD29+, CD34−, CD44+, CD45−, CD54+, CD90+, SH2+, SH3+, and SH4+. In another embodiment, the isolated placental stem cells are OCT-4+ and CD34−, and either SH3+ or SH4+. In another embodiment, the isolated placental stem cells are CD34− and either CD10+, CD29+, CD44+, CD54+, CD90+, or OCT-4+.

In another embodiment, isolated placental stem cells are CD200+ and OCT-4+. In a specific embodiment, the isolated placental stem cells are CD73+ and CD105+. In another specific embodiment, said isolated placental stem cells are HLA-G−. In another specific embodiment, said isolated CD200+, OCT-4+ placental stem cells are CD34−, CD38− or CD45−. In another specific embodiment, said isolated CD200+, OCT-4+ placental stem cells are CD34−, CD38− and CD45−. In another specific embodiment, said isolated CD200+, OCT-4+ placental stem cells are CD34−, CD38−, CD45−, CD73+, CD105+ and HLA-G−. In another specific embodiment, the isolated CD200+, OCT-4+ placental stem cells facilitate the production of one or more embryoid-like bodies by a population of placental cells that comprises the placental stem cells, when the population is cultured under conditions that allow the formation of embryoid-like bodies. In another specific embodiment, said isolated CD200+, OCT-4+ placental stem cells are isolated away from placental cells that are not said placental stem cells. In another specific embodiment, said isolated CD200+, OCT-4+ placental stem cells are isolated away from placental cells that do not display these characteristics.

In another embodiment, a cell population useful in the methods and compositions described herein is a population of cells comprising, e.g., that is enriched for, CD200+, OCT-4+ placental stem cells. In various embodiments, at least about 10%, at least about 20%, at least about 30%, at least about 40%, at least about 50%, or at least about 60% of cells in said cell population are isolated CD200+, OCT-4+ placental stem cells. In another embodiment, at least about 70% of said cells are said isolated CD200+, OCT-4+ placental stem cells. In another embodiment, at least about 80%, 90%, 95%, or 99% of cells in said cell population are said isolated CD200+, OCT-4+ placental stem cells. In a specific embodiment of the isolated populations, said isolated CD200+, OCT-4+ placental stem cells are additionally CD73+ and CD105+. In another specific embodiment, said isolated CD200+, OCT-4+ placental stem cells are additionally HLA-G−. In another specific embodiment, said isolated CD200+, OCT-4+ placental stem cells are additionally CD34−, CD38− and CD45−. In another specific embodiment, said isolated CD200+, OCT-4+ placental stem cells are additionally CD34−, CD38−, CD45−, CD73+, CD105+ and HLA-G−. In another specific embodiment, the cell population produces one or more embryoid-like bodies when cultured under conditions that allow the formation of embryoid-like bodies. In another specific embodiment, said cell population is isolated away from placental cells that are not isolated CD200+, OCT-4+ placental cells. In another specific embodiment, said cell population is isolated away from placental cells that do not display these markers.

In another embodiment, the isolated placental stem cells useful in the methods and compositions described herein are CD73+, CD105+ and HLA-G−. In another specific embodiment, the isolated CD73+, CD105+ and HLA-G− placental stem cells are additionally CD34−, CD38− or CD45−. In another specific embodiment, the isolated CD73+, CD105+, HLA-G− placental stem cells are additionally CD34−, CD38− and CD45−. In another specific embodiment, the isolated CD73+, CD105+, HLA-G− placental stem cells are additionally OCT-4+. In another specific embodiment, the isolated CD73+, CD105+, HLA-G− placental stem cells are additionally CD200+. In another specific embodiment, the isolated CD73+, CD105+, HLA-G− placental stem cells are additionally CD34−, CD38−, CD45−, OCT-4+ and CD200+. In another specific embodiment, the isolated CD73+, CD105+, HLA-G− placental stem cells facilitate the formation of embryoid-like bodies in a population of placental cells comprising said placental stem cells, when the population is cultured under conditions that allow the formation of embryoid-like bodies. In another specific embodiment, said the isolated CD73+, CD105+, HLA-G− placental stem cells are isolated away from placental cells that are not the isolated CD73+, CD105+, HLA-G− placental stem cells. In another specific embodiment, said the isolated CD73+, CD105+, HLA-G− placental stem cells are isolated away from placental cells that do not display these markers.

In another embodiment, a cell population useful in the methods and compositions described herein is a population of cells comprising, e.g., that is enriched for, isolated CD73+, CD105+ and HLA-G− placental stem cells. In various embodiments, at least about 10%, at least about 20%, at least about 30%, at least about 40%, at least about 50%, or at least about 60% of cells in said population of cells are isolated CD73+, CD105+, HLA-G− placental stem cells. In another embodiment, at least about 70% of cells in said population of cells are isolated CD73+, CD105+, HLA-G− placental stem cells. In another embodiment, at least about 90%, 95% or 99% of cells in said population of cells are isolated CD73+, CD105+, HLA-G− placental stem cells. In a specific embodiment of the above populations, said isolated CD73+, CD105+, HLA-G− placental stem cells are additionally CD34−, CD38− or CD45−. In another specific embodiment, said isolated CD73+, CD105+, HLA-G− placental stem cells are additionally CD34−, CD38− and CD45−. In another specific embodiment, said isolated CD73+, CD105+, HLA-G− placental stem cells are additionally OCT-4+. In another specific embodiment, said isolated CD73$^+$, CD105$^+$, HLA-G$^-$ placental stem cells are additionally CD200$^+$. In another specific embodiment, said isolated CD73$^+$, CD105$^+$, HLA-G$^-$ placental stem cells are additionally CD34$^-$, CD38$^-$, CD45$^-$, OCT-4$^+$ and CD200$^+$. In another specific embodiment, said cell population is isolated away from placental cells that are not CD73$^+$, CD105$^+$, HLA-G$^-$ placental stem cells. In another specific embodiment, said cell population is isolated away from placental cells that do not display these markers.

In another embodiment, the isolated placental stem cells are CD73$^+$ and CD105$^+$ and facilitate the formation of one or more embryoid-like bodies in a population of isolated placental cells comprising said CD73$^+$, CD105$^+$ cells when said population is cultured under conditions that allow formation of embryoid-like bodies. In another specific embodiment, said isolated CD73$^+$, CD105$^+$ placental stem cells are additionally CD34$^-$, CD38$^-$ or CD45$^-$. In another specific embodiment, said isolated CD73$^+$, CD105$^+$ placental stem cells are additionally CD34$^-$, CD38$^-$ and CD45$^-$. In another specific embodiment, said isolated CD73$^+$, CD105$^+$ placental stem cells are additionally OCT-4$^+$. In another specific embodiment, said isolated CD73$^+$, CD105$^+$ placental stem cells are additionally OCT-4$^+$, CD34$^-$, CD38$^-$ and CD45$^-$. In another specific embodiment, said isolated CD73$^+$, CD105$^+$ placental stem cells are isolated away from placental cells that are not said cells. In another specific embodiment, said isolated CD73$^+$, CD105$^+$ placental stem cells are isolated away from placental cells that do not display these characteristics.

In another embodiment, a cell population useful in the methods and compositions described herein is a population of cells comprising, e.g., that is enriched for, isolated placental stem cells that are CD73$^+$, CD105$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated CD73$^+$, CD105$^+$ placental stem cells. In another embodiment, at least about 70% of cells in said population of cells are said isolated CD73$^+$, CD105$^+$ placental stem cells. In another embodiment, at least about 90%, 95% or 99% of cells in said population of cells are said isolated CD73$^+$, CD105$^+$ placental stem cells. In a specific embodiment of the above populations, said isolated CD73$^+$, CD105$^+$ placental stem cells are additionally CD34$^-$, CD38$^-$ or CD45$^-$. In another specific embodiment, said isolated CD73$^+$, CD105$^+$ placental stem cells are additionally CD34$^-$, CD38$^-$ and CD45$^-$. In another specific embodiment, said isolated CD73$^+$, CD105$^+$ placental stem cells are additionally OCT-4$^+$. In another specific embodiment, said isolated CD73$^+$, CD105$^+$ placental stem cells are additionally CD200$^+$. In another specific embodiment, said isolated CD73$^+$, CD105$^+$ placental stem cells are additionally CD34$^-$, CD38$^-$, CD45$^-$, OCT-4$^+$ and CD200$^+$. In another specific embodiment, said cell population is isolated away from placental cells that are not said isolated CD73$^+$, CD105$^+$ placental stem cells. In another specific embodiment, said cell population is isolated away from placental cells that do not display these markers.

In another embodiment, the isolated placental stem cells are OCT-4$^+$ and facilitate formation of one or more embryoid-like bodies in a population of isolated placental stem cells comprising said placental stem cells when said population of cells is cultured under conditions that allow formation of embryoid-like bodies. In a specific embodiment, said isolated OCT-4$^+$ placental stem cells are additionally CD73$^+$ and CD105$^+$. In another specific embodiment, said isolated OCT-4$^+$ placental stem cells are additionally CD34$^-$, CD38$^-$, or CD45$^-$. In another specific embodiment, said isolated OCT-4$^+$ placental stem cells are additionally CD200$^+$. In another specific embodiment, said isolated OCT-4$^+$ placental stem cells are additionally CD73$^+$, CD105$^+$, CD200$^+$, CD34$^-$, CD38$^-$, and CD45$^-$. In another specific embodiment, said isolated OCT-4$^+$ placental stem cells are isolated away from placental cells that are not OCT-4$^+$ placental cells. In another specific embodiment, said isolated OCT-4$^+$ placental stem cells are isolated away from placental cells that do not display these characteristics.

In another embodiment, a cell population useful in the methods and compositions described herein is a population of cells comprising, e.g., that is enriched for, isolated placental stem cells that are OCT-4$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated OCT-4$^+$ placental stem cells. In another embodiment, at least about 70% of cells in said population of cells are said isolated OCT-4$^+$ placental stem cells. In another embodiment, at least about 80%, 90%, 95% or 99% of cells in said population of cells are said isolated OCT-4$^+$ placental stem cells. In a specific embodiment of the above populations, said isolated OCT-4$^+$ placental stem cells are additionally CD34$^-$, CD38$^-$ or CD45$^-$. In another specific embodiment, said isolated OCT-4$^+$ placental stem cells are additionally CD34$^-$, CD38$^-$ and CD45$^-$. In another specific embodiment, said isolated OCT-4$^+$ placental stem cells are additionally CD73$^+$ and CD105$^+$. In another specific embodiment, said isolated OCT-4$^+$ placental stem cells are additionally CD200$^+$. In another specific embodiment, said isolated OCT-4$^+$ placental stem cells are additionally CD73$^+$, CD105$^+$, CD200$^+$, CD34$^-$, CD38$^-$, and CD45$^-$. In another specific embodiment, said cell population is isolated away from placental cells that are not said placental stem cells. In another specific embodiment, said cell population is isolated away from placental cells that do not display these markers.

In another embodiment, the isolated placental stem cells useful in the methods and compositions described herein are isolated HLA-A,B,C$^+$, CD45$^-$, CD133$^-$ and CD34$^-$ placental stem cells. In another embodiment, a cell population useful in the methods and compositions described herein is a population of cells comprising isolated placental stem cells, wherein at least about 70%, at least about 80%, at least about 90%, at least about 95% or at least about 99% of cells in said population of cells are isolated HLA-A,B,C$^+$, CD45$^-$, CD133$^-$ and CD34$^-$ placental stem cells. In a specific embodiment, said isolated placental cell or population of isolated placental cells is isolated away from placental cells that are not HLA-A,B, C$^+$, CD45$^-$, CD133$^-$ and CD34$^-$ placental stem cells. In another specific embodiment, said isolated placental stem cells are non-maternal in origin. In another specific embodiment, said population of isolated placental stem cells are substantially free of maternal components; e.g., at least about 40%, 45%, 5-0%, 55%, 60%, 65%, 70%, 75%, 90%, 85%, 90%, 95%, 98% or 99% of said cells in said population of isolated placental stem cells are non-maternal in origin.

In another embodiment, the isolated placental stem cells useful in the methods and compositions described herein are isolated CD10$^+$, CD13$^+$, CD33$^+$, CD45$^-$, CD117$^-$ and CD133$^-$ placental stem cells. In another embodiment, a cell population useful in the methods and compositions described herein is a population of cells comprising isolated placental stem cells, wherein at least about 70%, at least about 80%, at least about 90%, at least about 95% or at least about 99% of cells in said population of cells are isolated CD10$^+$, CD13$^+$, CD33$^+$, CD45$^-$, CD117$^-$ and CD133$^-$ placental stem cells. In a specific embodiment, said isolated placental stem cells or population of isolated placental stem cells is isolated away from placental cells that are not said isolated placental stem cells. In another specific embodiment, said isolated CD10$^+$, CD13$^+$, CD33$^+$, CD45$^-$, CD117$^-$ and CD133$^-$ placental stem cells are non-maternal in origin, i.e., have the fetal genotype. In another specific embodiment, at least about 40%, 45%, 50%, 55%, 60%, 65%, 70%, 75%, 90%, 85%, 90%, 95%, 98% or 99% of said cells in said population of isolated placental stem cells, are non-maternal in origin. In another specific embodiment, said isolated placental stem cells or population of isolated placental stem cells are isolated away from placental cells that do not display these characteristics.

In another embodiment, the isolated placental stem cells are isolated CD10$^+$ CD33$^-$, CD44$^+$, CD45$^-$, and CD117$^-$ placental cells. In another embodiment, a cell population useful for the in the methods and compositions described herein is a population of cells comprising, e.g., enriched for, isolated placental cells, wherein at least about 70%, at least about 80%, at least about 90%, at least about 95% or at least about 99% of cells in said population of cells are isolated CD10$^+$ CD33$^-$, CD44$^+$, CD45$^-$, and CD11T placental cells. In a specific embodiment, said isolated placental cell or population of isolated placental cells is isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said placental stem cells in said cell population are non-maternal in origin. In another specific embodiment, said isolated placental stem cells or population of isolated placental stem cells is isolated away from placental cells that do not display these markers.

In another embodiment, the isolated placental stem cells useful in the methods and compositions described herein are isolated CD10$^+$ CD13$^-$, CD33$^-$, CD45$^-$, and CD117$^-$ placental stem cells. In another embodiment, a cell population useful in the methods and compositions described herein is a population of cells comprising, e.g., enriched for, isolated CD10$^+$, CD13$^-$, CD33$^-$, CD45$^-$, and CD11T placental stem cells, wherein at least about 70%, at least about 80%, at least about 90%, at least about 95% or at least about 99% of cells in said population are CD10+ CD13$^-$, CD33$^-$, CD45$^-$, and CD117$^-$ placental stem cells. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental stem cells or population of isolated placental stem cells is isolated away from placental cells that do not display these characteristics.

In another embodiment, the isolated placental stem cells useful in the methods and compositions described herein are HLA A,B,C$^+$, CD45$^-$, CD34$^-$, and CD133$^-$, and are additionally CD10$^+$, CD13$^+$, CD38$^+$, CD44$^+$, CD90$^+$, CD105$^+$, CD200$^+$ and/or HLA-G$^-$, and/or negative for CD117. In another embodiment, a cell population useful in the methods described herein is a population of cells comprising isolated placental stem cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated placental stem cells that are HLA A,B,C$^-$, CD45$^-$, CD34$^-$, CD133$^-$, and that are additionally positive for CD10, CD13, CD38, CD44, CD90, CD105, CD200, and/or negative for CD117 and/or HLA-G. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said placental stem cells in said cell population are non-maternal in origin. In another specific embodiment, said isolated placental stem cells or population of isolated placental stem cells are isolated away from placental cells that do not display these characteristics.

In another embodiment, the isolated placental stem cells are isolated placental stem cells that are CD200$^+$ and CD10$^+$, as determined by antibody binding, and CD117$^-$, as determined by both antibody binding and RT-PCR. In another embodiment, the isolated placental stem cells are isolated placental stem cells that are CD10$^+$, CD29$^-$, CD54$^+$, CD200$^+$, HLA-G$^-$, MHC class I$^+$ and β-2-microglobulin$^+$. In another embodiment, isolated placental stem cells useful in the methods and compositions described herein are placental stem cells wherein the expression of at least one cellular marker is at least two-fold higher than in an equivalent number of mesenchymal stem cells, e.g., bone marrow-derived mesenchymal stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated placental stem cells are isolated placental stem cells that are one or more of CD10$^+$, CD29$^+$, CD44$^+$, CD45$^-$, CD54/ICAM$^+$, CD62E$^-$, CD62L$^-$, CD62P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and/or PDL1$^{low}$. In a specific embodiment, the isolated placental stem cells are at least CD29$^+$ and CD54$^+$. In another specific embodiment, the isolated placental stem cells are at least CD44$^+$ and CD106$^+$. In another specific embodiment, the isolated placental stem cells are at least CD29$^+$.

In another embodiment, a cell population useful in the methods and compositions described herein comprises isolated placental stem cells, and at least 50%, 60%, 70%, 80%, 90%, 95%, 98% or 99% of the cells in said cell population are isolated placental stem cells that are one or more of CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{dim}$, CD184/CXCR4$^-$, β2-microglobulin$^{dim}$, HLA-I$^{dim}$, HLA-II$^-$, HLA-G$^{dim}$, and/or PDL1$^{dim}$ placental stem cells. In another specific embodiment, at least 50%, 60%, 70%, 80%, 90%, 95%, 98% or 99% of cells in said cell population are CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{dim}$, CD184/CXCR4$^-$, β2-microglobulin$^{dim}$, MHC-I$^{dim}$, MHC-II$^-$, HLA-G$^{dim}$, and PDL1$^{dim}$ placental stem cells. In certain embodiments, the placental stem cells express HLA-II markers when induced by interferon gamma (IFN-γ).

In another embodiment, the isolated placental stem cells useful in the methods and compositions described herein are isolated placental stem cells that are one or more, or all, of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, where ABC-p is a placenta-specific ABC transporter protein (also known as breast cancer resistance protein (BCRP) or as mitoxantrone resistance protein (MXR)), wherein said isolated placental stem cells are obtained by perfusion of a mammalian, e.g., human, placenta that has been drained of cord blood and perfused to remove residual blood.

In another specific embodiment of any of the above embodiments, expression of the recited cellular marker(s) (e.g., cluster of differentiation or immunogenic marker(s)) is determined by flow cytometry. In another specific embodiment, expression of the marker(s) is determined by RT-PCR.

Gene profiling confirms that isolated placental stem cells, and populations of isolated placental stem cells, are distinguishable from other cells, e.g., mesenchymal stem cells, e.g., bone marrow-derived mesenchymal stem cells. The isolated placental stem cells described herein can be distinguished from, e.g., bone marrow-derived mesenchymal stem cells on the basis of the expression of one or more genes, the expression of which is significantly higher in the isolated placental stem cells in comparison to bone marrow-derived mesenchymal stem cells. In particular, the isolated placental stem cells, useful in the methods of treatment provided herein, can be distinguished from bone marrow-derived mesenchymal stem cells on the basis of the expression of one or more genes, the expression of which is significantly higher (that is, at least twofold higher) in the isolated placental stem cells than in an equivalent number of bone marrow-derived mesenchymal stem cells, wherein the one or more gene comprise ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In certain specific embodiments, said expression of said one or more genes is determined, e.g., by RT-PCR or microarray analysis, e.g, using a U133-A microarray (Affymetrix).

In another specific embodiment, said isolated placental stem cells express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another specific embodiment, the isolated placental cell-specific gene is CD200.

Specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (F1110781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In certain specific embodiments, said isolated placental stem cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, F1110781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In specific embodiments, the placental stem cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells wherein said bone marrow-derived mesenchymal stem cells have undergone a number of passages in culture equivalent to the number of passages said isolated placental stem cells have undergone. In other specific embodiments, the placental stem cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells, wherein said bone marrow-derived mesenchymal stem cells have undergone a number of passages in culture equivalent to the number of passages said isolated placental stem cells have undergone.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental stem cells, to identify a population of cells as comprising at least a plurality of isolated placental stem cells, or the like. Populations of isolated placental stem cells, the identity of which is confirmed, can be clonal, e.g., populations of isolated placental stem cells expanded from a single isolated placental stem cells, or a mixed population of placental stem cells, e.g., a population of cells comprising isolated placental stem cells that are expanded from multiple isolated placental stem cells, or a population of cells comprising isolated placental stem cells, as described herein, and at least one other type of cell.

The level of expression of these genes can be used to select populations of isolated placental stem cells. For example, a population of cells, e.g., clonally-expanded placental stem cells, may be selected if the expression of one or more of the genes listed above is significantly higher in a sample from the population of cells than in an equivalent population of bone marrow-derived mesenchymal stem cells. Such selecting can be of a population from a plurality of isolated placental stem cells populations, from a plurality of cell populations, the identity of which is not known, etc.

Isolated placental stem cells can be selected on the basis of the level of expression of one or more such genes as compared to the level of expression in said one or more genes in, e.g., a bone marrow-derived mesenchymal stem cell control. In one embodiment, the level of expression of said one or more genes in a sample comprising an equivalent number of bone marrow-derived mesenchymal stem cells is used as a control. In another embodiment, the control, for isolated placental stem cells tested under certain conditions, is a numeric value representing the level of expression of said one or more genes in bone marrow-derived mesenchymal stem cells under said conditions.

The isolated placental stem cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× linoleic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

In certain embodiments of any of the placental stem cells disclosed herein, the cells are human. In certain embodiments of any of the placental cells disclosed herein, the cellular marker characteristics or gene expression characteristics are human markers or human genes.

In another specific embodiment of the isolated placental stem cells or populations of cells comprising the isolated placental stem cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of said isolated placental stem cells or populations of cells comprising the isolated placental stem cells, said cells or population are primary isolates. In another specific embodiment of the isolated placental stem cells, or populations of cells comprising isolated placental stem cells, that are disclosed herein, said isolated placental stem cells are fetal in origin (that is, have the fetal genotype).

In certain embodiments, said isolated placental stem cells do not differentiate during culturing in growth medium, i.e., medium formulated to promote proliferation, e.g., during proliferation in growth medium. In another specific embodiment, said isolated placental stem cells do not require a feeder layer in order to proliferate. In another specific embodiment, said isolated placental stem cells do not differentiate in culture in the absence of a feeder layer, solely because of the lack of a feeder cell layer.

In another embodiment, the isolated placental cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, between about 3% and about 25% of placental stem cells are positive for ALDH. In another embodiment, said isolated placental stem cells show at least three-fold, or at least five-fold, higher ALDH activity than a population of bone marrow-derived mesenchymal stem cells having about the same number of cells and cultured under the same conditions.

In certain embodiments of any of the populations of cells comprising the isolated placental stem cells described herein, the placental stem cells in said populations of cells are substantially free of cells having a maternal genotype; e.g., at least 40%, 45%, 50%, 55%, 60%, 65%, 70%, 75%, 80%, 85%, 90%, 95%, 98% or 99% of the placental stem cells in said population have a fetal genotype. In certain other embodiments of any of the populations of cells comprising the isolated placental stem cells described herein, the populations of cells comprising said placental stem cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated placental stem cells or cell populations comprising isolated placental stem cells, the karyotype of the cells, e.g., all of the cells, or at least about 95% or about 99% of the cells in said population, is normal. In another specific embodiment of any of the above placental stem cells or populations or placental stem cells, the placental stem cells are non-maternal in origin.

In a specific embodiment of any of the embodiments of placental cells disclosed herein, the placental cells are genetically stable, displaying a normal diploid chromosome count and a normal karyotype.

Isolated placental stem cells, or populations of isolated placental stem cells, bearing any of the above combinations of markers, can be combined in any ratio. Any two or more of the above isolated placental stem cells populations can be combined to form an isolated placental stem cell population. For example, a population of isolated placental stem cells can comprise a first population of isolated placental stem cells defined by one of the marker combinations described above, and a second population of isolated placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental stem cells or isolated placental stem cell populations can be combined.

Isolated placental stem cells useful in the methods and compositions described herein can be obtained, e.g., by disruption of placental tissue, with or without enzymatic digestion or perfusion. For example, populations of isolated placental stem cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental stem cells; and isolating said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental stem cells, contained within a population of cells obtained from perfusion of a placenta, are at least 50%, 60%, 70%, 80%, 90%, 95%, 99% or at least 99.5% of said population of placental stem cells. In another specific embodiment, the isolated placental stem cells collected by perfusion comprise fetal and maternal cells. In another specific embodiment, the isolated placental stem cells collected by perfusion are at least 50%, 60%, 70%, 80%, 90%, 95%, 99% or at least 99.5% fetal cells.

In another specific embodiment, provided herein is a composition comprising a population of the isolated placental stem cells, as described herein, collected (isolated) by perfusion, wherein said composition comprises at least a portion of the perfusion solution used to isolate the placental stem cells.

Populations of the isolated placental stem cells described herein can be produced by digesting placental tissue with a tissue-disrupting enzyme to obtain a population of placental cells comprising the placental stem cells, and isolating, or substantially isolating, a plurality of the placental stem cells from the remainder of said placental cells. The whole, or any part of, the placenta can be digested to obtain the isolated placental stem cells described herein. In specific embodiments, for example, said placental tissue can be a whole placenta (e.g., including an umbilical cord), an amniotic membrane, chorion, a combination of amnion and chorion, or a combination of any of the foregoing. In other specific embodiments, the tissue-disrupting enzyme is trypsin or collagenase. In various embodiments, the isolated placental stem cells, contained within a population of cells obtained from digesting a placenta, are at least 50%, 60%, 70%, 80%, 90%, 95%, 99% or at least 99.5% of said population of placental cells.

The populations of isolated placental stem cells described above, and populations of isolated placental stem cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more of the isolated placental stem cells. Populations of isolated placental stem cells useful in the methods of treatment described herein comprise at least 50%, 55%, 60%, 65%, 70%, 75%, 80%, 85%, 90%, 95%, 98%, or 99% viable isolated placental stem cells, e.g., as determined by, e.g., trypan blue exclusion.

For any of the above placental stem cells, or populations of placental stem cells, the cells or population of placental stem cells are, or can comprise, cells that have been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more.

In a specific embodiment of any of the above placental stem cells or placental stem cells populations, the karyotype of the cells, or at least about 95% or about 99% of the cells in said population, is normal. In another specific embodiment of any of the above placental stem cells or placental stem cells populations, the cells, or cells in the population of cells, are non-maternal in origin.

Isolated placental stem cells, or populations of isolated placental stem cells, bearing any of the above combinations of markers, can be combined in any ratio. Any two or more of the above placental stem cells populations can be isolated, or enriched, to form a placental stem cells population. For example, an population of isolated placental stem cells comprising a first population of placental stem cells defined by one of the marker combinations described above can be combined with a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cells populations can be combined.

In a specific embodiment of the above-mentioned placental stem cells, the placental stem cells constitutively secrete IL-6, IL-8 and monocyte chemoattractant protein (MCP-1).

The immunosuppressive pluralities of placental cells described above can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

In certain embodiments, the placental stem cells useful in the methods provided herein, do not express CD34, as detected by immunolocalization, after exposure to 1 to 100 ng/mL VEGF for 4 to 21 days. In a specific embodiment, said placental stem cells are adherent to tissue culture plastic. In another specific embodiment, said placental stem cells induce endothelial cells to form sprouts or tube-like structures, e.g., when cultured in the presence of an angiogenic factor such as vascular endothelial growth factor (VEGF), epithelial growth factor (EGF), platelet derived growth factor (PDGF) or basic fibroblast growth factor (bFGF), e.g., on a substrate such as MATRIGEL™.

In another aspect, the placental stem cells provided herein, or a population of cells, e.g., a population of placental stem cells, or a population of cells wherein at least about 50%, 60%, 70%, 80%, 90%, 95% or 98% of cells in said population of cells are placental stem cells, secrete one or more, or all, of VEGF, HGF, IL-8, MCP-3, FGF2, follistatin, G-CSF, EGF, ENA-78, GRO, IL-6, MCP-1, PDGF-BB, TIMP-2, uPAR, or galectin-1, e.g., into culture medium in which the cell, or cells, are grown. In another embodiment, the placental stem cells express increased levels of CD202b, IL-8 and/or VEGF under hypoxic conditions (e.g., less than about 5% $O_2$) compared to normoxic conditions (e.g., about 20% or about 21% $O_2$).

In another embodiment, any of the placental stem cells or populations of cells comprising placental stem cells described herein can cause the formation of sprouts or tube-like structures in a population of endothelial cells in contact with said placental stem cells. In a specific embodiment, the placental stem cells are co-cultured with human endothelial cells, which form sprouts or tube-like structures, or support the formation of endothelial cell sprouts, e.g., when cultured in the presence of extracellular matrix proteins such as collagen type I and IV, and/or angiogenic factors such as vascular endothelial growth factor (VEGF), epithelial growth factor (EGF), platelet derived growth factor (PDGF) or basic fibroblast growth factor (bFGF), e.g., in or on a substrate such as placental collagen or MATRIGEL™ for at least 4 days. In another embodiment, any of the populations of cells comprising placental stem cells, described herein, secrete angiogenic factors such as vascular endothelial growth factor (VEGF), hepatocyte growth factor (HGF), platelet derived growth factor (PDGF), basic fibroblast growth factor (bFGF), or Interleukin-8 (IL-8) and thereby can induce human endothelial cells to form sprouts or tube-like structures when cultured in the presence of extracellular matrix proteins such as collagen type I and IV e.g., in or on a substrate such as placental collagen or MATRIGEL™.

In another embodiment, any of the above populations of cells comprising placental stem cells secretes angiogenic factors. In specific embodiments, the population of cells secretes vascular endothelial growth factor (VEGF), hepatocyte growth factor (HGF), platelet derived growth factor (PDGF), basic fibroblast growth factor (bFGF), and/or interleukin-8 (IL-8). In other specific embodiments, the population of cells comprising placental stem cells secretes one or more angiogenic factors and thereby induces human endothelial cells to migrate in an in vitro wound healing assay. In other specific embodiments, the population of cells comprising placental stem cells induces maturation, differentiation or proliferation of human endothelial cells, endothelial progenitors, myocytes or myoblasts.

5.3.3 Selecting and Producing Placental Cell Populations

In certain embodiments, populations of placental stem cells can be selected, wherein the population is immunosuppressive. In one embodiment, for example, immunosuppressive placental stem cells can be selected from a plurality of placental cells, comprising selecting a population of placental cells wherein at least 10%, at least 20%, at least 30%, at least 40%, at least 50% at least 60%, at least 70%, at least 80%, at least 90%, or at least 95% of said cells are $CD10^+$, $CD34^-$, $CD105^+$, $CD200^+$ placental stem cells, and wherein said placental stem cells detectably suppresses T cell proliferation in a mixed lymphocyte reaction (MLR) assay. In a specific embodiment, said selecting comprises selecting placental stem cells that are also $CD45^-$ and $CD90^+$.

In another embodiment, provided herein is a method of selecting a plurality of immunosuppressive placental stem cells from a plurality of placental cells, comprising selecting a population of placental stem cells wherein at least 10%, at least 20%, at least 30%, at least 40%, at least 50% at least 60%, at least 70%, at least 80%, at least 90%, or at least 95% of said cells are $CD200^+$, $HLA-G^-$ placental stem cells, and wherein said placental stem cells detectably suppresses T cell proliferation in a mixed lymphocyte reaction (MLR) assay. In a specific embodiment, said selecting comprises selecting placental stem cells that are also $CD73^+$ and $CD105^+$. In another specific embodiment, said selecting comprises selecting placental stem cells that are also $CD34^-$, $CD38^-$ or $CD45^-$. In another specific embodiment, said selecting comprises selecting placental stem cells that are also $CD34^-$, $CD38^-$, $CD45^-$, $CD73^+$ and $CD105^+$. In another specific embodiment, said selecting also comprises selecting a plurality of placental cells, e.g., the placental stem cells described above, that forms one or more embryoid-like bodies when cultured under conditions that allow the formation of embryoid-like bodies.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are $CD73^+$, $CD105^+$, $CD200^+$ placental stem cells, and wherein said placental cells detectably suppresses T cell proliferation in a mixed lymphocyte reaction (MLR) assay. In a specific embodiment, said selecting comprises selecting placental stem cells that are also $HLA-G^-$. In another specific embodiment, said selecting comprises selecting placental stem cells that are also $CD34^-$, $CD38^-$ or $CD45^-$. In another specific embodiment, said selecting comprises selecting placental stem cells that are also $CD34^-$, $CD38^-$ and $CD45^-$. In another specific embodiment, said selecting comprises selecting placental stem cells that are also $CD34^-$, $CD38^-$, $CD45^-$, and $HLA-G^-$. In another specific embodiment, said selecting additionally comprises selecting a population of placental stem cells that produces one or more embryoid-like bodies when the population is cultured under conditions that allow the formation of embryoid-like bodies.

In another embodiment, also provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are $CD200^+$, $OCT-4^+$ placental stem cells, and wherein said placental cells detectably suppresses T cell proliferation in a mixed lymphocyte reaction (MLR) assay. In a specific embodiment, said selecting comprises selecting placental stem cells that are also $CD73^+$ and $CD105^+$. In another specific embodiment, said selecting comprises selecting placental stem cells that are also $HLA-G^-$. In another specific embodiment, said selecting comprises selecting placental stem cells that are also $CD34^-$, $CD38^-$ and $CD45^-$. In another specific embodiment, said selecting comprises selecting placental stem cells that are also $CD34^-$, $CD38^-$, $CD45^-$, $CD73^+$, $CD105^+$ and $HLA-G^-$.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are $CD73^+$, $CD105^+$ and $HLA-G^-$ placental stem cells, and wherein said placental cells detectably suppresses T cell proliferation in a mixed lymphocyte reaction (MLR) assay. In a specific embodiment, said selecting comprises selecting placental stem cells that are also $CD34^-$, $CD38^-$ or $CD45^-$. In another specific embodiment, said selecting comprises selecting placental stem cells that are also $CD34^-$, $CD38^-$ and $CD45^-$. In another specific embodiment, said selecting comprises selecting placental stem cells that are also $CD200^+$. In another specific embodiment, said selecting comprises selecting placental stem cells that are also $CD34^-$, $CD38^-$, $CD45^-$, $OCT-4^+$ and $CD200^+$.

In another embodiment, also provided herein is provides a method of selecting a plurality of immunosuppressive placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are $CD73^+$, $CD105^+$ placental stem cells, and wherein said plurality forms one or more embryoid-like bodies under conditions that allow formation of embryoid-like bodies. In a specific embodiment, said selecting comprises selecting placental stem cells that are also $CD34^-$, $CD38^-$ or $CD45^-$. In another specific embodiment, said selecting comprises selecting placental stem cells that are also $CD34^-$, $CD38^-$ and $CD45^-$. In another specific embodiment, said selecting comprises selecting placental stem cells that are also $OCT-4^+$. In a more specific embodiment, said selecting comprises selecting placental stem cells that are also $OCT-4^+$, $CD34^-$, $CD38^-$ and $CD45^-$.

In another embodiment, provided herein is a method of selecting a plurality of immunosuppressive placental stem cells from a plurality of placental cells, comprising selecting a plurality of placental stem cells wherein at least 10%, at least 20%, at least 30%, at least 40%, at least 50% at least 60%, at least 70%, at least 80%, at least 90%, or at least 95% of said isolated placental cells are OCT4$^+$ placental stem cells, and wherein said plurality forms one or more embryoid-like bodies under conditions that allow formation of embryoid-like bodies. In a specific embodiment, said selecting comprises selecting placental stem cells that are also CD73$^+$ and CD105$^+$. In another specific embodiment, said selecting comprises selecting placental stem cells that are also CD34$^-$, CD38$^-$, or CD45$^-$. In another specific embodiment, said selecting comprises selecting placental stem cells that are also CD200$^+$. In a more specific embodiment, said selecting comprises selecting placental stem cells that are also CD73$^+$, CD105$^+$, CD200$^+$, CD34$^-$, CD38$^-$, and CD45$^-$.

Immunosuppressive populations, or pluralities, of placental cells can be produced according to the methods provided herein. For example, provided herein is method of producing a cell population, comprising selecting any of the pluralities of placental stem cells described above, and isolating the plurality of placental cells from other cells, e.g., other placental cells. In a specific embodiment, provided herein is a method of producing a cell population comprising selecting placental stem cells, wherein said placental stem cells (a) adhere to a substrate, (b) express CD200 and do not express HLA-G; or express CD73, CD105, and CD200; or express CD200 and OCT-4; or express CD73, CD105, and do not express HLA-G; or express CD73 and CD105 and facilitate the formation of one or more embryoid-like bodies in a population of placental cells that comprise the placental stem cells, when said population is cultured under conditions that allow formation of embryoid-like bodies; or express OCT-4 and facilitate the formation of one or more embryoid-like bodies in a population of placental cells that comprise the placental stem cells, when said population is cultured under conditions that allow formation of embryoid-like bodies; and (c) detectably suppress CD4$^+$ or CD8$^+$ T cell proliferation in an MLR (mixed lymphocyte reaction) or regression assay; and selecting said placental stem cells, or isolating said placental stem cells from other cells to form a cell population.

In a more specific embodiment, immunosuppressive placental stem cells populations can be produced by a method comprising selecting placental stem cells that (a) adhere to a substrate, (b) express CD200 and do not express HLA-G, and (c) detectably suppress CD4$^+$ or CD8$^+$ T cell proliferation in an MLR (mixed lymphocyte reaction); and isolating said placental stem cells from other cells to form a cell population. In another specific embodiment, the method comprises selecting placental stem cells that (a) adhere to a substrate, (b) express CD73, CD105, and CD200, and (c) detectably suppress CD4$^+$ or CD8$^+$ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD200 and OCT-4, and (c) detectably suppress CD4$^+$ or CD8$^+$ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD73 and CD105, (c) form embryoid-like bodies when cultured under conditions allowing the formation of embryoid-like bodies, and (d) detectably suppress CD4$^+$ or CD8$^+$ T cell proliferation in an MLR; and isolating said placental stem cells from other cells to form a cell population. In another specific embodiment, the method comprises selecting placental stem cells that (a) adhere to a substrate, (b) express CD73 and CD105, and do not express HLA-G, and (c) detectably suppress CD4$^+$ or CD8$^+$ T cell proliferation in an MLR; and isolating said placental stem cells from other cells to form a cell population. In another specific embodiment, the method comprises selecting placental stem cells that (a) adhere to a substrate, (b) express OCT-4, (c) form embryoid-like bodies when cultured under conditions allowing the formation of embryoid-like bodies, and (d) detectably suppress CD4$^+$ or CD8$^+$ T cell proliferation in an MLR; and isolating said placental cells from other cells to form a cell population.

In a specific embodiment of the methods of producing an immunosuppressive placental stem cells population, said T cells and said placental stem cells are present in said MLR at a ratio of about 5:1. The placental stem cells used in the method can be derived from the whole placenta, or primarily from amnion, or amnion and chorion. In another specific embodiment, the placental stem cells suppress CD4$^+$ or CD8$^+$ T cell proliferation by at least 50%, at least 75%, at least 90%, or at least 95% in said MLR compared to an amount of T cell proliferation in said MLR in the absence of said placental stem cells. The method can additionally comprise the selection and/or production of a placental stem cells population capable of immunomodulation, e.g., suppression of the activity of, other immune cells, e.g., an activity of a natural killer (NK) cell.

5.3.4 Growth in Culture

The growth of the placental cells, e.g., the placental stem cells (PDACs) described herein, as for any mammalian cell, depends in part upon the particular medium selected for growth. Under optimum conditions, placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells provided herein, when cultured under appropriate conditions, can form embryoid-like bodies, that is, three-dimensional clusters of cells grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental cells thus facilitate the growth of one or more embryoid-like bodies in a population of placental cells that comprise the adherent placental cells. Mesenchymal stem cells, e.g., bone marrow-derived mesenchymal stem cells, do not develop embryoid-like bodies in culture.

5.3.5 Differentiation

The placental cells, useful in the methods of treating a CNS injury, e.g., a spinal cord injury or traumatic brain injury, provided herein, in certain embodiments are differentiable into different committed cell lineages. For example, in certain embodiments, the placental cells can be differentiated into cells of an adipogenic, chondrogenic, neurogenic, or osteogenic lineage. Such differentiation can be accomplished, e.g., by any method known in the art for differentiating, e.g., bone marrow-derived mesenchymal stem cells into similar cell lineages, or by methods described elsewhere herein. Specific methods of differentiating placental cells into particular cell lineages are disclosed in, e.g., U.S. Pat. No. 7,311,905, and in U.S. Patent Application Publication No. 2007/0275362, the disclosures of which are hereby incorporated by reference in their entireties.

The placental stem cells provided herein can exhibit the capacity to differentiate into a particular cell lineage in vitro, in vivo, or in vitro and in vivo. In a specific embodiment, the placental stem cells provided herein can be differentiated in vitro when placed in conditions that cause or promote differentiation into a particular cell lineage, but do not detectably differentiate in vivo, e.g., in a NOD-SCID mouse model.

5.4 Methods of Obtaining Placental Stem Cells 5.4.1 Stem Cell Collection Composition Placental stem cells can be collected and isolated according to the methods provided herein. Generally, placental stem cells are obtained from a mammalian placenta using a physiologically-acceptable solution, e.g., a stem cell collection composition. A stem cell collection composition is described in detail in related U.S. Patent Application Publication No. 20070190042.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, HDMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.4.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to placental stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.4.3 Physical Disruption and Enzymatic Digestion of Placental Tissue

In one embodiment, placental stem cells are collected from a mammalian placenta by physical disruption, e.g., enzymatic digestion, of the organ, e.g., using the stem cell collection composition described above. For example, the placenta, or a portion thereof, may be, e.g., crushed, sheared, minced, diced, chopped, macerated or the like, while in contact with, e.g., a buffer, medium or a stem cell collection composition, and the tissue subsequently digested with one or more enzymes. The placenta, or a portion thereof, may also be physically disrupted and digested with one or more enzymes, and the resulting material then immersed in, or mixed into, a buffer, medium or a stem cell collection composition. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

Typically, placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

Enzymatic digestion can be performed using single enzymes or combinations of enzymes. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the placental stem cells with the stem cell collection composition.

It will be appreciated that where an entire placenta, or portion of a placenta comprising both fetal and maternal cells (for example, where the portion of the placenta comprises the chorion or cotyledons) is digested to obtain placental stem cells, the placental cells collected will comprise a mix of placental cells derived from both fetal and maternal sources. Where a portion of the placenta that comprises no, or a negligible number of, maternal cells (for example, amnion) is used to obtain placental stem cells, the placental stem cells collected will comprise almost exclusively fetal placental stem cells.

5.4.4 Placental Perfusion

Placental stem cells can also be obtained by perfusion of the mammalian placenta. Methods of perfusing mammalian placenta to obtain stem cells are disclosed, e.g., in Hariri, U.S. Application Publication No. 2002/0123141, and in related U.S. Provisional Application No. 60/754,969, entitled "Improved Composition for Collecting and Preserving Placental Cells and Methods of Using the Composition" filed on Dec. 29, 2005.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood; this portion of the perfusion can be discarded. The perfusion fluid becomes more colorless as perfusion proceeds and the residual cord blood cells are washed out of the placenta.

The volume of perfusion liquid used to collect placental stem cells may vary depending upon the number of placental stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of placental stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where they are collectable, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Stem cells can be isolated from placenta by perfusion with a solution comprising one or more proteases or other tissue-disruptive enzymes. In a specific embodiment, a placenta or portion thereof is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental stem cells are washed after several minutes with a cold (e.g., 4° C.) stem cell collection composition described elsewhere herein.

Perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

5.4.5 Isolation, Sorting, and Characterization of Placental cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means removing at least 20%, 30%, 40%, 50%, 60%, 70%, 80%, 90%, 95% or 99% of the cells with which the placental stem cells are normally associated in the intact mammalian placenta.

Placental stem cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex).

In one embodiment of isolation of placental stem cells, aliquots of, for example, about 5-10×10$^6$ placental cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34 as compared to, for example, an isotype control; if so, the cell is $CD34^+$. Likewise, if a cell produces enough OCT-4 RNA to be detectable by RT-PCR, or significantly more OCT-4 RNA than a terminally-differentiated cell, the cell is $OCT-4^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted, e.g., further isolated, using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, placental stem cells can be sorted on the basis of expression of the markers CD34, CD38, CD44, CD45, CD73, CD105, OCT-4 and/or HLA-G, or any of the other markers listed elsewhere herein. This can be accomplished in connection with procedures to select stem cells on the basis of their adherence properties in culture. For example, adherence selection of placental stem cells can be accomplished before or after sorting on the basis of marker expression. In one embodiment, for example, placental stem cells can be sorted first on the basis of their expression of CD34; $CD34^-$ cells are retained, and cells that are $CD200^+$ or $HLA-G^+$, are separated from all other $CD34^-$ cells. In another embodiment, placental stem cells can be sorted based on their expression of CD200 and/or HLA-G, or lack thereof; for example, cells displaying either of these markers can be isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental stem cells are sorted by expression, or lack thereof, of CD200, HLA-G, CD73, CD105, CD34, CD38 and CD45, and placental stem cells that are $CD200^+$, $HLA-G^-$, $CD73^+$, $CD105^+$, $CD34^-$, $CD38^-$ and $CD45^-$ are isolated from other placental cells for further use.

In another embodiment, magnetic beads can be used to separate cells, e.g., separate placental stem cells from other placental cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture can be isolated from other placental cells. In another embodiment, $OCT-4^+$ placental cells that produce one or more embryoid-like bodies in culture are isolated from other placental cells.

In another embodiment, placental stem cells can be identified and characterized by a colony forming unit assay. Colony forming unit assays are commonly known in the art, such as MesenCult™ medium (Stem Cell Technologies, Inc., Vancouver British Columbia).

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.5 Culture of Placental Stem Cells 5.5.1 Culture Media

Isolated placental stem cells, or placental cell populations, or cells or placental tissue from which placental cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GlutaMAX™ and gentamicin; DMEM comprising 10% FBS, GlutaMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMIEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Any of the culture methods and media disclosed herein can be used to culture and propagate enhanced placental stem cells, as well.

5.5.2 Expansion and Proliferation of Placental Stem Cells

Once placental stem cells are isolated (e.g., separated from at least 50% of the placental cells with which the stem cell or population of stem cells is normally associated in vivo), the stem cell or population of stem cells can be proliferated and expanded in vitro. Similarly, once enhanced placental stem cells are produced, such cells can also be proliferated and expanded in vitro. For example, placental stem cells can be cultured in tissue culture containers, e.g., dishes, flasks, multiwell plates, or the like, for a sufficient time for the placental stem cells to proliferate to 70-90% confluence, that is, until the placental stem cells and their progeny occupy 70-90% of the culturing surface area of the tissue culture container.

Placental stem cells can be seeded in culture vessels at a density that allows cell growth. For example, the placental stem cells may be seeded at low density (e.g., about 1,000 to about 5,000 cells/cm$^2$) to high density (e.g., about 50,000 or more cells/cm$^2$). In a preferred embodiment, the placental stem cells are cultured at about 0 to about 5 percent by volume $CO_2$ in air. In some preferred embodiments, the placental stem cells are cultured at about 2 to about 25 percent $O_2$ in air, preferably about 5 to about 20 percent $O_2$ in air. The placental stem cells preferably are cultured at about 25° C. to about 40° C., preferably 37° C. The placental stem cells are preferably cultured in an incubator. The culture medium can be static or agitated, for example, using a bioreactor. Placental stem cells are preferably are grown under low oxidative stress (e.g., with addition of glutathione, ascorbic acid, catalase, tocopherol, N-acetylcysteine, or the like).

Once 70%-90% confluence is obtained, the placental stem cells may be passaged. For example, the cells can be enzymatically treated, e.g., trypsinized, using techniques well-known in the art, to separate them from the tissue culture surface. After removing the placental stem cells by pipetting and counting the cells, about 20,000-100,000 stem cells, preferably about 50,000 placental stem cells, are passaged to a new culture container containing fresh culture medium. Typically, the new medium is the same type of medium from which the stem cells were removed. Provided herein are populations of placental stem cells that have been passaged at least 1, 2, 3, 4, 5, 6, 7, 8, 9, 10, 12, 14, 16, 18, or 20 times, or more, and combinations of the same.

5.6 Preservation of Enhanced Placental Cells

Enhanced placental stem cells can be preserved, that is, placed under conditions that allow for long-term storage, or conditions that inhibit cell death by, e.g., apoptosis or necrosis.

Enhanced placental stem cells can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Composition for Collecting and Preserving Placental Cells and Methods of Using the Composition" filed on Dec. 25, 2005.

In one embodiment, provided herein is a method of preserving enhanced placental stem cells comprising contacting said enhanced placental stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of enhanced placental stem cells, as compared to a population of enhanced placental stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said enhanced placental stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said enhanced placental stem cells. In another more specific embodiment, said contacting is performed during freezing and thawing of said population of stem cells.

In another embodiment, enhanced placental stem cells can be preserved by a method comprising contacting said enhanced placental stem cells with an inhibitor of apoptosis and an organ-preserving compound, wherein said inhibitor of apoptosis is present in an amount and for a time sufficient to reduce or prevent apoptosis of the enhanced placental stem cells, as compared to enhanced placental stem cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof.

In another embodiment, placental stem cells, to be used to produce enhanced placental stem cells, are contacted with a stem cell collection composition comprising an apoptosis inhibitor and oxygen-carrying perfluorocarbon, organ-preserving compound, or combination thereof, during perfusion. In another embodiment, said placental stem cells, to be used to produce enhanced placental stem cells, are contacted during a process of tissue disruption, e.g., enzymatic digestion. In another embodiment, placental cells are contacted with said stem cell collection compound after collection by perfusion, or after collection by tissue disruption, e.g., enzymatic digestion.

Typically, during placental stem cell collection, enrichment and isolation, it is preferable to minimize or eliminate cell stress due to hypoxia and mechanical stress. In another embodiment of the method, therefore, placental stem cells, to be used to produce enhanced placental stem cells, are exposed to a hypoxic condition during collection, enrichment or isolation for less than six hours during said preservation, wherein a hypoxic condition is a concentration of oxygen that is less than normal blood oxygen concentration. In a more specific embodiment, said placental stem cells are exposed to said hypoxic condition for less than two hours during said preservation. In another more specific embodiment, said placental stem cells are exposed to said hypoxic condition for less than one hour, or less than thirty minutes, or is not exposed to a hypoxic condition, during collection, enrichment or isolation. In another specific embodiment, said placental stem cells are not exposed to shear stress during collection, enrichment or isolation.

The enhanced placental stem cells, as well as the placental stem cells to be used to produce enhanced placental stem cells, described herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, Plasmalyte, methylcellulose with or without glycerol. The stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C. In certain embodiments, enhanced placental stem cells provided herein are cryopreserved about 12, 24, 36, 48, 60 or 72 hours after being contacted with modulatory RNA molecules (e.g., transfection). In one embodiment, enhanced placental stem cells provided herein are cryopreserved about 24 hours after being contacted with modulatory RNA molecules (e.g., transfection).

5.7 Other Uses of Enhanced Placental Cells
5.7.1 Compositions Comprising Placental Cells The methods provided herein can use compositions comprising the enhanced placental stem cells, or biomolecules therefrom. In the same manner, the populations of enhanced placental stem cells provided herein can be combined with any physiologically-acceptable or medically-acceptable compound, composition or device for use in, e.g., research or therapeutics.

5.7.1.1 Cryopreserved Placental Cells

The immunosuppressive enhanced placental cells described herein can be preserved, for example, cryopreserved for later use. Methods for cryopreservation of cells, such as stem cells, are well known in the art. Enhanced placental cells can be prepared in a form that is easily administrable to an individual. For example, enhanced placental cells described herein can be contained within a container that is suitable for medical use. Such a container can be, for example, a sterile plastic bag, flask, jar, vial, or other container from which the placental cell population can be easily dispensed. For example, the container can be a blood bag or other plastic, medically-acceptable bag suitable for the intravenous administration of a liquid to a recipient. The container is preferably one that allows for cryopreservation of the enhanced placental cells.

Cryopreserved immunosuppressive enhanced placental cell populations can comprise placental stem cells derived from a single donor, or from multiple donors. The enhanced placental cells can be completely HLA-matched to an intended recipient, or partially or completely HLA-mismatched.

Thus, in one embodiment, provided herein is a composition comprising enhanced placental cells in a container. In a specific embodiment, the enhanced placental cells cryopreserved. In another specific embodiment, the container is a bag, flask, vial or jar. In more specific embodiment, said bag is a sterile plastic bag. In a more specific embodiment, said bag is suitable for, allows or facilitates intravenous administration of said enhanced placental cells. The bag can comprise multiple lumens or compartments that are interconnected to allow mixing of the enhanced placental cells and one or more other solutions, e.g., a drug, prior to, or during, administration. In another specific embodiment, the composition comprises one or more compounds that facilitate cryopreservation of the combined stem cell population. In another specific embodiment, said enhanced placental cells are contained within a physiologically-acceptable aqueous solution. In a more specific embodiment, said physiologically-acceptable aqueous solution is a 0.9% NaCl solution. In another specific embodiment, said enhanced placental cells are HLA-matched to a recipient of said enhanced placental cells. In another specific embodiment, said enhanced placental cells are at least partially HLA-mismatched to a recipient of said enhanced placental cells. In another specific embodiment, said enhanced placental cells are derived from placental stem cells from a plurality of donors.

5.7.1.2 Pharmaceutical Compositions

In another aspect, provided herein is a pharmaceutical composition for treating an individual having or at risk of developing a disease, disorder or condition having an inflammatory component, said pharmaceutical composition comprising a therapeutically effective amount of enhanced placental stem cells. In certain embodiments, said cells comprise or have been contacted with an effective amount of modulatory RNA molecules that, when compared to placental stem cells not contacted with said modulatory RNA molecules (i) suppress an amount of soluble IL-23 protein produced by peripheral blood mononuclear cells (PBMCs) in the presence of said enhanced placental stem cells; (ii) increase Cox-2 activity in said enhanced placental stem cells; (iii) increase an amount of PGE2 produced by said enhanced placental stem cells; or (iv) reduce the level a pro-inflammatory cytokine produced by enhanced placental stem cells, wherein the therapeutically effective amount is an amount sufficient to cause a detectable improvement in one or more symptoms of said disease, disorder or condition.

In another aspect, provided herein are enhanced placental stem cells that have been modified by the methods or modulatory RNA molecules provided herein.

Immunosuppressive enhanced placental cells can be formulated into pharmaceutical compositions for use in vivo. Such pharmaceutical compositions can comprise enhanced placental cells in a pharmaceutically-acceptable carrier, e.g., a saline solution or other accepted physiologically-acceptable solution for in vivo administration. Pharmaceutical compositions provided herein can comprise any of the enhanced placental cells described elsewhere herein. The pharmaceutical compositions can comprise fetal, maternal, or both fetal and maternal enhanced placental cells. The pharmaceutical compositions provided herein can further comprise enhanced placental cells produced from placental stem cells obtained from a single individual or placenta, or from a plurality of individuals or placentae.

The pharmaceutical compositions provided herein can comprise any immunosuppressive number of enhanced placental cells. For example, a single unit dose of enhanced placental cells can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more enhanced placental cells.

The pharmaceutical compositions provided herein can comprise populations of enhanced placental cells that comprise 50% viable enhanced placental cells or more (that is, at least 50% of the cells in the population are functional or living). Preferably, at least 60% of the cells in the population are viable. More preferably, at least 70%, 80%, 90%, 95%, or 99% of the enhanced placental cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

5.7.1.3 Matrices Comprising Enhanced Placental Cells

Further provided herein are matrices, hydrogels, scaffolds, and the like that comprise immunosuppressive enhanced placental cells. Enhanced placental cells provided herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% H$_2$O) amniotic membrane, chorionic membrane, substantially dry chorionic membrane, substantially dry amniotic and chorionic membrane, and the like. Preferred placental biomaterials on which enhanced placental cells can be seeded are described in Hariri, U.S. Application Publication No. 2004/0048796.

Placental cells provided herein can be suspended in a hydrogel solution suitable for, e.g., injection. Suitable hydrogels for such compositions include self-assembling peptides, such as RAD16. Enhanced placental stem cells can also be combined with, e.g., alginate or platelet-rich plasma, or other fibrin-containing matrices, for local injection. In one embodiment, a hydrogel solution comprising enhanced placental cells can be allowed to harden, for instance in a mold, to form a matrix having the cells dispersed therein for implantation. Enhanced placental cells in such a matrix can also be cultured so that the cells are mitotically expanded prior to implantation. The hydrogel can be, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the matrix comprises an in situ polymerizable gel (see, e.g., U.S. Patent Application Publication 2002/0022676; Anseth et al., *J. Control Release,* 78(1-3):199-209 (2002); Wang et al., *Biomaterials,* 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The enhanced placental cells can be seeded onto a three-dimensional framework or scaffold and implanted in vivo. Such a framework can be implanted in combination with any one or more growth factors, cells, drugs or other components that stimulate tissue formation or otherwise enhance or improve the practice of the methods of treatment described elsewhere herein.

Examples of scaffolds that can be used in the methods of treatment described herein include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly($\epsilon$-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, the scaffold is, or comprises, a nanofibrous scaffold, e.g., an electrospun nanofibrous scaffold. In a more specific embodiment, said nanofibrous scaffold comprises poly(L-lactic acid) (PLLA), type I collagen, a copolymer of vinylidene fluoride and trifluoroethylnee (PVDF-TrFE), poly(-caprolactone), poly(L-lactide-co-$\epsilon$-caprolactone) [P(LLA-CL)] (e.g., 75:25), and/or a copolymer of poly(3-hydroxybutyrate-co-3-hydroxyvalerate) (PHBV) and type I collagen. Methods of producing nanofibrous scaffolds, e.g., electrospun nanofibrous scaffolds, are known in the art. See, e.g., Xu et al., *Tissue Engineering* 10(7):1160-

1168 (2004); Xu et al., *Biomaterials* 25:877-886 (20040; Meng et al., *J. Biomaterials Sci., Polymer Edition* 18(1):81-94 (2007).

The enhanced placental stem cells described herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, enhanced placental cells can be seeded onto, or contacted with, a felt, which can be, e.g., composed of a multifilament yarn made from a bioabsorbable material such as PGA, PLA, PCL copolymers or blends, or hyaluronic acid.

The enhanced placental cells described herein can, in another embodiment, be seeded onto foam scaffolds that may be composite structures. Such foam scaffolds can be molded into a useful shape. In some embodiments, the framework is treated, e.g., with 0.1M acetic acid followed by incubation in polylysine, PBS, and/or collagen, prior to inoculation of the immunosuppressive placental cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with enhanced placental cells.

6. EXAMPLES

6.1 Example 1

PDACs Transfected with siRNAs of Human Nuclear Receptors Showed Enhanced Suppression of IL-23 by PBMCs This working example provided herein demonstrates the successful enhancement of placental stem cells. In particular, this example demonstrates that inhibition of the expression of human nuclear receptors in placental stem cells enhances the ability of such placental stem cells to suppress PBMC expression of IL-23.

6.1.1 Transfection of Placental Stem Cells

Reagents siPORT™ Amine Catalog #AM4503, Ambion; Silencer® Select Human Nuclear Hormone Receptor (HNR) siRNA Library V4, 0.25 nmol each siRNA, Cat #4397914, Ambion; Silencer® Negative Control No. 1 siRNA (50 µM) Catalog #AM4611, Ambion; Opti-Mem media Catalog#31985-062, Invitrogen; siRNA library Human ON-TARGETplus siRNA Nuclear Receptors Sub-Library Catalog #103400, Dharmacon; Dharmafect 3 Transfection Reagent Catalog#T-2003, Dharmacon; Dharmafect 1 Transfection Reagent Catalog #T-2001, Dharmacon; TaqMan® Gene Expression Cells-to-CT™ Kit, AM1728, Ambion; Bio-Plex Pro Human Cytokine HGF Set #171-B6008M, Bio-Rad; HGF ELISA, Catalog #KAC2211, Invitrogen; CellTiter 96® AQueous One Solution Cell Proliferation Assay (MTS) Catalog #G3580, Promega.

$CD34^-$, $CD10^+$, $CD105^+$, $CD200^+$, tissue culture plastic-adherent placental stem cells were transfected with human nuclear receptor siRNA libraries or control siRNA by direct or reverse transfection. The siRNA libraries and control siRNA were obtained from Ambion (Silencer® Select Human Nuclear Hormone Receptor (HNR) siRNA Library V4, 0.25 nmol each siRNA; Silencer® Negative Control No. 1 siRNA (50 µM)), and Dharmacon (siRNA library Human ON-TARGETplus siRNA Nuclear Receptors Sub-Library). Transfections were set up in a 96-well plate, and were carried out using 0.75-1.0% siPORT Amine transfection reagent (Ambion) or 0.5% Dharmafect 1 or 3 transfection reagent (Dharmafect) in a final volume of 100 uL at $8 \times 10^4$ to $1.2 \times 10^5$ cells/mL. The supernatants or cells were collected after 48 hours of incubation for functional tests. The efficiency of gene silencing by siRNAs was confirmed by quantitative RT-PCR using TaqMan® Gene Expression Cells-to-CT™ Kit (Ambion).

6.1.2 IL-23 Modulation Assay

PBMCs were collected from fresh buffy coat by Ficoll gradient centrifugation of the buffy coat at 300 g for 30 minutes. The layer containing PBMCs was removed, washed three times and counted.

The prepared PBMCs were diluted to $1 \times 10^6$/ml in RPMI-10% FBS complete media, supplemented with 10 ng/ml LPS. The supernatants were removed from the culture plate containing PDACs, and 200 microliters of the PBMC suspension was added to each well. After incubation at 37° C. overnight, the supernatants were collected for quantification of IL-23. The production of IL-23 was determined by IL-23 ELISA (eBioscience 88-7239) following the manufacturer's protocol.

Results siRNAs against six HNR genes (see Table 7) increased PDAC suppression of IL-23 production by PBMCs. The sequence and respective target for each siRNA are listed in Table 1. As shown in FIG. 1, compared to the vehicle control, PDACs treated with individual siRNAs targeting VDR (D3), NR4A3 (D4), NR0B2 (D5), NR1I2 (D6), NR1H3 (E1) or DNTTIP1 (E2) significantly reduced the amount of IL-23 produced by PBMCs exposed to or contacted with the ePSCs. Increased suppression of IL-23 production of PBMCs was confirmed in a separate experiment, where PDACs were treated with siRNA against VDR, NR0B2 or NR1H3 (see FIG. 2).

TABLE 7 siRNAs against six HNR genes enhanced PDAC suppression of IL-23 production by PBMCs in the presence of enhanced placental stem cells

| ID# | Symbol | Description | Entrez Gene Name | Location | Family |
|---|---|---|---|---|---|
| D3 | VDR | vitamin D (1,25-dihydroxyvitamin D3) receptor | vitamin D (1,25-dihydroxyvitamin D3) receptor | Nucleus | ligand-dependent nuclear receptor |
| D4 | NR4A3 | nuclear receptor subfamily 4, group A, member 3 | nuclear receptor subfamily 4, group A, member 3 | Nucleus | ligand-dependent nuclear receptor |
| D5 | NR0B2 | nuclear receptor subfamily 0, group B, member 2 | nuclear receptor subfamily 0, group B, member 2 | Nucleus | ligand-dependent nuclear receptor |
| D6 | NR1I2 | nuclear receptor subfamily 1, group I, member 2 | nuclear receptor subfamily 1, group I, member 2 | Nucleus | ligand-dependent nuclear receptor |
| E1 | NR1H3 | nuclear receptor subfamily 1, group H, member 3 | nuclear receptor subfamily 1, group H, member 3 | Nucleus | ligand-dependent nuclear receptor |
| E2 | DNTTIP1 | deoxynucleotidyltransferase, terminal, interacting protein 1 | deoxynucleotidyltransferase, terminal, interacting protein 1 | Nucleus | ligand-dependent nuclear receptor |

In a confirmation study, siRNAs targeting VDR, NR4A3, or NR1H3 showed more than 50% gene silencing, and siRNAs against DNTTIP1 showed ~95% of gene silencing, as determined by a quantitative RT-PCR analysis (see FIG. 3).

6.2 Example 2

PDACs Transfected with Anti-miRs Increased IL-1Beta-Induced PGE2 Production

6.2.1 Transfection of PDACs and PDAC Functional Assays

The example demonstrates that placental stem cells transfected with microRNA inhibitors of specific placental stem cell microRNAs increased prostaglandin-2 production by the placental stem cells upon induction by interferon-beta.

Reagents

Anti-miR miRNA Precursor Library Human V13 (Ambion AM17005); siPort Amine (Ambion AM4502); Recombinant Human IL-1B (Peprotech AF-200-01B); PGE2 ELISA Kit (R&D Systems SKG004B)

$CD34^-$, $CD10^+$, $CD105^+$, $CD200^+$, tissue culture plastic-adherent placental stem cells were thawed out in an equal volume of medium w/out antibiotics, and centrifuged at 400 g for 5 minutes. The supernatant was discarded and cells were resuspended in medium w/out antibiotics to ~$5\times10^5$/mL. Cells were then counted by Trypan Blue staining. The density of cells was adjusted with media w/out antibiotics to 3,500 cells per 80 µL (43.75 cells/µL). 80 4, of cells was dispensed into each well of a 96-well flat bottom plate using a liquid handling system. Cells were then incubated at 37° C. for 24 hrs. The transfections of the placental stem cells with Anti-miR inhibitors were set up in a 96-well plate, and were performed by direct or reverse transfection using 0.6% siPORT Amine transfection reagent (Ambion) in a final volume of 100 uL for 24 hours with 3,000 to 3,500 cells per well. 1 ng/mL of IL-1β (recombinant human IL-1β,) was then added to the cells for another 24 hours.

The supernatants were collected for PGE2 assay following manufacturer's protocol. The IL-23 modulation assay was performed with PBMCs following the protocol as in Example 2.

Results

The change in suppression of IL-23 protein produced by PBMCs in the presence of enhanced placental stem cells is summarized in Table 8 (the p value is noted as 0 when the value was less than 0.001). The percent suppression of IL-23 was calculated as follows: % suppression=((PBMC alone)–(PBMC+PDAC))/(PBMC alone)*100. The amount of IL-23 production from PBMC was around 2000 pg/mL.

TABLE 8

Change in suppression of soluble IL-23 protein produced by PBMCs in the presence of enhanced placental stem cells by miR inhibitors

| Target miR | Change vs. Avg IL-23 Suppression | p Value | Mature Sequence of Target miR | SEQ ID NO. |
|---|---|---|---|---|
| hsa-miR-183 | -38.25% | 0 | UAUGGCACUGGUAGAAUUCACU | 15 |
| hsa-miR-491-5p | -36.41% | 0.188 | AGUGGGGAACCCUUCCAUGAGG | 16 |
| hsa-miR-132* | -31.57% | 0.107 | ACCGUGGCUUUCGAUUGUUACU | 17 |
| hsa-miR-129-5p | -29.85% | 0 | CUUUUUGCGGUCUGGGCUUGC | 18 |
| hsa-miR-636 | -28.23% | 0.006 | UGUGCUUGCUCGUCCCGCCCGCA | 19 |

TABLE 8-continued

Change in suppression of soluble IL-23 protein produced by PBMCs in the presence of enhanced placental stem cells by miR inhibitors

| Target miR | Change vs. Avg IL-23 Suppression | p Value | Mature Sequence of Target miR | SEQ ID NO. |
|---|---|---|---|---|
| hsa-miR-100 | -25.71% | 0.002 | AACCCGUAGAUCCGAACUUGUG | 20 |
| hsa-miR-181a | -25.54% | 0 | AACAUUCAACGCUGUCGGUGAGU | 21 |
| hsa-miR-519a | -24.20% | 0.028 | AAAGUGCAUCCUUUUAGAGUGU | 22 |
| hsa-miR-338-3p | -23.27% | 0 | UCCAGCAUCAGUGAUUUUGUUG | 23 |
| hsa-miR-1179 | -23.25% | 0.102 | AAGCAUUCUUUCAUUGGUUGG | 24 |
| hsa-miR-521 | -20.59% | 0.017 | AACGCACUUCCCUUUAGAGUGU | 25 |
| hsa-miR-608 | -20.25% | 0.001 | AGGGGUGGUGUUGGGACAGCUCCGU | 26 |
| hsa-miR-1306 | -20.12% | 0.054 | ACGUUGGCUCUGGUGGUG | 27 |
| hsa-miR-543 | -19.91% | 0.062 | AAACAUUCGCGGUGCACUUCUU | 28 |
| hsa-miR-542-3p | -19.49% | 0 | UGUGACAGAUUGAUAACUGAAA | 29 |
| hsa-miR-23b | -17.07% | 0.001 | AUCACAUUGCCAGGGAUUACC | 30 |
| hsa-miR-299-3p | -15.30% | 0.052 | UAUGUGGGAUGGUAAACCGCUU | 31 |
| hsa-miR-597 | -15.13% | 0.096 | UGUGUCACUCGAUGACCACUGU | 32 |
| hsa-miR-1976 | -14.70% | 0.001 | CCUCCUGCCCUCCUUGCUGU | 33 |
| hsa-miR-1252 | -14.14% | 0 | AGAAGGAAAUUGAAUUCAUUUA | 34 |
| hsa-miR-510 | -14.13% | 0.082 | UACUCAGGAGAGUGGCAAUCAC | 35 |
| hsa-miR-1207-5p | -13.42% | 0.012 | UGGCAGGGAGGCUGGGAGGGG | 36 |
| hsa-miR-518a-3p | -13.16% | 0 | GAAAGCGCUUCCCUUUGCUGGA | 37 |
| hsa-miR-1250 | -13.01% | 0 | ACGGUGCUGGAUGUGGCCUUU | 38 |
| hsa-miR-1274a | -12.79% | 0 | GUCCCUGUUCAGGCGCCA | 39 |
| hsa-miR-141* | -12.58% | 0.064 | CAUCUUCCAGUACAGUGUUGGA | 40 |
| hsa-miR-9* | -12.58% | 0.05 | AUAAAGCUAGAUAACCGAAAGU | 41 |
| hsa-miR-566 | -12.38% | 0 | GGGCGCCUGUGAUCCCAAC | 42 |
| hsa-miR-142-5p | -12.13% | 0.027 | CAUAAAGUAGAAAGCACUACU | 43 |
| hsa-miR-23a* | -12.13% | 0 | GGGGUUCCUGGGGAUGGGAUUU | 44 |
| hsa-miR-519e* | -11.75% | 0.012 | UUCUCCAAAAGGGAGCACUUUC | 45 |
| hsa-miR-1292 | --11.64% | 0 | UGGGAACGGGUUCCGGCAGACGCUG | 46 |
| hsa-miR-96 | -11.63% | 0.037 | UUUGGCACUAGCACAUUUUUGCU | 47 |
| hsa-miR-886-3p | -10.25% | 0 | CGCGGGUGCUUACUGACCCUU | 48 |
| hsa-miR-216b | -10.10% | 0.028 | AAAUCUCUGCAGGCAAAUGUGA | 49 |
| hsa-miR-218-2* | -9.93% | 0.005 | CAUGGUUCUGUCAAGCACCGCG | 50 |
| hsa-miR-182 | -9.83% | 0 | UUUGGCAAUGGUAGAACUCACACU | 51 |

TABLE 8-continued

Change in suppression of soluble IL-23 protein produced by PBMCs in
the presence of enhanced placental stem cells by miR inhibitors

| Target miR | Change vs. Avg IL-23 Suppression | p Value | Mature Sequence of Target miR | SEQ ID NO. |
|---|---|---|---|---|
| hsa-miR-545* | -9.48% | 0 | UCAGUAAAUGUUUAUUAGAUGA | 52 |
| hsa-miR-517a | -9.19% | 0 | AUCGUGCAUCCCUUUAGAGUGU | 53 |
| hsa-miR-541* | -9.07% | 0 | AAAGGAUUCUGCUGUCGGUCCCACU | 54 |
| hsa-miR-1293 | -8.70% | 0.014 | UGGGUGGUCUGGAGAUUUGUGC | 55 |
| hsa-miR-339-5p | -8.45% | 0 | UCCCUGUCCUCCAGGAGCUCACG | 56 |
| hsa-miR-494 | -7.33% | 0 | UGAAACAUACACGGGAAACCUC | 57 |
| hsa-miR-196a* | -5.65% | 0 | CGGCAACAAGAAACUGCCUGAG | 58 |
| hsa-miR-371-5p | 7.34% | 0 | ACUCAAACUGUGGGGGCACU | 59 |
| hsa-miR-136* | 7.80% | 0.049 | CAUCAUCGUCUCAAAUGAGUCU | 60 |
| hsa-miR-214 | 7.89% | 0.032 | ACAGCAGGCACAGACAGGCAGU | 61 |
| hsa-miR-25* | 8.05% | 0 | AGGCGGAGACUUGGGCAAUUG | 62 |
| hsa-miR-452* | 8.94% | 0 | CUCAUCUGCAAAGAAGUAAGUG | 63 |
| hsa-miR-454* | 11.04% | 0 | ACCCUAUCAAUAUUGUCUCUGC | 64 |
| hsa-miR-548b-5p | 11.12% | 0 | AAAAGUAAUUGUGGUUUUGGCC | 65 |
| hsa-miR-10b* | 11.17% | 0.001 | ACAGAUUCGAUUCUAGGGGAAU | 66 |
| hsa-miR-218 | 11.19% | 0 | UUGUGCUUGAUCUAACCAUGU | 67 |
| hsa-miR-548m | 11.28% | 0 | CAAAGGUAUUGUGGUUUUUG | 68 |
| hsa-miR-520a-3p | 11.96% | 0.009 | AAAGUGCUUCCCUUUGGACUGU | 69 |
| hsa-miR-1323 | 12.29% | 0.097 | UCAAAACUGAGGGGCAUUUUCU | 70 |
| hsa-miR-24-2* | 12.67% | 0 | UGCCUACUGAGCUGAAACACAG | 71 |
| hsa-miR-613 | 13.16% | 0.171 | AGGAAUGUUCCUUCUUUGCC | 72 |
| hsa-miR-26a | 13.28% | 0.009 | UUCAAGUAAUCCAGGAUAGGCU | 73 |
| hsa-miR-193a-3p | 14.34% | 0 | AACUGGCCUACAAAGUCCCAGU | 74 |
| hsa-miR-1208 | 14.43% | 0.152 | UCACUGUUCAGACAGGCGGA | 75 |
| hsa-miR-767-5p | 15.47% | 0 | UGCACCAUGGUUGUCUGAGCAUG | 76 |
| hsa-miR-491-3p | 16.08% | 0.119 | CUUAUGCAAGAUUCCCUUCUAC | 77 |
| hsa-miR-626 | 16.14% | 0 | AGCUGUCUGAAAAUGUCUU | 78 |
| hsa-miR-216a | 16.79% | 0.009 | UAAUCUCAGCUGGCAACUGUGA | 79 |
| hsa-miR-151-5p | 18.39% | 0.013 | UCGAGGAGCUCACAGUCUAGU | 80 |
| hsa-miR-1282 | 19.20% | 0.011 | UCGUUUGCCUUUUUCUGCUU | 81 |
| hsa-miR-497* | 20.94% | 0 | CAAACCACACUGUGGUGUUAGA | 82 |
| hsa-miR-129-3p | 28.54% | 0.089 | AAGCCCUUACCCCAAAAAGCAU | 83 |

The change of PGE2 production in enhanced placental stem cells by miR inhibitors is summarized in Table 9. The change is expressed as % compared to negative control (p Value is noted as 0 when the value was less than 0.001). FIG. 4 shows that anti-miR inhibitors increased PGE2 secretion of PDACs by 15-50% compared to the negative control group (P<0.05; unpaired t-Test).

TABLE 9

Change of PGE2 production in enhanced placental stem cells by miR inhibitors

| Target miR | Change in PGE2 production (Compared to Negative Control) | p Value | Mature Sequence of Target miR | SEQ ID NO |
|---|---|---|---|---|
| hsa-miR-886-3p | -97.06 | 0 | CGCGGGUGCUUACUGACCCUU | 48 |
| hsa-miR-371-3p | -97.00 | 0 | AAGUGCCGCCAUCUUUUGAGUGU | 84 |
| hsa-miR-25* | -96.69 | 0 | AGGCGGAGACUUGGGCAAUUG | 62 |
| hsa-miR-376c | -96.23 | 0 | AACAUAGAGGAAAUUCCACGU | 85 |
| hsa-miR-888 | -94.55 | 0 | UACUCAAAAAGCUGUCAGUCA | 86 |
| hsa-miR-517b | -56.00 | 0 | UCGUGCAUCCCUUUAGAGUGUU | 87 |
| hsa-miR-433 | -54.45 | 0.013 | AUCAUGAUGGGCUCCUCGGUGU | 88 |
| hsa-miR-200a* | -54.17 | 0 | CAUCUUACCGGACAGUGCUGGA | 89 |
| hsa-miR-520a-5p | -51.23 | 0 | CUCCAGAGGGAAGUACUUUCU | 90 |
| hsa-miR-1286 | -48.41 | 0 | UGCAGGACCAAGAUGAGCCCU | 91 |
| hsa-miR-182* | -47.87 | 0 | UGGUUCUAGACUUGCCAACUA | 92 |
| hsa-miR-1273 | -45.38 | 0.014 | GGGCGACAAAGCAAGACUCUUUCUU | 93 |
| hsa-miR-1280 | -44.48 | 0.014 | UCCCACCGCUGCCACCC | 94 |
| hsa-miR-563 | -43.55 | 0.001 | AGGUUGACAUACGUUUCCC | 95 |
| hsa-miR-501-5p | -42.56 | 0 | AAUCCUUUGUCCCUGGGUGAGA | 96 |
| hsa-miR-448 | -40.98 | 0.04 | UUGCAUAUGUAGGAUGUCCCAU | 97 |
| hsa-miR-485-3p | -39.62 | 0 | GUCAUACACGGCUCUCCUCUCU | 98 |
| hsa-miR-29c | -39.62 | 0 | UAGCACCAUUUGAAAUCGGUUA | 99 |
| hsa-miR-548f | -36.65 | 0.043 | AAAAACUGUAAUUACUUUU | 100 |
| hsa-miR-1248 | -36.62 | 0 | ACCUUCUUGUAUAAGCACUGUGCUAAA | 101 |
| hsa-let-7d* | -35.72 | 0 | CUAUACGACCUGCUGCCUUUCU | 102 |
| hsa-miR-618 | -34.90 | 0 | AAACUCUACUUGUCCUUCUGAGU | 103 |
| hsa-miR-30c | -34.74 | 0 | UGUAAACAUCCUACACUCUCAGC | 104 |
| hsa-miR-136 | -34.50 | 0 | ACUCCAUUUGUUUUGAUGAUGGA | 105 |
| hsa-miR-181a | -33.46 | 0 | AACAUUCAACGCUGUCGGUGAGU | 21 |
| hsa-miR-26a | -32.94 | 0 | UUCAAGUAAUCCAGGAUAGGCU | 73 |
| hsa-miR-10a | -32.56 | 0.012 | UACCCUGUAGAUCCGAAUUUGUG | 106 |
| hsa-miR-557 | -32.47 | 0 | GUUUGCACGGGUGGGCCUUGUCU | 107 |
| hsa-miR-564 | -32.27 | 0.013 | AGGCACGGUGUCAGCAGGC | 108 |
| hsa-miR-520g | -31.72 | 0 | ACAAAGUGCUUCCCUUUAGAGUGU | 109 |
| hsa-miR-122* | -31.69 | 0.002 | AACGCCAUUAUCACACUAAAUA | 110 |
| hsa-miR-548k | -31.59 | 0 | AAAAGUACUUGCGGAUUUUGCU | 111 |
| hsa-miR-423-3p | -31.29 | 0.002 | AGCUCGGUCUGAGGCCCCUCAGU | 112 |
| hsa-miR-548j | -30.77 | 0 | AAAAGUAAUUGCGGUCUUUGGU | 113 |

TABLE 9-continued

Change of PGE2 production in enhanced placental stem cells by miR inhibitors

| Target miR | Change in PGE2 production (Compared to Negative Control) | p Value | Mature Sequence of Target miR | SEQ ID NO |
|---|---|---|---|---|
| hsa-miR-340* | -30.59 | 0 | UCCGUCUCAGUUACUUUAUAGC | 114 |
| hsa-miR-573 | -30.58 | 0.035 | CUGAAGUGAUGUGUAACUGAUCAG | 115 |
| hsa-miR-548i | -29.80 | 0.003 | AAAAGUAAUUGCGGAUUUUGCC | 116 |
| hsa-miR-555 | -29.54 | 0.001 | AGGGUAAGCUGAACCUCUGAU | 117 |
| hsa-miR-144 | -29.49 | 0.001 | UACAGUAUAGAUGAUGUACU | 118 |
| hsa-miR-567 | -29.37 | 0.003 | AGUAUGUUCUUCCAGGACAGAAC | 119 |
| hsa-miR-191* | -29.11 | 0.001 | GCUGCGCUUGGAUUUCGUCCCC | 120 |
| hsa-miR-566 | -28.90 | 0.001 | GGGCGCCUGUGAUCCCAAC | 42 |
| hsa-miR-335 | -28.84 | 0.005 | UCAAGAGCAAUAACGAAAAAUGU | 121 |
| hsa-miR-126* | -28.72 | 0.046 | CAUUAUUACUUUUGGUACGCG | 122 |
| hsa-miR-22* | -28.42 | 0.001 | AGUUCUUCAGUGGCAAGCUUUA | 123 |
| hsa-miR-572 | -28.18 | 0.001 | GUCCGCUCGGCGGUGGCCCA | 124 |
| hsa-miR-517c | -28.01 | 0.001 | AUCGUGCAUCCUUUUAGAGUGU | 125 |
| hsa-miR-380* | -27.92 | 0.015 | UGGUUGACCAUAGAACAUGCGC | 126 |
| hsa-miR-106a* | -27.76 | 0.031 | CUGCAAUGUAAGCACUUCUUAC | 127 |
| hsa-miR-519e | -27.53 | 0.004 | AAGUGCCUCCUUUUAGAGUGUU | 128 |
| hsa-miR-520c-3p | -27.18 | 0.004 | AAAGUGCUUCCUUUUAGAGGGU | 129 |
| hsa-miR-517* | -26.66 | 0.001 | CCUCUAGAUGGAAGCACUGUCU | 130 |
| hsa-miR-432* | -26.47 | 0.039 | CUGGAUGGCUCCUCCAUGUCU | 131 |
| hsa-miR-520e | -26.07 | 0.002 | AAAGUGCUUCCUUUUUGAGGG | 132 |
| hsa-miR-9* | -26.00 | 0 | AUAAAGCUAGAUAACCGAAAGU | 41 |
| hsa-miR-551a | -25.73 | 0.006 | GCGACCCACUCUUGGUUUCCA | 133 |
| hsa-miR-1471 | -25.54 | 0 | GCCCGCGUGUGGAGCCAGGUGU | 134 |
| hsa-miR-613 | -25.30 | 0.012 | AGGAAUGUUCCUUCUUUGCC | 72 |
| hsa-miR-562 | -25.28 | 0.002 | AAAGUAGCUGUACCAUUUGC | 135 |
| hsa-miR-922 | -25.02 | 0.001 | GCAGCAGAGAAUAGGACUACGUC | 136 |
| hsa-miR-216a | -24.79 | 0.022 | UAAUCUCAGCUGGCAACUGUGA | 79 |
| hsa-miR-499-5p | -24.37 | 0.023 | UUAAGACUUGCAGUGAUGUUU | 137 |
| hsa-miR-25 | -24.08 | 0.002 | CAUUGCACUUGUCUCGGUCUGA | 138 |
| hsa-miR-197 | -23.77 | 0.018 | UUCACCACCUUCUCCACCCAGC | 139 |
| hsa-miR-500* | -23.41 | 0.003 | AUGCACCUGGGCAAGGAUUCUG | 140 |
| hsa-miR-365* | -23.05 | 0 | AGGGACUUUCAGGGGCAGCUGU | 141 |
| hsa-miR-1247 | -22.96 | 0.022 | ACCCGUCCCGUUCGUCCCCGGA | 142 |
| hsa-miR-586 | -22.75 | 0.003 | UAUGCAUUGUAUUUUUAGGUCC | 143 |
| hsa-miR-548d-3p | -22.71 | 0.003 | CAAAAACCACAGUUUCUUUUGC | 144 |
| hsa-miR-27a* | -22.68 | 0.005 | AGGGCUUAGCUGCUUGUGAGCA | 145 |

TABLE 9-continued

Change of PGE2 production in enhanced placental stem cells by miR inhibitors

| Target miR | Change in PGE2 production (Compared to Negative Control) | p Value | Mature Sequence of Target miR | SEQ ID NO |
|---|---|---|---|---|
| hsa-miR-598 | -22.54 | 0.026 | UACGUCAUCGUUGUCAUCGUCA | 146 |
| hsa-miR-609 | -22.43 | 0.006 | AGGGUGUUUCUCUCAUCUCU | 147 |
| hsa-miR-132 | -22.04 | 0.004 | UAACAGUCUACAGCCAUGGUCG | 148 |
| hsa-miR-411* | -21.97 | 0 | UAUGUAACACGGUCCACUAACC | 149 |
| hsa-miR-135a | -21.85 | 0.004 | UAUGGCUUUUUAUUCCUAUGUGA | 150 |
| hsa-miR-31 | --21.83 | 0.004 | AGGCAAGAUGCUGGCAUAGCU | 151 |
| hsa-miR-181a* | -21.81 | 0.004 | ACCAUCGACCGUUGAUUGUACC | 152 |
| hsa-miR-1245 | -21.74 | 0 | AAGUGAUCUAAAGGCCUACAU | 153 |
| hsa-miR-758 | -21.26 | 0.005 | UUUGUGACCUGGUCCACUAACC | 154 |
| hsa-miR-924 | -21.22 | 0.001 | AGAGUCUUGUGAUGUCUUGC | 155 |
| hsa-miR-1246 | -21.19 | 0.015 | AAUGGAUUUUUGGAGCAGG | 156 |
| hsa-miR-23b | -21.16 | 0.005 | AUCACAUUGCCAGGGAUUACC | 30 |
| hsa-miR-631 | -20.40 | 0.006 | AGACCUGGCCCAGACCUCAGC | 157 |
| hsa-miR-1 | -20.21 | 0.006 | UGGAAUGUAAAGAAGUAUGUAU | 158 |
| hsa-miR-920 | -20.00 | 0 | GGGGAGCUGUGGAAGCAGUA | 159 |
| hsa-miR-589* | -19.95 | 0.006 | UCAGAACAAAUGCCGGUUCCCAGA | 160 |
| hsa-miR-638 | -19.86 | 0.006 | AGGGAUCGCGGGCGGGUGGCGGCCU | 161 |
| hsa-miR-1244 | -19.85 | 0 | AAGUAGUUGGUUUGUAUGAGAUGGUU | 162 |
| hsa-miR-328 | -19.71 | 0.047 | CUGGCCCUCUCUGCCCUUCCGU | 163 |
| hsa-let-7i | -19.65 | 0.007 | UGAGGUAGUAGUUUGUGCUGUU | 164 |
| hsa-miR-429 | -19.45 | 0.036 | UAAUACUGUCUGGUAAAACCGU | 165 |
| hsa-miR-380 | -19.40 | 0.007 | UAUGUAAUAUGGUCCACAUCUU | 166 |
| hsa-let-7b* | -19.15 | 0.01 | CUAUACAACCUACUGCCUUCCC | 167 |
| hsa-miR-614 | -18.73 | 0.009 | GAACGCCUGUUCUUGCCAGGUGG | 168 |
| hsa-miR-1225-5p | -18.71 | 0.002 | GUGGGUACGGCCCAGUGGGGGG | 169 |
| hsa-miR-545* | -18.55 | 0.036 | UCAGUAAAUGUUUAUUAGAUGA | 52 |
| hsa-miR-320c | -18.15 | 0.003 | AAAAGCUGGGUUGAGAGGGU | 170 |
| hsa-miR-579 | -18.12 | 0.01 | UUCAUUUGGUAUAAACCGCGAUU | 171 |
| hsa-miR-1282 | -18.01 | 0.05 | UCGUUUGCCUUUUUCUGCUU | 81 |
| hsa-miR-455-5p | -17.12 | 0.015 | UAUGUGCCUUUGGACUACAUCG | 172 |
| hsa-miR-615-3p | -16.81 | 0.014 | UCCGAGCCUGGGUCUCCCUCUU | 173 |
| hsa-miR-585 | -16.72 | 0.015 | UGGGCGUAUCUGUAUGCUA | 174 |
| hsa-miR-559 | -16.52 | 0.015 | UAAAGUAAAUAUGCACCAAAA | 175 |
| hsa-miR-561 | -16.09 | 0.037 | CAAAGUUUAAGAUCCUUGAAGU | 176 |
| hsa-miR-191 | -15.73 | 0.031 | CAACGGAAUCCCAAAAGCAGCUG | 177 |
| hsa-miR-187 | -15.63 | 0.028 | UCGUGUCUUGUGUUGCAGCCGG | 178 |
| hsa-miR-29b | -15.39 | 0.021 | UAGCACCAUUUGAAAUCAGUGUU | 179 |

TABLE 9-continued

Change of PGE2 production in enhanced placental stem cells by miR inhibitors

| Target miR | Change in PGE2 production (Compared to Negative Control) | p Value | Mature Sequence of Target miR | SEQ ID NO |
|---|---|---|---|---|
| hsa-miR-769-5p | -15.12 | 0.042 | UGAGACCUCUGGGUUCUGAGCU | 180 |
| hsa-miR-495 | 16.81 | 0.015 | AAACAAACAUGGUGCACUUCUU | 181 |
| hsa-miR-516a-3p | 17.46 | 0.017 | UGCUUCCUUUCAGAGGGU | 182 |
| hsa-miR-938 | 17.60 | 0.012 | UGCCCUUAAAGGUGAACCCAGU | 183 |
| hsa-miR-936 | 18.04 | 0.015 | ACAGUAGAGGGAGGAAUCGCAG | 184 |
| hsa-miR-373* | 18.18 | 0.01 | ACUCAAAAUGGGGCGCUUUCC | 185 |
| hsa-miR-1184 | 18.26 | 0.018 | CCUGCAGCGACUUGAUGGCUUCC | 186 |
| hsa-miR-122 | 18.47 | 0.009 | UGGAGUGUGACAAUGGUGUUUG | 187 |
| hsa-miR-208b | 18.98 | 0.002 | AUAAGACGAACAAAAGGUUUGU | 188 |
| hsa-miR-223* | 19.15 | 0.025 | CGUGUAUUUGACAAGCUGAGUU | 189 |
| hsa-miR-1972 | 19.20 | 0.018 | UCAGGCCAGGCACAGUGGCUCA | 190 |
| hsa-miR-520h | 19.70 | 0.008 | ACAAAGUGCUUCCCUUUAGAGU | 191 |
| hsa-miR-330-3p | 19.73 | 0.01 | GCAAAGCACACGGCCUGCAGAGA | 192 |
| hsa-miR-149 | 20.79 | 0 | UCUGGCUCCGUGUCUUCACUCCC | 193 |
| hsa-miR-7 | 21.30 | 0.005 | UGGAAGACUAGUGAUUUUGUUGU | 194 |
| hsa-miR-29b-2* | 22.10 | 0 | CUGGUUUCACAUGGUGGCUUAG | 195 |
| hsa-miR-520d-5p | 22.16 | 0 | CUACAAAGGGAAGCCCUUUC | 196 |
| hsa-miR-592 | 22.23 | 0.004 | UUGUGUCAAUAUGCGAUGAUGU | 197 |
| hsa-miR-940 | 22.50 | 0.004 | AAGGCAGGGCCCCCCGCUCCCC | 198 |
| hsa-miR-146b-3p | 22.58 | 0.003 | UGCCCUGUGGACUCAGUUCUGG | 199 |
| hsa-miR-518e* | 23.08 | 0.004 | CUCUAGAGGGAAGCGCUUUCUG | 200 |
| hsa-miR-1255a | 23.32 | 0 | AGGAUGAGCAAAGAAAGUAGAUU | 201 |
| hsa-miR-935 | 25.52 | 0 | CCAGUUACCGCUUCCGCUACCGC | 202 |
| hsa-miR-633 | 25.97 | 0.004 | CUAAUAGUAUCUACCACAAUAAA | 203 |
| hsa-miR-513a-5p | 26.20 | 0.008 | UUCACAGGGAGGUGUCAU | 204 |
| hsa-miR-361-3p | 26.53 | 0.001 | UCCCCCAGGUGUGAUUCUGAUUU | 205 |
| hsa-miR-194 | 26.62 | 0.017 | UGUAACAGCAACUCCAUGUGGA | 206 |
| hsa-miR-1185 | 26.72 | 0 | AGAGGAUACCCUUUGUAUGUU | 207 |
| hsa-miR-875-3p | 27.12 | 0.044 | CCUGGAAACACUGAGGUUGUG | 208 |
| hsa-miR-200a | 27.36 | 0.002 | UAACACUGUCUGGUAACGAUGU | 209 |
| hsa-miR-1201 | 27.67 | 0.002 | AGCCUGAUUAAACACAUGCUCUGA | 210 |
| hsa-miR-629 | 28.98 | 0 | UGGGUUUACGUUGGGAGAACU | 211 |
| hsa-miR-139-5p | 29.02 | 0 | UCUACAGUGCACGUGUCUCCAG | 212 |
| hsa-miR-504 | 30.84 | 0.04 | AGACCCUGGUCUGCACUCUAUC | 213 |
| hsa-miR-452 | 31.32 | 0 | AACUGUUUGCAGAGGAAACUGA | 214 |
| hsa-miR-517a | 32.41 | 0 | AUCGUGCAUCCCUUUAGAGUGU | 53 |

TABLE 9-continued

Change of PGE2 production in enhanced placental stem cells by miR inhibitors

| Target miR | Change in PGE2 production (Compared to Negative Control) | p Value | Mature Sequence of Target miR | SEQ ID NO |
|---|---|---|---|---|
| hsa-miR-543 | 33.29 | 0 | AAACAUUCGCGGUGCACUUCUU | 28 |
| hsa-miR-616* | 33.83 | 0.024 | ACUCAAAACCCUUCAGUGACUU | 215 |
| hsa-miR-651 | 34.09 | 0.024 | UUUAGGAUAAGCUUGACUUUUG | 216 |
| hsa-miR-1254 | 35.96 | 0 | AGCCUGGAAGCUGGAGCCUGCAGU | 217 |
| hsa-miR-339-3p | 37.00 | 0.007 | UGAGCGCCUCGACGACAGAGCCG | 218 |
| hsa-miR-510 | 37.14 | 0 | UACUCAGGAGAGUGGCAAUCAC | 35 |
| hsa-miR-181c* | 39.58 | 0 | AACCAUCGACCGUUGAGUGGAC | 219 |
| hsa-miR-19b-1* | 40.92 | 0.001 | AGUUUUGCAGGUUUGCAUCCAGC | 220 |
| hsa-miR-1274a | 42.43 | 0 | GUCCCUGUUCAGGCGCCA | 39 |
| hsa-miR-1294 | 42.66 | 0.006 | UGUGAGGUUGGCAUUGUUGUCU | 221 |
| hsa-miR-1306 | 43.90 | 0 | ACGUUGGCUCUGGUGGUG | 27 |
| hsa-miR-1226* | 44.07 | 0.019 | GUGAGGGCAUGCAGGCCUGGAUGGGG | 222 |
| hsa-miR-541* | 48.09 | 0.042 | AAAGGAUUCUGCUGUCGGUCCCACU | 54 |

6.3 Example 3

Mouse EAE Model for Testing Enhanced Placental Stem Cells

The immunosuppressive effect of ePSCs treated with modulatory RNA molecules such as siRNAs that confer additional immunosuppressive activity to the ePSCs, as compared to an equivalent number of unmodified placental stem cells, is assessed, e.g., using a murine experimental autoimmune encephalomyelitis (EAE) model for multiple sclerosis.

In a proof-of-concept study, C57BL/6 mice are separated into four groups of eight mice each.

Group 1 mice receive $1.5 \times 10^6$ placental stem cells (unmodified) at Day 0, 6 hours after inoculation with a fragment of monocyte-oligodendrocyte glycoprotein amino acids 35-55 ($MOG_{35-55}$, sequence MEVGWYRSPFSRVVH-LYRNGK (SEQ ID NO: 223)) in an amount previously determined to induce onset of EAE.

Group 2 mice receive $1.5 \times 10^6$ placental stem cells transfected with siRNAs comprising the sequences of SEQ ID NOS 1 and 2, at Day 6, prior to onset of symptoms.

Group 3 mice receive $1.5 \times 10^6$ placental stem cells transfected with siRNAs comprising the sequences of SEQ ID NOS 1 and 2 at Day 11 or Day 12, after early onset of EAE symptoms.

Group 4 mice receive $1.5 \times 10^6$ placental stem cells transfected with siRNAs comprising the sequences of SEQ ID NOS 3 and 4, at Day 6, prior to onset of symptoms.

Group 5 mice receive $1.5 \times 10^6$ placental stem cells transfected with siRNAs comprising the sequences of SEQ ID NOS 3 and 4 at Day 11 or Day 12, after early onset of EAE symptoms.

Group 6 mice receive $1.5 \times 10^6$ placental stem cells transfected with siRNAs comprising the sequences of SEQ ID NOS 5 and 6, at Day 6, prior to onset of symptoms.

Group 7 mice receive $1.5 \times 10^6$ placental stem cells transfected with siRNAs comprising the sequences of SEQ ID NOS 5 and 6 at Day 11 or Day 12, after early onset of EAE symptoms.

Group 8 mice receive $1.5 \times 10^6$ placental stem cells transfected with siRNAs comprising the sequences of SEQ ID NOS 7 and 8, at Day 6, prior to onset of symptoms.

Group 9 mice receive $1.5 \times 10^6$ placental stem cells transfected with siRNAs comprising the sequences of SEQ ID NOS 7 and 8 at Day 11 or Day 12, after early onset of EAE symptoms.

Group 10 mice receive $1.5 \times 10^6$ placental stem cells transfected with siRNAs comprising the sequences of SEQ ID NOS 9 and 10, at Day 6, prior to onset of symptoms.

Group 11 mice receive $1.5 \times 10^6$ placental stem cells transfected with siRNAs comprising the sequences of SEQ ID NOS 9 and 10 at Day 11 or Day 12, after early onset of EAE symptoms.

Group 12 mice receive $1.5 \times 10^6$ placental stem cells transfected with siRNAs comprising the sequences of SEQ ID NOS 11 and 12, at Day 6, prior to onset of symptoms.

Group 13 mice receive $1.5 \times 10^6$ placental stem cells transfected with siRNAs comprising the sequences of SEQ ID NOS 11 and 12 at Day 11 or Day 12, after early onset of EAE symptoms.

Group 14 mice receive $1.5 \times 10^6$ placental stem cells transfected with siRNAs comprising the sequences of SEQ ID NOS 13 and 14, at Day 6, prior to onset of symptoms.

Group 15 mice receive $1.5 \times 10^6$ placental stem cells transfected with siRNAs comprising the sequences of SEQ ID NOS 13 and 14 at Day 11 or Day 12, after early onset of EAE symptoms.

Control Group 16 mice receive vehicle at Day 0, Day 6 and Day 12.

Control Group 17 mice receive no $MOG_{35-55}$.

The immunosuppressive activity of the ePSCs (Groups 2-15) can be measured by the abrogation of symptom development in comparison with Groups 1, 16 and 17.

6.4 Example 4

Down-Regulation of VDR and NR4A3 in Placental Stem Cells Showed Enhanced Suppression of IL-23 Produced by PBMCs This example demonstrates suppression of peripheral blood mononuclear cell (PBMC) IL-23 production by enhanced placental stem cells (ePSCs) treated with short hairpin RNA (shRNA) targeting vitamin D (1,25-dihydroxyvitamin D3) receptor (VDR) or nuclear receptor subfamily 4, group A, member 3 (NR4A3) genes.

IL-23 Assay:

Freshly isolated PBMCs from buffy coat were stimulated with LPS at 10 ng/ml for overnight at 37° C. and added to pre-attached PDACs in the plate for co-culture overnight. IL-23 in the culture supernatant was measured by IL-23 ELISA kit (eBioscience) following the manufacturer's protocol. The "percent Suppression" (see Tables 9 and 10) was calculated as follows: % suppression=("LPS-treated PBMCs"–"PDAC:PBMCs co-culture")/"LPS-treated PBMCs"*100%.

Viral Transduction in PDACs:

Early passage (P2) CD10+, CD34−, CD105+, CD200+ placental stem cells were thawed and plated at a density of 4,000 cells/cm2 in DMEM media supplemented with 10% FBS in a 100 mm cell culture dish. The next day the media was removed and the viral particles were added at 25-50 MOI in serum-free and antibiotics-free media supplemented with Polybrene (0.6 μg/mL) in a total volume of 3 mL. After 4 hours of incubation (37° C., 5% $CO_2$), 12 mL of complete media was added to the culture dish. The media was replaced with DMEM media supplemented with 10% FBS and Puromycin (1.0 μg/mL) after 24-48 hours of incubation. The culture was checked every 2-3 days for confluence to collect cells in the next passage (P3) when the culture reached confluency, or to change the media with DMEM media supplemented with 10% FBS and Puromycin (1.0 μg/mL).

The viral particles used in this study contain GIPZ lentiviral shRNAmir constructs from Open Biosystems with the following genes (or non-silencing control): non-Silencing Control (Cat#RHS4348, Lot EV16118, titer 3.69E8 to/ml); targeting NR4A3 (Open Biosystems Cat#VGH5523-100994599, Lot HV111111, titer 2.84E8 tu/mL) or targeting VDR (Open Biosystems Cat#VGH5523-101070492, Lot KV121001, titer 2.50E8 tu/mL). The sequences for the shRNAmirs are listed in Table 9.

Results

Suppression of IL-23 produced by PBMC in the presence of enhanced placental stem cells is showed in Tables 11A-B. The gene silencing efficiency of both VDR and NR4A3 was >90% as compared to the non-targeting controls (NTP-shRNA or NTP2-shRNA).

TABLE 10

DNA sequences encoding shRNAmirs

| shRNAmirs | | Sequence | SEQ ID No. |
| --- | --- | --- | --- |
| VDR: V3LHS_337628 | Harpin sequence | TGCTGTTGACAGTGAGCGCCCG CGTCAGTGACGTGACCAATAGT GAAGCCACAGATGTATTGGTCA CGTCACTGACGCGGTTGCCTAC TGCCTCGGA | 224 |
| | Mature Sense Sequence | CGCGTCAGTGACGTGACCA | 225 |
| NR4A3: V3LHS_348138 | Harpin sequence | TGCTGTTGACAGTGAGCGACCC AAAGAAGATCAGACATTATAGT GAAGCCACAGATGTATAATGTC TGATCTTCTTTGGGGTGCCTAC TGCCTCGGA | 226 |
| | Mature Sense Sequence | CCAAAGAAGATCAGACATT | 227 |

TABLE 11A

Suppression of IL-23 produced by PBMC (from Donor #1) in the presence of enhanced placental stem cells

| Name | #PDACs | Mean IL-23 (pg/mL) | Std Dev | % Suppression |
| --- | --- | --- | --- | --- |
| LPS-treated PBMCs | — | 482 | 58.951 | |
| PDACs | 2500 cells | 275 | 111 | 43% |
| NTP2-shRNA | | 116 | 7 | 76% |
| VDR-shRNA | | 33 | 1 | 93% |
| PDACs | 5000 cells | 233 | 18 | 52% |
| NTP2-shRNA | | 142 | 32 | 71% |
| VDR-shRNA | | 36 | 1 | 92% |
| PDACs | 10000 cells | 246 | 79 | 49% |
| NTP2-shRNA | | 103 | 23 | 79% |
| VDR-shRNA | | 30 | 11 | 94% |

TABLE 11B

Suppression of IL-23 produced by PBMC (from Donor #2) in the presence of enhanced placental stem cells

| Name | #PDACs | Mean IL-23 (pg/mL) | Std Dev | % Suppression |
| --- | --- | --- | --- | --- |
| LPS-treated PBMCs | — | 217.78 | 23.33 | |
| PDACs | 2000 cells | 63.64 | 15.00 | 70.78% |
| NTP-shRNA | | 68.97 | 7.72 | 68.33% |
| NTP2-shRNA | | 35.54 | 4.25 | 83.68% |
| NR4A3 shRNA | | 24.62 | 19.03 | 88.70% |
| VDR-shRNA | | 30.68 | 6.95 | 85.91% |
| PDACs | 3000 cells | 20.103 | 6.965 | 90.77% |
| NTP-shRNA | | 16.521 | 16.65 | 92.41% |
| NTP2-shRNA | | 9.509 | 8.444 | 95.63% |

TABLE 11B-continued

Suppression of IL-23 produced by PBMC (from Donor #2) in the presence of enhanced placental stem cells

| Name | #PDACs | Mean IL-23 (pg/mL) | Std Dev | % Suppression |
|---|---|---|---|---|
| NR4A3-shRNA | | 3.079 | — | 98.59% |
| VDR-shRNA | | Below detection | — | — |

6.5 Example 5

Modulation of IL-23 Production of LPS-Stimulated PBMCs in the Presence of PDACs This example demonstrates that $CD10^+$, $CD34^-$, $CD105^+$, $CD200^+$ placental stem cells transfected with certain microRNA mimics showed enhanced suppression of IL-23 produced by LPS-stimulated PBMCs.

Briefly, PDACs were seeded on Day 0 at 3,000 cells/well in DMEM media+10% FBS without antibiotics. On Day 1, cells were transfected with 30 nM miR mimics using SiPort Amine Transfection Reagent (Ambion, Cat #AM4502) at a ratio of 1:2 of miR mimics:Amine Transfection Reagent (2× of the manufacturer's recommended concentration). On Day 2, the transfection media was removed and replaced with 10% FBS-RPMI media. On Day 3, the supernatants were collected and frozen for the IL-23 suppression assay and RNA was extracted from the modified cells. RNA (mRNA and miRNA) was extracted and purified using Ambion's mirVana miRNA Isolation Kit (Ambion, Cat #1566) and the Taqman MicroRNA Cells-to-Ct Kit (Ambion, Cat #4391848) according to manufacturer's recommended procedure. miR and target gene modification were evaluated using Taqman Expression Assays. For the IL-23 suppression assay, the supernatants were thawed and added to freshly isolated PBMCs from buffy coat that were stimulated with LPS at 10 ng/ml for overnight at 37° C. The IL-23 in the culture supernatant was measured by IL-23 ELISA kit from eBioscience. The "percent Suppression" of IL-23 (see Table 12) was calculated as follows: % suppression=("LPS-treated PBMCs"–"PDAC:PBMCs co-culture")/"LPS-treated PBMCs"*100%. The negative control was calculated without the inclusion of outliers.

Results

The results are shown in Table 12. The transfection of placental stem cells with miR-1, miR-129-3p, miR-129-5p, miR-24, and miR-218 mimics resulted in successful knock-up of microRNAs (2.89-4,860 fold increase), knock-down of target genes (2.06-24.2% decrease in Twinfilin-1, NR4A3, and VDR), and augmentation of IL-23 suppression (13.5-18.4% absolute increase) with LPS-stimulated PBMCs. The transfection of placental stem cells with miR-24-1* and miR-218-1* also resulted in successful miR knock-up and IL-23 suppression augmentation. These results are consistent with the data of placental stem cells treated with miRNA inhibitors, which are summarized in Example 1, above.

TABLE 12

Summary of suppression of IL-23 produced by LPS-stimulated PBMCs by placental stem cells transfected with microRNA mimics

| | | qPCR | | Absolute Change in IL-23 % Suppression (Test Suppression %- Ctl Suppression %) | | | |
|---|---|---|---|---|---|---|---|
| | | NR4A3/VDR KD | miR Knock-up | miR | | | SEQ |
| Target Gene | microRNA | Percent Decrease | microRNA Fold Change | Mimics vs. Neg Ctl | vs. Avg Veh Ctl | Mature sequence of target miR | ID NO |
| Twinfilin-1 | hsa-miR-1 | 24.16 | 506.49 | 38.12 | 17.33 | UGGAAUGUAAAGAAGUAUGUAU | 228 |
| NR4A3 | hsa-miR-129-3p | 18.86 | 4,860.00 | 34.33 | 13.54 | AAGCCCUUACCCCAAAAAGCAU | 83 |
| | hsa-miR-129-5p | 2.06 | 3,810.12 | 37.77 | 16.98 | CUUUUUGCGGUCUGGGCUUGC | 18 |
| | hsa-miR-129* | 24.15 | 953.05 | 19.19 | -1.60 | AAGCCCUUACCCCAAAAAGUAU | 229 |
| | hsa-miR-24 | 17.32 | 2.89 | 38.78 | 17.99 | UGGCUCAGUUCAGCAGGAACAG | 230 |
| | hsa-miR-24-1* | -31.04 | 613.79 | 39.82 | 19.03 | UGCCUACUGAGCUGAUAUCAGU | 231 |
| | hsa-miR-24-2* | -30.12 | 341.95 | 16.01 | -4.78 | UGCCUACUGAGCUGAAACACAG | 71 |
| VDR | hsa-miR-218 | 21.36 | 25.61 | 39.17 | 18.38 | UUGUGCUUGAUCUAACCAUGU | 67 |
| | hsa-miR-281-1* | -9.04 | 14,009.91 | 25.42 | 4.63 | AUGGUUCCGUCAAGCACCAUGG | 232 |
| | hsa-miR-281-2* | 11.98 | 171,905.48 | -71.55 | -92.34 | CAUGGUUCUGUCAAGCACCGCG | 50 |
| | hsa-miR-183 | 17.64 | 18,990.37 | -228.11 | -248.90 | UAUGGCACUGGUAGAAUUCACU | 233 |
| | hsa-miR-183* | -6.51 | 1,758.84 | -42.66 | -63.45 | GUGAAUUACCGAAGGGCCAUAA | 234 |

EQUIVALENTS

The compositions and methods disclosed herein are not to be limited in scope by the specific embodiments described herein. Indeed, various modifications of the compositions and methods in addition to those described will become apparent to those skilled in the art from the foregoing description and accompanying figures. Such modifications are intended to fall within the scope of the appended claims.

Various publications, patents and patent applications are cited herein, the disclosures of

What is claimed:

1. A method of treating an individual having or at risk of developing a disease, disorder or condition having an inflammatory component, comprising administering to the individual a therapeutically effective amount of enhanced placental stem cells,
wherein said enhanced placental stem cells comprise or have been contacted with an effective amount of modulatory RNA molecules that decrease expression of one or more human nuclear receptors in said enhanced placental stem cells, resulting in suppression of soluble IL-23 protein produced by peripheral blood mononuclear cells (PBMCs) in the presence of said enhanced placental stem cells compared to placental stem cells not contacted with said modulatory RNA molecules,
wherein said modulatory RNA molecules are small interfering RNAs (siRNAs), microRNA inhibitors (miR inhibitors), or micro RNA mimics (miR mimics),
wherein said one or more human nuclear receptors is selected from the group consisting of: vitamin D receptor (VDR); nuclear receptor subfamily 4, group A, member 3 (NR4A3); nuclear receptor subfamily 0, group B, member 2 (NR0B2); nuclear receptor subfamily 1, group 1, member 2 (NR1I2); nuclear receptor subfamily 1, group H, member 3 (NR1H3); and deoxynucleotidyltransferase, terminal, interacting protein 1 (DNTTIP1), and
wherein the therapeutically effective amount is an amount sufficient to cause a detectable improvement in one or more symptoms of said disease, disorder or condition.

2. The method of claim 1, wherein said modulatory RNA molecules are siRNAs.

3. The method of claim 1, wherein said modulatory RNA molecules are selected from a library.

4. The method of claim 3, wherein said library is a human nuclear receptor library, human phosphatase siRNA library, or an anti-miR library.

5. The method of claim 1, wherein said placental stem cells are $CD10^-$, $CD34^-$, $CD105^+$, $CD200^+$ placental stem cells.

6. The method of claim 1, wherein said placental stem cells express CD200 and do not express HLA-G, or express CD73, CD105, and CD200, or express CD200 and OCT-4, or express CD73 and CD105 and do not express HLA-G.

7. The method of claim 5, wherein said placental stem cells are additionally $CD90^+$ and $CD45^-$.

8. The method of claim 5, wherein said placental stem cells are additionally $CD80^-$ and $CD86^-$.

* * * * *

```
                        SEQUENCE LISTING

<160> NUMBER OF SEQ ID NOS: 234

<210> SEQ ID NO 1
<211> LENGTH: 21
<212> TYPE: DNA
<213> ORGANISM: Artificial Sequence
<220> FEATURE:
<223> OTHER INFORMATION: sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 1
ggaugcuaau gaaacuggun n                                                 21

<210> SEQ ID NO 2
<211> LENGTH: 21
<212> TYPE: DNA
<213> ORGANISM: Artificial Sequence
<220> FEATURE:
<223> OTHER INFORMATION: Antisense siRNA sequence
<220> FEATURE:
<223> OTHER INFORMATION: RNA/DNA hybrid
<220> FEATURE:
<221> NAME/KEY: misc_feature
<222> LOCATION: 20
<223> OTHER INFORMATION: n = g
<220> FEATURE:
<221> NAME/KEY: misc_feature
<222> LOCATION: 21
<223> OTHER INFORMATION: n = t

<400> SEQUENCE: 2
accaguuuca uuagcauccn n                                                 21

<210> SEQ ID NO 3
<211> LENGTH: 21
<212> TYPE: DNA
<213> ORGANISM: Artificial Sequence
<220> FEATURE:
<223> OTHER INFORMATION: Sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 3
ggaacauaau gauaaagcan n                                                 21

<210> SEQ ID NO 4
<211> LENGTH: 21
<212> TYPE: DNA
<213> ORGANISM: Artificial Sequence
<220> FEATURE:
<223> OTHER INFORMATION: Antisense siRNA sequence
<220> FEATURE:
<223> OTHER INFORMATION: RNA/DNA hybrid
<220> FEATURE:
<221> NAME/KEY: misc_feature
```

```
<222> LOCATION: 20, 21
<223> OTHER INFORMATION: n = a

<400> SEQUENCE: 4
ugcuuuauca uuauguuccn n                                              21

<210> SEQ ID NO 5
<211> LENGTH: 21
<212> TYPE: DNA
<213> ORGANISM: Artificial Sequence
<220> FEATURE:
<223> OTHER INFORMATION: Sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 5
agaucacugu aucaccucun n                                              21

<210> SEQ ID NO 6
<211> LENGTH: 21
<212> TYPE: DNA
<213> ORGANISM: Artificial Sequence
<220> FEATURE:
<223> OTHER INFORMATION: Antisense siRNA sequence
<220> FEATURE:
<223> OTHER INFORMATION: RNA/DNA hybrid
<220> FEATURE:
<221> NAME/KEY: misc_feature
<222> LOCATION: 20
<223> OTHER INFORMATION: n = g
<220> FEATURE:
<221> NAME/KEY: misc_feature
<222> LOCATION: 21
<223> OTHER INFORMATION: n = a

<400> SEQUENCE: 6
agaggugaua cagugaucun n                                              21

<210> SEQ ID NO 7
<211> LENGTH: 21
<212> TYPE: DNA
<213> ORGANISM: Artificial Sequence
<220> FEATURE:
<223> OTHER INFORMATION: Sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 7
agaucuugau uauuccagan n                                              21

<210> SEQ ID NO 8
<211> LENGTH: 21
<212> TYPE: DNA
<213> ORGANISM: Artificial Sequence
<220> FEATURE:
<223> OTHER INFORMATION: Antisense siRNA sequence
<220> FEATURE:
<223> OTHER INFORMATION: RNA/DNA hybrid
<220> FEATURE:
<221> NAME/KEY: misc_feature
<222> LOCATION: 20
<223> OTHER INFORMATION: n = c
<220> FEATURE:
```

<221> NAME/KEY: misc_feature
<222> LOCATION: 21
<223> OTHER INFORMATION: n = t

<400> SEQUENCE: 8
ucuggaauaa ucaagaucun n                                                     21

<210> SEQ ID NO 9
<211> LENGTH: 21
<212> TYPE: DNA
<213> ORGANISM: Artificial Sequence
<220> FEATURE:
<223> OTHER INFORMATION: Sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 9
cggugcccag cauacucaan n                                                     21

<210> SEQ ID NO 10
<211> LENGTH: 21
<212> TYPE: DNA
<213> ORGANISM: Artificial Sequence
<220> FEATURE:
<223> OTHER INFORMATION: Antisense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = g

<400> SEQUENCE: 10
uugaguaugc ugggcaccgn n                                                     21

<210> SEQ ID NO 11
<211> LENGTH: 21
<212> TYPE: DNA
<213> ORGANISM: Artificial Sequence
<220> FEATURE:
<223> OTHER INFORMATION: Sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 11
ggcuaucacu ucaaugucan n                                                     21

<210> SEQ ID NO 12
<211> LENGTH: 21
<212> TYPE: DNA
<213> ORGANISM: Artificial Sequence
<220> FEATURE:
<223> OTHER INFORMATION: Antisense siRNA sequence
<220> FEATURE:
<223> OTHER INFORMATION: RNA/DNA hybrid
<220> FEATURE:
<221> NAME/KEY: misc_feature
<222> LOCATION: 20
<223> OTHER INFORMATION: n = a
<220> FEATURE:
<221> NAME/KEY: misc_feature
<222> LOCATION: 21
<223> OTHER INFORMATION: n = g

```
<400> SEQUENCE: 12
ugacauugaa gugauagccn n                                              21

<210> SEQ ID NO 13
<211> LENGTH: 21
<212> TYPE: DNA
<213> ORGANISM: Artificial Sequence
<220> FEATURE:
<223> OTHER INFORMATION: Sense siRNA sequence
<220> FEATURE:
<223> OTHER INFORMATION: RNA/DNA hybrid
<220> FEATURE:
<221> NAME/KEY: misc_feature
<222> LOCATION: 20, 21
<223> OTHER INFORMATION: n = t

<400> SEQUENCE: 13
ccuuggaaca uaaugauaan n                                              21

<210> SEQ ID NO 14
<211> LENGTH: 21
<212> TYPE: DNA
<213> ORGANISM: Artificial Sequence
<220> FEATURE:
<223> OTHER INFORMATION: Antisense siRNAsequence
<220> FEATURE:
<223> OTHER INFORMATION: RNA/DNA hybrid
<220> FEATURE:
<221> NAME/KEY: misc_feature
<222> LOCATION: 20
<223> OTHER INFORMATION: n = g
<220> FEATURE:
<221> NAME/KEY: misc_feature
<222> LOCATION: 21
<223> OTHER INFORMATION: n = t

<400> SEQUENCE: 14
uuaucauuau guuccaaggn n                                              21

<210> SEQ ID NO 15
<211> LENGTH: 22
<212> TYPE: RNA
<213> ORGANISM: Artificial Sequence
<220> FEATURE:
<223> OTHER INFORMATION: Mature hsa-miR-183 sequence

<400> SEQUENCE: 15
uauggcacug guagaauuca cu                                             22

<210> SEQ ID NO 16
<211> LENGTH: 22
<212> TYPE: RNA
<213> ORGANISM: Artificial Sequence
<220> FEATURE:
<223> OTHER INFORMATION: Mature hsa-miR-491-5p sequence

<400> SEQUENCE: 16
aguggggaac ccuuccauga gg                                             22

<210> SEQ ID NO 17
<211> LENGTH: 22
<212> TYPE: RNA
<213> ORGANISM: Artificial Sequence
<220> FEATURE:
<223> OTHER INFORMATION: Mature hsa-miR-132* sequence

<400> SEQUENCE: 17
```
accguggcuu ucgauuguua cu    22

<210> SEQ ID NO 18
<211> LENGTH: 21
<212> TYPE: RNA
<213> ORGANISM: Artificial Sequence
<220> FEATURE:
<223> OTHER INFORMATION: Mature hsa-miR-129-5p sequence

<400> SEQUENCE: 18
cuuuuugcgg ucugggcuug c    21

<210> SEQ ID NO 19
<211> LENGTH: 23
<212> TYPE: RNA
<213> ORGANISM: Artificial Sequence
<220> FEATURE:
<223> OTHER INFORMATION: Mature hsa-miR-636 sequence

<400> SEQUENCE: 19
ugugcuugcu cgucccgccc gca    23

<210> SEQ ID NO 20
<211> LENGTH: 22
<212> TYPE: RNA
<213> ORGANISM: Artificial Sequence
<220> FEATURE:
<223> OTHER INFORMATION: Mature hsa-miR-100 sequence

<400> SEQUENCE: 20
aacccguaga uccgaacuug ug    22

<210> SEQ ID NO 21
<211> LENGTH: 23
<212> TYPE: RNA
<213> ORGANISM: Artificial Sequence
<220> FEATURE:
<223> OTHER INFORMATION: Mature hsa-miR-181a sequence

<400> SEQUENCE: 21
aacauucaac gcugucggug agu    23

<210> SEQ ID NO 22
<211> LENGTH: 22
<212> TYPE: RNA
<213> ORGANISM: Artificial Sequence
<220> FEATURE:
<223> OTHER INFORMATION: Mature hsa-miR-519a sequence

<400> SEQUENCE: 22
aaagugcauc cuuuuagagu gu    22

<210> SEQ ID NO 23
<211> LENGTH: 22
<212> TYPE: RNA
<213> ORGANISM: Artificial Sequence
<220> FEATURE:
<223> OTHER INFORMATION: Mature hsa-miR-338-3p sequence

<400> SEQUENCE: 23
uccagcauca gugauuuugu ug    22

<210> SEQ ID NO 24
<211> LENGTH: 21
<212> TYPE: RNA
<213> ORGANISM: Artificial Sequence

```
<220> FEATURE:
<223> OTHER INFORMATION: Mature hsa-miR-1179 sequence

<400> SEQUENCE: 24
aagcauucuu ucauugguug g                                              21

<210> SEQ ID NO 25
<211> LENGTH: 22
<212> TYPE: RNA
<213> ORGANISM: Artificial Sequence
<220> FEATURE:
<223> OTHER INFORMATION: Mature hsa-miR-521 sequence

<400> SEQUENCE: 25
aacgcacuuc ccuuuagagu gu                                             22

<210> SEQ ID NO 26
<211> LENGTH: 25
<212> TYPE: RNA
<213> ORGANISM: Artificial Sequence
<220> FEATURE:
<223> OTHER INFORMATION: Mature hsa-miR-608 sequence

<400> SEQUENCE: 26
aggggugguc uugggacagc uccgu                                          25

<210> SEQ ID NO 27
<211> LENGTH: 18
<212> TYPE: RNA
<213> ORGANISM: Artificial Sequence
<220> FEATURE:
<223> OTHER INFORMATION: Mature hsa-miR-1306 sequence

<400> SEQUENCE: 27
acguuggcuc ugguggug                                                  18

<210> SEQ ID NO 28
<211> LENGTH: 22
<212> TYPE: RNA
<213> ORGANISM: Artificial Sequence
<220> FEATURE:
<223> OTHER INFORMATION: Mature hsa-miR-543 sequence

<400> SEQUENCE: 28
aaacauucgc ggugcacuuc uu                                             22

<210> SEQ ID NO 29
<211> LENGTH: 22
<212> TYPE: RNA
<213> ORGANISM: Artificial Sequence
<220> FEATURE:
<223> OTHER INFORMATION: Mature hsa-miR-542-3p sequence

<400> SEQUENCE: 29
ugugacagau ugauaacuga aa                                             22

<210> SEQ ID NO 30
<211> LENGTH: 21
<212> TYPE: RNA
<213> ORGANISM: Artificial Sequence
<220> FEATURE:
<223> OTHER INFORMATION: Mature hsa-miR-23b sequence

<400> SEQUENCE: 30
aucacauugc cagggauuac c                                              21
```

```
<210> SEQ ID NO 31
<211> LENGTH: 22
<212> TYPE: RNA
<213> ORGANISM: Artificial Sequence
<220> FEATURE:
<223> OTHER INFORMATION: Mature hsa-miR-299-3p sequence

<400> SEQUENCE: 31 uauguggau gguaaaccgc uu                                          22

<210> SEQ ID NO 32
<211> LENGTH: 22
<212> TYPE: RNA
<213> ORGANISM: Artificial Sequence
<220> FEATURE:
<223> OTHER INFORMATION: Mature hsa-miR-597 sequence

<400> SEQUENCE: 32 ugugcacuc gaugaccacu gu                                          22

<210> SEQ ID NO 33
<211> LENGTH: 20
<212> TYPE: RNA
<213> ORGANISM: Artificial Sequence
<220> FEATURE:
<223> OTHER INFORMATION: Mature hsa-miR-1976 sequence

<400> SEQUENCE: 33
ccuccugccc uccuugcugu                                            20

<210> SEQ ID NO 34
<211> LENGTH: 22
<212> TYPE: RNA
<213> ORGANISM: Artificial Sequence
<220> FEATURE:
<223> OTHER INFORMATION: Mature hsa-miR-1252 sequence

<400> SEQUENCE: 34
agaaggaaau ugaauucauu ua                                         22

<210> SEQ ID NO 35
<211> LENGTH: 22
<212> TYPE: RNA
<213> ORGANISM: Artificial Sequence
<220> FEATURE:
<223> OTHER INFORMATION: Mature hsa-miR-510 sequence

<400> SEQUENCE: 35
uacucaggag aguggcaauc ac                                         22

<210> SEQ ID NO 36
<211> LENGTH: 21
<212> TYPE: RNA
<213> ORGANISM: Artificial Sequence
<220> FEATURE:
<223> OTHER INFORMATION: Mature hsa-miR-1207-5p sequence

<400> SEQUENCE: 36
uggcagggag gcugggaggg g                                          21

<210> SEQ ID NO 37
<211> LENGTH: 22
<212> TYPE: RNA
<213> ORGANISM: Artificial Sequence
<220> FEATURE:
<223> OTHER INFORMATION: Mature hsa-miR-518a-3p sequence
```

```
<400> SEQUENCE: 37
gaaagcgcuu cccuuugcug ga                                              22

<210> SEQ ID NO 38
<211> LENGTH: 21
<212> TYPE: RNA
<213> ORGANISM: Artificial Sequence
<220> FEATURE:
<223> OTHER INFORMATION: Mature hsa-miR-1250 sequence

<400> SEQUENCE: 38
acggugcugg auguggccuu u                                               21

<210> SEQ ID NO 39
<211> LENGTH: 18
<212> TYPE: RNA
<213> ORGANISM: Artificial Sequence
<220> FEATURE:
<223> OTHER INFORMATION: Mature hsa-miR-1274a sequence

<400> SEQUENCE: 39
gucccuguuc aggcgcca                                                   18

<210> SEQ ID NO 40
<211> LENGTH: 22
<212> TYPE: RNA
<213> ORGANISM: Artificial Sequence
<220> FEATURE:
<223> OTHER INFORMATION: Mature hsa-miR-141* sequence

<400> SEQUENCE: 40
caucuuccag uacaguguug ga                                              22

<210> SEQ ID NO 41
<211> LENGTH: 22
<212> TYPE: RNA
<213> ORGANISM: Artificial Sequence
<220> FEATURE:
<223> OTHER INFORMATION: Mature hsa-miR-9* sequence

<400> SEQUENCE: 41
auaaagcuag auaaccgaaa gu                                              22

<210> SEQ ID NO 42
<211> LENGTH: 19
<212> TYPE: RNA
<213> ORGANISM: Artificial Sequence
<220> FEATURE:
<223> OTHER INFORMATION: Mature hsa-miR-566 sequence

<400> SEQUENCE: 42
gggcgccugu gaucccaac                                                  19

<210> SEQ ID NO 43
<211> LENGTH: 21
<212> TYPE: RNA
<213> ORGANISM: Artificial Sequence
<220> FEATURE:
<223> OTHER INFORMATION: Mature hsa-miR-142-5p sequence

<400> SEQUENCE: 43
cauaaaguag aaagcacuac u                                               21

<210> SEQ ID NO 44
```

```
<211> LENGTH: 22
<212> TYPE: RNA
<213> ORGANISM: Artificial Sequence
<220> FEATURE:
<223> OTHER INFORMATION: Mature hsa-miR-23a* sequence

<400> SEQUENCE: 44
gggguuccug gggaugggau uu                                               22

<210> SEQ ID NO 45
<211> LENGTH: 22
<212> TYPE: RNA
<213> ORGANISM: Artificial Sequence
<220> FEATURE:
<223> OTHER INFORMATION: Mature hsa-miR-519e* sequence

<400> SEQUENCE: 45
uucuccaaaa gggagcacuu uc                                               22

<210> SEQ ID NO 46
<211> LENGTH: 25
<212> TYPE: RNA
<213> ORGANISM: Artificial Sequence
<220> FEATURE:
<223> OTHER INFORMATION: Mature hsa-miR-1292 sequence

<400> SEQUENCE: 46
ugggaacggg uuccggcaga cgcug                                            25

<210> SEQ ID NO 47
<211> LENGTH: 23
<212> TYPE: RNA
<213> ORGANISM: Artificial Sequence
<220> FEATURE:
<223> OTHER INFORMATION: Mature hsa-miR-96 sequence

<400> SEQUENCE: 47
uuuggcacua gcacauuuuu gcu                                              23

<210> SEQ ID NO 48
<211> LENGTH: 21
<212> TYPE: RNA
<213> ORGANISM: Artificial Sequence
<220> FEATURE:
<223> OTHER INFORMATION: Mature hsa-miR-886-3p sequence

<400> SEQUENCE: 48
cgcgggugcu uacugacccu u                                                21

<210> SEQ ID NO 49
<211> LENGTH: 22
<212> TYPE: RNA
<213> ORGANISM: Artificial Sequence
<220> FEATURE:
<223> OTHER INFORMATION: Mature hsa-miR-216b sequence

<400> SEQUENCE: 49
aaaucucugc aggcaaaugu ga                                               22

<210> SEQ ID NO 50
<211> LENGTH: 22
<212> TYPE: RNA
<213> ORGANISM: Artificial Sequence
<220> FEATURE:
<223> OTHER INFORMATION: Mature hsa-miR-218-2* sequence

<400> SEQUENCE: 50
```

```
caugguucug ucaagcaccg cg                                             22

<210> SEQ ID NO 51
<211> LENGTH: 24
<212> TYPE: RNA
<213> ORGANISM: Artificial Sequence
<220> FEATURE:
<223> OTHER INFORMATION: Mature hsa-miR-182 sequence

<400> SEQUENCE: 51
uuuggcaaug guagaacuca cacu                                           24

<210> SEQ ID NO 52
<211> LENGTH: 22
<212> TYPE: RNA
<213> ORGANISM: Artificial Sequence
<220> FEATURE:
<223> OTHER INFORMATION: Mature hsa-miR-545* sequence

<400> SEQUENCE: 52
ucaguaaaug uuuauuagau ga                                             22

<210> SEQ ID NO 53
<211> LENGTH: 22
<212> TYPE: RNA
<213> ORGANISM: Artificial Sequence
<220> FEATURE:
<223> OTHER INFORMATION: Mature hsa-miR-517a sequence

<400> SEQUENCE: 53
aucgugcauc ccuuuagagu gu                                             22

<210> SEQ ID NO 54
<211> LENGTH: 25
<212> TYPE: RNA
<213> ORGANISM: Artificial sequence
<220> FEATURE:
<223> OTHER INFORMATION: Mature hsa-miR-541* sequence

<400> SEQUENCE: 54
aaaggauucu gcugucgguc ccacu                                          25

<210> SEQ ID NO 55
<211> LENGTH: 22
<212> TYPE: RNA
<213> ORGANISM: Artificial Sequence
<220> FEATURE:
<223> OTHER INFORMATION: Mature hsa-miR-1293 sequence

<400> SEQUENCE: 55
uggguggucu ggagauuugu gc                                             22

<210> SEQ ID NO 56
<211> LENGTH: 23
<212> TYPE: RNA
<213> ORGANISM: Artificial Sequence
<220> FEATURE:
<223> OTHER INFORMATION: Mature hsa-miR-339-5p sequence

<400> SEQUENCE: 56
ucccuguccu ccaggagcuc acg                                            23

<210> SEQ ID NO 57
<211> LENGTH: 22
<212> TYPE: RNA
```

```
<213> ORGANISM: Artificial Sequence
<220> FEATURE:
<223> OTHER INFORMATION: Mature hsa-miR-494 sequence

<400> SEQUENCE: 57
ugaaacauac acgggaaacc uc                                           22

<210> SEQ ID NO 58
<211> LENGTH: 22
<212> TYPE: RNA
<213> ORGANISM: Artificial Sequence
<220> FEATURE:
<223> OTHER INFORMATION: Mature hsa-miR-196a* sequence

<400> SEQUENCE: 58
cggcaacaag aaacugccug ag                                           22

<210> SEQ ID NO 59
<211> LENGTH: 20
<212> TYPE: RNA
<213> ORGANISM: Artificial Sequence
<220> FEATURE:
<223> OTHER INFORMATION: Mature hsa-miR-371-5p sequence

<400> SEQUENCE: 59
acucaaacug uggggcacu                                               20

<210> SEQ ID NO 60
<211> LENGTH: 22
<212> TYPE: RNA
<213> ORGANISM: Artificial Sequence
<220> FEATURE:
<223> OTHER INFORMATION: Mature hsa-miR-136* sequence

<400> SEQUENCE: 60
caucaucguc ucaaaugagu cu                                           22

<210> SEQ ID NO 61
<211> LENGTH: 22
<212> TYPE: RNA
<213> ORGANISM: Artificial Sequence
<220> FEATURE:
<223> OTHER INFORMATION: Mature hsa-miR-214 sequence

<400> SEQUENCE: 61
acagcaggca cagacaggca gu                                           22

<210> SEQ ID NO 62
<211> LENGTH: 21
<212> TYPE: RNA
<213> ORGANISM: Artificial Sequence
<220> FEATURE:
<223> OTHER INFORMATION: Mature hsa-miR-25* sequence

<400> SEQUENCE: 62
aggcggagac uugggcaauu g                                            21

<210> SEQ ID NO 63
<211> LENGTH: 22
<212> TYPE: RNA
<213> ORGANISM: Artificial Sequence
<220> FEATURE:
<223> OTHER INFORMATION: Mature hsa-miR-452* sequence

<400> SEQUENCE: 63
cucaucugca aagaaguaag ug                                           22
```

```
<210> SEQ ID NO 64
<211> LENGTH: 22
<212> TYPE: RNA
<213> ORGANISM: Artificial Sequence
<220> FEATURE:
<223> OTHER INFORMATION: Mature hsa-miR-454* sequence

<400> SEQUENCE: 64
acccuaucaa uauugucucu gc                                              22

<210> SEQ ID NO 65
<211> LENGTH: 22
<212> TYPE: RNA
<213> ORGANISM: Artificial Sequence
<220> FEATURE:
<223> OTHER INFORMATION: Mature hsa-miR-548b-5p sequence

<400> SEQUENCE: 65
aaaaguaauu gugguuuugg cc                                              22

<210> SEQ ID NO 66
<211> LENGTH: 22
<212> TYPE: RNA
<213> ORGANISM: Artificial Sequence
<220> FEATURE:
<223> OTHER INFORMATION: Mature hsa-miR-10b* sequence

<400> SEQUENCE: 66
acagauucga uucuagggga au                                              22

<210> SEQ ID NO 67
<211> LENGTH: 21
<212> TYPE: RNA
<213> ORGANISM: Artificial Sequence
<220> FEATURE:
<223> OTHER INFORMATION: Mature hsa-miR-218 sequence

<400> SEQUENCE: 67
uugugcuuga ucuaaccaug u                                               21

<210> SEQ ID NO 68
<211> LENGTH: 21
<212> TYPE: RNA
<213> ORGANISM: Artificial Sequence
<220> FEATURE:
<223> OTHER INFORMATION: Mature hsa-miR-548m sequence

<400> SEQUENCE: 68
caaagguauu gugguuuuu g                                                21

<210> SEQ ID NO 69
<211> LENGTH: 22
<212> TYPE: RNA
<213> ORGANISM: Artificial Sequence
<220> FEATURE:
<223> OTHER INFORMATION: Mature hsa-miR-520a-3p sequence

<400> SEQUENCE: 69
aaagugcuuc ccuuuggacu gu                                              22

<210> SEQ ID NO 70
<211> LENGTH: 22
<212> TYPE: RNA
<213> ORGANISM: Artificial sequence
<220> FEATURE:
```

```
<223> OTHER INFORMATION: Mature hsa-miR-1323 sequence

<400> SEQUENCE: 70
ucaaaacuga ggggcauuuu cu                                              22

<210> SEQ ID NO 71
<211> LENGTH: 22
<212> TYPE: RNA
<213> ORGANISM: Artificial Sequence
<220> FEATURE:
<223> OTHER INFORMATION: Mature hsa-miR-24-2* sequence

<400> SEQUENCE: 71
ugccuacuga gcugaaacac ag                                              22

<210> SEQ ID NO 72
<211> LENGTH: 20
<212> TYPE: RNA
<213> ORGANISM: Artificial Sequence
<220> FEATURE:
<223> OTHER INFORMATION: Mature hsa-miR-613 sequence

<400> SEQUENCE: 72
aggaauguuc cuucuuugcc                                                 20

<210> SEQ ID NO 73
<211> LENGTH: 22
<212> TYPE: RNA
<213> ORGANISM: Artificial Sequence
<220> FEATURE:
<223> OTHER INFORMATION: Mature hsa-miR-26a sequence

<400> SEQUENCE: 73
uucaaguaau ccaggauagg cu                                              22

<210> SEQ ID NO 74
<211> LENGTH: 22
<212> TYPE: RNA
<213> ORGANISM: Artificial Sequence
<220> FEATURE:
<223> OTHER INFORMATION: Mature hsa-miR-193a-3p sequence

<400> SEQUENCE: 74
aacuggccua caaaguccca gu                                              22

<210> SEQ ID NO 75
<211> LENGTH: 20
<212> TYPE: RNA
<213> ORGANISM: Artificial Sequence
<220> FEATURE:
<223> OTHER INFORMATION: Mature hsa-miR-1208 sequence

<400> SEQUENCE: 75
ucacuguuca gacaggcgga                                                 20

<210> SEQ ID NO 76
<211> LENGTH: 23
<212> TYPE: RNA
<213> ORGANISM: Artificial Sequence
<220> FEATURE:
<223> OTHER INFORMATION: Mature hsa-miR-767-5p sequence

<400> SEQUENCE: 76
ugcaccaugg uugucugagc aug                                             23
```

-continued

```
<210> SEQ ID NO 77
<211> LENGTH: 22
<212> TYPE: RNA
<213> ORGANISM: Artificial Sequence
<220> FEATURE:
<223> OTHER INFORMATION: Mature hsa-miR-491-3p sequence

<400> SEQUENCE: 77
cuuaugcaag auucccuucu ac                                              22

<210> SEQ ID NO 78
<211> LENGTH: 19
<212> TYPE: RNA
<213> ORGANISM: Artificial Sequence
<220> FEATURE:
<223> OTHER INFORMATION: Mature hsa-miR-626 sequence

<400> SEQUENCE: 78
agcugucuga aaaugucuu                                                  19

<210> SEQ ID NO 79
<211> LENGTH: 22
<212> TYPE: RNA
<213> ORGANISM: Artificial Sequence
<220> FEATURE:
<223> OTHER INFORMATION: Mature hsa-miR-216a sequence

<400> SEQUENCE: 79
uaaucucagc uggcaacugu ga                                              22

<210> SEQ ID NO 80
<211> LENGTH: 21
<212> TYPE: RNA
<213> ORGANISM: Artificial Sequence
<220> FEATURE:
<223> OTHER INFORMATION: Mature hsa-miR-151-5p sequence

<400> SEQUENCE: 80
ucgaggagcu cacagucuag u                                               21

<210> SEQ ID NO 81
<211> LENGTH: 20
<212> TYPE: RNA
<213> ORGANISM: Artificial Sequence
<220> FEATURE:
<223> OTHER INFORMATION: Mature hsa-miR-1282 sequence

<400> SEQUENCE: 81
ucguuugccu uuucugcuu                                                  20

<210> SEQ ID NO 82
<211> LENGTH: 22
<212> TYPE: RNA
<213> ORGANISM: Artificial Sequence
<220> FEATURE:
<223> OTHER INFORMATION: Mature hsa-miR-497* sequence

<400> SEQUENCE: 82
caaaccacac uguggguuua ga                                              22

<210> SEQ ID NO 83
<211> LENGTH: 22
<212> TYPE: RNA
<213> ORGANISM: Artificial Sequence
<220> FEATURE:
<223> OTHER INFORMATION: Mature hsa-miR-129-3p sequence
```

```
<400> SEQUENCE: 83
aagcccuuac cccaaaaagc au                                             22

<210> SEQ ID NO 84
<211> LENGTH: 23
<212> TYPE: RNA
<213> ORGANISM: Artificial Sequence
<220> FEATURE:
<223> OTHER INFORMATION: Mature hsa-miR-371-3p sequence

<400> SEQUENCE: 84
aagugccgcc aucuuugag ugu                                             23

<210> SEQ ID NO 85
<211> LENGTH: 21
<212> TYPE: RNA
<213> ORGANISM: Artificial Sequence
<220> FEATURE:
<223> OTHER INFORMATION: Mature hsa-miR-376c sequence

<400> SEQUENCE: 85
aacauagagg aaauuccacg u                                              21

<210> SEQ ID NO 86
<211> LENGTH: 21
<212> TYPE: RNA
<213> ORGANISM: Artificial Sequence
<220> FEATURE:
<223> OTHER INFORMATION: Mature hsa-miR-888 sequence

<400> SEQUENCE: 86
uacucaaaaa gcugucaguc a                                              21

<210> SEQ ID NO 87
<211> LENGTH: 22
<212> TYPE: RNA
<213> ORGANISM: Artificial Sequence
<220> FEATURE:
<223> OTHER INFORMATION: Mature hsa-miR-517b sequence

<400> SEQUENCE: 87
ucgugcaucc cuuuagagug uu                                             22

<210> SEQ ID NO 88
<211> LENGTH: 22
<212> TYPE: RNA
<213> ORGANISM: Artificial Sequence
<220> FEATURE:
<223> OTHER INFORMATION: Mature hsa-miR-433 sequence

<400> SEQUENCE: 88
aucaugaugg gcuccucggu gu                                             22

<210> SEQ ID NO 89
<211> LENGTH: 22
<212> TYPE: RNA
<213> ORGANISM: Artificial Sequence
<220> FEATURE:
<223> OTHER INFORMATION: Mature hsa-miR-200a* sequence

<400> SEQUENCE: 89
caucuuaccg gacagugcug ga                                             22

<210> SEQ ID NO 90
<211> LENGTH: 21
```

```
<212> TYPE: RNA
<213> ORGANISM: Artificial Sequence
<220> FEATURE:
<223> OTHER INFORMATION: Mature hsa-miR-520a-5p sequence

<400> SEQUENCE: 90
cuccagaggg aaguacuuuc u                                              21

<210> SEQ ID NO 91
<211> LENGTH: 21
<212> TYPE: RNA
<213> ORGANISM: Artificial Sequence
<220> FEATURE:
<223> OTHER INFORMATION: Mature hsa-miR-1286 sequence

<400> SEQUENCE: 91
ugcaggacca agaugagccc u                                              21

<210> SEQ ID NO 92
<211> LENGTH: 21
<212> TYPE: RNA
<213> ORGANISM: Artificial Sequence
<220> FEATURE:
<223> OTHER INFORMATION: Mature hsa-miR-182* sequence

<400> SEQUENCE: 92
ugguucuaga cuugccaacu a                                              21

<210> SEQ ID NO 93
<211> LENGTH: 25
<212> TYPE: RNA
<213> ORGANISM: Artificial Sequence
<220> FEATURE:
<223> OTHER INFORMATION: Mature hsa-miR-1273 sequence

<400> SEQUENCE: 93
gggcgacaaa gcaagacucu uucuu                                          25

<210> SEQ ID NO 94
<211> LENGTH: 17
<212> TYPE: RNA
<213> ORGANISM: Artificial Sequence
<220> FEATURE:
<223> OTHER INFORMATION: Mature hsa-miR-1280 sequence

<400> SEQUENCE: 94
ucccaccgcu gccaccc                                                   17

<210> SEQ ID NO 95
<211> LENGTH: 19
<212> TYPE: RNA
<213> ORGANISM: Artificial Sequence
<220> FEATURE:
<223> OTHER INFORMATION: Mature hsa-miR-563 sequence

<400> SEQUENCE: 95
agguugacau acguuuccc                                                 19

<210> SEQ ID NO 96
<211> LENGTH: 22
<212> TYPE: RNA
<213> ORGANISM: Artificial Sequence
<220> FEATURE:
<223> OTHER INFORMATION: Mature hsa-miR-501-5p sequence

<400> SEQUENCE: 96
```
aauccuuugu cccuggguga ga                                        22

<210> SEQ ID NO 97
<211> LENGTH: 22
<212> TYPE: RNA
<213> ORGANISM: Artificial Sequence
<220> FEATURE:
<223> OTHER INFORMATION: Mature hsa-miR-448 sequence

<400> SEQUENCE: 97
uugcauaugu aggauguccc au                                        22

<210> SEQ ID NO 98
<211> LENGTH: 22
<212> TYPE: RNA
<213> ORGANISM: Artificial sequence
<220> FEATURE:
<223> OTHER INFORMATION: Mature hsa-miR-485-3p sequence

<400> SEQUENCE: 98
gucauacacg gcucuccucu cu                                        22

<210> SEQ ID NO 99
<211> LENGTH: 22
<212> TYPE: RNA
<213> ORGANISM: Artificial Sequence
<220> FEATURE:
<223> OTHER INFORMATION: Mature hsa-miR-29c sequence

<400> SEQUENCE: 99
uagcaccauu ugaaaucggu ua                                        22

<210> SEQ ID NO 100
<211> LENGTH: 19
<212> TYPE: RNA
<213> ORGANISM: Artificial Sequence
<220> FEATURE:
<223> OTHER INFORMATION: Mature hsa-miR-548f sequence

<400> SEQUENCE: 100
aaaaacugua auuacuuuu                                            19

<210> SEQ ID NO 101
<211> LENGTH: 27
<212> TYPE: RNA
<213> ORGANISM: Artificial Sequence
<220> FEATURE:
<223> OTHER INFORMATION: Mature hsa-miR-1248 sequence

<400> SEQUENCE: 101
accuucuugu auaagcacug ugcuaaa                                   27

<210> SEQ ID NO 102
<211> LENGTH: 22
<212> TYPE: RNA
<213> ORGANISM: Artificial Sequence
<220> FEATURE:
<223> OTHER INFORMATION: Mature hsa-let-7d* sequence

<400> SEQUENCE: 102
cuauacgacc ugcugccuuu cu                                        22

<210> SEQ ID NO 103
<211> LENGTH: 23
<212> TYPE: RNA
<213> ORGANISM: Artificial Sequence

```
<220> FEATURE:
<223> OTHER INFORMATION: Mature hsa-miR-618 sequence

<400> SEQUENCE: 103
aaacucuacu uguccuucug agu                                              23

<210> SEQ ID NO 104
<211> LENGTH: 23
<212> TYPE: RNA
<213> ORGANISM: Artificial Sequence
<220> FEATURE:
<223> OTHER INFORMATION: Mature hsa-miR-30c sequence

<400> SEQUENCE: 104
uguaaacauc cuacacucuc agc                                              23

<210> SEQ ID NO 105
<211> LENGTH: 23
<212> TYPE: RNA
<213> ORGANISM: Artificial Sequence
<220> FEATURE:
<223> OTHER INFORMATION: Mature hsa-miR-136 sequence

<400> SEQUENCE: 105
acuccauuug uuuugaugau gga                                              23

<210> SEQ ID NO 106
<211> LENGTH: 23
<212> TYPE: RNA
<213> ORGANISM: Artificial Sequence
<220> FEATURE:
<223> OTHER INFORMATION: Mature hsa-miR-10a sequence

<400> SEQUENCE: 106
uacccuguag auccgaauuu gug                                              23

<210> SEQ ID NO 107
<211> LENGTH: 23
<212> TYPE: RNA
<213> ORGANISM: Artificial Sequence
<220> FEATURE:
<223> OTHER INFORMATION: Mature hsa-miR-557 sequence

<400> SEQUENCE: 107
guuugcacgg gugggccuug ucu                                              23

<210> SEQ ID NO 108
<211> LENGTH: 19
<212> TYPE: RNA
<213> ORGANISM: Artificial sequence
<220> FEATURE:
<223> OTHER INFORMATION: Mature hsa-miR-564 sequence

<400> SEQUENCE: 108
aggcacggug ucagcaggc                                                   19

<210> SEQ ID NO 109
<211> LENGTH: 24
<212> TYPE: RNA
<213> ORGANISM: Artificial Sequence
<220> FEATURE:
<223> OTHER INFORMATION: Mature hsa-miR-520g sequence

<400> SEQUENCE: 109
acaaagugcu ucccuuuaga gugu                                             24
```

```
<210> SEQ ID NO 110
<211> LENGTH: 22
<212> TYPE: RNA
<213> ORGANISM: Artificial Sequence
<220> FEATURE:
<223> OTHER INFORMATION: Mature hsa-miR-122* sequence

<400> SEQUENCE: 110
aacgccauua ucacacuaaa ua                                              22

<210> SEQ ID NO 111
<211> LENGTH: 22
<212> TYPE: RNA
<213> ORGANISM: Artificial Sequence
<220> FEATURE:
<223> OTHER INFORMATION: Mature hsa-miR-548k sequence

<400> SEQUENCE: 111
aaaaguacuu gcggauuuug cu                                              22

<210> SEQ ID NO 112
<211> LENGTH: 23
<212> TYPE: RNA
<213> ORGANISM: Artificial Sequence
<220> FEATURE:
<223> OTHER INFORMATION: Mature hsa-miR-423-3p sequence

<400> SEQUENCE: 112
agcucggucu gaggccccuc agu                                             23

<210> SEQ ID NO 113
<211> LENGTH: 22
<212> TYPE: RNA
<213> ORGANISM: Artificial Sequence
<220> FEATURE:
<223> OTHER INFORMATION: Mature hsa-miR-548j sequence

<400> SEQUENCE: 113
aaaaguaauu gcggucuuug gu                                              22

<210> SEQ ID NO 114
<211> LENGTH: 22
<212> TYPE: RNA
<213> ORGANISM: Artificial Sequence
<220> FEATURE:
<223> OTHER INFORMATION: Mature hsa-miR-340* sequence

<400> SEQUENCE: 114
uccgucucag uuacuuuaua gc                                              22

<210> SEQ ID NO 115
<211> LENGTH: 24
<212> TYPE: RNA
<213> ORGANISM: Artificial Sequence
<220> FEATURE:
<223> OTHER INFORMATION: Mature hsa-miR-573 sequence

<400> SEQUENCE: 115
cugaagugau guguaacuga ucag                                            24

<210> SEQ ID NO 116
<211> LENGTH: 22
<212> TYPE: RNA
<213> ORGANISM: Artificial Sequence
<220> FEATURE:
<223> OTHER INFORMATION: Mature hsa-miR-548i sequence
```

```
<400> SEQUENCE: 116
aaaaguaauu gcggauuuug cc                                           22

<210> SEQ ID NO 117
<211> LENGTH: 21
<212> TYPE: RNA
<213> ORGANISM: Artificial Sequence
<220> FEATURE:
<223> OTHER INFORMATION: Mature hsa-miR-555 sequence

<400> SEQUENCE: 117
aggguaagcu gaaccucuga u                                            21

<210> SEQ ID NO 118
<211> LENGTH: 20
<212> TYPE: RNA
<213> ORGANISM: Artificial Sequence
<220> FEATURE:
<223> OTHER INFORMATION: Mature hsa-miR-144 sequence

<400> SEQUENCE: 118
uacaguauag augauguacu                                              20

<210> SEQ ID NO 119
<211> LENGTH: 23
<212> TYPE: RNA
<213> ORGANISM: Artificial Sequence
<220> FEATURE:
<223> OTHER INFORMATION: Mature hsa-miR-567 sequence

<400> SEQUENCE: 119
aguauguucu uccaggacag aac                                          23

<210> SEQ ID NO 120
<211> LENGTH: 22
<212> TYPE: RNA
<213> ORGANISM: Artificial Sequence
<220> FEATURE:
<223> OTHER INFORMATION: Mature hsa-miR-191* sequence

<400> SEQUENCE: 120
gcugcgcuug gauuucgucc cc                                           22

<210> SEQ ID NO 121
<211> LENGTH: 23
<212> TYPE: RNA
<213> ORGANISM: Artificial Sequence
<220> FEATURE:
<223> OTHER INFORMATION: Mature hsa-miR-335 sequence

<400> SEQUENCE: 121
ucaagagcaa uaacgaaaaa ugu                                          23

<210> SEQ ID NO 122
<211> LENGTH: 21
<212> TYPE: RNA
<213> ORGANISM: Artificial Sequence
<220> FEATURE:
<223> OTHER INFORMATION: Mature hsa-miR-126* sequence

<400> SEQUENCE: 122
cauuauuacu uuugguacgc g                                            21

<210> SEQ ID NO 123
```

```
<211> LENGTH: 22
<212> TYPE: RNA
<213> ORGANISM: Artificial Sequence
<220> FEATURE:
<223> OTHER INFORMATION: Mature hsa-miR-22* sequence

<400> SEQUENCE: 123
aguucuucag uggcaagcuu ua                                              22

<210> SEQ ID NO 124
<211> LENGTH: 20
<212> TYPE: RNA
<213> ORGANISM: Artificial Sequence
<220> FEATURE:
<223> OTHER INFORMATION: Mature hsa-miR-572 sequence

<400> SEQUENCE: 124
guccgcucgg cgguggccca                                                 20

<210> SEQ ID NO 125
<211> LENGTH: 22
<212> TYPE: RNA
<213> ORGANISM: Artificial Sequence
<220> FEATURE:
<223> OTHER INFORMATION: Mature hsa-miR-517c sequence

<400> SEQUENCE: 125
aucgugcauc cuuuuagagu gu                                              22

<210> SEQ ID NO 126
<211> LENGTH: 22
<212> TYPE: RNA
<213> ORGANISM: Artificial Sequence
<220> FEATURE:
<223> OTHER INFORMATION: Mature hsa-miR-380* sequence

<400> SEQUENCE: 126
ugguugacca uagaacaugc gc                                              22

<210> SEQ ID NO 127
<211> LENGTH: 22
<212> TYPE: RNA
<213> ORGANISM: Artificial Sequence
<220> FEATURE:
<223> OTHER INFORMATION: Mature hsa-miR-106a* sequence

<400> SEQUENCE: 127
cugcaaugua agcacuucuu ac                                              22

<210> SEQ ID NO 128
<211> LENGTH: 22
<212> TYPE: RNA
<213> ORGANISM: Artificial Sequence
<220> FEATURE:
<223> OTHER INFORMATION: Mature hsa-miR-519e sequence

<400> SEQUENCE: 128
aagugccucc uuuuagagug uu                                              22

<210> SEQ ID NO 129
<211> LENGTH: 22
<212> TYPE: RNA
<213> ORGANISM: Artificial Sequence
<220> FEATURE:
<223> OTHER INFORMATION: Mature hsa-miR-520c-3p sequence

<400> SEQUENCE: 129
```

-continued aaagugcuuc cuuuuagagg gu                                    22

<210> SEQ ID NO 130
<211> LENGTH: 22
<212> TYPE: RNA
<213> ORGANISM: Artificial Sequence
<220> FEATURE:
<223> OTHER INFORMATION: Mature hsa-miR-517* sequence

<400> SEQUENCE: 130
ccucuagaug gaagcacugu cu                                    22

<210> SEQ ID NO 131
<211> LENGTH: 21
<212> TYPE: RNA
<213> ORGANISM: Artificial Sequence
<220> FEATURE:
<223> OTHER INFORMATION: Mature hsa-miR-432* sequence

<400> SEQUENCE: 131
cuggauggcu ccuccauguc u                                     21

<210> SEQ ID NO 132
<211> LENGTH: 21
<212> TYPE: RNA
<213> ORGANISM: Artificial Sequence
<220> FEATURE:
<223> OTHER INFORMATION: Mature hsa-miR-520e sequence

<400> SEQUENCE: 132
aaagugcuuc cuuuuugagg g                                     21

<210> SEQ ID NO 133
<211> LENGTH: 21
<212> TYPE: RNA
<213> ORGANISM: Artificial Sequence
<220> FEATURE:
<223> OTHER INFORMATION: Mature hsa-miR-551a sequence

<400> SEQUENCE: 133
gcgacccacu cuugguuucc a                                     21

<210> SEQ ID NO 134
<211> LENGTH: 22
<212> TYPE: RNA
<213> ORGANISM: Artificial Sequence
<220> FEATURE:
<223> OTHER INFORMATION: Mature hsa-miR-1471 sequence

<400> SEQUENCE: 134
gcccgcgugu ggagccaggu gu                                    22

<210> SEQ ID NO 135
<211> LENGTH: 20
<212> TYPE: RNA
<213> ORGANISM: Artificial Sequence
<220> FEATURE:
<223> OTHER INFORMATION: Mature hsa-miR-562 sequence

<400> SEQUENCE: 135
aaaguagcug uaccauuugc                                       20

<210> SEQ ID NO 136
<211> LENGTH: 23
<212> TYPE: RNA

```
<213> ORGANISM: Artificial Sequence
<220> FEATURE:
<223> OTHER INFORMATION: Mature hsa-miR-922 sequence

<400> SEQUENCE: 136
gcagcagaga auaggacuac guc                                           23

<210> SEQ ID NO 137
<211> LENGTH: 21
<212> TYPE: RNA
<213> ORGANISM: Artificial Sequence
<220> FEATURE:
<223> OTHER INFORMATION: Mature hsa-miR-499-5p sequence

<400> SEQUENCE: 137
uuaagacuug cagugauguu u                                             21

<210> SEQ ID NO 138
<211> LENGTH: 22
<212> TYPE: RNA
<213> ORGANISM: Artificial Sequence
<220> FEATURE:
<223> OTHER INFORMATION: Mature hsa-miR-25 sequence

<400> SEQUENCE: 138
cauugcacuu gucucggucu ga                                            22

<210> SEQ ID NO 139
<211> LENGTH: 22
<212> TYPE: RNA
<213> ORGANISM: Artificial Sequence
<220> FEATURE:
<223> OTHER INFORMATION: Mature hsa-miR-197 sequence

<400> SEQUENCE: 139
uucaccaccu ucuccaccca gc                                            22

<210> SEQ ID NO 140
<211> LENGTH: 22
<212> TYPE: RNA
<213> ORGANISM: Artificial Sequence
<220> FEATURE:
<223> OTHER INFORMATION: Mature hsa-miR-500* sequence

<400> SEQUENCE: 140
augcaccugg gcaaggauuc ug                                            22

<210> SEQ ID NO 141
<211> LENGTH: 22
<212> TYPE: RNA
<213> ORGANISM: Artificial Sequence
<220> FEATURE:
<223> OTHER INFORMATION: Mature hsa-miR-365* sequence

<400> SEQUENCE: 141
agggacuuuc aggggcagcu gu                                            22

<210> SEQ ID NO 142
<211> LENGTH: 22
<212> TYPE: RNA
<213> ORGANISM: Artificial Sequence
<220> FEATURE:
<223> OTHER INFORMATION: Mature hsa-miR-1247 sequence

<400> SEQUENCE: 142
acccgucccg uucgucccg ga                                             22
```

```
<210> SEQ ID NO 143
<211> LENGTH: 22
<212> TYPE: RNA
<213> ORGANISM: Artificial Sequence
<220> FEATURE:
<223> OTHER INFORMATION: Mature hsa-miR-586 sequence

<400> SEQUENCE: 143
uaugcauugu auuuuuaggu cc                                              22

<210> SEQ ID NO 144
<211> LENGTH: 22
<212> TYPE: RNA
<213> ORGANISM: Artificial Sequence
<220> FEATURE:
<223> OTHER INFORMATION: Mature hsa-miR-548d-3p sequence

<400> SEQUENCE: 144
caaaaaccac aguuucuuuu gc                                              22

<210> SEQ ID NO 145
<211> LENGTH: 22
<212> TYPE: RNA
<213> ORGANISM: Artificial Sequence
<220> FEATURE:
<223> OTHER INFORMATION: Mature hsa-miR-27a* sequence

<400> SEQUENCE: 145
agggcuuagc ugcuugugag ca                                              22

<210> SEQ ID NO 146
<211> LENGTH: 22
<212> TYPE: RNA
<213> ORGANISM: Artificial Sequence
<220> FEATURE:
<223> OTHER INFORMATION: Mature hsa-miR-598 sequence

<400> SEQUENCE: 146
uacgucaucg uugucaucgu ca                                              22

<210> SEQ ID NO 147
<211> LENGTH: 20
<212> TYPE: RNA
<213> ORGANISM: Artificial Sequence
<220> FEATURE:
<223> OTHER INFORMATION: Mature hsa-miR-609 sequence

<400> SEQUENCE: 147
aggguguuuc ucucaucucu                                                 20

<210> SEQ ID NO 148
<211> LENGTH: 22
<212> TYPE: RNA
<213> ORGANISM: Artificial Sequence
<220> FEATURE:
<223> OTHER INFORMATION: Mature hsa-miR-132 sequence

<400> SEQUENCE: 148
uaacagucua cagccauggu cg                                              22

<210> SEQ ID NO 149
<211> LENGTH: 22
<212> TYPE: RNA
<213> ORGANISM: Artificial Sequence
<220> FEATURE:
```

```
<223> OTHER INFORMATION: Mature hsa-miR-411* sequence

<400> SEQUENCE: 149
uauguaacac gguccacuaa cc                                              22

<210> SEQ ID NO 150
<211> LENGTH: 23
<212> TYPE: RNA
<213> ORGANISM: Artificial Sequence
<220> FEATURE:
<223> OTHER INFORMATION: Mature hsa-miR-135a sequence

<400> SEQUENCE: 150
uauggcuuuu uauuccuaug uga                                             23

<210> SEQ ID NO 151
<211> LENGTH: 21
<212> TYPE: RNA
<213> ORGANISM: Artificial Sequence
<220> FEATURE:
<223> OTHER INFORMATION: Mature hsa-miR-31 sequence

<400> SEQUENCE: 151
aggcaagaug cuggcauagc u                                               21

<210> SEQ ID NO 152
<211> LENGTH: 22
<212> TYPE: RNA
<213> ORGANISM: Artificial Sequence
<220> FEATURE:
<223> OTHER INFORMATION: Mature hsa-miR-181a* sequence

<400> SEQUENCE: 152
accaucgacc guugauugua cc                                              22

<210> SEQ ID NO 153
<211> LENGTH: 21
<212> TYPE: RNA
<213> ORGANISM: Artificial Sequence
<220> FEATURE:
<223> OTHER INFORMATION: Mature hsa-miR-1245 sequence

<400> SEQUENCE: 153
aagugaucua aaggccuaca u                                               21

<210> SEQ ID NO 154
<211> LENGTH: 22
<212> TYPE: RNA
<213> ORGANISM: Artificial Sequence
<220> FEATURE:
<223> OTHER INFORMATION: Mature hsa-miR-758 sequence

<400> SEQUENCE: 154
uuugugaccu gguccacuaa cc                                              22

<210> SEQ ID NO 155
<211> LENGTH: 20
<212> TYPE: RNA
<213> ORGANISM: Artificial Sequence
<220> FEATURE:
<223> OTHER INFORMATION: Mature hsa-miR-924 sequence

<400> SEQUENCE: 155
agagucuugu gaugucuugc                                                 20
```

```
<210> SEQ ID NO 156
<211> LENGTH: 19
<212> TYPE: RNA
<213> ORGANISM: Artificial Sequence
<220> FEATURE:
<223> OTHER INFORMATION: Mature hsa-miR-1246 sequence

<400> SEQUENCE: 156
aauggauuuu uggagcagg                                                 19

<210> SEQ ID NO 157
<211> LENGTH: 21
<212> TYPE: RNA
<213> ORGANISM: Artificial Sequence
<220> FEATURE:
<223> OTHER INFORMATION: Mature hsa-miR-631 sequence

<400> SEQUENCE: 157
agaccuggcc cagaccucag c                                              21

<210> SEQ ID NO 158
<211> LENGTH: 22
<212> TYPE: RNA
<213> ORGANISM: Artificial Sequence
<220> FEATURE:
<223> OTHER INFORMATION: Mature hsa-miR-1 sequence

<400> SEQUENCE: 158
uggaauguaa agaaguaugu au                                             22

<210> SEQ ID NO 159
<211> LENGTH: 20
<212> TYPE: RNA
<213> ORGANISM: Artificial Sequence
<220> FEATURE:
<223> OTHER INFORMATION: Mature hsa-miR-920 sequence

<400> SEQUENCE: 159
ggggagcugu ggaagcagua                                                20

<210> SEQ ID NO 160
<211> LENGTH: 24
<212> TYPE: RNA
<213> ORGANISM: Artificial Sequence
<220> FEATURE:
<223> OTHER INFORMATION: Mature hsa-miR-589* sequence

<400> SEQUENCE: 160
ucagaacaaa ugccgguucc caga                                           24

<210> SEQ ID NO 161
<211> LENGTH: 25
<212> TYPE: RNA
<213> ORGANISM: Artificial Sequence
<220> FEATURE:
<223> OTHER INFORMATION: Mature hsa-miR-638 sequence

<400> SEQUENCE: 161
agggaucgcg ggcggguggc ggccu                                          25

<210> SEQ ID NO 162
<211> LENGTH: 26
<212> TYPE: RNA
<213> ORGANISM: Artificial Sequence
<220> FEATURE:
<223> OTHER INFORMATION: Mature hsa-miR-1244 sequence
```

```
<400> SEQUENCE: 162
aaguaguugg uuuguaugag auugguu                                          26

<210> SEQ ID NO 163
<211> LENGTH: 22
<212> TYPE: RNA
<213> ORGANISM: Artificial Sequence
<220> FEATURE:
<223> OTHER INFORMATION: Mature hsa-miR-328 sequence

<400> SEQUENCE: 163
cuggcccucu cugcccuucc gu                                               22

<210> SEQ ID NO 164
<211> LENGTH: 22
<212> TYPE: RNA
<213> ORGANISM: Artificial Sequence
<220> FEATURE:
<223> OTHER INFORMATION: Mature hsa-let-7i sequence

<400> SEQUENCE: 164
ugagguagua guuugugcug uu                                               22

<210> SEQ ID NO 165
<211> LENGTH: 22
<212> TYPE: RNA
<213> ORGANISM: Artificial Sequence
<220> FEATURE:
<223> OTHER INFORMATION: Mature hsa-miR-429 sequence

<400> SEQUENCE: 165
uaauacuguc ugguaaaacc gu                                               22

<210> SEQ ID NO 166
<211> LENGTH: 22
<212> TYPE: RNA
<213> ORGANISM: Artificial Sequence
<220> FEATURE:
<223> OTHER INFORMATION: Mature hsa-miR-380 sequence

<400> SEQUENCE: 166
uauguaauau gguccacauc uu                                               22

<210> SEQ ID NO 167
<211> LENGTH: 22
<212> TYPE: RNA
<213> ORGANISM: Artificial Sequence
<220> FEATURE:
<223> OTHER INFORMATION: Mature hsa-let-7b* sequence

<400> SEQUENCE: 167
cuauacaacc uacugccuuc cc                                               22

<210> SEQ ID NO 168
<211> LENGTH: 23
<212> TYPE: RNA
<213> ORGANISM: Artificial Sequence
<220> FEATURE:
<223> OTHER INFORMATION: Mature hsa-miR-614 sequence

<400> SEQUENCE: 168
gaacgccugu ucuugccagg ugg                                              23

<210> SEQ ID NO 169
<211> LENGTH: 22
```

```
<212> TYPE: RNA
<213> ORGANISM: Artificial Sequence
<220> FEATURE:
<223> OTHER INFORMATION: Mature hsa-miR-1225-5p sequence

<400> SEQUENCE: 169
guggguacgg cccagugggg gg                                              22

<210> SEQ ID NO 170
<211> LENGTH: 20
<212> TYPE: RNA
<213> ORGANISM: Artificial Sequence
<220> FEATURE:
<223> OTHER INFORMATION: Mature hsa-miR-320c sequence

<400> SEQUENCE: 170
aaaagcuggg uugagagggu                                                 20

<210> SEQ ID NO 171
<211> LENGTH: 23
<212> TYPE: RNA
<213> ORGANISM: Artificial Sequence
<220> FEATURE:
<223> OTHER INFORMATION: Mature hsa-miR-579 sequence

<400> SEQUENCE: 171
uucauuuggu auaaaccgcg auu                                             23

<210> SEQ ID NO 172
<211> LENGTH: 22
<212> TYPE: RNA
<213> ORGANISM: Artificial Sequence
<220> FEATURE:
<223> OTHER INFORMATION: Mature hsa-miR-455-5p sequence

<400> SEQUENCE: 172
uaugugccuu uggacuacau cg                                              22

<210> SEQ ID NO 173
<211> LENGTH: 22
<212> TYPE: RNA
<213> ORGANISM: Artificial Sequence
<220> FEATURE:
<223> OTHER INFORMATION: Mature hsa-miR-615-3p sequence

<400> SEQUENCE: 173
uccgagccug ggucucccuc uu                                              22

<210> SEQ ID NO 174
<211> LENGTH: 19
<212> TYPE: RNA
<213> ORGANISM: Artificial Sequence
<220> FEATURE:
<223> OTHER INFORMATION: Mature hsa-miR-585 sequence

<400> SEQUENCE: 174
ugggcguauc uguaugcua                                                  19

<210> SEQ ID NO 175
<211> LENGTH: 21
<212> TYPE: RNA
<213> ORGANISM: Artificial Sequence
<220> FEATURE:
<223> OTHER INFORMATION: Mature hsa-miR-559 sequence

<400> SEQUENCE: 175
```
uaaaguaaau augcaccaaa a          21

<210> SEQ ID NO 176
<211> LENGTH: 22
<212> TYPE: RNA
<213> ORGANISM: Artificial sequence
<220> FEATURE:
<223> OTHER INFORMATION: Mature hsa-miR-561 sequence

<400> SEQUENCE: 176
caaaguuuaa gauccuugaa gu          22

<210> SEQ ID NO 177
<211> LENGTH: 23
<212> TYPE: RNA
<213> ORGANISM: Artificial Sequence
<220> FEATURE:
<223> OTHER INFORMATION: Mature hsa-miR-191 sequence

<400> SEQUENCE: 177
caacggaauc ccaaaagcag cug          23

<210> SEQ ID NO 178
<211> LENGTH: 22
<212> TYPE: RNA
<213> ORGANISM: Artificial Sequence
<220> FEATURE:
<223> OTHER INFORMATION: Mature hsa-miR-187 sequence

<400> SEQUENCE: 178
ucgugucuug uguugcagcc gg          22

<210> SEQ ID NO 179
<211> LENGTH: 23
<212> TYPE: RNA
<213> ORGANISM: Artificial Sequence
<220> FEATURE:
<223> OTHER INFORMATION: Mature hsa-miR-29b sequence

<400> SEQUENCE: 179
uagcaccauu ugaaaucagu guu          23

<210> SEQ ID NO 180
<211> LENGTH: 22
<212> TYPE: RNA
<213> ORGANISM: Artificial Sequence
<220> FEATURE:
<223> OTHER INFORMATION: Mature hsa-miR-769-5p sequence

<400> SEQUENCE: 180
ugagaccucu ggguucugag cu          22

<210> SEQ ID NO 181
<211> LENGTH: 22
<212> TYPE: RNA
<213> ORGANISM: Artificial Sequence
<220> FEATURE:
<223> OTHER INFORMATION: Mature hsa-miR-495 sequence

<400> SEQUENCE: 181
aaacaaacau ggugcacuuc uu          22

<210> SEQ ID NO 182
<211> LENGTH: 18
<212> TYPE: RNA
<213> ORGANISM: Artificial Sequence

```
<220> FEATURE:
<223> OTHER INFORMATION: Mature hsa-miR-516a-3p sequence

<400> SEQUENCE: 182
ugcuuccuuu cagagggu                                                        18

<210> SEQ ID NO 183
<211> LENGTH: 22
<212> TYPE: RNA
<213> ORGANISM: Artificial Sequence
<220> FEATURE:
<223> OTHER INFORMATION: Mature hsa-miR-938 sequence

<400> SEQUENCE: 183
ugcccuuaaa ggugaaccca gu                                                   22

<210> SEQ ID NO 184
<211> LENGTH: 22
<212> TYPE: RNA
<213> ORGANISM: Artificial Sequence
<220> FEATURE:
<223> OTHER INFORMATION: Mature hsa-miR-936 sequence

<400> SEQUENCE: 184
acaguagagg gaggaaucgc ag                                                   22

<210> SEQ ID NO 185
<211> LENGTH: 22
<212> TYPE: RNA
<213> ORGANISM: Artificial Sequence
<220> FEATURE:
<223> OTHER INFORMATION: Mature hsa-miR-373* sequence

<400> SEQUENCE: 185
acucaaaaug ggggcgcuuu cc                                                   22

<210> SEQ ID NO 186
<211> LENGTH: 23
<212> TYPE: RNA
<213> ORGANISM: Artificial Sequence
<220> FEATURE:
<223> OTHER INFORMATION: Mature hsa-miR-1184 sequence

<400> SEQUENCE: 186
ccugcagcga cuugauggcu ucc                                                  23

<210> SEQ ID NO 187
<211> LENGTH: 22
<212> TYPE: RNA
<213> ORGANISM: Artificial Sequence
<220> FEATURE:
<223> OTHER INFORMATION: Mature hsa-miR-122 sequence

<400> SEQUENCE: 187
uggaguguga caaugguguu ug                                                   22

<210> SEQ ID NO 188
<211> LENGTH: 22
<212> TYPE: RNA
<213> ORGANISM: Artificial Sequence
<220> FEATURE:
<223> OTHER INFORMATION: Mature hsa-miR-208b sequence

<400> SEQUENCE: 188
auaagacgaa caaaagguuu gu                                                   22
```

```
<210> SEQ ID NO 189
<211> LENGTH: 22
<212> TYPE: RNA
<213> ORGANISM: Artificial Sequence
<220> FEATURE:
<223> OTHER INFORMATION: Mature hsa-miR-223* sequence

<400> SEQUENCE: 189
cguguauuug acaagcugag uu                                              22

<210> SEQ ID NO 190
<211> LENGTH: 22
<212> TYPE: RNA
<213> ORGANISM: Artificial Sequence
<220> FEATURE:
<223> OTHER INFORMATION: Mature hsa-miR-1972 sequence

<400> SEQUENCE: 190
ucaggccagg cacaguggcu ca                                              22

<210> SEQ ID NO 191
<211> LENGTH: 22
<212> TYPE: RNA
<213> ORGANISM: Artificial Sequence
<220> FEATURE:
<223> OTHER INFORMATION: Mature hsa-miR-520h sequence

<400> SEQUENCE: 191
acaaagugcu ucccuuuaga gu                                              22

<210> SEQ ID NO 192
<211> LENGTH: 23
<212> TYPE: RNA
<213> ORGANISM: Artificial Sequence
<220> FEATURE:
<223> OTHER INFORMATION: Mature hsa-miR-330-3p sequence

<400> SEQUENCE: 192
gcaaagcaca cggccugcag aga                                             23

<210> SEQ ID NO 193
<211> LENGTH: 23
<212> TYPE: RNA
<213> ORGANISM: Artificial Sequence
<220> FEATURE:
<223> OTHER INFORMATION: Mature hsa-miR-149 sequence

<400> SEQUENCE: 193
ucuggcuccg ugucuucacu ccc                                             23

<210> SEQ ID NO 194
<211> LENGTH: 23
<212> TYPE: RNA
<213> ORGANISM: Artificial Sequence
<220> FEATURE:
<223> OTHER INFORMATION: Mature hsa-miR-7 sequence

<400> SEQUENCE: 194
uggaagacua gugauuuugu ugu                                             23

<210> SEQ ID NO 195
<211> LENGTH: 22
<212> TYPE: RNA
<213> ORGANISM: Artificial Sequence
<220> FEATURE:
<223> OTHER INFORMATION: Mature hsa-miR-29b-2* sequence
```

```
<400> SEQUENCE: 195
cugguuucac augguggcuu ag                                          22

<210> SEQ ID NO 196
<211> LENGTH: 20
<212> TYPE: RNA
<213> ORGANISM: Artificial Sequence
<220> FEATURE:
<223> OTHER INFORMATION: Mature hsa-miR-520d-5p sequence

<400> SEQUENCE: 196
cuacaaaggg aagcccuuuc                                             20

<210> SEQ ID NO 197
<211> LENGTH: 22
<212> TYPE: RNA
<213> ORGANISM: Artificial Sequence
<220> FEATURE:
<223> OTHER INFORMATION: Mature hsa-miR-592 sequence

<400> SEQUENCE: 197
uugugucaau augcgaugau gu                                          22

<210> SEQ ID NO 198
<211> LENGTH: 21
<212> TYPE: RNA
<213> ORGANISM: Artificial Sequence
<220> FEATURE:
<223> OTHER INFORMATION: Mature hsa-miR-940 sequence

<400> SEQUENCE: 198
aaggcagggc ccccgcuccc c                                           21

<210> SEQ ID NO 199
<211> LENGTH: 22
<212> TYPE: RNA
<213> ORGANISM: Artificial Sequence
<220> FEATURE:
<223> OTHER INFORMATION: Mature hsa-miR-146b-3p sequence

<400> SEQUENCE: 199
ugcccugugg acucaguucu gg                                          22

<210> SEQ ID NO 200
<211> LENGTH: 22
<212> TYPE: RNA
<213> ORGANISM: Artificial Sequence
<220> FEATURE:
<223> OTHER INFORMATION: Mature hsa-miR-518e* sequence

<400> SEQUENCE: 200
cucuagaggg aagcgcuuuc ug                                          22

<210> SEQ ID NO 201
<211> LENGTH: 23
<212> TYPE: RNA
<213> ORGANISM: Artificial Sequence
<220> FEATURE:
<223> OTHER INFORMATION: Mature hsa-miR-1255a sequence

<400> SEQUENCE: 201
aggaugagca aagaaaguag auu                                         23

<210> SEQ ID NO 202
```

```
<211> LENGTH: 23
<212> TYPE: RNA
<213> ORGANISM: Artificial Sequence
<220> FEATURE:
<223> OTHER INFORMATION: Mature hsa-miR-935 sequence

<400> SEQUENCE: 202
ccaguuaccg cuuccgcuac cgc                                          23

<210> SEQ ID NO 203
<211> LENGTH: 23
<212> TYPE: RNA
<213> ORGANISM: Artificial Sequence
<220> FEATURE:
<223> OTHER INFORMATION: Mature hsa-miR-633 sequence

<400> SEQUENCE: 203
cuaauaguau cuaccacaau aaa                                          23

<210> SEQ ID NO 204
<211> LENGTH: 18
<212> TYPE: RNA
<213> ORGANISM: Artificial Sequence
<220> FEATURE:
<223> OTHER INFORMATION: Mature hsa-miR-513a-5p sequence

<400> SEQUENCE: 204
uucacaggga ggugucau                                                18

<210> SEQ ID NO 205
<211> LENGTH: 23
<212> TYPE: RNA
<213> ORGANISM: Artificial Sequence
<220> FEATURE:
<223> OTHER INFORMATION: Mature hsa-miR-361-3p sequence

<400> SEQUENCE: 205 uccccaggu gugauucuga uuu                                           23

<210> SEQ ID NO 206
<211> LENGTH: 22
<212> TYPE: RNA
<213> ORGANISM: Artificial Sequence
<220> FEATURE:
<223> OTHER INFORMATION: Mature hsa-miR-194 sequence

<400> SEQUENCE: 206
uguaacagca acuccaugug ga                                           22

<210> SEQ ID NO 207
<211> LENGTH: 21
<212> TYPE: RNA
<213> ORGANISM: Artificial Sequence
<220> FEATURE:
<223> OTHER INFORMATION: Mature hsa-miR-1185 sequence

<400> SEQUENCE: 207
agaggauacc cuuuguaugu u                                            21

<210> SEQ ID NO 208
<211> LENGTH: 21
<212> TYPE: RNA
<213> ORGANISM: Artificial Sequence
<220> FEATURE:
<223> OTHER INFORMATION: Mature hsa-miR-875-3p sequence

<400> SEQUENCE: 208
```

```
ccuggaaaca cugagguugu g                                         21

<210> SEQ ID NO 209
<211> LENGTH: 22
<212> TYPE: RNA
<213> ORGANISM: Artificial Sequence
<220> FEATURE:
<223> OTHER INFORMATION: Mature hsa-miR-200a sequence

<400> SEQUENCE: 209
uaacacuguc ugguaacgau gu                                        22

<210> SEQ ID NO 210
<211> LENGTH: 24
<212> TYPE: RNA
<213> ORGANISM: Artificial Sequence
<220> FEATURE:
<223> OTHER INFORMATION: Mature hsa-miR-1201 sequence

<400> SEQUENCE: 210
agccugauua aacacaugcu cuga                                      24

<210> SEQ ID NO 211
<211> LENGTH: 21
<212> TYPE: RNA
<213> ORGANISM: Artificial Sequence
<220> FEATURE:
<223> OTHER INFORMATION: Mature hsa-miR-629 sequence

<400> SEQUENCE: 211
uggguuuacg uugggagaac u                                         21

<210> SEQ ID NO 212
<211> LENGTH: 22
<212> TYPE: RNA
<213> ORGANISM: Artificial Sequence
<220> FEATURE:
<223> OTHER INFORMATION: Mature hsa-miR-139-5p sequence

<400> SEQUENCE: 212
ucuacagugc acgugucucc ag                                        22

<210> SEQ ID NO 213
<211> LENGTH: 22
<212> TYPE: RNA
<213> ORGANISM: Artificial Sequence
<220> FEATURE:
<223> OTHER INFORMATION: Mature hsa-miR-504 sequence

<400> SEQUENCE: 213
agacccuggu cugcacucua uc                                        22

<210> SEQ ID NO 214
<211> LENGTH: 22
<212> TYPE: RNA
<213> ORGANISM: Artificial Sequence
<220> FEATURE:
<223> OTHER INFORMATION: Mature hsa-miR-452 sequence

<400> SEQUENCE: 214
aacuguuugc agaggaaacu ga                                        22

<210> SEQ ID NO 215
<211> LENGTH: 22
<212> TYPE: RNA
```

```
<213> ORGANISM: Artificial Sequence
<220> FEATURE:
<223> OTHER INFORMATION: Mature hsa-miR-616* sequence

<400> SEQUENCE: 215
acucaaaacc cuucagugac uu                                              22

<210> SEQ ID NO 216
<211> LENGTH: 22
<212> TYPE: RNA
<213> ORGANISM: Artificial Sequence
<220> FEATURE:
<223> OTHER INFORMATION: Mature hsa-miR-651 sequence

<400> SEQUENCE: 216
uuuaggauaa gcuugacuuu ug                                              22

<210> SEQ ID NO 217
<211> LENGTH: 24
<212> TYPE: RNA
<213> ORGANISM: Artificial Sequence
<220> FEATURE:
<223> OTHER INFORMATION: Mature hsa-miR-1254 sequence

<400> SEQUENCE: 217
agccuggaag cuggagccug cagu                                            24

<210> SEQ ID NO 218
<211> LENGTH: 23
<212> TYPE: RNA
<213> ORGANISM: Artificial Sequence
<220> FEATURE:
<223> OTHER INFORMATION: Mature hsa-miR-339-3p sequence

<400> SEQUENCE: 218
ugagcgccuc gacgacagag ccg                                             23

<210> SEQ ID NO 219
<211> LENGTH: 22
<212> TYPE: RNA
<213> ORGANISM: Artificial Sequence
<220> FEATURE:
<223> OTHER INFORMATION: Mature hsa-miR-181c* sequence

<400> SEQUENCE: 219
aaccaucgac cguugagugg ac                                              22

<210> SEQ ID NO 220
<211> LENGTH: 23
<212> TYPE: RNA
<213> ORGANISM: Artificial Sequence
<220> FEATURE:
<223> OTHER INFORMATION: Mature hsa-miR-19b-1* sequence

<400> SEQUENCE: 220
aguuuugcag guuugcaucc agc                                             23

<210> SEQ ID NO 221
<211> LENGTH: 22
<212> TYPE: RNA
<213> ORGANISM: Artificial Sequence
<220> FEATURE:
<223> OTHER INFORMATION: Mature hsa-miR-1294 sequence

<400> SEQUENCE: 221
ugugagguug gcauuguugu cu                                              22
```

<210> SEQ ID NO 222
<211> LENGTH: 26
<212> TYPE: RNA
<213> ORGANISM: Artificial Sequence
<220> FEATURE:
<223> OTHER INFORMATION: Mature hsa-miR-1226* sequence

<400> SEQUENCE: 222
gugagggcau gcaggccugg augggg                                          26

<210> SEQ ID NO 223
<211> LENGTH: 21
<212> TYPE: PRT
<213> ORGANISM: Artificial Sequence
<220> FEATURE:
<223> OTHER INFORMATION: MOG35-55

<400> SEQUENCE: 223

Met Glu Val Gly Trp Tyr Arg Ser Pro Phe Ser Arg Val Val His Leu
1               5                   10                  15

Tyr Arg Asn Gly Lys
            20

<210> SEQ ID NO 224
<211> LENGTH: 97
<212> TYPE: DNA
<213> ORGANISM: Artificial Sequence
<220> FEATURE:
<223> OTHER INFORMATION: Hairpin sequence of shRNAmir targeting VDR

<400> SEQUENCE: 224
tgctgttgac agtgagcgcc cgcgtcagtg acgtgaccaa tagtgaagcc acagatgtat     60
tggtcacgtc actgacgcgg ttgcctactg cctcgga                             97

<210> SEQ ID NO 225
<211> LENGTH: 19
<212> TYPE: DNA
<213> ORGANISM: Artificial Sequence
<220> FEATURE:
<223> OTHER INFORMATION: Mature sense sequence of shRNAmir targeting VDR

<400> SEQUENCE: 225
cgcgtcagtg acgtgacca                                                 19

<210> SEQ ID NO 226
<211> LENGTH: 97
<212> TYPE: DNA
<213> ORGANISM: Artificial Sequence
<220> FEATURE:
<223> OTHER INFORMATION: Hairpin sequence of shRNAmir targeting NR4A3

<400> SEQUENCE: 226
tgctgttgac agtgagcgac ccaaagaaga tcagacatta tagtgaagcc acagatgtat     60
aatgtctgat cttctttggg gtgcctactg cctcgga                             97

<210> SEQ ID NO 227
<211> LENGTH: 19
<212> TYPE: DNA
<213> ORGANISM: Artificial Sequence
<220> FEATURE:
<223> OTHER INFORMATION: Mature sense sequence of shRNAmir targeting
      NR4A3

<400> SEQUENCE: 227

```
ccaaagaaga tcagacatt                                                19
```

<210> SEQ ID NO 228
<211> LENGTH: 22
<212> TYPE: RNA
<213> ORGANISM: Artificial Sequence
<220> FEATURE:
<223> OTHER INFORMATION: Mature hsa-miR-1 sequence

<400> SEQUENCE: 228

```
uggaauguaa agaaguaugu au                                            22
```

<210> SEQ ID NO 229
<211> LENGTH: 22
<212> TYPE: RNA
<213> ORGANISM: Artificial Sequence
<220> FEATURE:
<223> OTHER INFORMATION: Mature hsa-miR-129* sequence

<400> SEQUENCE: 229

```
aagcccuuac cccaaaaagu au                                            22
```

<210> SEQ ID NO 230
<211> LENGTH: 22
<212> TYPE: RNA
<213> ORGANISM: Artificial Sequence
<220> FEATURE:
<223> OTHER INFORMATION: Mature hsa-miR-24 sequence

<400> SEQUENCE: 230

```
uggcucaguu cagcaggaac ag                                            22
```

<210> SEQ ID NO 231
<211> LENGTH: 22
<212> TYPE: RNA
<213> ORGANISM: Artificial Sequence
<220> FEATURE:
<223> OTHER INFORMATION: Mature hsa-miR-24-1* sequence

<400> SEQUENCE: 231

```
ugccuacuga gcugauauc agu                                            22
```

<210> SEQ ID NO 232
<211> LENGTH: 22
<212> TYPE: RNA
<213> ORGANISM: Artificial Sequence
<220> FEATURE:
<223> OTHER INFORMATION: Mature hsa-miR-218-1* sequence

<400> SEQUENCE: 232

```
augguuccgu caagcaccau gg                                            22
```

<210> SEQ ID NO 233
<211> LENGTH: 22
<212> TYPE: RNA
<213> ORGANISM: Artificial Sequence
<220> FEATURE:
<223> OTHER INFORMATION: Mature hsa-miR-183 sequence

<400> SEQUENCE: 233

```
uauggcacug guagaauuca cu                                            22
```

<210> SEQ ID NO 234
<211> LENGTH: 22
<212> TYPE: RNA

```
<213> ORGANISM: Artificial Sequence
<220> FEATURE:
<223> OTHER INFORMATION: Mature hsa-miR-183* sequence

<400> SEQUENCE: 234
gugaauuacc gaagggccau aa                                              22
```